US012612408B2

(12) United States Patent
Wang et al.

(10) Patent No.: US 12,612,408 B2
(45) Date of Patent: Apr. 28, 2026

(54) PYRAZOLONE-FUSED PYRIMIDINE COMPOUND, PREPARATION METHOD FOR SAME AND APPLICATIONS THEREOF

(71) Applicant: SHANGHAI PHARMACEUTICALS HOLDING CO., LTD., Shanghai (CN)

(72) Inventors: Qian Wang, Shanghai (CN); Sijie Shu, Shanghai (CN); Guangxin Xia, Shanghai (CN); Hui Ge, Shanghai (CN); Bingbin Zhang, Shanghai (CN); Guoyong Huo, Shanghai (CN); Lin Zhang, Shanghai (CN); Chen Shi, Shanghai (CN); Jiangsong Lou, Shanghai (CN); Chi Zhang, Shanghai (CN); Zhihui Zhang, Shanghai (CN); Yu Mao, Shanghai (CN); Jianxin Yu, Shanghai (CN); Ying Ke, Shanghai (CN); Yanjun Liu, Shanghai (CN)

(73) Assignee: Shanghai Pharmaceuticals Holding Co., Ltd., Shanghai (CN)

( * ) Notice: Subject to any disclaimer, the term of this patent is extended or adjusted under 35 U.S.C. 154(b) by 1056 days.

(21) Appl. No.: 17/622,579

(22) PCT Filed: Jun. 28, 2020

(86) PCT No.: PCT/CN2020/098611

§ 371 (c)(1),
(2) Date: Dec. 23, 2021

(87) PCT Pub. No.: WO2020/259703

PCT Pub. Date: Dec. 30, 2020

(65) Prior Publication Data

US 2022/0259210 A1 Aug. 18, 2022

(30) Foreign Application Priority Data

Jun. 28, 2019 (CN) ........................ 201910579671.0

(51) Int. Cl.

| | |
|---|---|
| ***C07D 487/04*** | (2006.01) |
| ***A61K 31/519*** | (2006.01) |
| ***A61K 45/06*** | (2006.01) |
| ***A61P 35/00*** | (2006.01) |

(52) U.S. Cl.

CPC .......... *C07D 487/04* (2013.01); *A61K 31/519* (2013.01); *A61K 45/06* (2013.01); *A61P 35/00* (2018.01)

(58) Field of Classification Search

CPC ..... C07D 487/04; A61P 35/00; A61K 31/519; A61K 45/06

See application file for complete search history.

(56) References Cited

U.S. PATENT DOCUMENTS

| | | | | |
|---|---|---|---|---|
| 7,241,763 | B2 | 7/2007 | Lacrampe et al. | |
| 7,834,019 | B2 | 11/2010 | Sagara et al. | |
| 7,935,708 | B2 * | 5/2011 | Sagara | A61K 31/4162 548/364.7 |
| 7,947,695 | B2 | 5/2011 | Freyne et al. | |
| 8,288,396 | B2 | 10/2012 | Goto et al. | |
| 8,507,505 | B2 | 8/2013 | Bamba et al. | |
| 10,766,902 | B2 | 9/2020 | Burkamp et al. | |
| 10,947,238 | B2 | 3/2021 | Reigan et al. | |
| 10,954,253 | B2 | 3/2021 | Qian et al. | |
| 11,124,518 | B2 | 9/2021 | Huang et al. | |
| 11,261,192 | B2 | 3/2022 | Huang et al. | |
| 11,299,493 | B2 | 4/2022 | Chakravarty et al. | |
| 2010/0105674 | A1 | 4/2010 | Deanda, Jr. et al. | |
| 2010/0113445 | A1 | 5/2010 | Deanda, Jr. et al. | |
| 2020/0017528 | A1 | 1/2020 | Qian et al. | |
| 2021/0061807 | A1 | 3/2021 | Chen | |

FOREIGN PATENT DOCUMENTS

| | | |
|---|---|---|
| CN | 101432284 A | 5/2009 |
| CN | 109422754 A | 3/2019 |
| CN | 109810111 A | 5/2019 |

(Continued)

OTHER PUBLICATIONS

Esposito, Francesca, et al. "Wee1 kinase: a potential target to overcome tumor resistance to therapy." International Journal of Molecular Sciences 22.19 (2021): 10689. (Year: 2021).*

Wang, Zizhuo, et al. "An update of predictive biomarkers related to WEE1 inhibition in cancer therapy." Journal of Cancer Research and Clinical Oncology 150.1 (2024): 13. (Year: 2024).*

American Cancer Society. "Breast Cancer Risk and Prevention". https://www.cancer.org/content/dam/CRC/PDF/Public/8578.00.pdf. Accessed Apr. 18, 2025. (Year: 2025).*

(Continued)

*Primary Examiner* — James H Alstrum-Acevedo
*Assistant Examiner* — Justin Christopher Sanchez

(57) ABSTRACT

Disclosed are a pyrazolone-fused pyrimidine compound, a preparation method for same and applications thereof. Provided in the present invention is the pyrazolone-fused pyrimidine compound as represented by formula (II). The compound has improved inhibitory activity with respect to WEE1 kinase.

II

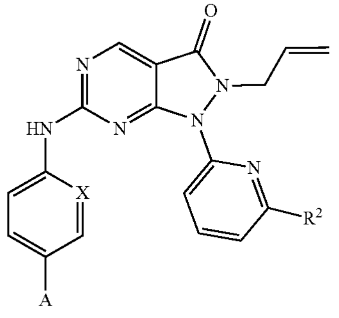

20 Claims, No Drawings

(56) References Cited

FOREIGN PATENT DOCUMENTS

| | | | |
|---|---|---|---|
| WO | 2004007499 | A1 | 1/2004 |
| WO | 2006074985 | A1 | 7/2006 |
| WO | 2007126122 | A1 | 11/2007 |
| WO | 2007126128 | A1 | 11/2007 |
| WO | 2008115738 | A1 | 9/2008 |
| WO | 2008115742 | A1 | 9/2008 |
| WO | 2010067886 | A1 | 6/2010 |
| WO | 2010098367 | A1 | 9/2010 |
| WO | 2017075629 | A2 | 5/2017 |
| WO | 2018011569 | A1 | 1/2018 |
| WO | 2018133829 | A1 | 7/2018 |
| WO | 2019028008 | A1 | 2/2019 |
| WO | 2019037678 | A1 | 2/2019 |
| WO | 2019074979 | A1 | 4/2019 |
| WO | 2019165204 | A1 | 8/2019 |
| WO | 2020/259703 | A1 | 12/2020 |

OTHER PUBLICATIONS

American Cancer Society. "Osteosarcoma Caused, Risk Factors, and Prevention". https://www.cancer.org/content/dam/CRC/PDF/Public/8769.00.pdf. Accessed Apr. 18, 2025. (Year: 2025).*

National Center for Biotechnology Information. "PubChem Compound Summary for CID 105533627, Ethyl 4-(4-aminophenyl)cyclohexane-1-carboxylate" PubChem, https://pubchem.ncbi.nlm.nih.gov/compound/Ethyl-4-_4-aminophenyl_cyclohexane-1-carboxylate. Accessed Apr. 18, 2025. (Year: 2025).*

International Search Report for International Patent Application No. PCT/CN2020/098611, mailed Sep. 30, 2020.

Written Opinion for International Patent Application No. PCT/CN2020/098611, mailed Sep. 30, 2020.

"1780635-51-9", STN Registry, Jun. 15, 2015 (Jun. 15, 2015), DOI: 20200904173416X.

"1700621-59-5", STN Registry, May 7, 2015 (May 7, 2015), DOI: 20200904173454X.

"1935415-74-9", STN Registry, Jun. 20, 2016 (Jun. 20, 2016), DOI: 20200904173330X.

"1780952-51-3", STN Registry, Jun. 15, 2015 (Jun. 15, 2015), DOI: 20200904173538X.

"1391259-46-3", STN Registry, Aug. 15, 2012 (Aug. 15, 2012), DOI: 20200904173616X.

"1391234-19-7", STN Registry, Aug. 15, 2012 (Aug. 15, 2012), DOI: 20200904173650X.

"1391201-09-4", STN Registry, Aug. 15, 2012 (Aug. 15, 2012), DOI: 20200904173717X.

"1391021-25-2", STN Registry, Aug. 14, 2012 (Aug. 14, 2012), DOI: 20200904173744X.

"1049004-35-4", STN Registry, Sep. 12, 2008 (Sep. 12, 2008), DOI: 20200904173823X.

"1049004-05-8", STN Registry, Sep. 12, 2008 (Sep. 12, 2008), DOI: 20200904173859X.

"892492-28-3", STN Registry, Jul. 13, 2006 (Jul. 13, 2006), DOI: 20200904173934X.

"892492-16-9", STN Registry, Jul. 13, 2006 (Jul. 13, 2006), DOI: 20200904174009X.

"854446-70-1", STN Registry, Jul. 11, 2005 (Jul. 11, 2005), DOI: 20200904174040X.

"854446-68-7", STN Registry, Jul. 11, 2005 (Jul. 11, 2005), DOI: 20200904174106X.

"31352-37-1", STN Registry, Nov. 16, 1984 (Nov. 16, 1984), DOI: 20200904174138X.

"62485-63-6", STN Registry, Nov. 16, 1984 (Nov. 16, 1984), DOI: 20200904174203X.

"1780635-51-9", *STN Registry*, Jun. 15, 2015.

"1700621-59-5", *STN Registry*, May 7, 2015.

"1935415-74-9", *STN Registry*, Jun. 20, 2016.

"1780952-51-3", *STN Registry*, Jun. 15, 2015.

"1391259-46-3", *STN Registry*, Aug. 15, 2012.

"1391234-19-7", *STN Registry*, Aug. 15, 2012.

"1391201-09-4", *STN Registry*, Aug. 15, 2012.

"1391021-25-2", *STN Registry*, Aug. 14, 2012.

"1049004-35-4", *STN Registry*, Sep. 12, 2008.

"1049004-05-8", *STN Registry*, Sep. 12, 2008.

"892492-28-3", *STN Registry*, Jul. 13, 2006.

"892492-16-9", *STN Registry*, Jul. 13, 2006.

"854446-70-1", *STN Registry*, Jul. 11, 2005.

"854446-68-7", *STN Registry*, Jul. 11, 2005.

"31352-37-1", *STN Registry*, Nov. 16, 1984.

"62485-63-6", *STN Registry*, Nov. 16, 1984.

International Search Report from PCT/CN2020/098611, mailed Sep. 30, 2020 (11 pages, English Translation).

Written Opinion of the International Searching Authority from PCT/CN2020/098611, mailed Sep. 30, 2020 (11 pages, English).

International Search Report from PCT/CN2020/112034, mailed Nov. 25, 2020 (9 pages, English Translation).

Written Opinion of the International Searching Authority from PCT/CN2020/112034, mailed Nov. 25, 2020 (7 pages, English).

Berge, et al., "Pharmaceutical Salts," Journal of Pharmaceutical Sciences, vol. 66, No. 1, Jan. 1977, 19 pages.

International Preliminary Report on Patentability received for PCT Patent Application No. PCT/CN2020/098611, mailed on Jan. 6, 2022, 21 pages (14 Pages of English Translation and 7 pages of Original Document).

* cited by examiner

PYRAZOLONE-FUSED PYRIMIDINE COMPOUND, PREPARATION METHOD FOR SAME AND APPLICATIONS THEREOF

The present application claims the priority of Chinese patent application 201910579671.0 filed on Jun. 28, 2019. The contents of the Chinese patent application are incorporated herein by reference in their entireties.

TECHNICAL FIELD

The present disclosure relates to a pyrazolone-fused pyrimidine compound, a preparation method therefor and an application thereof.

BACKGROUND

Cell cycle is closely related to DNA damage repair process. Cell cycle refers to the whole process of cell division, which is divided into two stages: interphase and mitotic phase (M). Cell cycle checkpoint is a key point to regulate the cell cycle, its main function is to ensure that every event in the cycle can be completed on time and orderly, and to adjust the cell state to adapt to the external environment. The main checkpoints of cells are as follows: 1) G1/S checkpoint, which is called R (restriction) point in mammals and controls cells from static G1 phase to DNA synthesis phase; 2) S-phase checkpoint: whether DNA replication is completed; 3) G2/M checkpoint: it is the control point that regulates the cell to enter the division stage; 4) middle-late checkpoint: also called spindle assembly checkpoint, if the centromere is not connected to the spindle correctly, it will cause the interruption of cell cycle. If there is abnormality in some processes of cell division cycle, such as DNA damage, the checkpoint will sense in time and start repair. P53 protein is an important protein that regulates G1 checkpoint, when DNA is damaged, P53 protein prevents cells from entering S phase and activates DNA repair mechanism, which is very important for maintaining the integrity of cell genome. However, since P53 mutation often exists in tumor cells, which makes G1 checkpoint defective, therefore, the regulation of cell division cycle in P53 mutated cells depends on G2/M checkpoint. WEE1 kinase is a cell cycle regulatory protein, which can regulate the phosphorylation state of cyclin-dependent kinase 1 (CDK1), thus regulating the activity of CDK1 and cyclin B complex, realizing the regulation of cell cycle, and playing an important role in regulating DNA damage checkpoints. WEE1 is a key gene in G2/M phase block, plays an important monitoring role, and is overexpressed in some cancers, inhibition or downregulation of WEE1 kinase may trigger mitotic catastrophe, so WEE1 kinase inhibitors have a key role in anticancer therapy and have become a hot spot for the development of anticancer drugs.

International patent applications WO2019037678, WO2019028008, WO2018133829, WO2010098367, WO2010067886, WO2008115742, WO2008115738, WO2007126122, WO2007126128 WO2004007499 and others have disclosed part of small molecule WEE1 kinase inhibitors, but there are no small molecule WEE1 kinase inhibitors on the market, and there is still a need in the art to develop new WEE1 kinase inhibitors with good anticancer activity and high safety.

DETAILED DESCRIPTION

The technical problem to be solved by the present disclosure is that the existing compounds with inhibitory activity against WEE1 kinase have a single structure, therefore, the present disclosure provides a pyrazolone-fused pyrimidine compound, a preparation method therefor and an application thereof, and the compound has a better inhibitory activity against WEE1 kinase.

The present disclosure provides a pyrazolone-fused pyrimidine compound represented by formula II, a pharmaceutically acceptable salt thereof, a solvate thereof, a solvate of the pharmaceutically acceptable salt thereof, a metabolite thereof or a prodrug thereof:

II

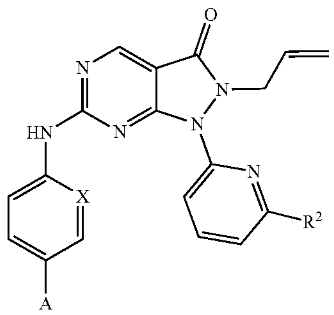

wherein, A is $C_3$-$C_{20}$ cycloalkyl substituted by one or two $R^1$;

X is CH or N;

$R^1$ is independently halogen, —$OR^{1-1}$, —$SR^{1-2}$, —CN, —$NR^{1-3}R^{1-4}$, —C(═O)$R^{1-5}$, —C(═$NR^{1-6}$)$R^{1-7}$, ═N—O—$R^{1-9}$ (wherein "═" refers to the substitution of two hydrogens on the methylene of the cycloalkyl) or "$C_2$-$C_7$ alkenyl, $C_2$-$C_8$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-8}$;

$R^{1-1}$ is independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-1-1}$;

$R^{1-1-1}$ is independently halogen, hydroxyl, amino, mercapto, cyano, $C_1$-$C_7$ alkyl, $C_1$-$C_7$alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-1-1-1}$"; $R^{1-1-1-1}$ is independently $C_1$-$C_7$ alkyl or $C_3$-$C_{14}$ cycloalkyl;

$R^{1-2}$ is independently hydrogen, "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-2-1}$;

$R^{1-2-1}$ is independently hydrogen, halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-2-1-1}$"; $R^{1-2-1-1}$ is independently $C_1$-$C_7$ alkyl or $C_3$-$C_{14}$ cycloalkyl;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2$$NR^{1-3-7}R^{1-3-8}$, —C(═O)$NR^{1-3-9}R^{1-3-10}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

or, $R^{1-3}$ and $R^{1-4}$ together with the nitrogen atom they are attached to form a $C_3$-$C_{14}$ heterocycloalkyl optionally substituted by one, two or three $R^{1-3-12}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-13}$)—; $R^{1-3-13}$ is independently $C_1$-$C_7$ alkyl or $C_3$-$C_{14}$ cycloalkyl;

$R^{1-3-1}$ and $R^{1-3-2}$ are independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$; $R^{1-3-1-1}$ is independently $C_1$-$C_7$ alkyl or $C_3$-$C_{14}$ cycloalkyl;

$R^{1-3-3}$ is independently hydrogen, —CN, $C_1$-$C_7$ alkyl, $C_2$-$C_7$ alkenyl, $C_2$-$C_7$ alkynyl or $C_3$-$C_{14}$ cycloalkyl;

$R^{1-3-5}$, $R^{1-3-6}$, $R^{1-3-7}$, $R^{1-3-8}$, $R^{1-3-9}$ and $R^{1-3-10}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-3-5}$ and $R^{1-3-6}$ together with the nitrogen atom they are attached to form a $C_3$-$C_{14}$ heterocycloalkyl optionally substituted by one, two or three $R^{1-3-5-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-5-2}$)—; $R^{1-3-5-1}$ is independently $C_1$-$C_7$ alkyl or $C_3$-$C_{14}$ cycloalkyl; $R^{1-3-5-2}$ is independently $C_1$-$C_7$ alkyl or $C_3$-$C_{14}$ cycloalkyl;

or, $R^{1-3-7}$ and $R^{1-3-8}$ together with the nitrogen atom they are attached to form a $C_3$-$C_{14}$ heterocycloalkyl optionally substituted by one, two or three $R^{1-3-7-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-7-2}$)—; $R^{1-3-7-1}$ is independently $C_1$-$C_7$ alkyl or $C_3$-$C_{14}$ cycloalkyl; $R^{1-3-7-2}$ is independently $C_1$-$C_7$ alkyl or $C_3$-$C_{14}$ cycloalkyl;

or, $R^{1-3-9}$ and $R^{1-3-10}$ together with the nitrogen atom they are attached to form a $C_3$-$C_{14}$ heterocycloalkyl optionally substituted by one, two or three $R^{1-3-9-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-9-2}$)—; $R^{1-3-9-1}$ is independently $C_1$-$C_7$ alkyl or $C_3$-$C_{14}$ cycloalkyl; $R^{1-3-9-2}$ is independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$". $R^{1-3-11-1}$ is independently $C_1$-$C_7$ alkyl or $C_3$-$C_{14}$ cycloalkyl;

$R^{1-3-12}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or amino substituted by one or two $R^{1-3-12-1}$; $R^{1-3-12-1}$ is independently $C_1$-$C_7$ alkyl or $C_3$-$C_{14}$ cycloalkyl;

$R^{15}$ is independently hydrogen, —$NR^{1-5-1}R^{1-5-2}$, —$OR^{1-5-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-5-1}$ and $R^{1-5-2}$ together with the nitrogen atom they are attached to form a $C_3$-$C_{14}$ heterocycloalkyl optionally substituted by one, two or three $R^{1-5-1-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-5-1-2}$)—; $R^{1-5-1-1}$ is independently $C_1$-$C_7$ alkyl or $C_3$-$C_{14}$ cycloalkyl; $R^{1-5-1-2}$ is independently $C_1$-$C_7$ alkyl or $C_3$-$C_{14}$ cycloalkyl;

$R^{1-5-3}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$". $R^{1-5-4-1}$ is independently $C_1$-$C_7$ alkyl or $C_3$-$C_{14}$ cycloalkyl;

$R^{1-6}$ is independently hydrogen, —CN, —OH or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-6-1}$;

$R^{1-6-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or amino substituted by one or two $R^{1-6-1-1}$; $R^{1-6-1-1}$ is independently $C_1$-$C_7$ alkyl or $C_3$-$C_{14}$ cycloalkyl;

$R^{1-7}$ is independently hydrogen, —$OR^{1-7-1}$, —$NR^{1-7-2}R^{1-7-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-7-4}$;

$R^{1-7-1}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-7-2}$ and $R^{1-7-3}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-7-2-2}$)—; $R^{1-7-2-1}$ is independently $C_1$-$C_7$ alkyl or $C_3$-$C_{14}$ cycloalkyl; $R^{1-7-2-2}$ is independently $C_1$-$C_7$ alkyl or $C_3$-$C_{14}$ cycloalkyl;

$R^{1-7-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-7-4-1}$". $R^{1-7-4-1}$ is independently $C_1$-$C_7$ alkyl or $C_3$-$C_{14}$ cycloalkyl;

$R^{1-8}$ is independently oxo, halogen, —OH, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^{1-9}$ is independently hydrogen or $C_1$-$C_7$ alkyl;

$R^2$ is —$OR^{2-1}$, cyano, carboxyl; or "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-1}$ is $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{2-2}$ is independently halogen, hydroxyl, amino, $C_1$-$C_7$ alkyl, $C_1$-$C_7$ alkoxy, $C_3$-$C_{14}$ cycloalkyl or $C_3$-$C_{14}$ heterocycloalkyl;

in any one of the above cases, the heteroatoms in the $C_3$-$C_{14}$ heterocycloalkyl, $C_1$-$C_7$ heteroaryl are independently selected from one or more of boron, silicon, oxygen, sulfur, selenium, nitrogen and phosphorus; the number of heteroatoms is independently 1, 2, 3 or 4.

In a certain scheme, some substituents in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof may further have the following definitions, and the definitions of substituents not involved below are as described in any of the above schemes (hereinafter referred to as "in a certain scheme"):

When A is $C_3$-$C_{20}$ cycloalkyl substituted by one or two $R^1$, the $C_3$-$C_{20}$ cycloalkyl is for example $C_3$-$C_{20}$ monocyclic cycloalkyl, $C_3$-$C_{20}$ spiro cycloalkyl, $C_3$-$C_{20}$ fused cycloalkyl or $C_3$-$C_{20}$ bridged cycloalkyl.

The $C_3$-$C_{20}$ monocyclic cycloalkyl is for example $C_3$-$C_6$ monocyclic cycloalkyl, for example cyclopropyl, cyclobutyl, cyclopentyl or cyclohexyl, for example cyclohexyl.

The $C_3$-$C_{20}$ bridged cycloalkyl is for example $C_5$-$C_8$ bridged cycloalkyl, for example

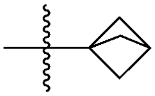

or

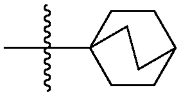

.

In a certain scheme:

When A is $C_3$-$C_{20}$ cycloalkyl substituted by one or two $R^1$, the $C_3$-$C_{20}$ cycloalkyl is for example $C_3$-$C_{20}$ saturated cycloalkyl.

In a certain scheme:

When A is $C_3$-$C_{20}$ cycloalkyl substituted by one $R^1$, the A is for example

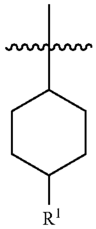

or

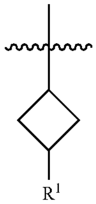

.

the

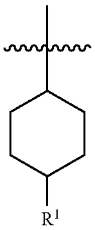

is for example

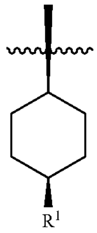

and/or

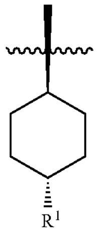

, for example,

"

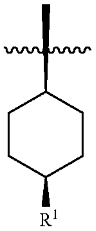

and

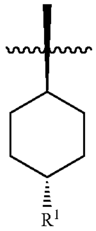

, the ratio of

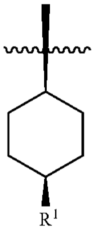

and

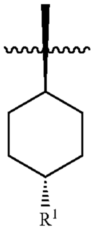

is 1:1".

the

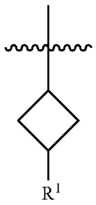

is for example

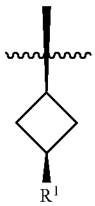

and/or

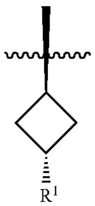

, for example,

“ 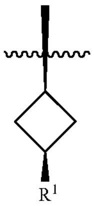 and 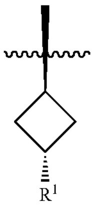 , the ratio of

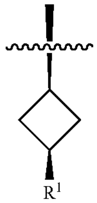 and 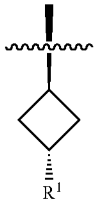

is 1:1”.

In a certain scheme:

When $R^1$ is independently $C_3$-$C_{14}$ heterocycloalkyl, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, “$C_3$-$C_9$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S” and which is connected to a benzene ring by a nitrogen atom, for example, azetidinyl, morpholinyl, piperidinyl or piperazinyl.

The azetidinyl is for example

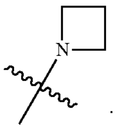 .

The morpholinyl is for example

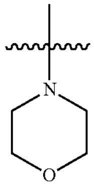 .

The piperidinyl is for example

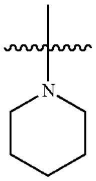 or 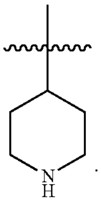 .

The piperazinyl is for example

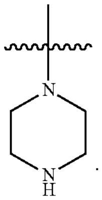 .

In a certain scheme:

When $R^1$ is independently $C_3$-$C_{14}$ heterocycloalkyl, the heteroatom of the $C_3$-$C_{14}$ heterocycloalkyl may not be substituted.

In a certain scheme:

When $R^1$ is independently $C_3$-$C_{14}$ heterocycloalkyl, the methylene in the $C_3$-$C_{14}$ heterocycloalkyl may not be substituted.

In a certain scheme:

When $R^1$ is independently $C_3$-$C_{14}$ heterocycloalkyl substituted by one $R^{1-8}$, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, “$C_3$-$C_9$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S” and which is connected to a benzene ring by a nitrogen atom, for example, azetidinyl,

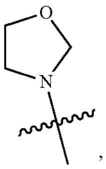 [SMILES: *N1CCOC1] , morpholinyl, piperidinyl or piperazinyl.

The azetidinyl is for example

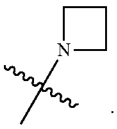 .

The morpholinyl is for example

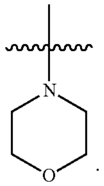

The piperidinyl is for example

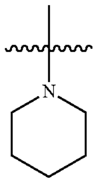

or

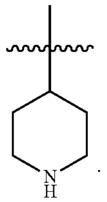

The piperazinyl is for example

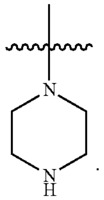

In a certain scheme:

When $R^1$ is independently $C_3$-$C_{14}$ heterocycloalkyl substituted by one $R^{1-8}$, the heteroatom of the $C_3$-$C_{14}$ heterocycloalkyl may not be substituted except $R^{1-8}$.

In a certain scheme:

When $R^1$ is independently $C_3$-$C_{14}$ heterocycloalkyl substituted by one $R^{1-8}$, the methylene in the $C_3$-$C_{14}$ heterocycloalkyl may not be substituted.

In a certain scheme:

When $R^1$ is independently $C_3$-$C_{14}$ heterocycloalkyl substituted by one $R^{1-8}$, the $C_3$-$C_{14}$ heterocycloalkyl substituted by one $R^{1-8}$ may be

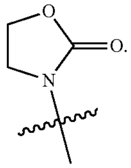 [SMILES: *N1CCOC1=O]

In a certain scheme:

When $R^{1-3}$ and $R^{1-4}$ are independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-3-1}$ is independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-3-2}$ is $C_3$-$C_{14}$ cycloalkyl, the $C_3$-$C_{14}$ cycloalkyl is for example $C_3$-$C_{14}$ monocyclic cycloalkyl, for example $C_3$-$C_6$ monocyclic cycloalkyl, for example cyclopropyl, cyclobutyl, cyclopentyl or cyclohexyl, for example cyclopropyl.

In a certain scheme:

When $R^{1-3-2}$ is $C_3$-$C_{14}$ cycloalkyl, the $C_3$-$C_{14}$ cycloalkyl is for example $C_3$-$C_{14}$ saturated cycloalkyl.

In a certain scheme:

When $R^{1-5}$ is independently $C_3$-$C_{14}$ heterocycloalkyl, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, "$C_3$-$C_9$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S" and which is connected to a benzene ring by a nitrogen atom, for example, azetidinyl.

The azetidinyl is for example

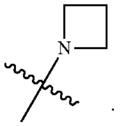

In a certain scheme:

When $R^{1-5}$ is independently $C_3$-$C_{14}$ heterocycloalkyl, the heteroatom of the $C_3$-$C_{14}$ heterocycloalkyl may not be substituted.

In a certain scheme:

When $R^{1-5}$ is independently $C_3$-$C_{14}$ heterocycloalkyl, the methylene in the $C_3$-$C_{14}$ heterocycloalkyl may not be substituted.

In a certain scheme:

When $R^{1-5-1}$ and $R^{1-5-2}$ are independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-1-1}$ and $R^{1-5-2}$ are independently $C_3$-$C_{14}$ cycloalkyl, the $C_3$-$C_{14}$ cycloalkyl is for example $C_3$-$C_{14}$ monocyclic cycloalkyl, $C_3$-$C_{14}$ spiro cycloalkyl, $C_3$-$C_{14}$ fused cycloalkyl or $C_3$-$C_{14}$ bridged cycloalkyl.

The $C_3$-$C_{14}$ monocyclic cycloalkyl is for example $C_3$-$C_6$ monocyclic cycloalkyl, for example cyclopropyl, cyclobutyl, cyclopentyl or cyclohexyl, for example cyclobutyl, cyclopentyl or cyclohexyl.

The $C_3$-$C_{14}$ bridged cycloalkyl is for example $C_5$-$C_5$ bridged cycloalkyl, for example

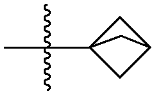

or

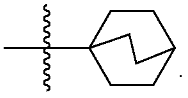

In a certain scheme:

When $R^{1-5-1}$ and $R^{1-5-2}$ are independently $C_3$-$C_{14}$ cycloalkyl, the $C_3$-$C_{14}$ cycloalkyl is for example $C_3$-$C_{14}$ saturated cycloalkyl.

In a certain scheme:

When $R^{1-5-3}$ is independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-9}$ is independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^2$ is $C_2$-$C_7$ alkyl optionally substituted by one, two or three $R^{2-2}$, the $C_2$-$C_7$ alkyl is for example $C_2$-$C_4$ alkyl, for example ethyl, n-propyl, isopropyl, n-butyl, isobutyl, sec-butyl or tert-butyl, for example isopropyl.

In a certain scheme:

When $R^2$ is $C_2$-$C_7$ alkyl substituted by one $R^{2-2}$, $R^{2-2}$ is hydroxyl; the $C_2$-$C_7$ alkyl substituted by one $R^{2-2}$ is for example

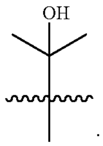

In a certain scheme:

When $R^2$ is $C_3$-$C_{14}$ heterocycloalkyl optionally substituted by one, two or three $R^{2-2}$, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, "$C_3$-$C_9$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S" and which is connected to a benzene ring by a nitrogen atom, for example, oxetanyl.

The morpholinyl oxetanyl is for example oxetan-3-yl.

In a certain scheme:

When $R^2$ is $C_3$-$C_{14}$ heterocycloalkyl optionally substituted by one, two or three $R^{2-2}$, the heteroatom of the $C_3$-$C_{14}$ heterocycloalkyl may not be substituted except $R^{2-2}$.

In a certain scheme:

When $R^2$ is $C_3$-$C_{14}$ heterocycloalkyl optionally substituted by one, two or three $R^{2-2}$, the methylene in the $C_3$-$C_{14}$ heterocycloalkyl may not be substituted.

In a certain scheme:

When $R^2$ is $C_3$-$C_{14}$ heterocycloalkyl substituted by one $R^{2-2}$, $R^{2-2}$ is halogen or hydroxyl; the $C_3$-$C_{14}$ heterocycloalkyl substituted by one $R^{2-2}$ is for example

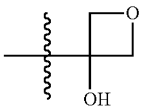 or 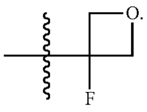

In a certain scheme:

The ratio of each isomer in the pyrazolone-fused pyrimidine compound represented by formula II may be equal, for example, racemate.

In a certain scheme:

The atoms in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof may all exist in their natural abundance.

In a certain scheme:

A is $C_3$-$C_{20}$ cycloalkyl substituted by one $R^1$.

In a certain scheme:

A is

"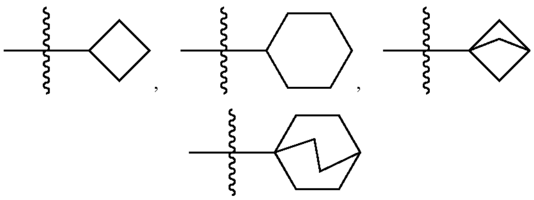 or substituted by one or two $R^1$".

In a certain scheme:

A is

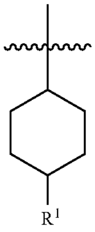 or 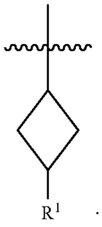

In a certain scheme:

$R^1$ is independently halogen, —CN, —$NR^{1-3}R^{1-4}$, —C(═O)$R^{1-5}$, —C(═$NR^{1-6}$)$R^{1-7}$, ═N—O—$R^{1-9}$ or "$C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-8}$.

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2$$NR^{1-3-7}R^{1-3-8}$, —C(═O)$NR^{1-3-9}R^{1-3-10}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

- $R^{1-3-1}$ and $R^{1-3-2}$ are independently "$C_1$-$C_7$ alkyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$"; $R^{1-3-1-1}$ is independently $C_1$-$C_7$ alkyl;
- $R^{1-3-3}$ is independently hydrogen;
- $R^{1-3-1}$, $R^{1-3-6}$, $R^{1-3-7}$, $R^{1-3-1}$, $R^{1-3-9}$ and $R^{1-3-10}$ are independently hydrogen, $C_1$-$C_7$ alkyl or $C_3$-$C_{14}$ cycloalkyl;
- $R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;
- $R^{1-5}$ is independently hydrogen, —$NR^{1-5-1}R^{1-5-2}$, —$OR^{1-5-3}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-5-4}$;
- $R^{1-5-1}$ and $R^{1-5-2}$ are independently hydrogen, $C_1$-$C_7$ alkyl or $C_3$-$C_{14}$ cycloalkyl;
- $R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently oxo, halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^{1-9}$ is independently hydrogen or $C_1$-$C_7$ alkyl.

In a certain scheme:

$R^1$ is independently halogen, —CN, —$NR^{1-3}R^{1-4}$, —C(═O)$R^{1-5}$, —C(═$NR^{1-6}$)$R^{1-7}$ or "$C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-8}$;

$R^{1-3}$ and $R^{1-4}$ are independently hydrogen, —S(═O)$_2$$R^{1-3-1}$, —C(═O)$R^{1-3-2}$, —C(═$NR^{1-3-3}$)$NR^{1-3-5}R^{1-3-6}$, —S(═O)$_2$$NR^{1-3-7}R^{1-3-8}$, —C(═O)$NR^{1-3-9}R^{1-3-10}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

$R^{1-3-1}$ and $R^{1-3-2}$ are independently "$C_1$-$C_7$ alkyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl.

In a certain scheme:

$R^1$ is independently cyano, halogen, —$NR^{1-3}R^{1-4}$, —C(═O)$R^{1-5}$, —C(═$NR^{1-6}$)$R^{1-7}$, ═N—O—$R^{1-9}$, $C_1$-$C_7$ heteroaryl or "$C_3$-$C_{14}$ heterocycloalkyl optionally substituted by one $R^{1-8}$".

In a certain scheme:

$R^1$ is independently cyano, halogen, —$NR^{1-3}R^{1-4}$, —C(═O)$R^{1-5}$, —C(═$NR^{1-6}$)$R^{1-7}$, $C_1$-$C_7$ heteroaryl or $C_3$-$C_{14}$ heterocycloalkyl.

In a certain scheme:

$R^1$ is —CN, —$NR^{1-3}R^{1-4}$, —C(═O)$R^{1-5}$, ═N—O—$R^{1-9}$, or "$C_3$-$C_{14}$ heterocycloalkyl optionally substituted by one $R^{1-8}$".

In a certain scheme:

$R^1$ is independently —$NR^{1-3}R^{1-4}$, —C(═O)$R^{1-5}$ or $C_3$-$C_{14}$ heterocycloalkyl.

In a certain scheme:

$R^{1-3}$ and $R^{1-4}$ are independently hydrogen, —S(═O)$_2$$R^{1-3-1}$, —C(═O)$R^{1-3-2}$, —C(═$NR^{1-3-3}$)$NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen.

In a certain scheme:

$R^{1-3}$ and $R^{1-4}$ are independently hydrogen, —S(═O)$_2$$R^{1-3-1}$ or $C_1$-$C_7$ alkyl; $R^{1-3-1}$ is independently $C_1$-$C_7$ alkyl.

In a certain scheme:

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl.

In a certain scheme:

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen.

In a certain scheme:

$R^{1-8}$ is independently oxo.

In a certain scheme:

$R^{1-9}$ is independently hydrogen or $C_1$-$C_7$ alkyl.

In a certain scheme:

$R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-2}$ is independently halogen or hydroxyl.

In a certain scheme:

$R^2$ is "$C_2$-$C_7$ alkyl or $C_3$-$C_{14}$ heterocycloalkyl substituted by one $R^{2-2}$"; $R^{2-2}$ is halogen or hydroxyl.

In a certain scheme:

$R^2$ is "$C_2$-$C_7$ alkyl or $C_3$-$C_{14}$ heterocycloalkyl substituted by one $R^{2-2}$"; $R^{2-2}$ is hydroxyl.

In a certain scheme:

$R^2$ is

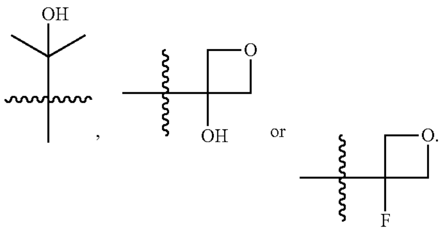

, or

In a certain scheme:

X is N.

In a certain scheme:

$R^1$ is $=N-O-R^{1-9}$; $R^{1-9}$ is independently hydrogen or $C_1$-$C_7$ alkyl.

In a certain scheme:

$R^{1-3-5}$, $R^{1-3-6}$, $R^{1-3-7}$, $R^{1-3-8}$, $R^{1-3-9}$ and $R^{1-3-10}$ are hydrogen.

In a certain scheme:

A is

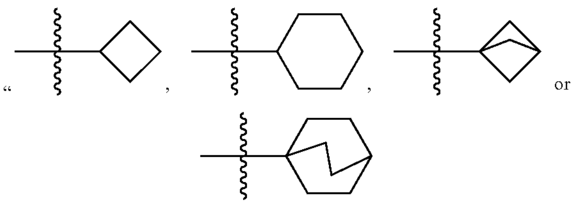

" , , or substituted by one or two $R^1$";

X is CH or N;

$R^1$ is independently halogen, —CN, $-NR^{1-3}R^{1-4}$, $-C(=O)R^{1-5}$, $-C(=NR^{1-6})R^{1-7}$, $=N-O-R^{1-9}$ or "$C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-8}$.

$R^{1-3}$ and $R^{1-4}$ are independently hydrogen, $-S(=O)_2R^{1-3-1}$, $-C(=O)R^{1-3-2}$, $-C(=NR^{1-3-3})NR^{1-3-5}R^{1-3-6}$, $-S(=O)_2NR^{1-3-7}R^{1-3-8}$, $-C(=O)NR^{1-3-9}R^{1-3-10}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

$R^{1-3-1}$ and $R^{1-3-2}$ are independently "$C_1$-$C_7$ alkyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently hydrogen, $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-5}$ is independently hydrogen, $-NR^{1-5-1}R^{1-5-2}$, $-OR^{1-5-3}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, $-NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently oxo, halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^{1-9}$ is independently hydrogen or $C_1$-$C_7$ alkyl;

$R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-2}$ is independently halogen or hydroxyl;

in any one of the above cases, the heteroatoms in the $C_3$-$C_{14}$ heterocycloalkyl, $C_1$-$C_7$ heteroaryl are independently selected from one or more of boron, silicon, oxygen, sulfur, selenium, nitrogen and phosphorus; the number of heteroatoms is independently 1, 2, 3 or 4.

In a certain scheme:

A is $C_3$-$C_{20}$ cycloalkyl substituted by one or two $R^1$;

X is CH or N;

$R^1$ is independently cyano, halogen, $-NR^{1-3}R^{1-4}$, $-C(=O)R^{1-5}$, $-C(=NR^{1-6})R^{1-7}$, $=N-O-R^{1-9}$, $C_1$-$C_7$ heteroaryl or "$C_3$-$C_{14}$ heterocycloalkyl" optionally substituted by one $R^{1-8}$.

$R^{1-3}$ and $R^{1-4}$ are independently hydrogen, $-S(=O)_2R^{1-3-1}$, $-C(=O)R^{1-3-2}$, $-C(=NR^{1-3}$-3)$NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is independently $-NR^{1-5-1}R^{1-5-2}$, $-OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is halogen or hydroxyl.

In a certain scheme:

A is $C_3$-$C_{20}$ cycloalkyl substituted by one $R^1$;

X is CH or N;

$R^1$ is —CN, $-NR^{1-3}R^{1-4}$, $-C(=O)R^{1-5}$, $=N-O-R^{1-9}$, or "$C_3$-$C_{14}$ heterocycloalkyl" optionally substituted by one $R^{1-8}$.

$R^{1-3}$ and $R^{1-4}$ are independently hydrogen, $-S(=O)_2R^{1-3-1}$, $-C(=O)R^{1-3-2}$, $-C(=NR^{1-3-3})NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl.

In a certain scheme:

A is $C_3$-$C_{20}$ cycloalkyl substituted by one $R^1$;

X is CH or N;

$R^1$ is —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$.

$R^{1-3}$ and $R^{1-4}$ are independently hydrogen, —S(═O)$_2R^{1-3-1}$, —C(═O)$R^{1-3-2}$, —C(═$NR^{1-3}$-3)$NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl;

$R^{1-5-1}$ and $R^{1-5-2}$ are independently hydrogen, $C_1$-$C_7$ alkyl or $C_3$-$C_{14}$ cycloalkyl;

$R^{1-5-3}$ is hydrogen;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl.

In a certain scheme:

A is

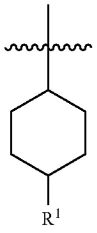
or
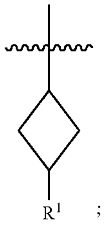
;

X is CH or N;

$R^1$ is —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$.

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl.

In a certain scheme:

A is

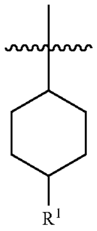
or
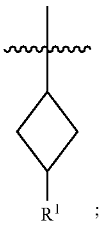
;

X is CH or N;

$R^1$ is independently —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$.

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$ or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is independently —$NR^{1-5-1}R^{1-5-2}$, —$OR^{1-5-3}$, or $C_3$-$C_{14}$ heterocycloalkyl;

$R^{1-5-1}$ and $R^{1-5-2}$ are independently hydrogen, $C_1$-$C_7$ alkyl, or $C_3$-$C_{14}$ cycloalkyl;

$R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is

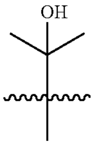
,
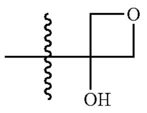
or
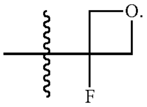

In a certain scheme, the pyrazolone-fused pyrimidine compound represented by formula II may be a pyrazolone-fused pyrimidine compound represented by formula I:

I

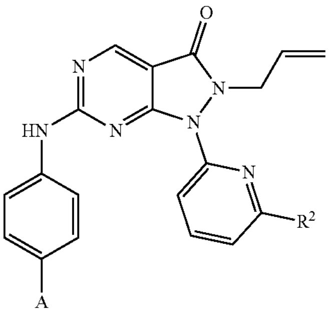

wherein, A is $C_3$-$C_{20}$ cycloalkyl substituted by one or two $R^1$;

$R^1$ is independently halogen, —$OR^{1-1}$, —$SR^{1-2}$, —CN, —$NR^{1-3}R^{1-4}$, —C(═O)$R^{1-5}$, —C(═$NR^{1-6}$)$R^{1-7}$ or “$C_2$-$C_7$ alkenyl, $C_2$-$C_8$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-8}$;

$R^{1-1}$ is independently “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl” optionally substituted by one, two or three $R^{1-1-1}$;

$R^{1-1-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-1-1-1}$”; $R^{1-1-1}$ is independently $C_1$-$C_7$ alkyl or $C_3$-$C_{14}$ cycloalkyl;

$R^{1-2}$ is independently “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl” optionally substituted by one, two or three $R^{1-2-1}$;

$R^{1-2-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-2-1-1}$”, $R^{1-2-1-1}$ is independently $C_1$-$C_7$ alkyl or $C_3$-$C_{14}$ cycloalkyl;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2$$NR^{1-3-7}R^{1-3-8}$, —C(═O)$NR^{1-3-9}R^{1-3-10}$ or “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-3-11}$;

or, $R^{1-3}$ and $R^{1-4}$ together with the nitrogen atom they are attached to form a $C_3$-$C_{14}$ heterocycloalkyl optionally substituted by one, two or three $R^{1-3-12}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-13}$)—; $R^{1-3-13}$ is independently a $C_1$-$C_7$ alkyl or $C_3$-$C_{14}$ cycloalkyl;

$R^{1-3-1}$ and $R^{1-3-2}$ are independently “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl or $C_6$-$C_{10}$ aryl optionally substituted by one or two $R^{1-3-1-1}$”; $R^{1-3-1-1}$ is independently $C_1$-$C_7$ alkyl or $C_3$-$C_{14}$ cycloalkyl;

$R^{1-3-3}$ is independently hydrogen, —CN, $C_1$-$C_7$ alkyl, $C_2$-$C_7$ alkenyl, $C_2$-$C_7$ alkynyl or $C_3$-$C_{14}$ cycloalkyl;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-3-5}$ and $R^{1-3-6}$ together with the nitrogen atom they are attached to form a $C_3$-$C_{14}$ heterocycloalkyl optionally substituted by one, two or three $R^{1-3-5}$-1; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-5-2}$)—; $R^{1-3-5-1}$ is independently $C_1$-$C_7$ alkyl or $C_3$-$C_{14}$ cycloalkyl; $R^{1-3-5-2}$ is independently $C_1$-$C_7$ alkyl or $C_3$-$C_{14}$ cycloalkyl;

or, $R^{1-3-7}$ and $R^{1-3-8}$ together with the nitrogen atom they are attached to form a $C_3$-$C_{14}$ heterocycloalkyl optionally substituted by one, two or three $R^{1-3-7-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-7-2}$)—; $R^{1-3-7-1}$ is independently $C_1$-$C_7$ alkyl or $C_3$-$C_{14}$ cycloalkyl; $R^{1-3-7-2}$ is independently $C_1$-$C_7$ alkyl or $C_3$-$C_{14}$ cycloalkyl;

or, $R^{1-3-9}$ and $R^{1-3-10}$ together with the nitrogen atom they are attached to form a $C_3$-$C_{14}$ heterocycloalkyl optionally substituted by one, two or three $R^{1-3-9}$-1; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-9-2}$)—; $R^{1-3-9-1}$ is independently $C_1$-$C_7$ alkyl or $C_3$-$C_{14}$ cycloalkyl; $R^{1-3-9-2}$ is independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-3-11-1}$” $R^{1-3-11-1}$ is independently $C_1$-$C_7$ alkyl or $C_3$-$C_{14}$ cycloalkyl;

$R^{1-3-12}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-3-12-1}$”; $R^{1-3-12-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl optionally substituted” by one, two or three $R^{1-5-4}$;

$R^{1-5-1}$ and $R^{1-5-2}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-5-1}$ and $R^{1-5-2}$ together with the nitrogen atom they are attached to form a $C_3$-$C_{14}$ heterocycloalkyl optionally substituted by one, two or three $R^{1-5-1-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-5-1-2}$)—; $R^{1-5-1-1}$ is independently $C_1$-$C_7$ alkyl or $C_3$-$C_{14}$ cycloalkyl; $R^{1-5-1-2}$ is independently $C_1$-$C_7$ alkyl or $C_3$-$C_{14}$ cycloalkyl;

$R^{1-5-3}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-5-4}$-1”. $R^{1-5-4-1}$ is independently $C_1$-$C_7$ alkyl or $C_3$-$C_{14}$ cycloalkyl;

$R^{1-6}$ is independently hydrogen, —CN, —OH or “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl” optionally substituted by one, two or three $R^{1-6-1}$;

$R^{1-6-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-6-1-1}$”; $R^{1-6-1-1}$ is independently $C_1$-$C_7$ alkyl or $C_3$-$C_{14}$ cycloalkyl;

$R^{1-7}$ is independently hydrogen, —$OR^{1-7-1}$, —$NR^{1-7-2}$ $R^{1-7-3}$ or “$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-7-4}$;

$R^{1-7-1}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-7-2}$ and $R^{1-7-3}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-7-2-2}$)—; $R^{1-7-2-1}$ is independently $C_1$-$C_7$ alkyl or $C_3$-$C_{14}$ cycloalkyl; $R^{1-7-2-2}$ is independently $C_1$-$C_7$ alkyl or $C_3$-$C_{14}$ cycloalkyl;

$R^{1-7-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-7-4-1}$". $R^{1-7-4-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^2$ is —$OR^{2-1}$, cyano, carboxyl, or "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-1}$ is $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{2-2}$ is independently halogen, hydroxyl, amino, $C_1$-$C_7$ alkyl, $C_1$-$C_7$ alkoxy, $C_3$-$C_{14}$ cycloalkyl or $C_3$-$C_{14}$ heterocycloalkyl;

in any one of the above cases, the heteroatoms in the $C_3$-$C_{14}$ heterocycloalkyl, $C_1$-$C_7$ heteroaryl are independently selected from one or more of boron, silicon, oxygen, sulfur, selenium, nitrogen and phosphorus; the number of heteroatoms is independently 1, 2, 3 or 4.

In a certain scheme, some substituents in the pyrazolone-fused pyrimidine compound represented by formula I, the pharmaceutically acceptable salt thereof, the solvate thereof, the solvate of the pharmaceutically acceptable salt thereof, the metabolite thereof or the prodrug thereof may further have the following definitions, and the definitions of substituents not involved below are as described in any of the above schemes (hereinafter referred to as "in a certain scheme"):

When A is $C_3$-$C_{20}$ cycloalkyl substituted by one or two $R^1$, the $C_3$-$C_{20}$ cycloalkyl is for example $C_3$-$C_{20}$ monocyclic cycloalkyl, $C_3$-$C_{20}$ spiro cycloalkyl, $C_3$-$C_{20}$ fused cycloalkyl or $C_3$-$C_{20}$ bridged cycloalkyl.

The $C_3$-$C_{20}$ monocyclic cycloalkyl is for example $C_3$-$C_6$ monocyclic cycloalkyl, for example cyclopropyl, cyclobutyl, cyclopentyl or cyclohexyl, for example cyclohexyl.

The $C_3$-$C_{20}$ bridged cycloalkyl is for example $C_5$-$C_8$ bridged cycloalkyl, for example

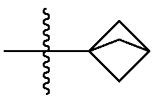 or 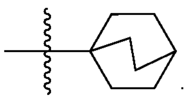 .

In a certain scheme:

When A is $C_3$-$C_{20}$ cycloalkyl substituted by one or two $R^1$, the $C_3$-$C_{20}$ cycloalkyl is for example $C_3$-$C_{20}$ saturated cycloalkyl.

In a certain scheme:

When A is $C_3$-$C_{20}$ cycloalkyl substituted by one $R^1$, the A is for example

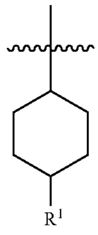 or 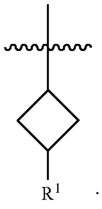 .

The

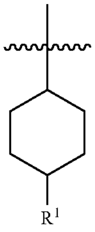

is for example

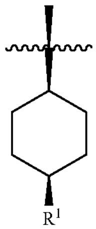 and/or 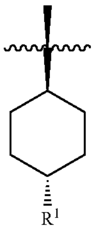 , for example,

" 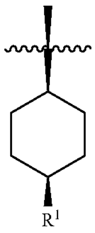 and 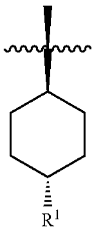 , the ratio of

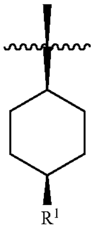 and 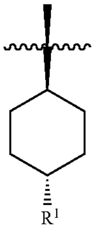

is 1:1”.

The

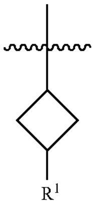

is for example

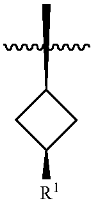 and/or 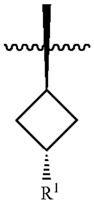, for example,

“ 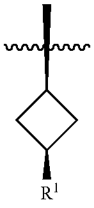 and 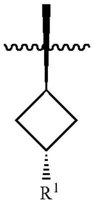, the ratio of

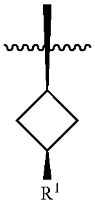 and 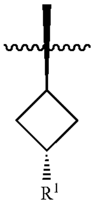

is 1:1”.

In a certain scheme:

When R[1] is independently $C_3$-$C_{14}$ heterocycloalkyl, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, “$C_3$-$C_9$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S”, for example, “$C_3$-$C_5$ monocyclic heterocycloalkyl having one or two heteroatoms selected from one or two of N, O and S” and which is connected to a benzene ring by a nitrogen atom, for example, azetidinyl, morpholinyl, piperidinyl or piperazinyl.

The azetidinyl is for example

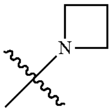.

The morpholinyl is for example

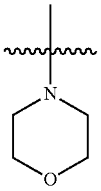.

The piperidinyl is for example or

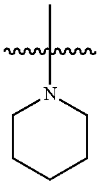 or 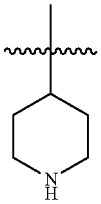.

The piperazinyl is for example H

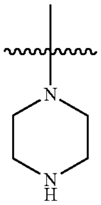.

In a certain scheme:

When R[1] is independently $C_3$-$C_{14}$ heterocycloalkyl, the heteroatom of the $C_3$-$C_{14}$ heterocycloalkyl may not be substituted.

In a certain scheme:

When R[1] is independently $C_3$-$C_{14}$ heterocycloalkyl, the methylene in the $C_3$-$C_{14}$ heterocycloalkyl may not be substituted.

In a certain scheme:

When $R^{1-3}$ and $R^{1-4}$ are independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-3-1}$ is independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-5}$ is independently $C_3$-$C_{14}$ heterocycloalkyl, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, "$C_3$-$C_9$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S" and which is connected to a benzene ring by a nitrogen atom, for example, azetidinyl.

The azetidinyl is for example

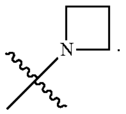 [SMILES: *N1CCC1]

In a certain scheme:

When $R^{1-5}$ is independently $C_3$-$C_{14}$ heterocycloalkyl, the heteroatom of the $C_3$-$C_{14}$ heterocycloalkyl may not be substituted.

In a certain scheme:

When $R^{1-5}$ is independently $C_3$-$C_{14}$ heterocycloalkyl, the methylene in the $C_3$-$C_{14}$ heterocycloalkyl may not be substituted.

In a certain scheme:

When $R^{1-5-1}$ and $R^{1-5-2}$ are independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^{1-5-1}$ and $R^{1-5-2}$ are independently $C_3$-$C_{14}$ cycloalkyl, the $C_3$-$C_{14}$ cycloalkyl is for example $C_3$-$C_{14}$ monocyclic cycloalkyl, $C_3$-$C_{14}$ spiro cycloalkyl, $C_3$-$C_{14}$ fused cycloalkyl or $C_3$-$C_{14}$ bridged cycloalkyl.

The $C_3$-$C_{14}$ monocyclic cycloalkyl is for example $C_3$-$C_6$ monocyclic cycloalkyl, for example cyclopropyl, cyclobutyl, cyclopentyl or cyclohexyl, for example cyclobutyl, cyclopentyl or cyclohexyl.

The $C_3$-$C_{14}$ bridged cycloalkyl is for example $C_5$-$C_5$ bridged cycloalkyl, for example

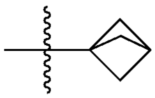 or 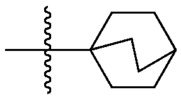

In a certain scheme:

When $R^{1-5-1}$ and $R^{1-5-2}$ are independently $C_3$-$C_{14}$ cycloalkyl, the $C_3$-$C_{14}$ cycloalkyl is for example $C_3$-$C_{14}$ saturated cycloalkyl.

In a certain scheme:

When $R^{1-5-3}$ is independently $C_1$-$C_7$ alkyl, the $C_1$-$C_7$ alkyl is for example $C_1$-$C_3$ alkyl, for example methyl, ethyl, n-propyl or isopropyl.

In a certain scheme:

When $R^2$ is $C_2$-$C_7$ alkyl optionally substituted by one, two or three $R^{2-2}$, the $C_2$-$C_7$ alkyl is for example $C_2$-$C_4$ alkyl, for example ethyl, n-propyl, isopropyl, n-butyl, isobutyl, sec-butyl or tert-butyl, for example isopropyl.

In a certain scheme:

When $R^2$ is $C_2$-$C_7$ alkyl substituted by one $R^{2-2}$, $R^{2-2}$ is hydroxyl; the $C_2$-$C_7$ alkyl substituted by one $R^{2-2}$ is for example

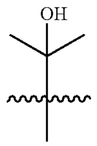

In a certain scheme:

When $R^2$ is $C_3$-$C_{14}$ heterocycloalkyl optionally substituted by one, two or three $R^{2-2}$, the $C_3$-$C_{14}$ heterocycloalkyl is for example $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl.

The $C_3$-$C_{14}$ monocyclic heterocycloalkyl is, for example, "$C_3$-$C_9$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S", for example, "$C_3$-$C_5$ monocyclic heterocycloalkyl having one or two heteroatoms selected from one or two of N, O and S" and which is connected to a benzene ring by a nitrogen atom, for example, oxetanyl.

The morpholinyl oxetanyl is for example oxetan-3-yl.

In a certain scheme:

When $R^2$ is $C_3$-$C_{14}$ heterocycloalkyl optionally substituted by one, two or three $R^{2-2}$, the heteroatom of the $C_3$-$C_{14}$ heterocycloalkyl may not be substituted except $R^{2-2}$.

In a certain scheme:

When $R^2$ is $C_3$-$C_{14}$ heterocycloalkyl optionally substituted by one, two or three $R^{2-2}$, the methylene in the $C_3$-$C_{14}$ heterocycloalkyl may not be substituted.

In a certain scheme:

When $R^2$ is $C_3$-$C_{14}$ heterocycloalkyl substituted by one $R^{2-2}$, $R^{2-2}$ is halogen or hydroxyl; the $C_3$-$C_{14}$ heterocycloalkyl substituted by one $R^{2-2}$ is for example

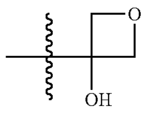 or 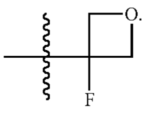

In a certain scheme:

The ratio of each isomer in the pyrazolone-fused pyrimidine compound represented by formula I may be equal, for example, racemate.

In a certain scheme:

The atoms in the pyrazolone-fused pyrimidine compound represented by formula I, the pharmaceutically acceptable salt thereof, the solvate thereof, the solvate of the pharmaceutically acceptable salt thereof, the metabolite thereof or the prodrug thereof may all exist in their natural abundance.

In a certain scheme:

A is

“ 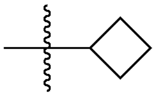, 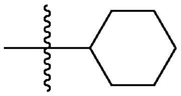,

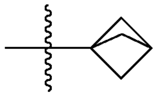 or 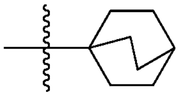

substituted by one or two $R^1$”.

In a certain scheme:

A is $C_3$-$C_{20}$ cycloalkyl substituted by one $R^1$.

In a certain scheme:

A is

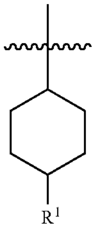 or 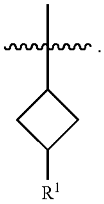.

In a certain scheme:

$R^1$ is independently halogen, —CN, —$NR^{1-3}R^{1-4}$, —C(═O)$R^{1-5}$, —C(═$NR^{1-6}$)$R^{1-7}$ or “$C_3$-$C_{14}$ cycloalkyl, $C_3$-$C_{14}$ heterocycloalkyl, $C_6$-$C_{10}$ aryl, or $C_1$-$C_7$ heteroaryl” optionally substituted by one, two or three $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2NR^{1-3-7}R^{1-3-8}$, —C(═O)$NR^{1-3-9}R^{1-3-10}$, or “$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-3-11}$.

$R^{1-3-1}$ and $R^{1-3-2}$ are independently “$C_1$-$C_7$ alkyl, $C_3$-$C_{14}$ cycloalkyl, $C_3$-$C_{14}$ heterocycloalkyl or $C_6$-$C_{10}$ aryl” optionally substituted by one or two $R^{1-3-1-1}$”; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-3-11-1}$”; $R^{1-3-11-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or “$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-5-4-1}$”; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-8-1}$”; $R^{1-8-1}$ is independently $C_1$-$C_7$ alkyl or $C_3$-$C_{14}$ cycloalkyl.

In a certain scheme:

$R^1$ is independently cyano, halogen, —$NR^{1-3}R^{1-4}$, C(═O)$R^{1-5}$, —C(═$NR^{1-6}$)$R^{1-7}$, $C_1$-$C_7$ heteroaryl or $C_3$-$C_{14}$ heterocycloalkyl.

In a certain scheme:

$R^1$ is independently —$NR^{1-3}R^{1-4}$, C(═O)$R^{1-5}$ or $C_3$-$C_{14}$ heterocycloalkyl.

In a certain scheme:

$R^{1-3}$ and $R^{1-4}$ are independently hydrogen, —S(═O)$_2$ $R^{1-3-1}$ or $C_1$-$C_7$ alkyl; $R^{1-3-1}$ is independently $C_1$-$C_7$ alkyl.

In a certain scheme:

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl.

In a certain scheme:

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen.

In a certain scheme:

$R^2$ is “$C_2$-$C_7$ alkyl, $C_3$-$C_{14}$ cycloalkyl or $C_3$-$C_{14}$ heterocycloalkyl” optionally substituted by one, two or three $R^{2-2}$;

$R^{2-2}$ is independently halogen or hydroxyl.

In a certain scheme:

$R^2$ is “$C_2$-$C_7$ alkyl or $C_3$-$C_{14}$ heterocycloalkyl substituted by one $R^{2-2}$”; $R^{2-2}$ is halogen or hydroxyl.

In a certain scheme:

$R^2$ is “$C_2$-$C_7$ alkyl or $C_3$-$C_{14}$ heterocycloalkyl substituted by one $R^{2-2}$”; $R^{2-2}$ is hydroxyl.

In a certain scheme:

$R^2$ is

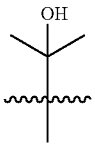, 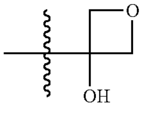 or 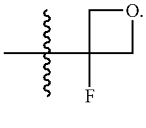.

In a certain scheme:

A is

“ 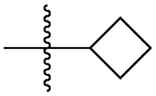, 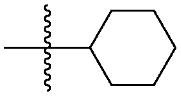, 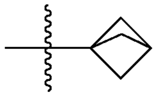 or 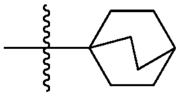

substituted by one or two $R^1$”;

$R^1$ is independently halogen, —CN, —$NR^{1-3}R^{1-4}$, —C(═O)$R^{1-5}$, —C(═$NR^{1-6}$)$R^{1-7}$ or “$C_3$-$C_{14}$ cycloalkyl, $C_3$-$C_{14}$ heterocycloalkyl, $C_6$-$C_{10}$ aryl, or $C_1$-$C_7$ heteroaryl” optionally substituted by one, two or three $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2$$NR^{1-3-7}R^{1-3-8}$, —C(═O)$NR^{1-3-9}R^{1-3-10}$ or “$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-3-11}$;

$R^{1-3-1}$ and $R^{1-3-2}$ are independently “$C_1$-$C_7$ alkyl, $C_3$-$C_{14}$ cycloalkyl, $C_3$-$C_{14}$ heterocycloalkyl or $C_6$-$C_{10}$ aryl” optionally substituted by one or two $R^{1-3-1-1}$; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-3-1}$”; $R^{1-3-11-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or “$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl” optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-5-4-1}$”; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with the nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or “amino substituted by one or two $R^{1-8-1}$”; $R^{1-8-1}$ is independently $C_1$-$C_7$ alkyl or $C_3$-$C_{14}$ cycloalkyl;

$R^2$ is “$C_2$-$C_7$ alkyl, $C_3$-$C_{14}$ cycloalkyl or $C_3$-$C_{14}$ heterocycloalkyl” optionally substituted by one, two or three $R^{2-2}$;

$R^{2-2}$ is independently halogen or hydroxyl;

in any one of the above cases, the heteroatoms in the $C_3$-$C_{14}$ heterocycloalkyl, $C_1$-$C_7$ heteroaryl are independently selected from one or more of boron, silicon, oxygen, sulfur, selenium, nitrogen and phosphorus; the number of heteroatoms is independently 1, 2, 3 or 4.

In a certain scheme:

A is $C_3$-$C_{20}$ cycloalkyl substituted by one or two $R^1$;

$R^1$ is independently cyano, halogen, —$NR^{1-3}R^{1-4}$, —C(═O)$R^{1-5}$, —C(═$NR^{1-6}$)$R^{1-7}$, $C_1$-$C_7$ heteroaryl or $C_3$-$C_{14}$ heterocycloalkyl;

$R^{1-3}$ and $R^{1-4}$ are independently hydrogen, —S(═O)$_2$ $R^{1-3-1}$ or $C_1$-$C_7$ alkyl; $R^{1-3-1}$ is independently $C_1$-$C_7$ alkyl;

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

$R^2$ is “$C_2$-$C_7$ alkyl or $C_3$-$C_{14}$ heterocycloalkyl substituted by one $R^{2-2}$”; $R^{2-2}$ is halogen or hydroxyl.

In a certain scheme:

A is $C_3$-$C_{20}$ cycloalkyl substituted by one $R^1$;

$R^1$ is —$NR^{1-3}R^{1-4}$, —C(═O)$R^{1-5}$ or $C_3$-$C_{14}$ heterocycloalkyl;

$R^{1-3}$ and $R^{1-4}$ are independently hydrogen, —S(═O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is $C_2$-$C_7$ alkyl or $C_3$-$C_{14}$ heterocycloalkyl substituted by one $R^{2-2}$; $R^{2-2}$ is hydroxyl.

In a certain scheme:

A is $C_3$-$C_{20}$ cycloalkyl substituted by one $R^1$;

$R^1$ is —$NR^{1-3}R^{1-4}$, —C(═O)$R^{1-5}$ or $C_3$-$C_{14}$ heterocycloalkyl;

$R^{1-3}$ and $R^{1-4}$ are independently hydrogen, —S(═O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen;

$R^2$ is “$C_2$-$C_7$ alkyl or $C_3$-$C_{14}$ heterocycloalkyl substituted by one $R^{2-2}$”; $R^{2-2}$ is hydroxyl.

In a certain scheme:

A is

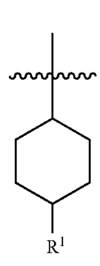 or 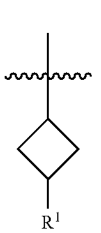;

$R^1$ is —$NR^{1-3}R^{1-4}$, —C(═O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl.

In a certain scheme:

A is

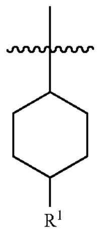

or

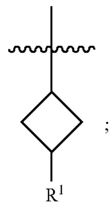

;

$R^1$ is —$NR^{1-3}R^{1-4}$, —C(=O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is

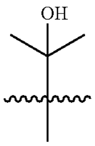

,

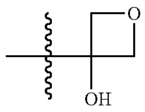

or

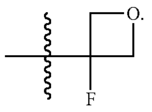

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

1-1

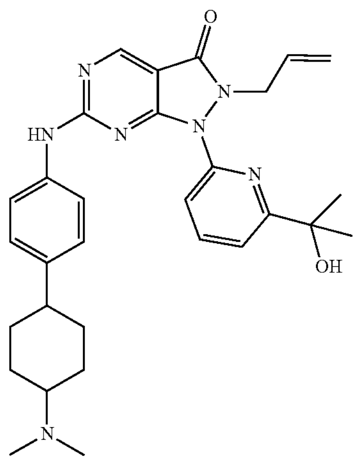

, 1-2

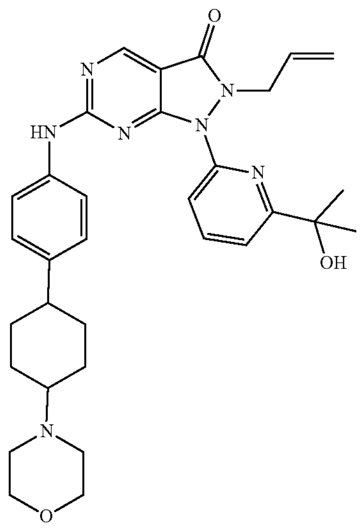

, 1-3

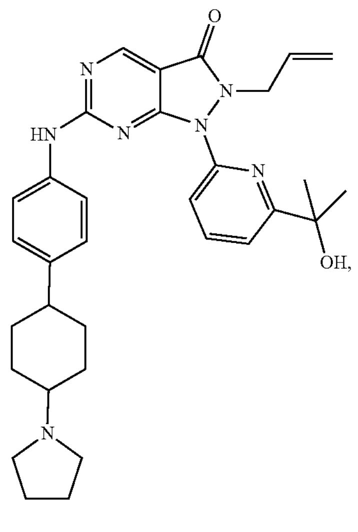

1-4
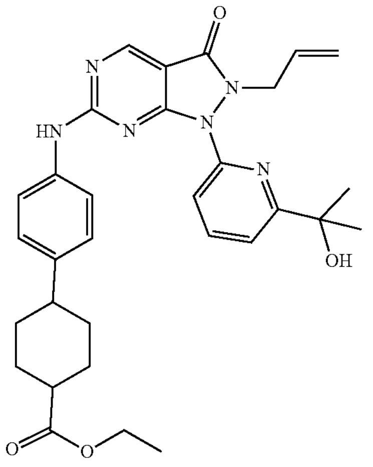
,
1-5
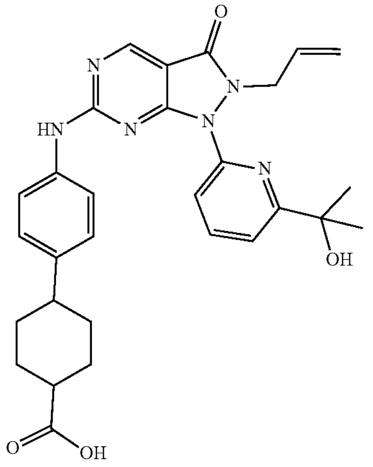
,
1-6
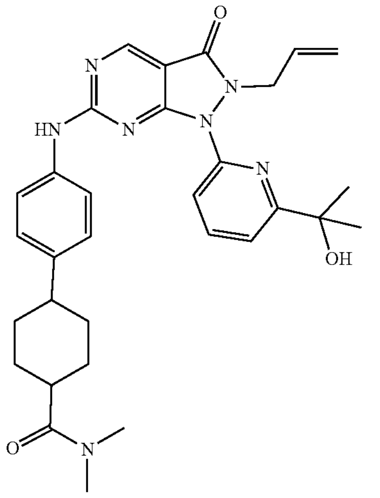
,
1-7
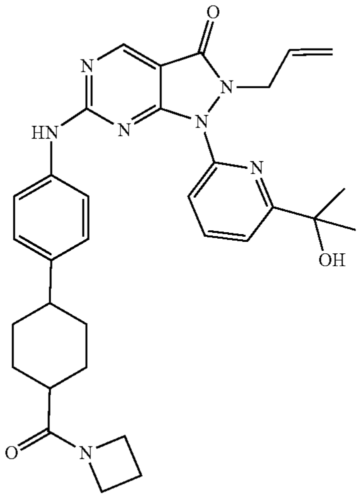
,
1-8
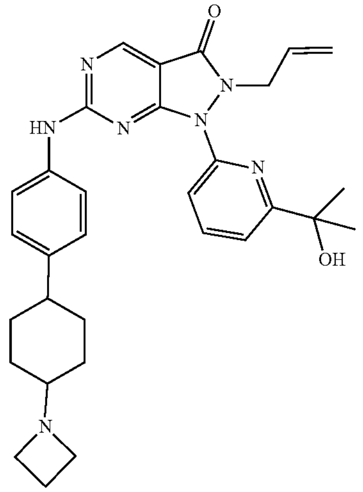
,
1-9
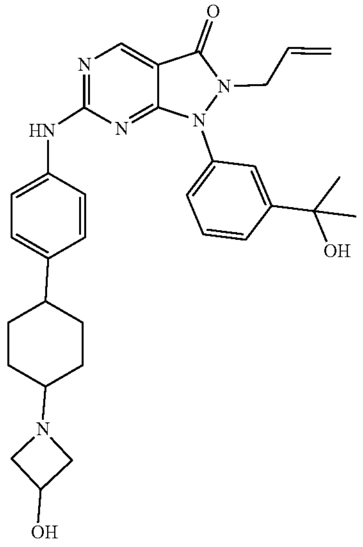
, 1-10
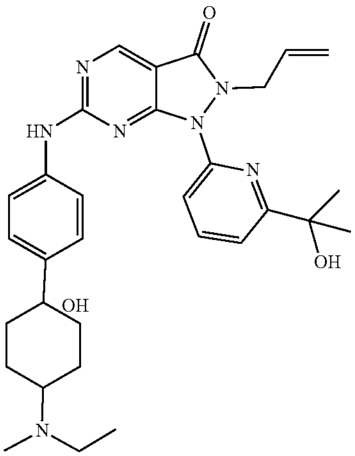
,
1-11
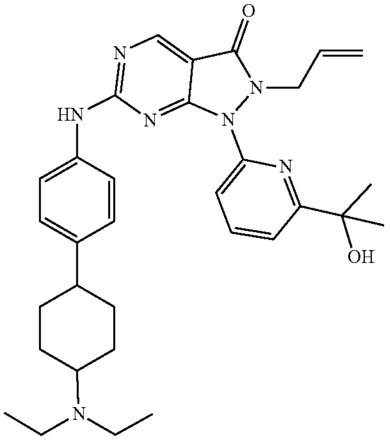
,
1-12
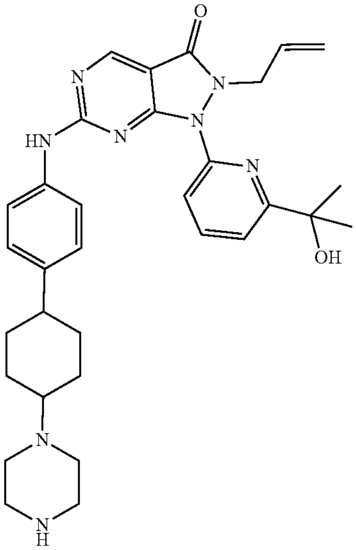
,
1-13
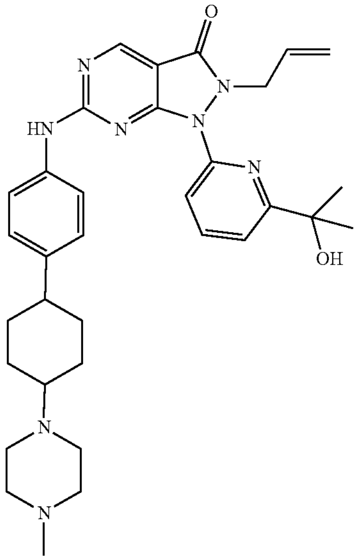
,
1-14
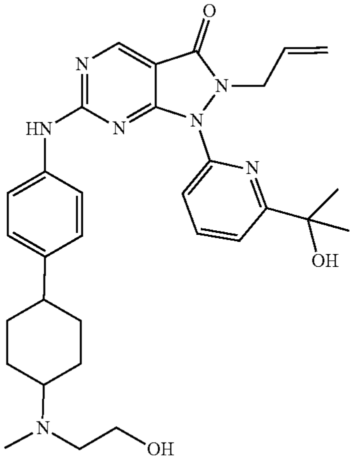
,
1-15
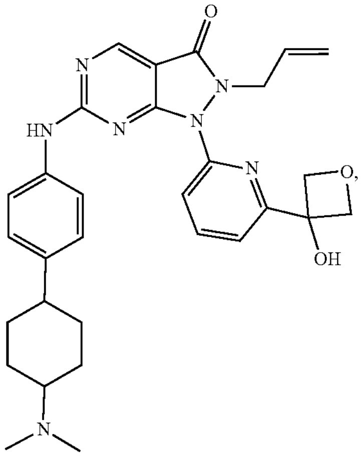
, -continued
1-16
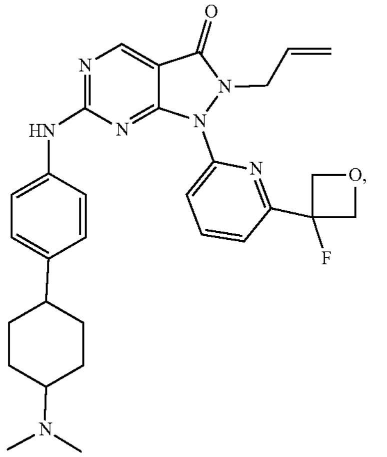
1-17
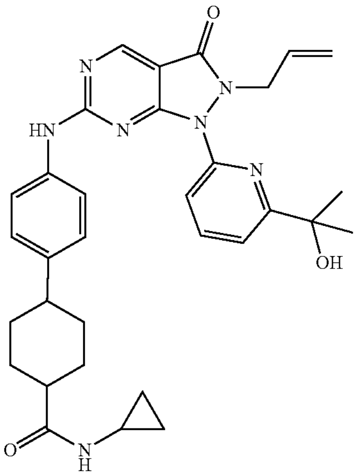
.
1-18
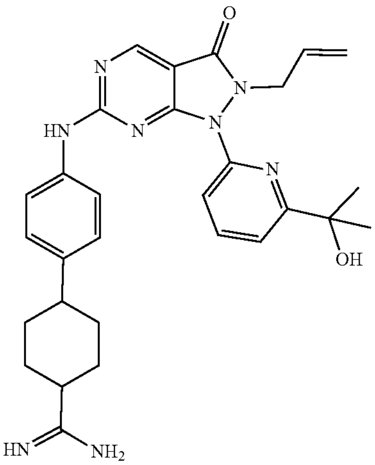
,
-continued
1-19
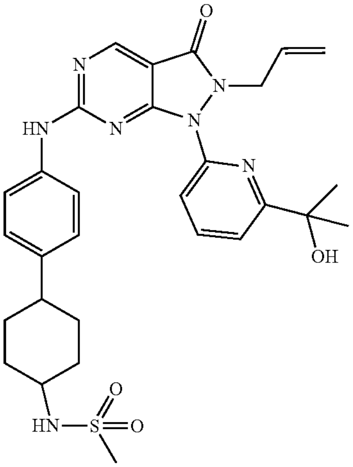
,
1-20
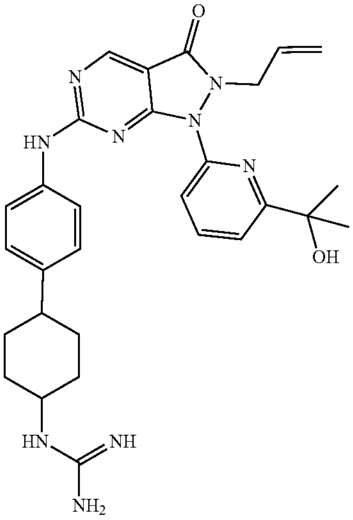
,
1-21
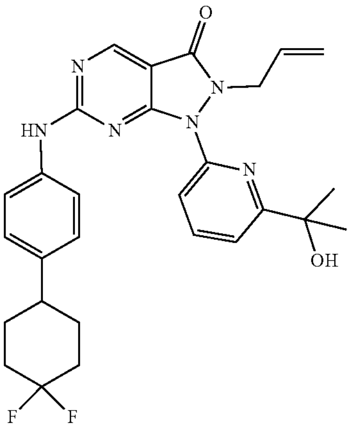
, -continued
1-22
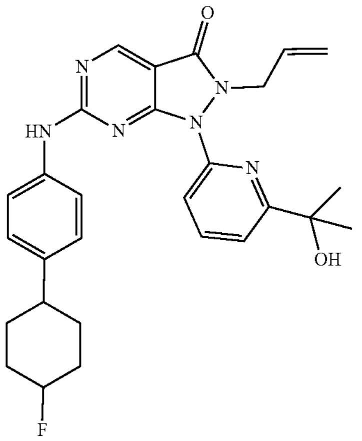
.
1-23
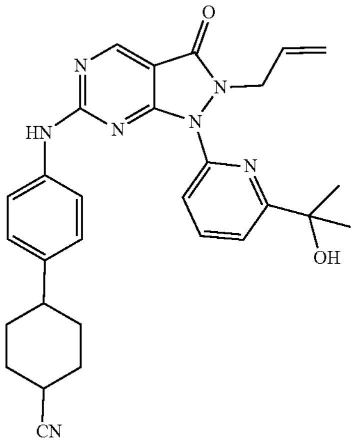
.
1-24
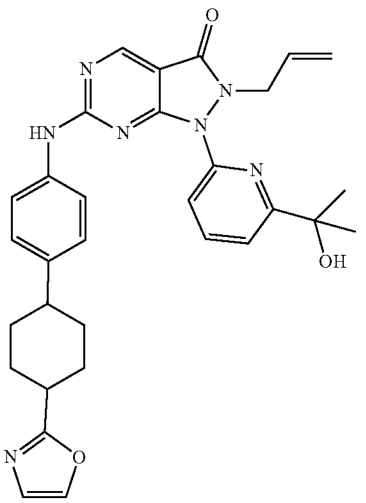
.
-continued
1-25
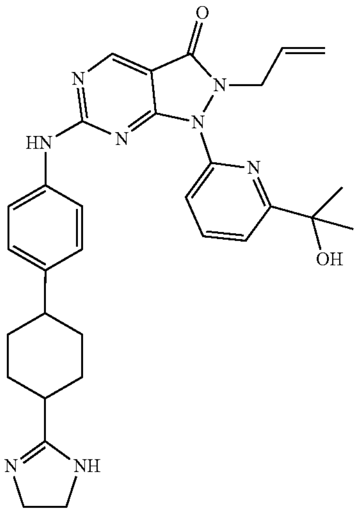
,
1-26
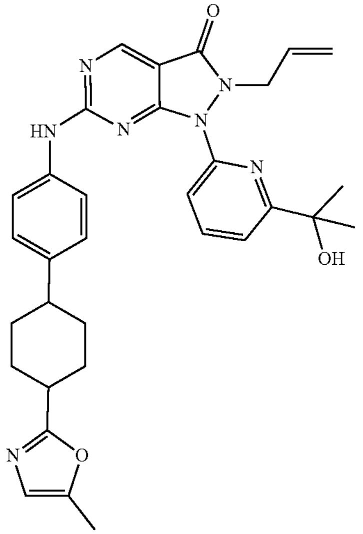
,
1-27
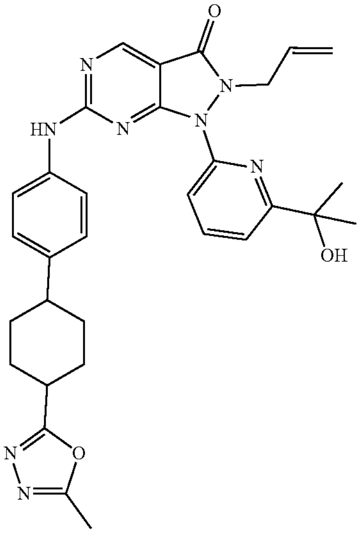
, -continued
1-28
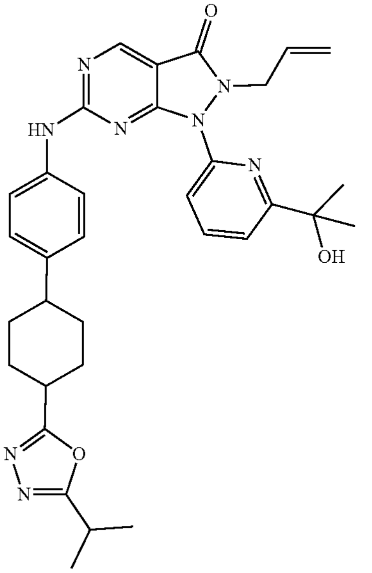
,
1-29
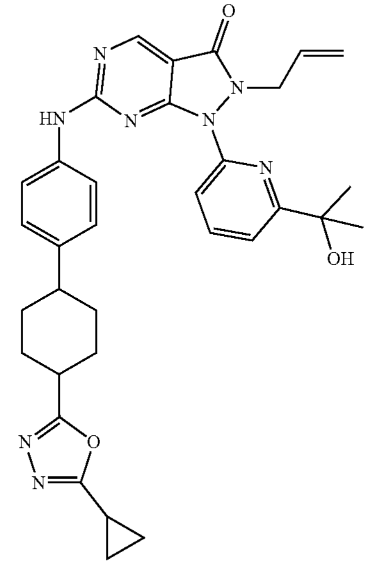
-continued
1-30
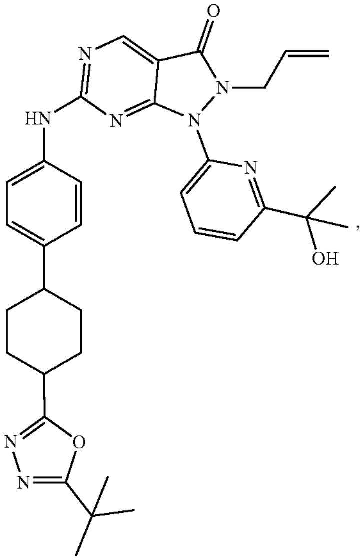
,
1-31
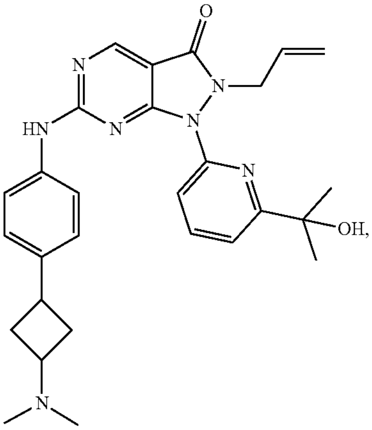
,
1-32
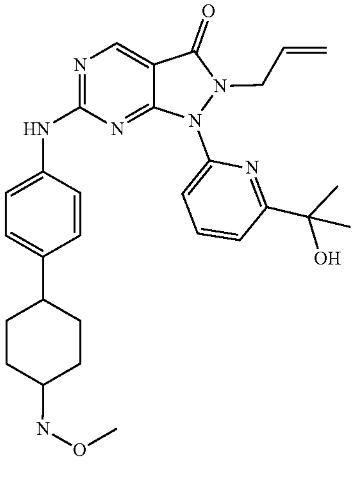
, -continued
1-33
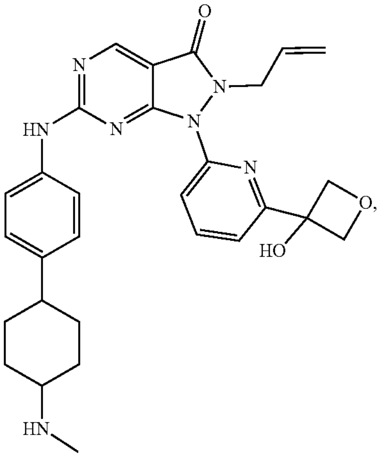
1-34
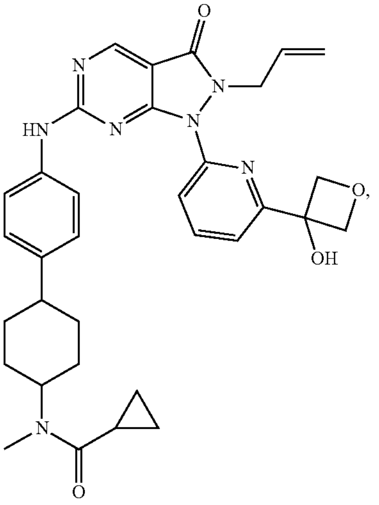
1-35
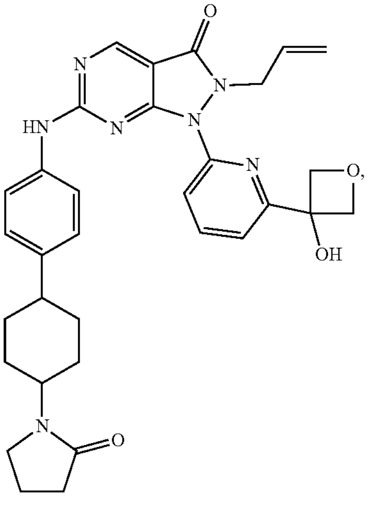
-continued
1-36
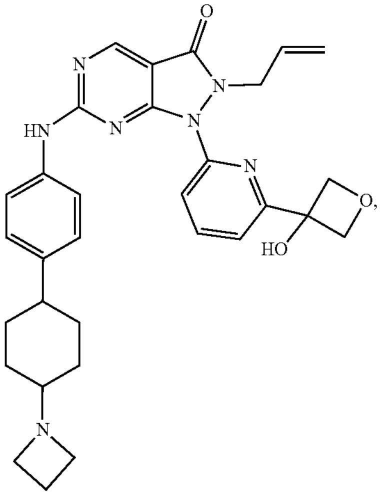
1-37
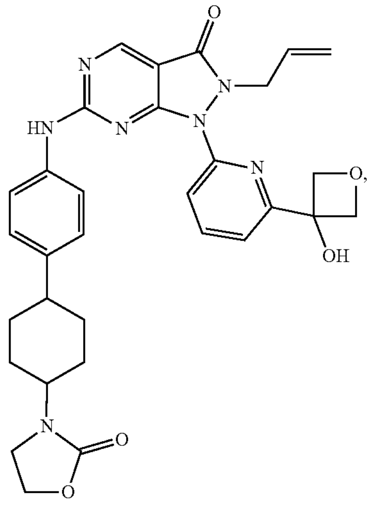
1-38
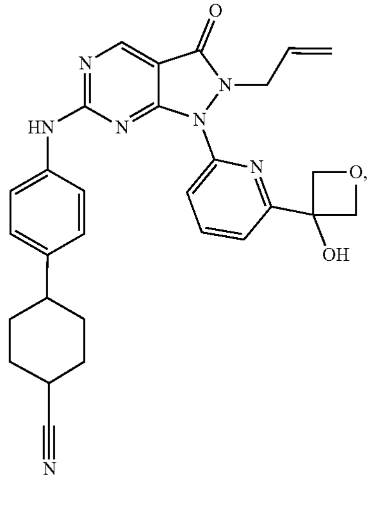

-continued 1-39

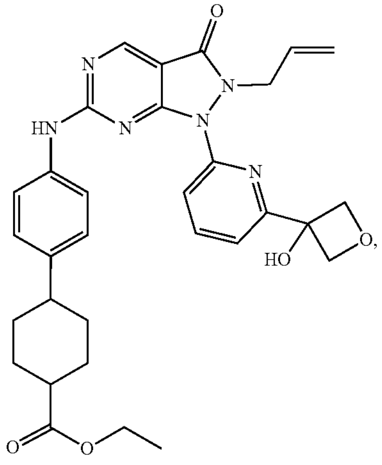

1-40

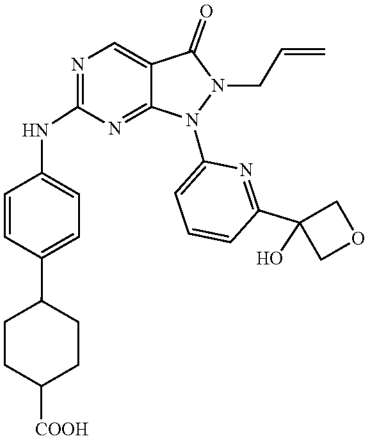

and 1-41

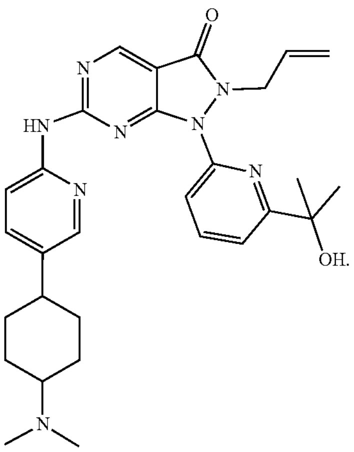

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

I-2

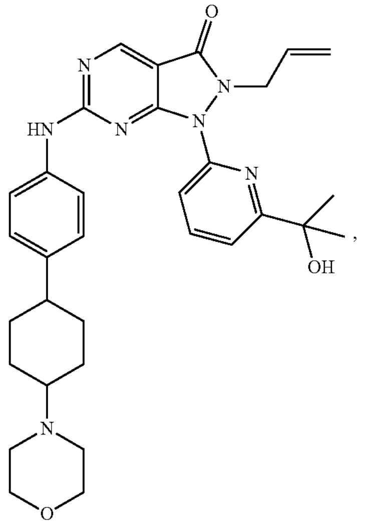

its $^{1}H$ NMR (400 MHz, MeOD) is δ 8.85 (s, 1H), 8.00 (t, J=7.9 Hz, 1H), 7.80 (d, J=8.1 Hz, 1H), 7.68 (d, J=7.7 Hz, 1H), 7.62 (d, J=8.6 Hz, 2H), 7.28 (d, J=8.6 Hz, 2H), 5.78-5.68 (m, 1H), 5.06 (d, J=10.3 Hz, 1H), 4.95 (s, 1H), 4.82 (s, 2H), 3.82-3.76 (m, 1H), 2.81 (s, 1H), 2.71 (s, 3H), 2.49 (s, 1H), 2.08 (d, J=10.9 Hz, 3H), 1.94 (d, J=15.0 Hz, 3H), 1.72 (s, 4H), 1.59 (d, J=7.0 Hz, 6H);

I-4

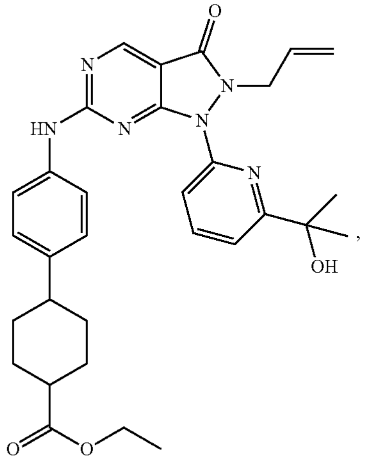

its $^{1}H$ NMR (400 MHz, $CDCl_3$) is δ 8.87 (d, J=2.1 Hz, 1H), 7.91 (td, J=7.9, 1.5 Hz, 1H), 7.78 (d, J=8.0 Hz, 1H), 7.54 (t, J=7.9 Hz, 2H), 7.39 (d, J=7.7 Hz, 1H), 7.21 (d, J=8.5 Hz, 2H), 5.72 (ddt, J=16.4, 10.2, 6.2 Hz, 1H), 5.07 (dd, J=10.2, 1.1 Hz, 1H), 4.96 (dd, J=17.1, 1.2 Hz, 1H), 4.77 (d, J=6.2 Hz, 2H), 4.25-4.10 (m, 2H), 3.95 (s, 1H), 2.73 (s, 1H), 2.56 (dt, J=15.5, 10.8 Hz, 1H), 2.28 (d, J=7.9 Hz, 1H), 2.14 (d, J=10.6 Hz, 1H), 2.05-1.97 (m, 1H), 1.78 (dd, J=19.0, 8.5 Hz, 1H), 1.67 (dt, J=10.1, 6.1 Hz, 3H), 1.61 (s, 6H), 1.59-1.44 (m, 1H), 1.34-1.26 (m, 3H);

I-5

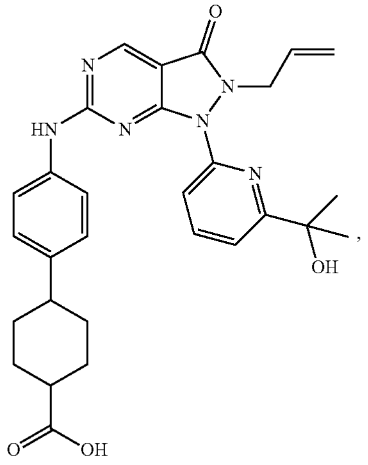

its $^1H$ NMR (400 MHz, MeOD) is δ 8.84 (d, J=1.4 Hz, 1H), 8.00 (td, J=7.9, 4.0 Hz, 1H), 7.83-7.76 (m, 1H), 7.67 (dd, J=7.7, 0.7 Hz, 1H), 7.60 (dd, J=8.4, 5.7 Hz, 2H), 7.19 (dd, J=13.2, 8.6 Hz, 2H), 5.73 (ddd, J=17.0, 6.1, 4.1 Hz, 1H), 5.08-5.03 (m, 1H), 4.95 (d, J=1.3 Hz, 1H), 4.86-4.79 (m, 2H), 2.72 (s, 1H), 2.58 (s, 1H), 2.27 (d, J=6.7 Hz, 1H), 2.13 (d, J=10.0 Hz, 1H), 1.96 (d, J=10.2 Hz, 1H), 1.80-1.66 (m, 4H), 1.64-1.52 (m, 7H);

I-6

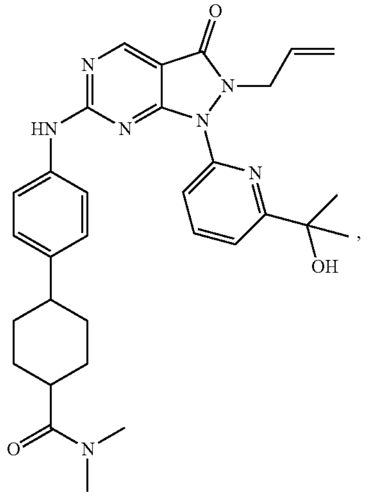

its $^1H$ NMR (400 MHz, $CDCl_3$) is δ 8.86 (d, J=4.2 Hz, 1H), 7.97-7.88 (m, 1H), 7.79 (d, J=8.0 Hz, 1H), 7.53 (dd, J=12.3, 8.5 Hz, 2H), 7.39 (d, J=7.6 Hz, 1H), 7.28-7.15 (m, 2H), 5.80-5.65 (m, 1H), 5.06 (d, J=10.0 Hz, 1H), 4.95 (d, J=17.1 Hz, 1H), 4.77 (d, J=6.0 Hz, 2H), 3.10 (d, J=12.1 Hz, 3H), 2.98 (s, 3H), 2.67-2.57 (m, 1H), 2.14 (dd, J=20.9, 10.3 Hz, 1H), 2.06-1.97 (m, 2H), 1.92 (d, J=14.0 Hz, 1H), 1.78-1.66 (m, 4H), 1.61 (s, 6H), 1.49 (dd, J=22.8, 12.2 Hz, 1H);

I-7

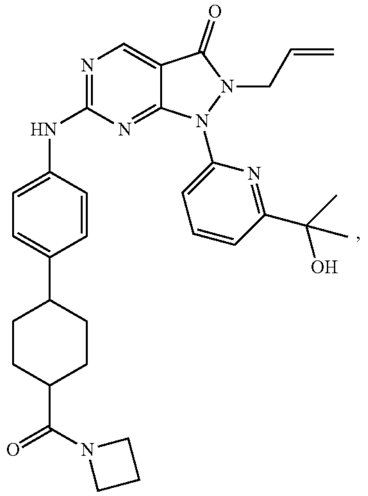

its $^1H$ NMR (400 MHz, $CDCl_3$) is δ 8.85 (d, J=4.7 Hz, 1H), 7.91 (dt, J=10.7, 7.9 Hz, 1H), 7.78 (d, J=7.8 Hz, 1H), 7.53 (dd, J=12.0, 8.5 Hz, 2H), 7.39 (dd, J=7.6, 2.4 Hz, 1H), 7.22 (dd, J=19.5, 8.5 Hz, 2H), 5.71 (ddt, J=16.4, 10.2, 6.2 Hz, 1H), 5.06 (d, J=10.2 Hz, 1H), 4.95 (d, J=17.1 Hz, 1H), 4.77 (d, J=6.1 Hz, 2H), 4.21 (dd, J=16.4, 8.6 Hz, 2H), 4.10-4.02 (m, 2H), 2.63-2.52 (m, 2H), 2.35-2.20 (m, 2H), 2.15-2.07 (m, 1H), 2.00 (dd, J=13.4, 3.0 Hz, 2H), 1.92-1.83 (m, 1H), 1.79-1.63 (m, 4H), 1.60 (s, 6H), 1.48 (ddd, J=24.7, 12.5, 2.5 Hz, 1H);

I-8

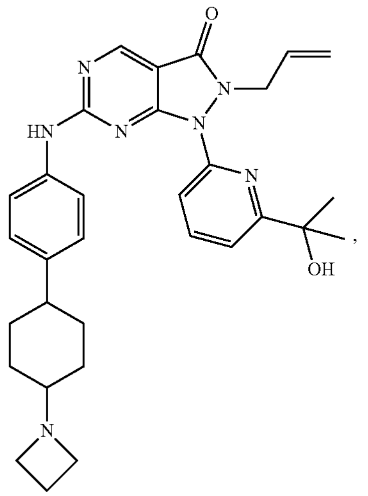

its $^1H$ NMR (400 MHz, $CDCl_3$) is δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H);

I-17

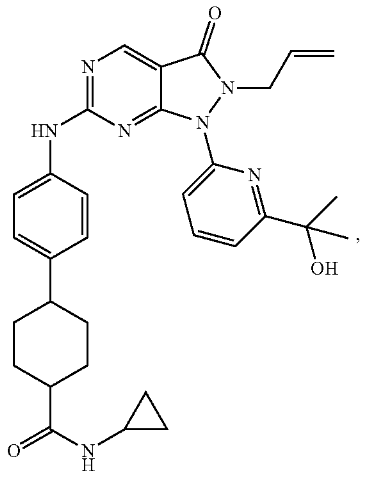

its $^1$H NMR (400 MHz, $CDCl_3$) is δ 8.84 (d, J=3.7 Hz, 1H), 7.94 (dd, J=14.8, 6.9 Hz, 1H), 7.76 (d, J=7.9 Hz, 1H), 7.58-7.50 (m, 2H), 7.42 (dd, J=7.5, 4.1 Hz, 1H), 7.22 (dd, J=15.8, 8.5 Hz, 2H), 5.71 (dd, J=11.5, 5.4 Hz, 2H), 5.07 (d, J=10.2 Hz, 1H), 4.95 (d, J=17.1 Hz, 1H), 4.77 (d, J=6.1 Hz, 2H), 2.82-2.72 (m, 1H), 2.60 (s, 1H), 2.12-2.01 (m, 3H), 1.92 (d, J=12.5 Hz, 1H), 1.81-1.67 (m, 3H), 1.62 (s, 6H), 1.54-1.43 (m, 1H), 0.93-0.78 (m, 3H), 0.52 (s, 2H);

I-19

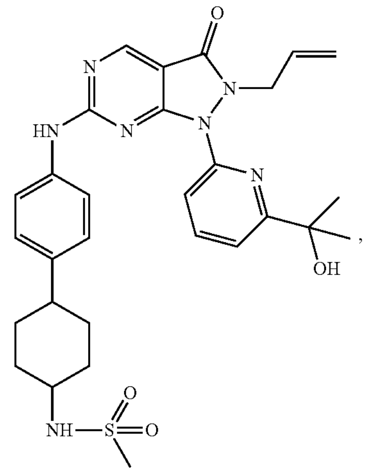

its $^1$H NMR (400 MHz, $CDCl_3$) is δ 8.88 (s, 1H), 7.91 (t, J=7.9 Hz, 1H), 7.77 (d, J=7.9 Hz, 1H), 7.56 (d, J=8.5 Hz, 2H), 7.40 (d, J=7.4 Hz, 1H), 7.19 (d, J=8.5 Hz, 2H), 5.78-5.66 (m, 1H), 5.07 (dd, J=10.2, 1.0 Hz, 1H), 4.96 (dd, J=17.1, 1.2 Hz, 1H), 4.77 (d, J=6.2 Hz, 2H), 4.42 (d, J=7.6 Hz, 1H), 3.49-3.35 (m, 1H), 3.04 (s, 3H), 2.57-2.46 (m, 1H), 2.29-2.17 (m, 2H), 2.05-1.96 (m, 8H), 1.56-1.65 (m, 2H), 1.41-1.50 (m, 2H);

I-20

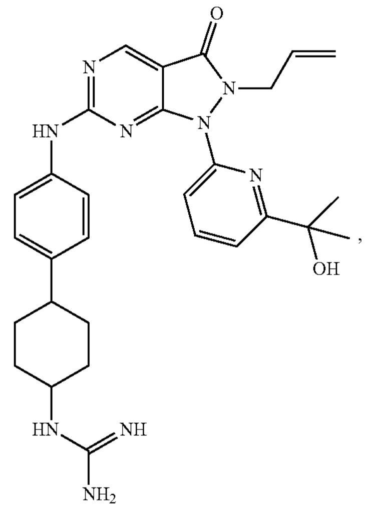

its $^1$H NMR (400 MHz, MeOD) is δ 8.84 (s, 1H), 8.02 (m, 1H), 7.80 (m, 1H), 7.72-7.58 (m, 3H), 7.25 (m, 2H), 5.73 (ddt, J=16.5, 10.3, 6.1 Hz, 1H), 5.05 (dd, J=10.2, 1.0 Hz, 1H), 4.95 (d, 1H), 4.83 (d, J=6.1 Hz, 2H), 3.54-3.42 (m, 1H), 2.59 (m, 1H), 2.14 (m, 1H), 1.98 (m, 2H), 1.83 (m, 1H), 1.68 (m, 2H), 1.60 (s, 6H), 1.50 (m, 2H);

I-23

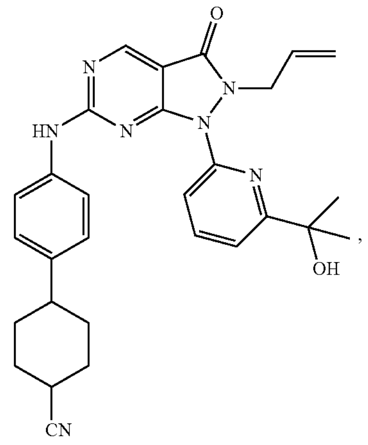

its $^1$H NMR (400 MHz, DMSO) is δ 10.28 (s, 1H), 8.88 (d, J=1.8 Hz, 1H), 8.09-7.97 (m, 1H), 7.75 (d, J=8.4 Hz, 1H), 7.66 (dd, J=20.6, 8.5 Hz, 3H), 7.19 (dd, J=11.1, 8.7 Hz, 2H), 5.74-5.61 (m, 1H), 5.00 (d, J=10.2 Hz, 1H), 4.82 (d, J=17.1 Hz, 1H), 4.69 (d, J=5.5 Hz, 2H), 3.23 (s, 1H), 2.74 (t, J=12.1 Hz, 1H), 2.53 (s, 1H), 2.12 (d, J=10.1 Hz, 1H), 1.98 (d, J=13.2 Hz, 1H), 1.82 (d, J=13.2 Hz, 2H), 1.77-1.57 (m, 3H), 1.49 (d, J=18.2 Hz, 6H);

I-31

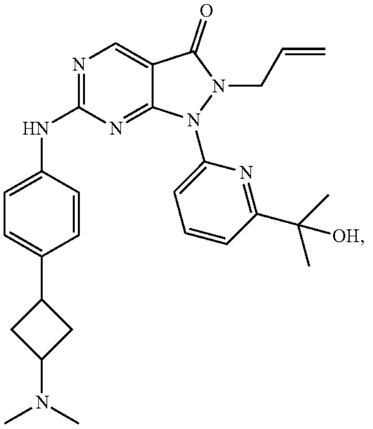

its $^1$H NMR (400 MHz, DMSO) is δ 10.27 (s, 1H), 8.89 (s, 1H), 8.12 (s, 1H), 7.74 (dd, J=22.6, 8.3 Hz, 3H), 7.64 (d, J=7.3 Hz, 1H), 7.37 (d, J=8.5 Hz, 2H), 5.76-5.61 (m, 1H), 5.34 (s, 1H), 5.01 (dd, J=10.3, 1.2 Hz, 1H), 4.84 (d, J=17.1 Hz, 1H), 4.70 (d, J=5.7 Hz, 2H), 3.62 (s, 1H), 3.12 (s, 1H), 2.71-2.58 (m, 8H), 2.38 (d, J=9.2 Hz, 2H), 1.47 (s, 6H), 1.32-1.24 (m, 1H);

I-32

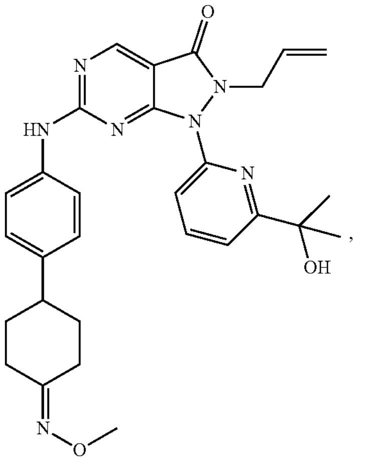

its $^1$H NMR (400 MHz, DMSO) is δ 10.26 (s, 1H), 8.88 (s, 1H), 8.07 (t, J=7.8 Hz, 1H), 7.76 (d, J=8.0 Hz, 1H), 7.65 (dd, J=14.5, 7.9 Hz, 2H), 7.22 (d, J=8.5 Hz, 2H), 5.74-5.60 (m, 1H), 5.35 (s, 1H), 5.00 (d, J=10.3 Hz, 1H), 4.83 (d, J=17.1 Hz, 1H), 4.69 (d, J=5.6 Hz, 2H), 3.74 (s, 3H), 3.24-3.15 (m, 1H), 2.77 (t, J=12.0 Hz, 1H), 2.37 (d, J=14.0 Hz, 1H), 2.25 (td, J=13.4, 4.6 Hz, 1H), 1.99-1.84 (m, 3H), 1.67-1.50 (m, 2H), 1.49 (d, J=14.0 Hz, 6H);

I-33

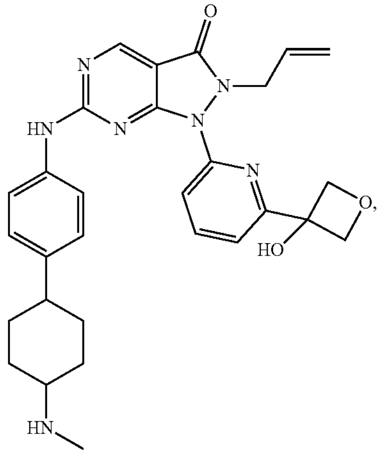

its $^1$H NMR (400 MHz, MeOD) is δ 8.86 (s, 0H), 8.11-8.01 (m, 1H), 7.94 (d, J=7.9 Hz, 2H), 7.67 (d, J=7.6 Hz, 2H), 7.62 (d, J=8.6 Hz, 2H), 7.28 (d, J=8.5 Hz, 2H), 5.83-5.74 (m, 1H), 5.09 (dd, J=7.9, 4.4 Hz, 3H), 4.98 (dd, J=17.1, 1.3 Hz, 2H), 4.85 (d, J=6.7 Hz, 2H), 2.87 (s, 1H), 2.64 (s, 1H), 2.47 (s, 3H), 1.97-1.67 (m, 8H);

I-34

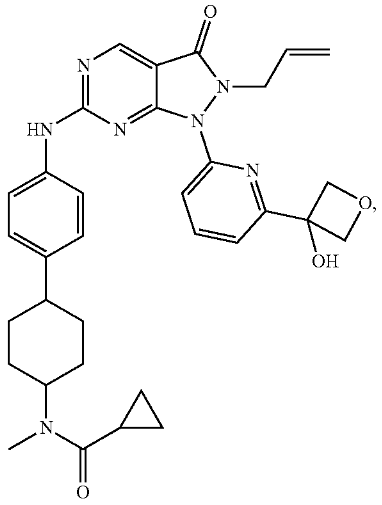

its $^1$H NMR (400 MHz, MeOD) is δ 8.87 (d, J=6.6 Hz, 1H), 8.06 (t, J=7.9 Hz, 1H), 7.95 (d, J=7.9 Hz, 1H), 7.68 (dd, J=7.8, 5.4 Hz, 2H), 7.61 (d, J=8.6 Hz, 1H), 7.41 (d, J=8.4 Hz, 1H), 7.24 (t, J=8.7 Hz, 1H), 5.84-5.72 (m, 1H), 5.09 (d, J=6.2 Hz, 2H), 5.07 (d, J=1.3 Hz, 1H), 5.02-4.94 (m, 2H), 4.90 (s, 2H), 4.84 (d, J=6.7 Hz, 2H), 3.15 (d, J=2.6 Hz, 1H), 3.08 (s, 1H), 2.95 (s, 1H), 2.71 (s, 1H), 2.43 (s, 1H), 1.93-2.03 (m, 3H), 1.76 (s, 2H), 1.51 (s, 1H), 1.31 (d, J=4.3 Hz, 3H), 0.89 (dd, J=20.1, 9.0 Hz, 4H);

I-35

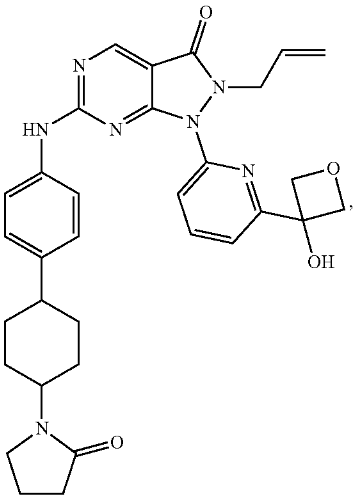

its $^1H$ NMR (400 MHz, $CDCl_3$) is δ 8.87-8.79 (m, 1H), 8.14-8.07 (m, 1H), 8.04-7.96 (m, 1H), 7.89-7.80 (m, 1H), 7.61-7.50 (m, 2H), 7.38-7.32 (m, 1H), 7.25-7.19 (m, 1H), 7.01 (t, J=3.4 Hz, 1H), 5.72 (ddd, J=16.6, 11.1, 8.6 Hz, 1H), 5.17-5.09 (m, 2H), 5.04-4.98 (m, 1H), 4.98-4.92 (m, 1H), 4.87-4.77 (m, 2H), 4.73-4.64 (m, 2H), 4.20-4.06 (m, 1H), 3.47-3.38 (m, 1H), 3.38-3.29 (m, 1H), 3.05-2.98 (m, 1H), 2.49-2.35 (m, 2H), 2.27-2.17 (m, 1H), 2.07-1.86 (m, 4H), 1.75-1.60 (m, 3H);

I-37

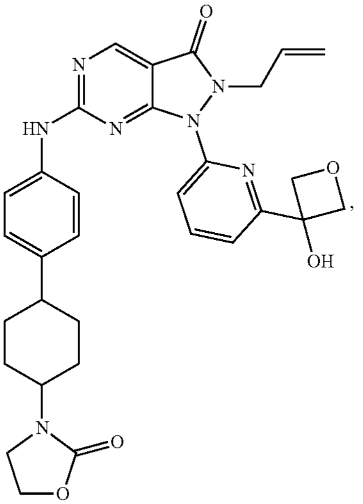

its $^1H$ NMR (400 MHz, $CDCl_3$) is δ 8.77 (s, 1H), 8.16-8.07 (m, 1H), 8.03 (d, J=7.6 Hz, 1H), 7.83-7.75 (m, 1H), 7.56 (dd, J=12.6, 6.1 Hz, 2H), 7.33 (d, J=8.5 Hz, 1H), 7.21 (d, J=8.5 Hz, 1H), 5.72 (dd, J=17.0, 10.3 Hz, 1H), 5.13 (dd, J=9.1, 6.1 Hz, 2H), 4.96 (d, J=17.0 Hz, 2H), 4.81 (d, J=7.2 Hz, 2H), 4.69 (d, J=6.2 Hz, 2H), 4.41-4.28 (m, 2H), 3.86 (s, 1H), 3.77 (t, J=6.6 Hz, 1H), 3.63-3.50 (m, 2H), 2.98 (m, 1H), 2.15 (m, 1H), 1.97 (dd, J=18.9, 9.6 Hz, 2H), 1.78 (d, J=5.0 Hz, 2H), 1.65 (d, J=8.7 Hz, 2H);

I-38

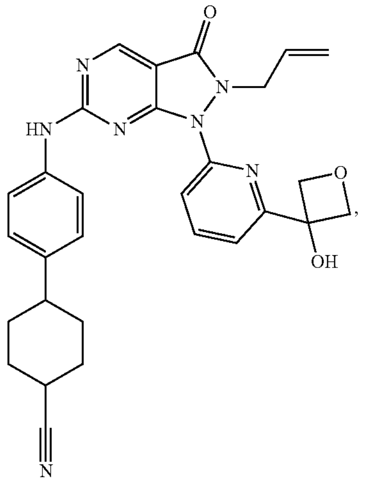

its $^1H$ NMR (400 MHz, $CDCl_3$) is δ 8.69 (s, 1H), 8.18 (d, J=8.0 Hz, 1H), 8.10 (dd, J=17.9, 7.6 Hz, 1H), 7.81-7.72 (m, 1H), 7.63-7.49 (m, 2H), 7.25 (d, J=8.4 Hz, 1H), 7.19 (d, J=8.3 Hz, 1H), 5.70 (d, J=6.8 Hz, 1H), 5.15 (d, J=10.1 Hz, 1H), 5.14-5.07 (m, 1H), 4.95 (d, J=16.6 Hz, 1H), 4.83 (t, J=6.7 Hz, 2H), 4.71 (s, 2H), 2.54 (dd, J=24.9, 12.6 Hz, 2H), 2.30 (d, J=11.2 Hz, 1H), 2.18 (d, J=13.5 Hz, 1H), 2.02 (d, J=12.9 Hz, 1H), 1.96-1.80 (m, 2H), 1.78 (d, J=16.1 Hz, 1H), 1.49 (dd, J=26.4, 11.2 Hz, 2H);

I-39

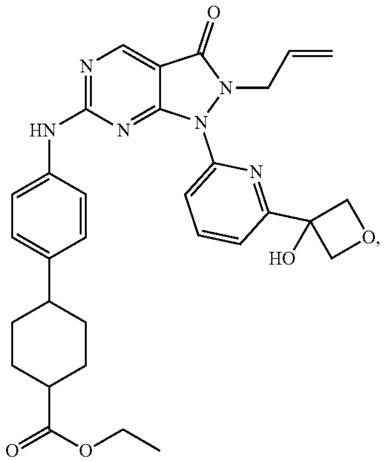

its $^1H$ NMR (400 MHz, Methanol-$d_4$) is δ 8.85 (d, J=1.1 Hz, 1H), 8.05 (td, J=7.9, 4.8 Hz, 1H), 7.96-7.86 (m, 1H), 7.67 (d, J=7.6 Hz, 1H), 7.59 (ddd, J=9.2, 4.6, 2.3 Hz, 2H), 7.25-7.19 (m, 1H), 7.19-7.11 (m, 1H), 5.78 (ddt, J=16.5, 10.1, 6.1 Hz, 1H), 5.12-5.07 (m, 2H), 5.06 (t, J=1.3 Hz, 1H), 4.98 (dd, J=17.0, 1.4 Hz, 1H), 4.90 (d, J=1.4 Hz, 2H), 4.25-4.19 (m, 1H), 4.14 (dd, J=14.1, 7.1 Hz, 1H), 2.34-2.12 (m, 2H), 2.07 (dd, J=17.0, 4.1 Hz, 1H), 1.99-1.82 (m, 1H), 1.74-1.65 (m, 2H), 1.65-1.53 (m, 2H), 1.31 (d, J=4.2 Hz, 3H), 1.29-1.25 (m, 2H);

I-40

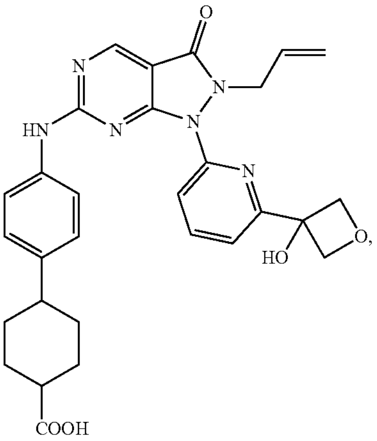

its $^1$H NMR (400 MHz, Methanol-$d_4$) is δ 8.84 (s, 1H), 8.05 (t, J=7.9 Hz, 1H), 7.92 (d, J=8.1 Hz, 1H), 7.66 (dd, J=7.6, 0.9 Hz, 1H), 7.63-7.53 (m, 2H), 7.22-7.14 (m, 2H), 5.84-5.74 (m, 1H), 5.10-5.07 (m, 2H), 5.06 (q, J=1.3 Hz, 1H), 4.98 (dq, J=17.0, 1.4 Hz, 1H), 4.89 (dt, J=6.1, 1.4 Hz, 2H), 2.71 (d, J=6.9 Hz, 1H), 2.59 (s, 1H), 2.24 (dd, J=16.4, 7.8 Hz, 2H), 2.04 (d, J=8.5 Hz, 1H), 1.73 (td, J=10.9, 6.8 Hz, 6H).

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

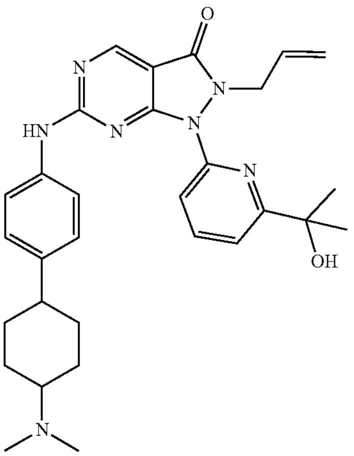
,

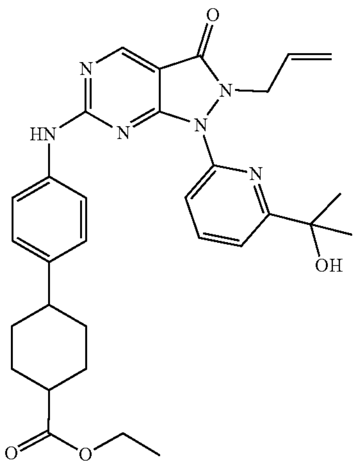
,

-continued

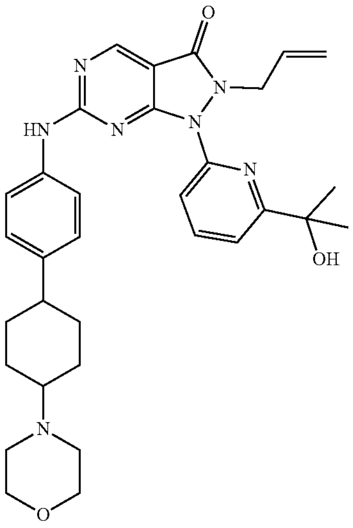
,

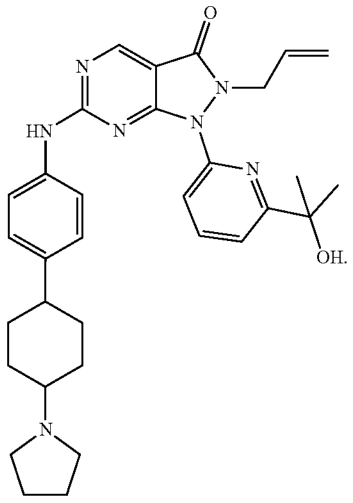
.

-continued
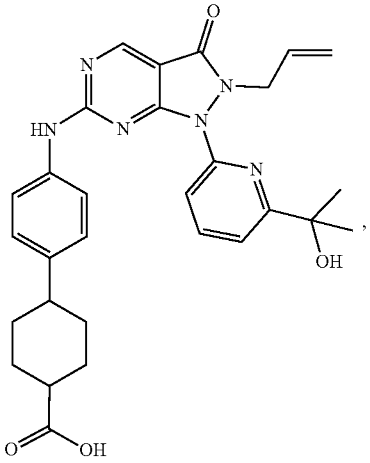
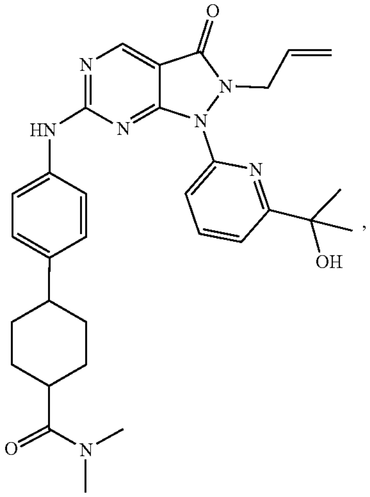
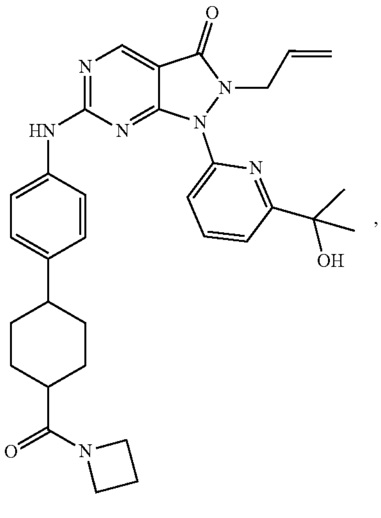
-continued
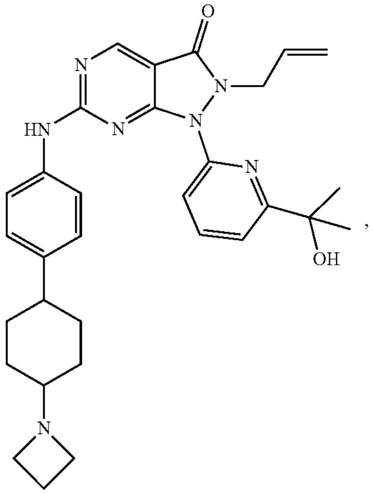
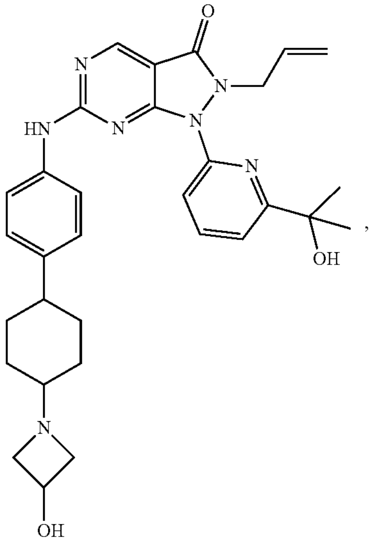
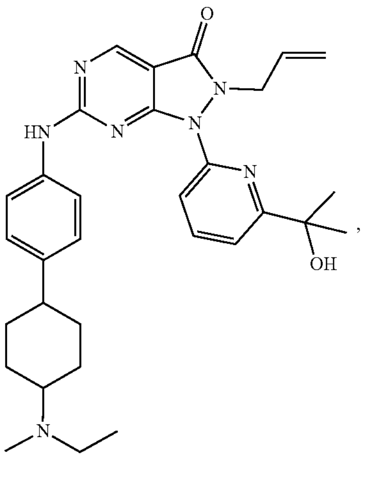

-continued
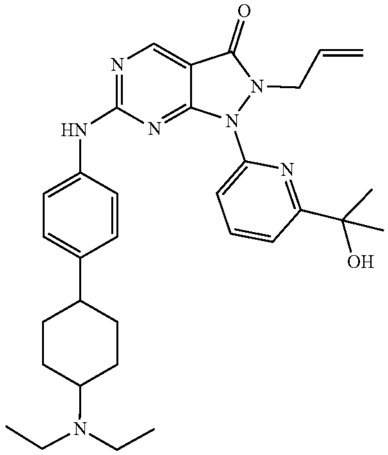
,
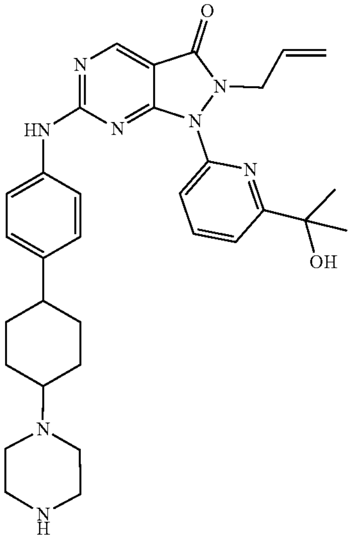
,
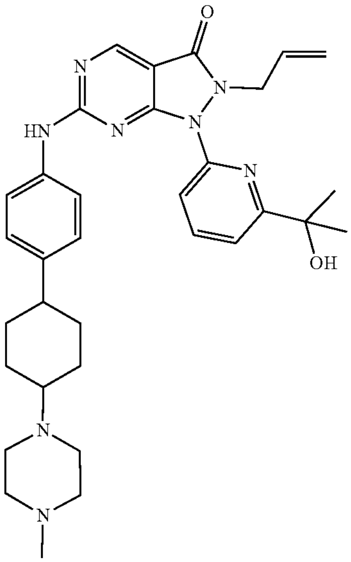
,
-continued
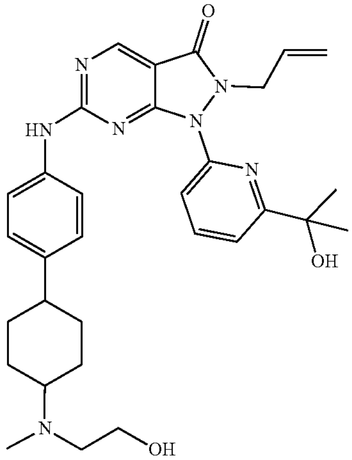
,
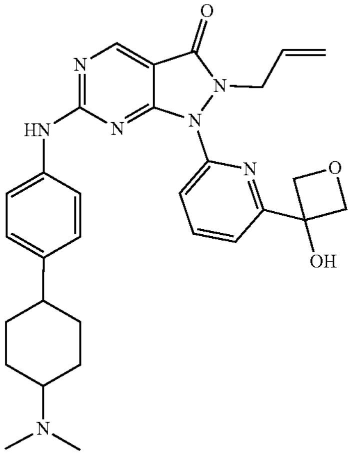
,
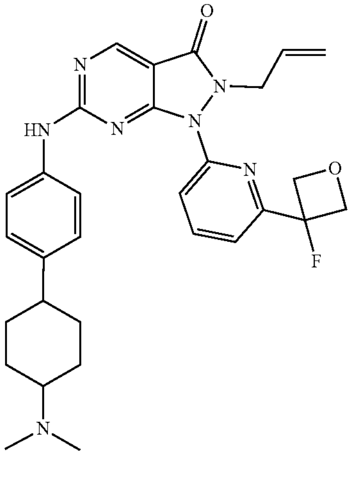
, -continued
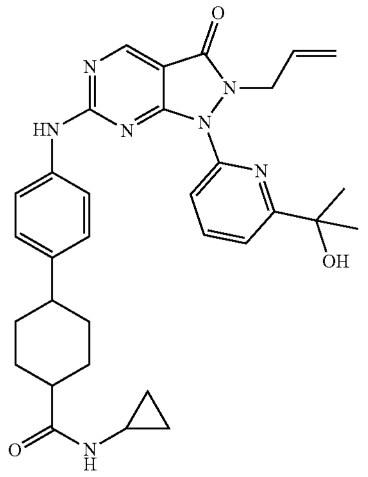
,
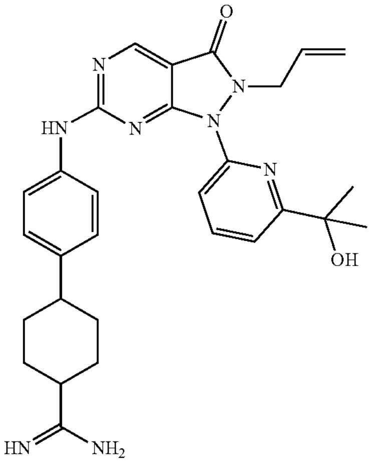
,
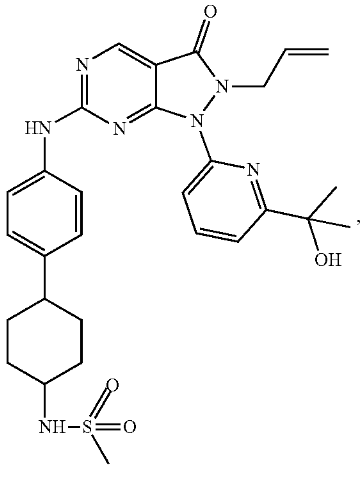
,
-continued
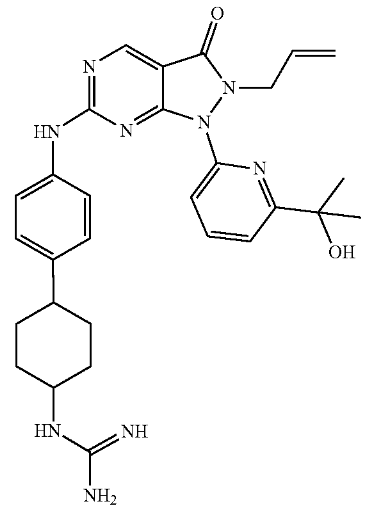
,
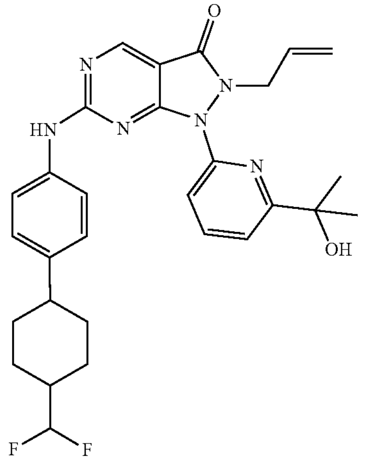
,
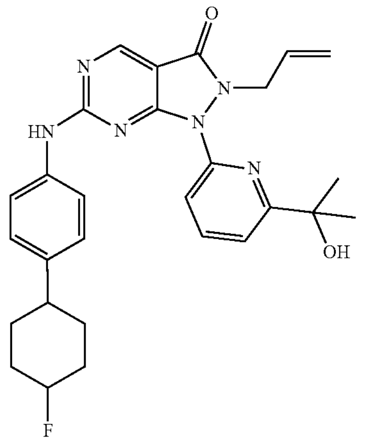
, -continued
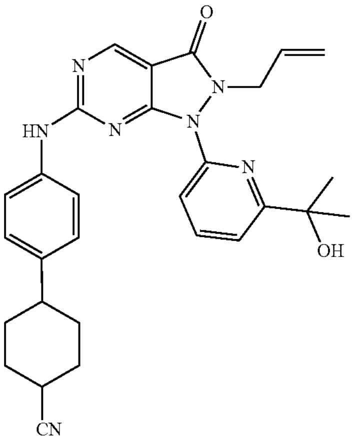
,
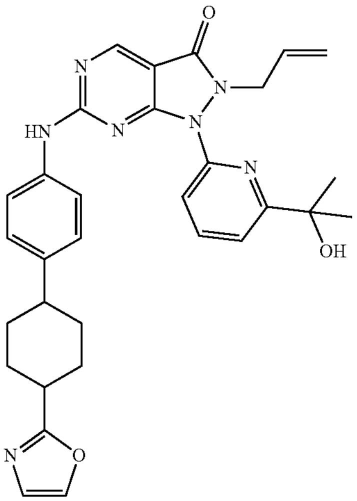
,
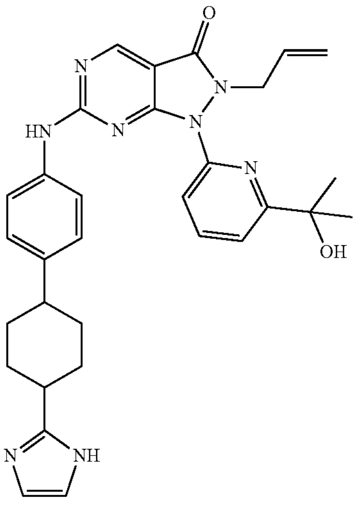
,
-continued
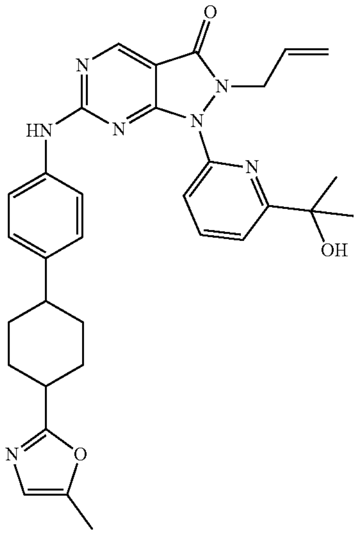
,
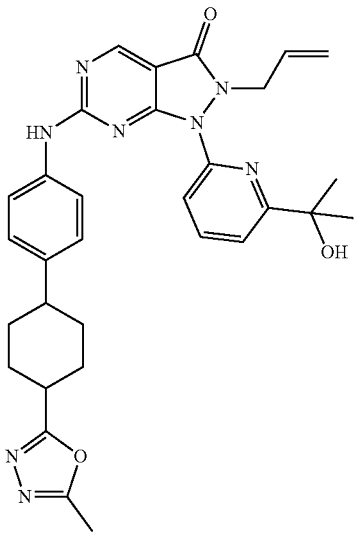
,
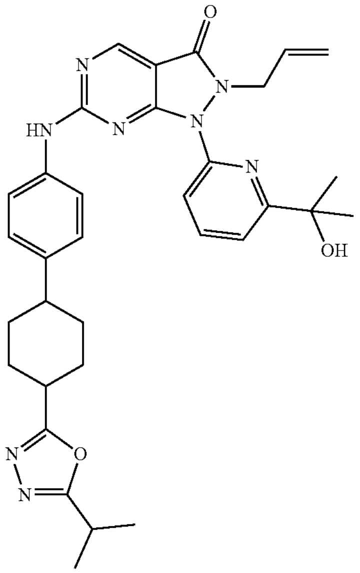
, -continued
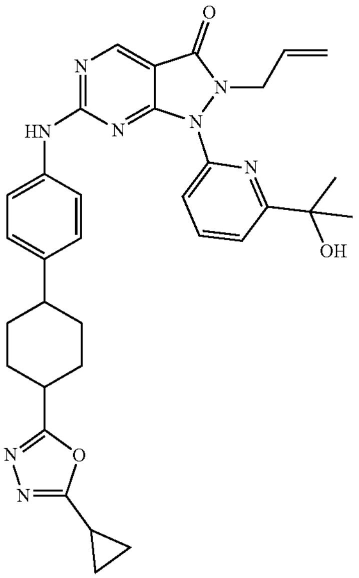
,
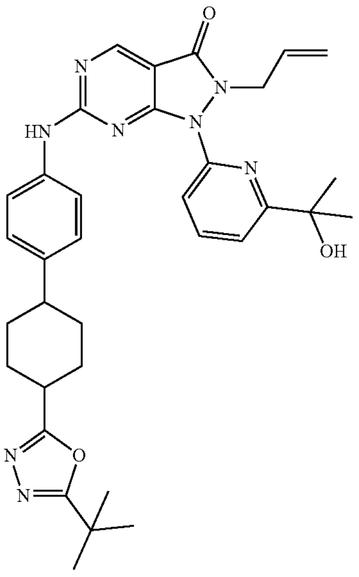
,
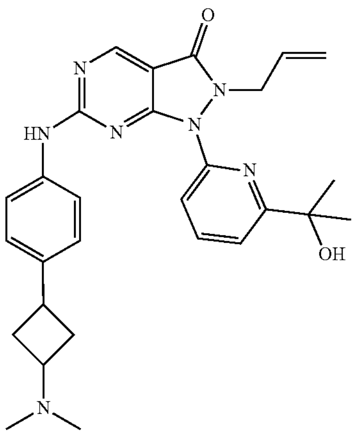
,
-continued
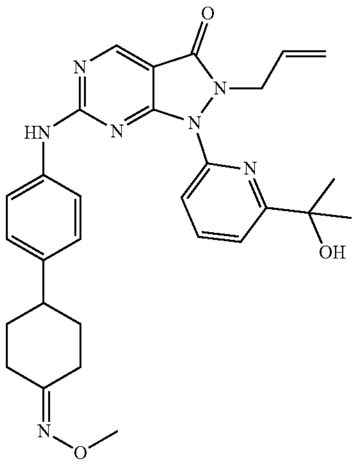
,
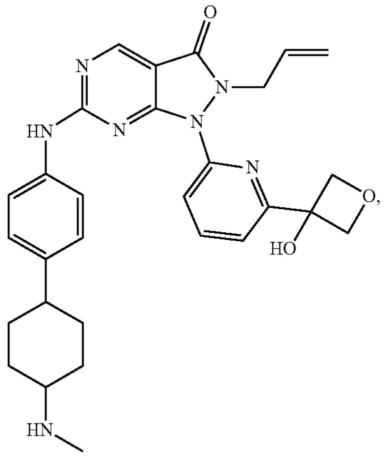
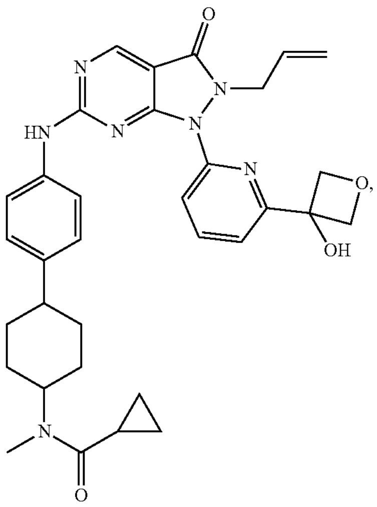

-continued
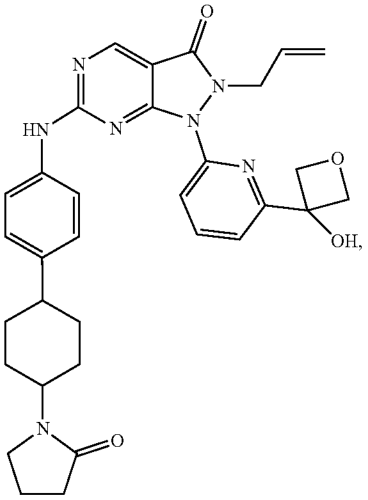
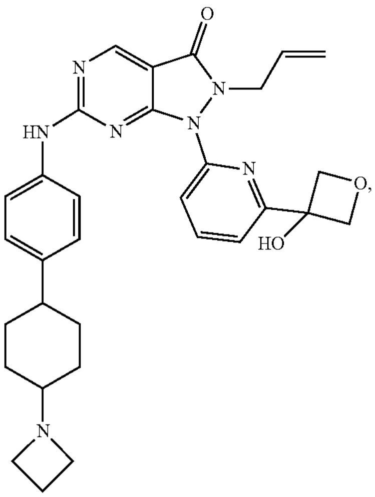
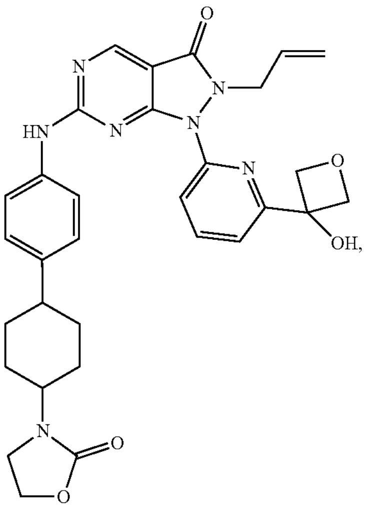
-continued
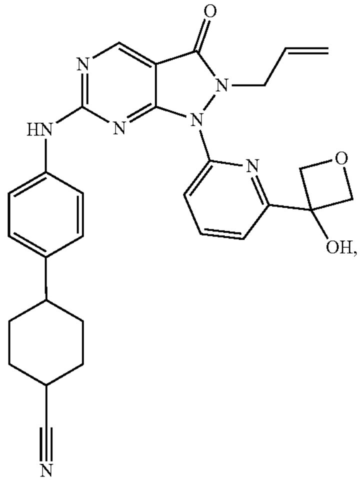
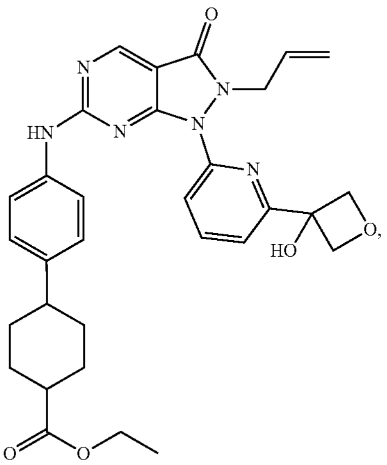
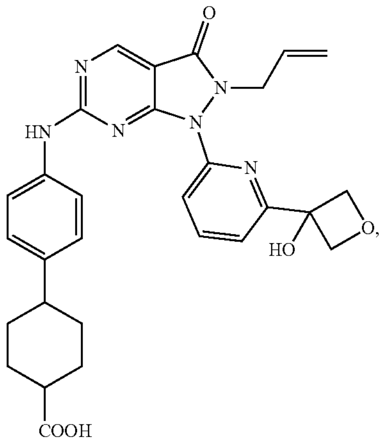
and -continued

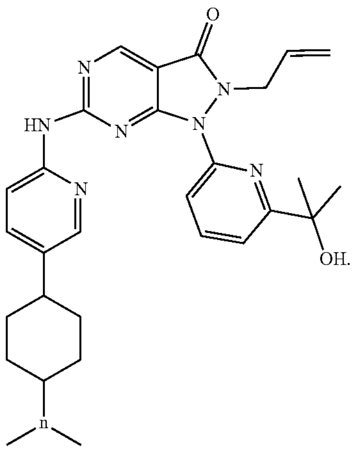

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

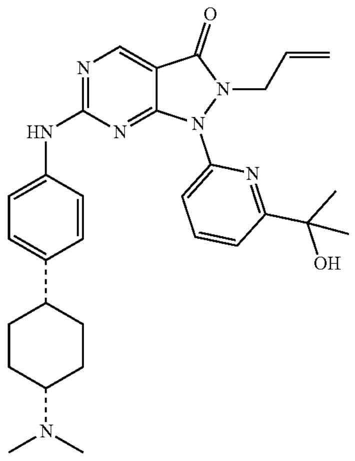

(I-1-1), its $^{1}$H NMR (400 MHz, MeOD) is δ 8.85 (s, 1H), 8.46 (s, 2H), 7.99 (t, J=7.9 Hz, 1H), 7.79 (d, J=8.0 Hz, 1H), 7.65 (dd, J=16.6, 8.1 Hz, 3H), 7.22 (d, J=8.6 Hz, 2H), 5.73 (ddt, J=16.3, 10.2, 6.1 Hz, 1H), 5.05 (dd, J=10.3, 1.1 Hz, 1H), 4.93 (dd, J=17.1, 1.3 Hz, 1H), 4.82 (d, J=6.1 Hz, 2H), 2.90 (s, 6H), 2.60 (d, J=8.4 Hz, 1H), 2.21 (s, 2H), 2.10 (d, J=10.6 Hz, 2H), 1.70 (d, J=11.4 Hz, 4H), 1.59 (s, 6H);

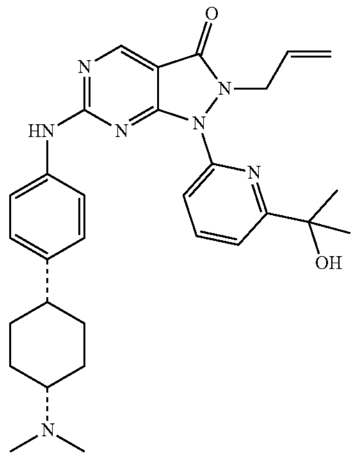

(I-1-2), its $^{1}$H NMR (400 MHz, $CDCl_3$) is δ 8.86 (s, 1H), 8.54 (s, 1H), 7.95 (t, J=7.9 Hz, 1H), 7.75 (d, J=8.0 Hz, 1H), 7.59 (d, J=8.5 Hz, 2H), 7.43 (d, J=7.6 Hz, 1H), 7.32 (d, J=8.5 Hz, 2H), 5.72 (ddt, J=16.5, 10.3, 6.2 Hz, 1H), 5.06 (d, J=10.2 Hz, 1H), 4.95 (dd, J=17.1, 1.0 Hz, 1H), 4.75 (d, J=6.1 Hz, 2H), 3.05 (m, 1H), 2.93 (m, 1H), 2.68 (s, 6H), 2.32 (m, 2H), 1.84 (m, 6H), 1.60 (s, 6H);

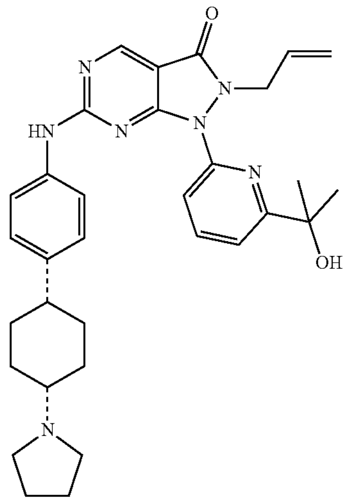

(I-3-1), its $^{1}$H NMR (400 MHz, $CDCl_3$) is δ 8.87 (s, 1H), 7.90 (t, J=7.9 Hz, 1H), 7.78 (d, J=8.0 Hz, 1H), 7.53 (d, J=8.5 Hz, 2H), 7.39 (dd, J=7.6, 0.5 Hz, 1H), 7.20 (d, J=8.5 Hz, 2H), 5.72 (ddt, J=16.4, 10.2, 6.2 Hz, 1H), 5.06 (dd, J=10.2, 1.0 Hz, 1H), 4.95 (dd, J=17.1, 1.2 Hz, 1H), 4.76 (d, J=6.2 Hz, 2H), 4.04 (s, 1H), 2.66 (m, 4H), 2.58-2.47 (m, 1H), 2.16 (m, 4H), 1.96 (m, 2H), 1.87-1.78 (m, 4H), 1.60 (s, 6H), 1.58-1.39 (m, 4H);

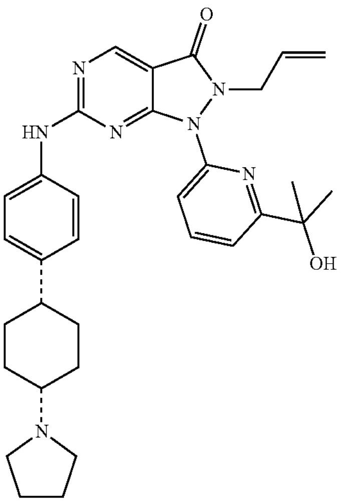

(I-3-2), its $^1$H NMR (400 MHz, $CDCl_3$) is δ 8.87 (s, 1H), 7.92 (t, J=7.9 Hz, 1H), 7.80 (d, J=8.0 Hz, 1H), 7.52 (d, J=8.5 Hz, 2H), 7.38 (d, J=7.6 Hz, 1H), 7.29 (t, J=4.2 Hz, 2H), 5.79-5.66 (m, 1H), 5.06 (dd, J=10.2, 1.0 Hz, 1H), 4.96 (dd, J=17.1, 1.2 Hz, 1H), 4.77 (d, J=6.2 Hz, 2H), 4.02 (s, 1H), 2.70-2.50 (m, 5H), 2.26 (s, 1H), 1.98 (m, 4H), 1.82 (s, 4H), 1.69-1.56 (m, 10H);

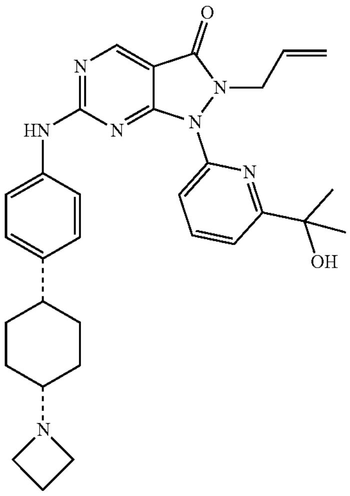

(I-8-1), its $^1$H NMR (400 MHz, $CDCl_3$) is δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H);

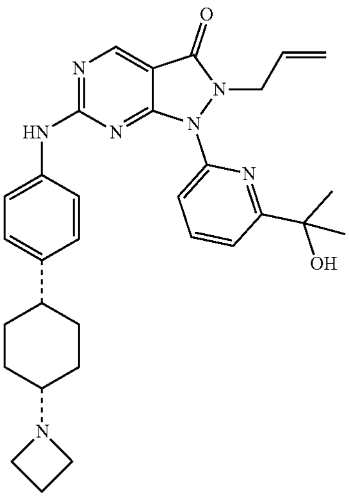

(I-8-2), its $^1$H NMR (400 MHz, $CDCl_3$) is δ8.87 (s, 1H), 7.92 (d, J=7.8 Hz, 1H), 7.80 (d, J=8.0 Hz, 1H), 7.52 (d, J=8.4 Hz, 2H), 7.39 (d, J=7.6 Hz, 1H), 7.29-7.25 (m, 2H), 5.82-5.63 (m, 1H), 5.12-4.91 (m, 2H), 4.78 (d, J=6.2 Hz, 2H), 4.01 (s, 1H), 3.17 (s, 4H), 2.53 (s, 1H), 2.33 (s, 1H), 2.06 (d, J=4.4 Hz, 2H), 1.89 (d, J=11.6 Hz, 2H), 1.75 (d, J=14.1 Hz, 2H), 1.59 (d, J=17.2 Hz, 8H), 1.46 (t, J=13.1 Hz, 2H);

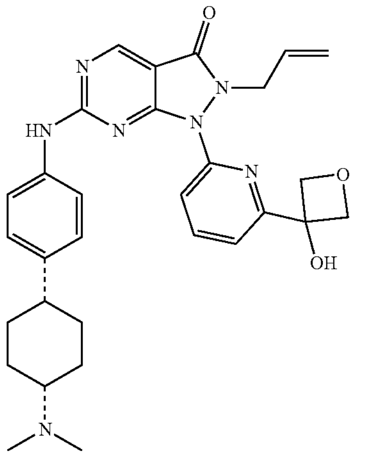

(I-15-1), its $^1$H NMR (400 MHz, MeOD) is δ 8.84 (s, 1H), 8.04 (t, J=7.9 Hz, 1H), 7.92 (d, J=8.1 Hz, 1H), 7.67 (d, J=7.6 Hz, 1H), 7.60 (d, J=8.6 Hz, 2H), 7.21 (d, J=8.6 Hz, 2H), 5.78 (ddt, J=16.3, 10.3, 6.1 Hz, 1H), 5.12-5.05 (m, 3H), 4.98 (dd, J=17.1, 1.3 Hz, 1H), 4.89 (d, J=6.1 Hz, 2H), 4.84 (s, 2H), 3.68 (s, 2H), 2.97-2.86 (m, 1H), 2.66 (s, 6H), 2.60-2.50 (m, 1H), 2.15 (d, J=8.6 Hz, 2H), 2.04 (d, J=9.0 Hz, 2H), 1.66-1.54 (m, 4H);

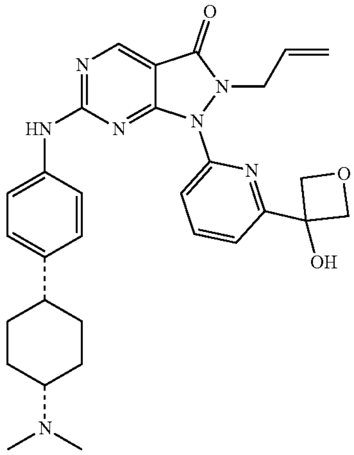

(I-15-2), its $^{1}$H NMR (400 MHz, MeOD) is δ 8.83 (s, 1H), 8.04 (t, J=7.9 Hz, 1H), 7.92 (d, J=8.0 Hz, 1H), 7.67-7.62 (m, 1H), 7.59 (d, J=8.6 Hz, 2H), 7.29 (d, J=8.5 Hz, 2H), 5.76 (ddt, J=16.3, 10.2, 6.1 Hz, 1H), 5.10-5.02 (m, 3H), 4.96 (dd, J=17.1, 1.3 Hz, 1H), 4.87 (d, J=6.8 Hz, 2H), 4.82 (d, J=6.8 Hz, 2H), 2.73 (d, J=4.2 Hz, 1H), 2.29 (d, J=21.9 Hz, 7H), 2.04-1.90 (m, 4H), 1.66 (dd, J=15.6, 6.1 Hz, 4H);

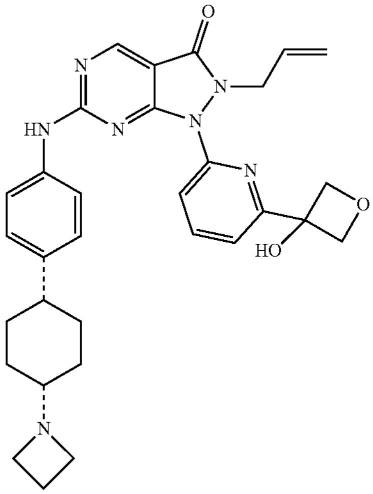

(I-36-1), its $^{1}$H NMR (400 MHz, $CDCl_3$) is δ 8.88 (d, J=2.6 Hz, 1H), 8.09 (dd, J=15.0, 7.8 Hz, 1H), 7.99-7.83 (m, 2H), 7.54 (t, J=9.5 Hz, 2H), 7.39 (d, J=8.7 Hz, 1H), 7.21 (d, J=8.5 Hz, 1H), 5.74 (dq, J=10.5, 5.9 Hz, 1H), 5.12 (t, J=8.8 Hz, 3H), 4.99 (d, J=17.1 Hz, 1H), 4.80 (d, J=6.3 Hz, 2H), 4.67 (d, J=6.0 Hz, 2H), 3.39-3.24 (m, 4H), 2.60-2.34 (m, 3H), 2.14 (dt, J=14.0, 6.8 Hz, 3H), 1.96 (d, J=10.8 Hz, 4H), 1.55-1.37 (m, 2H), 1.27-1.12 (m, 2H);

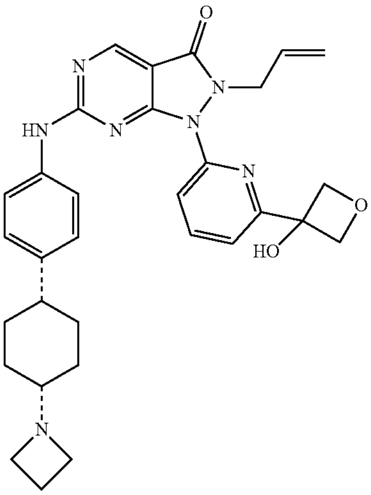

(I-36-2), its $^{1}$H NMR (400 MHz, MeOD) is δ 8.86 (s, 1H), 8.02 (dt, J=24.0, 7.9 Hz, 3H), 7.64 (dd, J=27.1, 8.1 Hz, 3H), 7.27 (t, J=8.6 Hz, 2H), 7.01-6.91 (m, 3H), 6.72-6.64 (m, 3H), 5.79 (ddd, J=16.3, 11.2, 6.1 Hz, 1H), 5.10-5.05 (m, 2H), 4.85 (d, J=6.8 Hz, 2H), 2.57 (d, J=10.7 Hz, 1H), 2.48-2.28 (m, 3H), 2.23-2.06 (m, 3H), 1.98-1.71 (m, 6H), 1.58 (dd, J=23.2, 12.9 Hz, 3H), 1.44 (ddd, J=16.1, 13.2, 3.5 Hz, 2H), 1.19-1.00 (m, 2H);

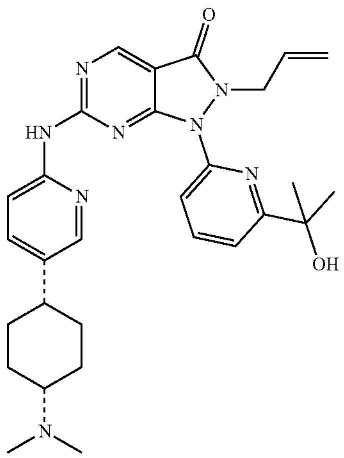

(I-41-1), its $^{1}$H NMR (400 MHz, Chloroform-d) is δ 9.00 (s, 1H), 8.30 (d, J=8.6 Hz, 1H), 8.22 (d, J=2.4 Hz, 1H), 7.96 (t, J=7.9 Hz, 1H), 7.73 (dd, J=8.1, 0.8 Hz, 1H), 7.55 (dd, J=8.7, 2.4 Hz, 1H), 7.44 (dd, J=7.7, 0.8 Hz, 1H), 5.77-5.66 (m, 1H), 5.12-5.05 (m, 1H), 4.97 (dq, J=17.0, 1.4 Hz, 1H), 4.76 (dt, J=6.3, 1.3 Hz, 2H), 2.70 (s, 1H), 2.56 (s, 6H), 2.23 (q, J=9.5 Hz, 4H), 2.11-2.01 (m, 4H), 1.58 (t, J=10.3 Hz, 6H);

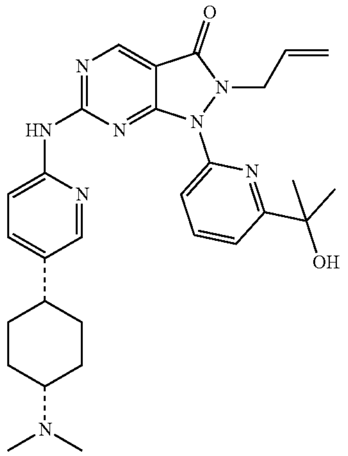

(I-41-2), its $^1$H NMR (400 MHz, Chloroform-d) is δ8.99 (s, 1H), 8.54 (s, 1H), 8.32 (d, J=8.7 Hz, 1H), 8.26 (d, J=2.4 Hz, 1H), 8.10 (t, J=7.7 Hz, 1H), 7.92 (s, 1H), 7.78 (dd, J=8.1, 0.8 Hz, 1H), 7.47-7.41 (m, 1H), 5.79-5.71 (m, 1H), 5.08 (dq, J=10.1, 1.2 Hz, 1H), 4.97 (dq, J=17.0, 1.3 Hz, 1H), 4.77 (dt, J=6.2, 1.4 Hz, 2H), 3.99 (s, 1H), 2.75 (d, J=11.0 Hz, 1H), 2.52 (s, 6H), 2.32-2.18 (m, 1H), 2.09 (d, J=14.4 Hz, 4H), 1.31 (d, J=22.8 Hz, 4H);

wherein, ⁄ means that the cis-trans conformation is uncertain.

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

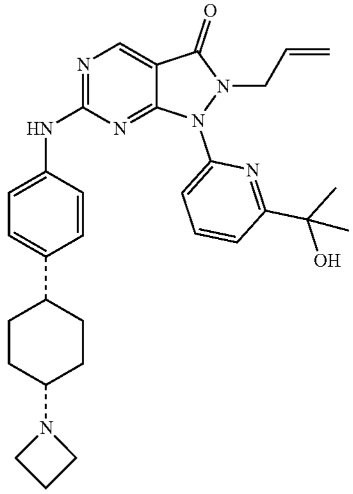

(I-8-1), its $^1$H NMR (400 MHz, $CDCl_3$) has a peak of 1.23-1.08;

wherein, ⁄ means that the cis-trans conformation is uncertain.

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

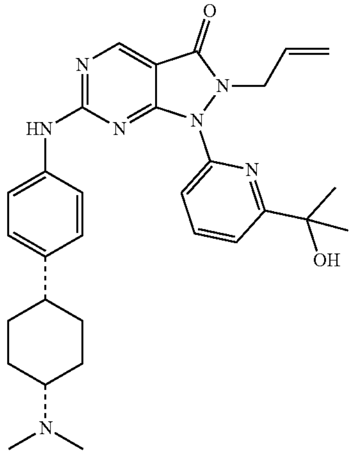

(I-1-1) with a retention time of 10.55 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

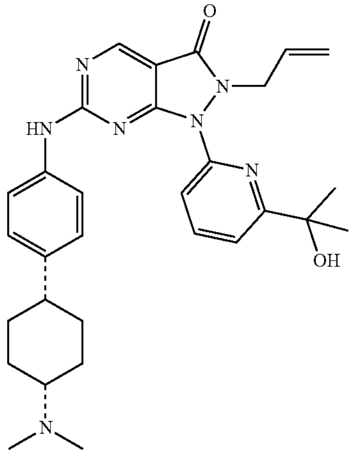

(I-1-2) with a retention time of 10.78 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

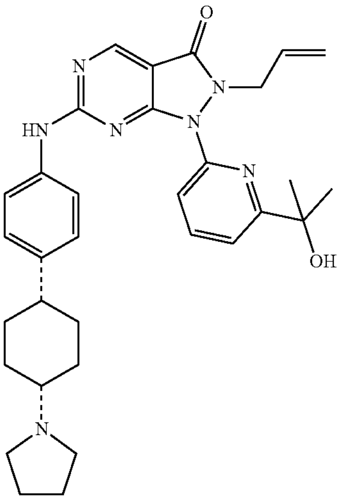

(I-3-1) with a retention time of 11.01 min under the following conditions: Agilent 1260 high performance liquid chromatograph; mobile phase A: water (0.1% formic acid), mobile phase B: acetonilrile; column time: 15 min; column type: Waters' Xselect, 5 μm, 4.6×250 mm; gradient elution, 5% mobile phase B→50% mobile phase B;

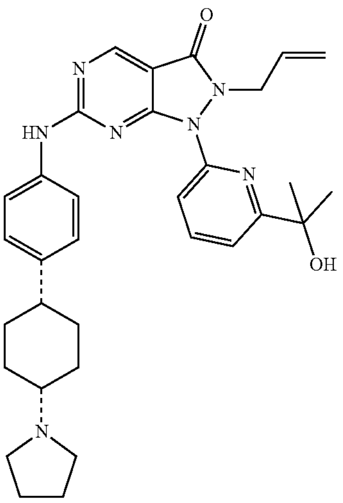

(I-3-2) with a retention time of 11.20 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

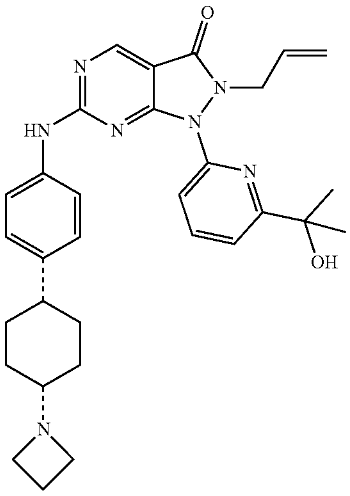

(I-8-1) with a retention time of 10.78 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

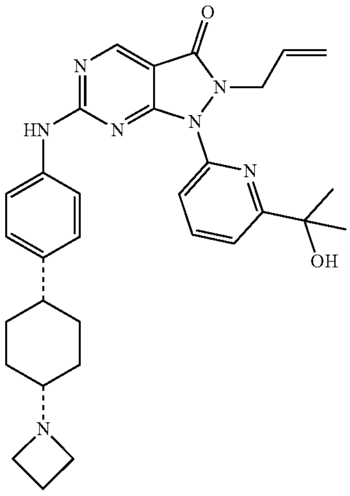

(I-8-2) with a retention time of 11.00 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

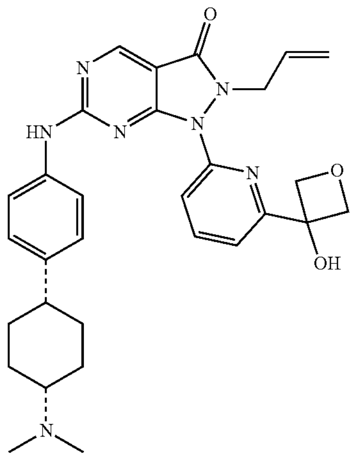

(I-15-1) with a retention time of 7.02 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

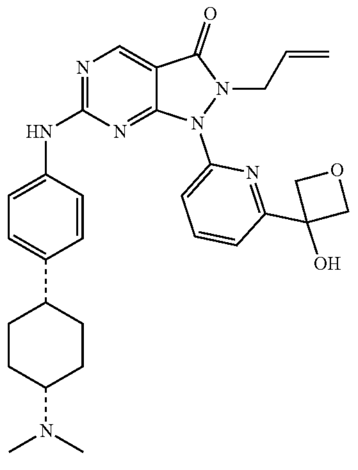

(I-15-2) with a retention time of 7.16 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

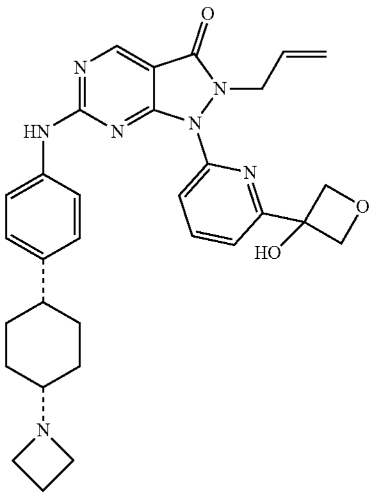

(I-36-1) with a retention time of 7.14 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

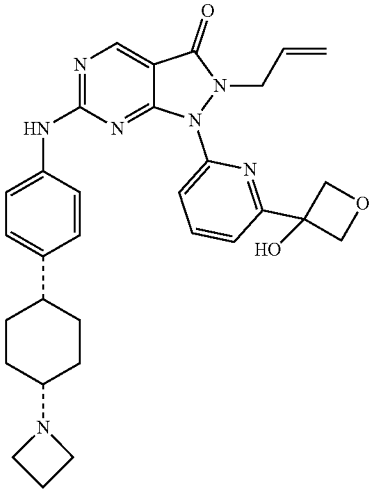

(I-36-2) with a retention time of 7.15 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

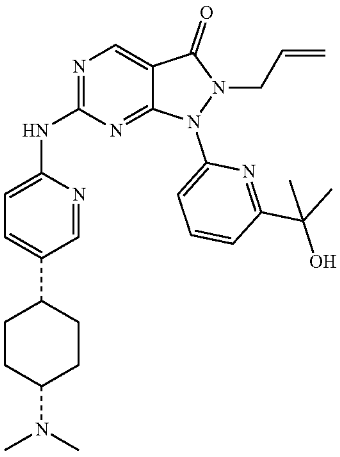 [SMILES: C=CCn1c(=O)c2cnc(Nc3ccc([C@H]4CC[C@@H](N(C)C)CC4)cn3)nc2n1-c1cccc(C(C)(C)O)n1]

(I-41-1) with a retention time of 6.17 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

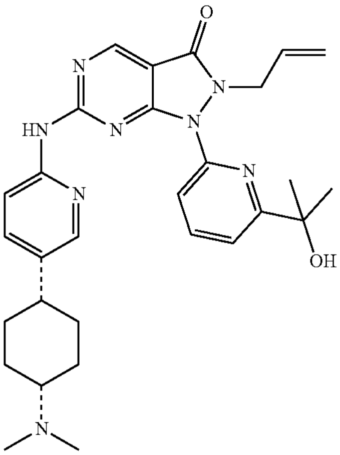

(I-41-2) with a retention time of 6.28 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

wherein, 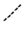 means that the cis-trans conformation is uncertain.

In a certain scheme, in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof, the pyrazolone-fused pyrimidine compound represented by formula II is any of the following compounds:

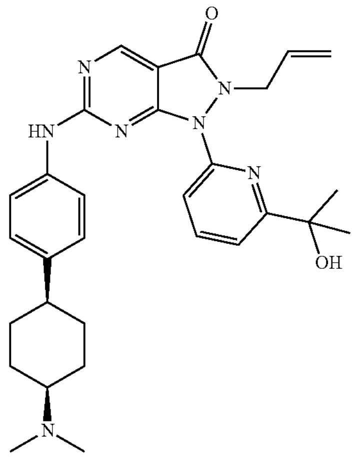

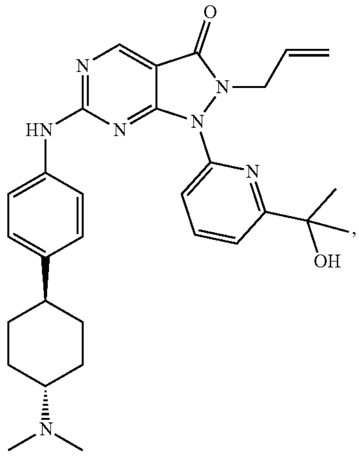

,

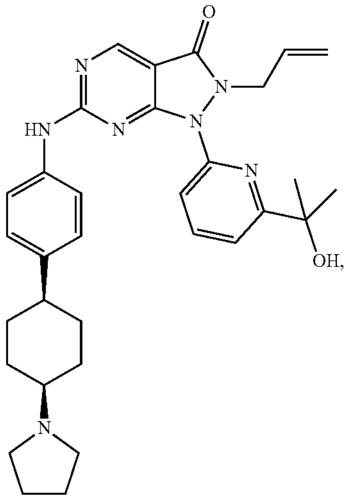

,

-continued
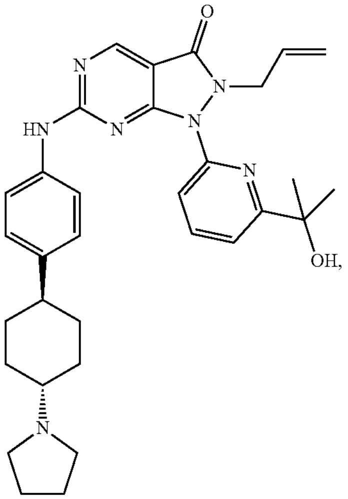
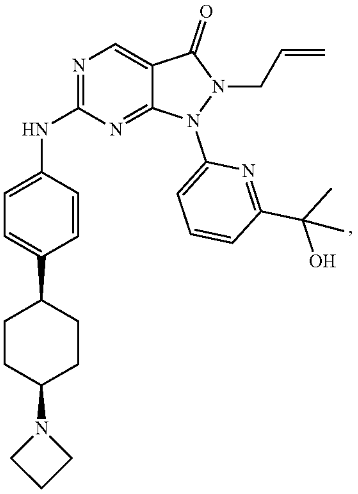
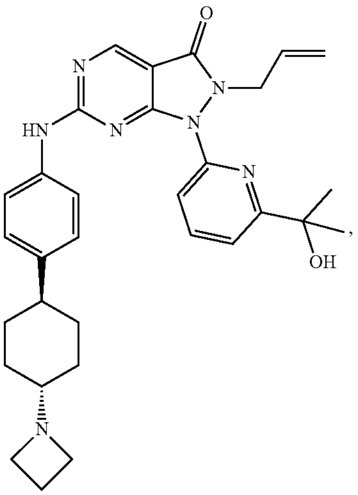
-continued
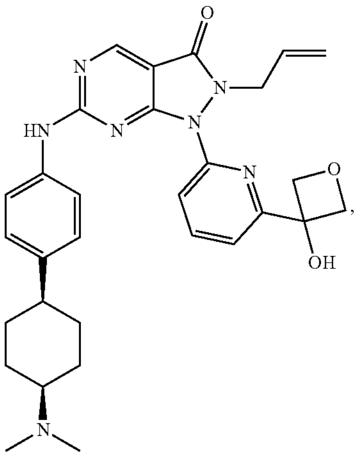
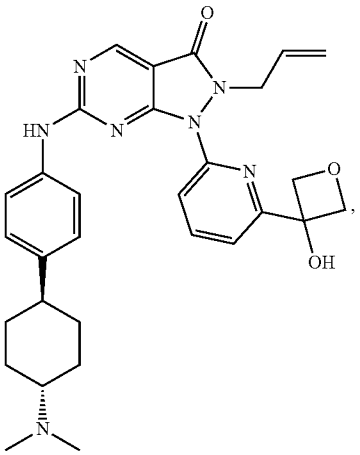
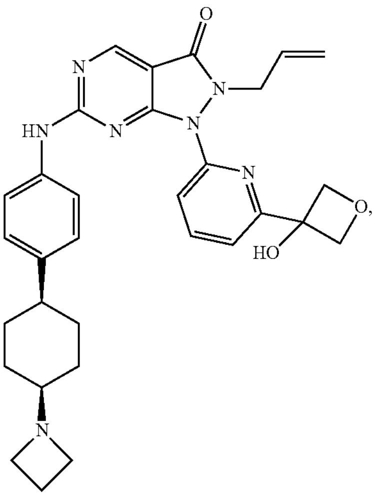

-continued

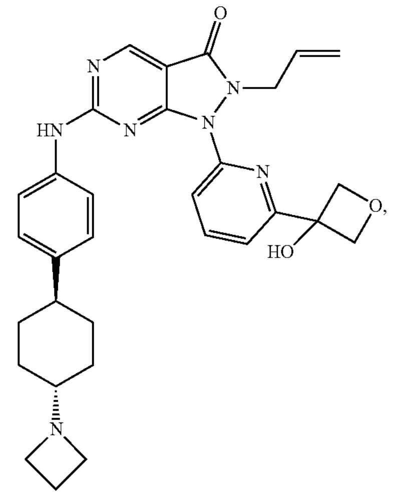

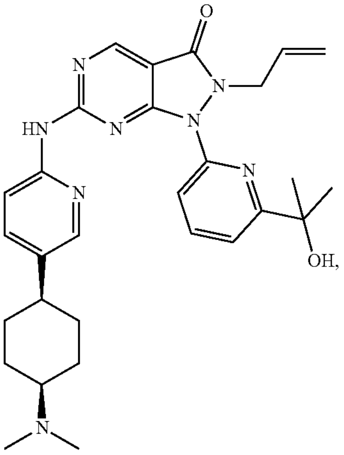

and

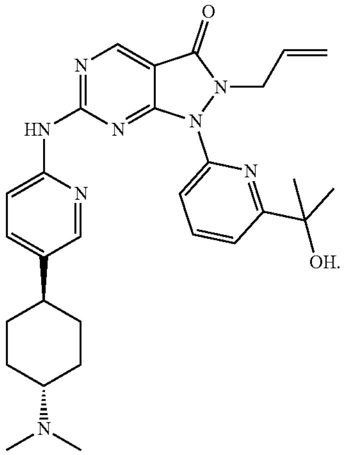

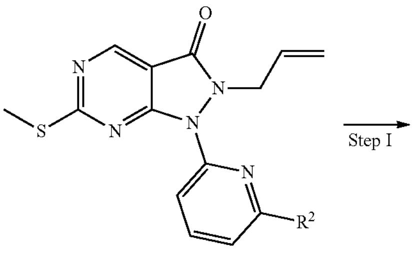

II-1A

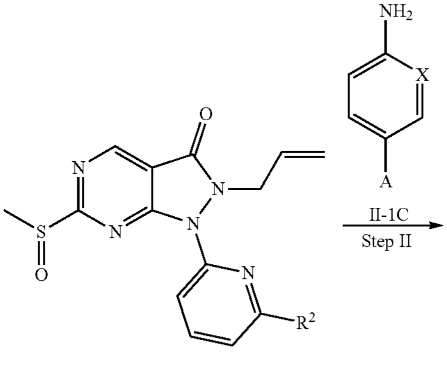

II-1B

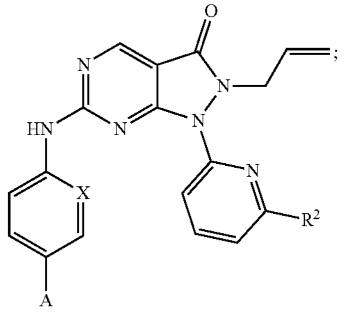

II

The present disclosure also provides a preparation method of the compound II, the method is any of the following methods:

method 1, comprising the following steps: step I, oxidizing compound II-1A by an oxidant in an organic solvent to obtain compound II-1B; step II, reacting compound II-1B with compound II-1C in an organic solvent and under alkaline conditions to obtain compound II;

method 2, comprising the following steps: step I, hydrolyzing compound II-2A ($R^1$ is —(C═O)—O—$C_2H_5$) to obtain compound II-2B ($R^1$ is —(C═O)—OH); step II, a condensation reaction is carried out between compound II-2B and an amino compound in an organic solvent to obtain compound II ($R^1$ is —(C═O)—$NR^{1-5-1}R^{1-5-2}$).

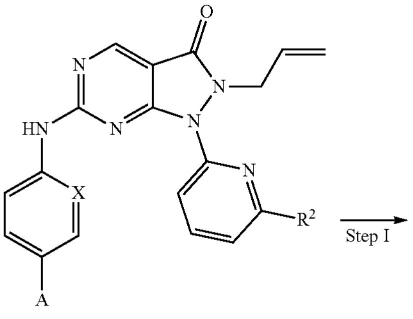

II-2A

-continued

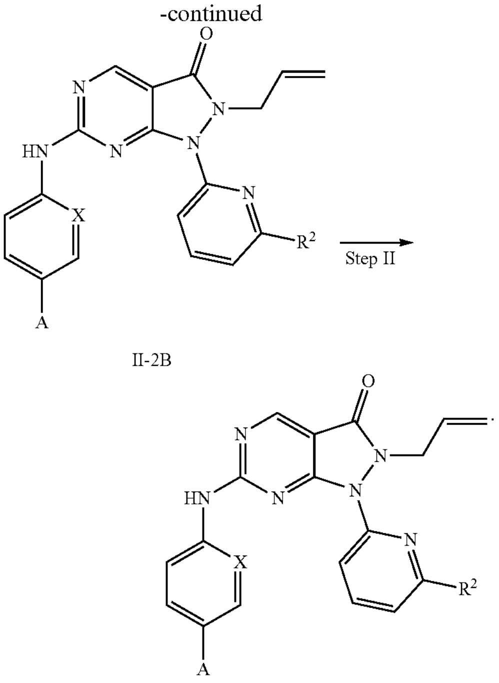

II-2B

II

The conditions and steps of the reaction described in method 1 may be conventional conditions and steps in the art. The following reaction conditions are particularly preferred in the present disclosure:

Step 1, the organic solvent is preferably one or more of methanol, dichloromethane, acetonitrile, toluene and DMF, more preferably dichloromethane or toluene; the oxidant may be an oxidant commonly used in the art to oxidize thioether to sulfoxide, preferably m-chloroperoxybenzoic acid (m-CPBA); the molar ratio of compound II-1A to m-CPBA is preferably 1:(1-1.2), the reaction time is preferably 1-12 hours, and the reaction temperature is preferably 0° C.-35° C.

Step 2, the organic solvent is preferably dichloromethane or toluene; the alkaline condition is preferably an organic base such as N,N-diisopropylethylamine (DIPEA) or triethylamine, more preferably N,N-diisopropylethylamine (DIPEA); the molar ratio of compound II-1B, compound II-1C and DIPEA is preferably 1:1:2, the reaction time is preferably 0-12 hours, and the reaction temperature is preferably 0° C.-35° C.

The conditions and steps of the reaction described in method 2 may be conventional conditions and steps in the art. The following reaction conditions are particularly preferred in the present disclosure:

Step I, the hydrolysis reaction conditions are any suitable reaction conditions commonly used in the art, such as alkaline hydrolysis or acid hydrolysis, and alkaline hydrolysis is for example sodium hydroxide hydrolysis or lithium hydroxide hydrolysis.

Step II, the amino compound may be a primary or secondary amine; the organic solvent is preferably dichloromethane or DMF; the condensation reaction is carried out under any suitable reaction conditions commonly used in the art, such as EDCI/HOBT/DIPEA or HATU/DIPEA.

The present disclosure also provides a compound represented by formula II-1C:

II-1C

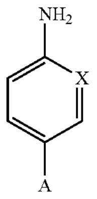

wherein, X is CH or N, A is defined as above.

In a certain scheme, the compound represented by formula II-1C may be any of the following compounds:

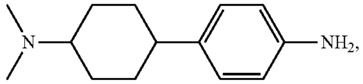
,
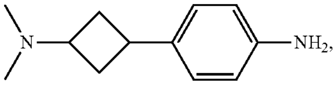
,
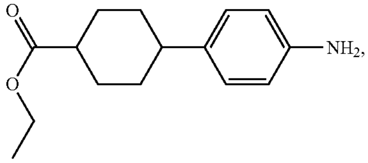
,
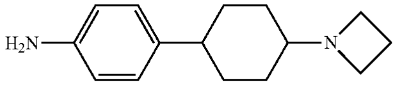
,
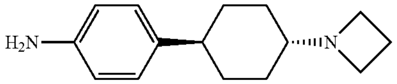
,
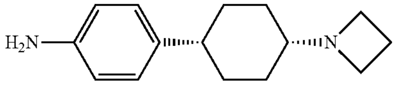
,
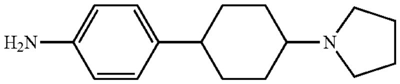
,
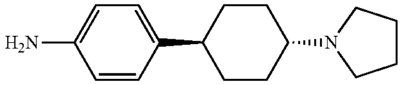
and
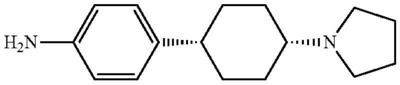
.

In a certain scheme, the compound represented by formula II-1C may be any of the following compounds:

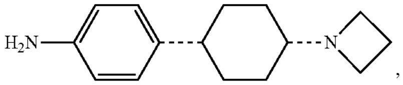
, its $^1H$ NMR (400 MHz, $CDCl_3$) is δ 7.08-6.96 (m, 2H), 6.70-6.60 (m, 2H), 3.57 (s, 2H), 3.22 (t, J=7.0 Hz, 4H), 2.38 (tt, J=12.1, 3.2 Hz, 1H), 2.15-1.95 (m, 5H), 1.95-1.81 (m, 4H), 1.51-1.30 (m, 2H), 1.21-1.04 (m, 2H);

or,

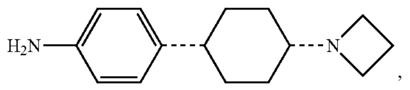

its $^1$H NMR (400 MHz, MeOD) is δ 7.10-6.97 (m, 2H), 6.74-6.63 (m, 2H), 4.22-4.08 (t, J=8.0 Hz, 4H), 3.47-3.38 (m, 1H), 2.61-2.52 (m, 1H), 2.52-2.28 (m, 2H), 1.92-1.62 (m, 8H).

The present disclosure also provides a preparation method of the compound represented by formula II-1C, the method is any of the following methods:

method A: step I, protecting amino N of compound II-1C1 in an organic solvent under alkaline condition to obtain compound II-1C2; step II, a Suzuki reaction is carried out between compound II-1C2 and compound II-1C3 to obtain compound II-1C4; step III, removing the ketal of compound II-1C4 to obtain compound II-1C5; step IV, a reductive amination reaction is carried out with compound II-1C5 to obtain compound II-1C6; step V, removing the amino protecting group PG with a reducing agent and reducing the double bond simultaneously to obtain compound II-1C;

Reaction formula 1

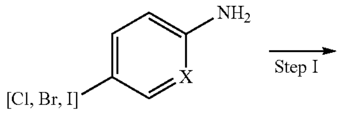

II-1C1

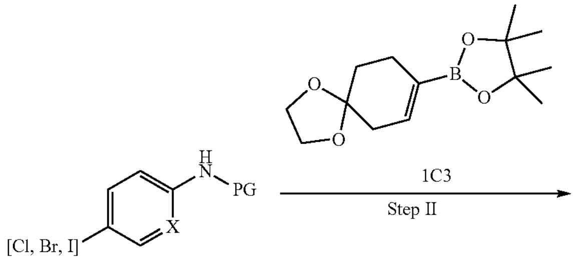

II-1C2

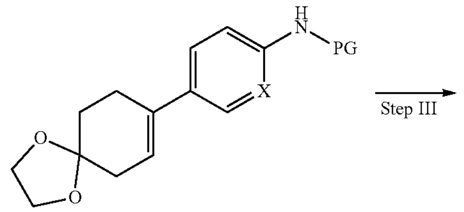

II-1C4

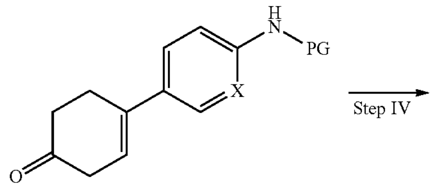

II-1C5

-continued

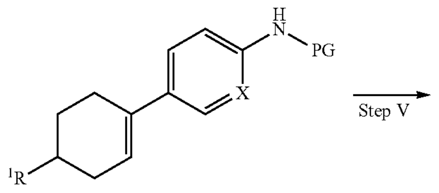

II-1C6

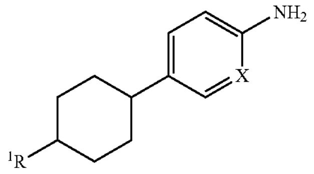

II-1C wherein, PG is an amino protecting group, $R^1$ is —$NR^{1-3}R^{1-4}$, and $R^{1-3}$ and $R^{1-4}$ are defined as above;

method B, comprising the following steps: step I, a Suzuki reaction is carried out between compound II-1C' and compound II-1C2' to obtain compound II-1C3'; step II, a reduction reaction is carried out with compound II-1C3' to obtain compound II-1C;

Reaction formula 2

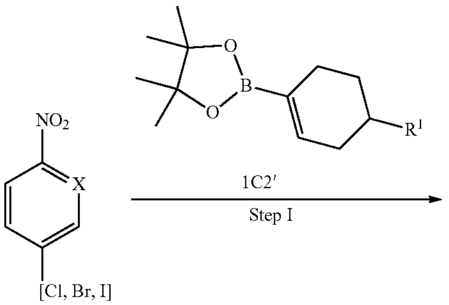

II-1C1'

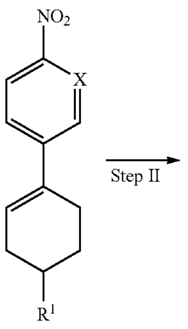

II-1C3'

-continued

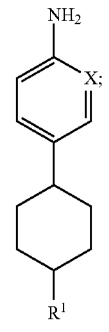

II-1C wherein, $R^1$ is —C(═O)$R^{1-5}$, $R^{1-5}$ is defined as above;

method C, comprising the following steps: step I, a reductive amination reaction is carried out with compound II-1C1" (ring A is oxo-$C_4$-$C_6$ cycloalkyl) to obtain compound II-1C2" ($R^1$ is —$NR^{1-3}R^{1-4}$); step II, a Buchwald reaction is carried out between compound II-1C2" and benzophenone imine to obtain compound II-1C3" ($R^1$ is —$NR^{1-3}R^{1-4}$); step III, removing the diphenyl of compound II-1C3" to obtain compound II-1C;

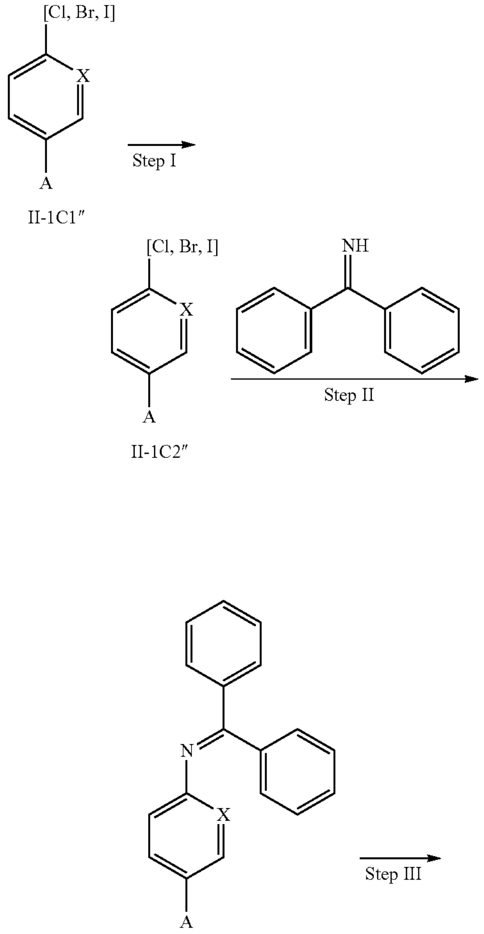

II-1C1"

II-1C2"

II-1C3"

-continued

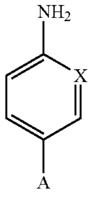

II-1C wherein, A, $R^{1-3}$ and $R^{1-4}$ are defined as above.

The conditions and steps of the reaction described in method A may be conventional conditions and steps in the art. The following reaction conditions are particularly preferred in the present disclosure:

Step I, the amino protecting group PG may be any suitable amino protecting group commonly used in the art, preferably Cbz, which is intended to protect compound II-1C1 from certain reactive groups (e.g., amino groups) on it when it is involved in the reaction. The compound II-1C1 is preferably a bromide or an iodide.

Step II, the Suzuki reaction conditions are any suitable reaction conditions commonly used in the art. The Suzuki reaction conditions are preferably $Pd(Ph_3P)_4$ or $Pd(dppf)Cl_2$, potassium carbonate, 1,2-dimethoxyethane or dioxane.

Step III, the ketal removal conditions are any suitable reaction conditions commonly used in the art, the removal is preferably carried out using hydrochloric acid, and the reaction temperature is preferably 50° C.-100° C.

Step IV, the reductive amination reaction conditions are any suitable reaction conditions commonly used in the art, and the reducing agent is preferably sodium triacetoxyborohydride.

Step V, the conditions for removing the amino protection group PG with the reducing agent and simultaneously reducing the double bond can be the conventional conditions of the method in the art. The amino protecting group PG, such as benzyl or Cbz, preferably Cbz. The reducing agent is preferably palladium carbon/hydrogen.

The conditions and steps of the reaction described in method B may be conventional conditions and steps in the art. The following reaction conditions are particularly preferred in the present disclosure:

Step I, the Suzuki reaction conditions are any suitable reaction conditions commonly used in the art. The Suzuki reaction conditions are preferably $Pd(Ph_3P)_4$ or $Pd(dppf)Cl_2$, potassium carbonate, 1,2-dimethoxyethane or dioxane.

Step II, the reduction reaction conditions are any suitable reaction conditions commonly used in the art to reduce both nitro and double bonds, such as palladium carbon/hydrogen, palladium carbon/ammonium formate, palladium carbon/hydrazine hydrate.

The conditions and steps of the reaction described in method C may be conventional conditions and steps in the art. The following reaction conditions are particularly preferred in the present disclosure:

Step I, the reductive amination reaction conditions are any suitable reaction conditions commonly used in the art, and the reducing agent is preferably sodium triacetoxyborohydride.

Step II, the Buchwald reaction conditions are any suitable reaction conditions commonly used in the art. The Buchwald reaction conditions are preferably $Pd_2(dba)_3$/sodium tert-butoxide/Binap.

Step III, the reaction conditions for removing diphenyl are any suitable reaction conditions commonly used in the art, and the reaction conditions are preferably sodium acetate/hydroxylamine hydrochloride.

The present disclosure also provides a preparation method of the compound I, which is any of the following methods:

method 1, comprising the following steps: step I, oxidizing compound 1A with an oxidant in an organic solvent to obtain compound 1B; step II, reacting compound 1B with compound 1C in an organic solvent and under alkaline conditions to obtain compound I;

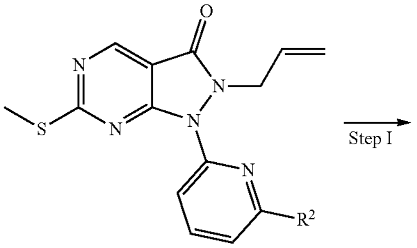

1A

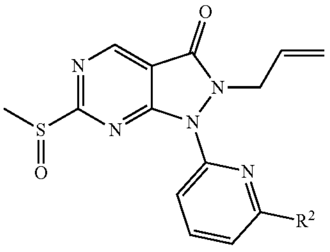

1B

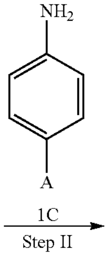

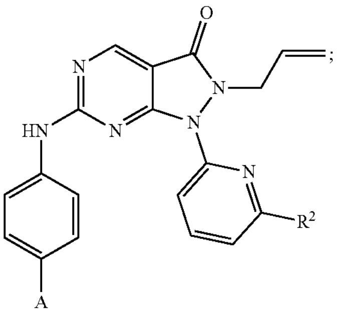

I method 2, comprising the following steps: step I, hydrolyzing compound 2A ($R^1$ is —(C═O)—O—$C_2H_5$) to obtain compound 2B ($R^1$ is —(C═O)—OH); step II, an condensation reaction is carried out between compound 2B and an amino compound in an organic solvent to obtain compound I ($R^1$ is —(C═O)—$NR^{1-5-1}R^{1-5-2}$);

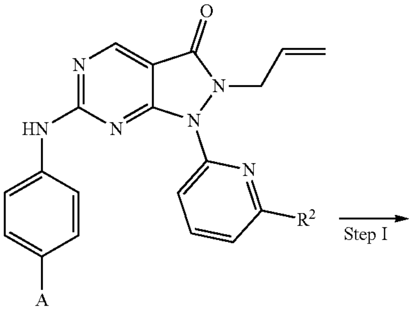

2A

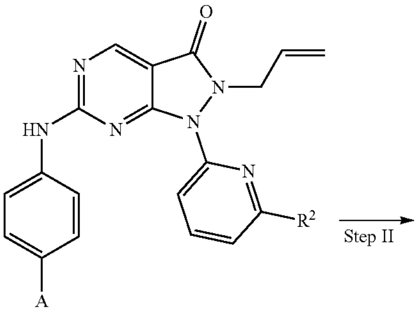

2B

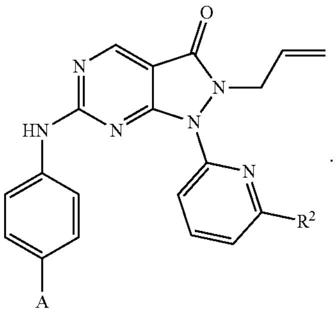

I

The conditions and steps of the reaction described in method 1 may be conventional conditions and steps in the art. The following reaction conditions are particularly preferred in the present disclosure:

Step 1, the organic solvent is preferably one or more of methanol, dichloromethane, acetonitrile, toluene and DMF, more preferably dichloromethane or toluene; the oxidant may be an oxidant commonly used in the art to oxidize thioether to sulfoxide, preferably m-chloroperoxybenzoic acid (m-CPBA); the molar ratio of compound 1A to m-CPBA is preferably 1:(1-1.2), the reaction time is preferably 1-12 hours, and the reaction temperature is preferably 0° C.-35° C.

Step 2, the organic solvent is preferably dichloromethane or toluene; the alkaline condition is preferably an organic base such as N,N-diisopropylethylamine (DIPEA) or triethylamine, more preferably N,N-diisopropylethylamine (DIPEA); the molar ratio of compound 1B, compound 1C and DIPEA is preferably 1:1:2, the reaction time is preferably 0-12 hours, and the reaction temperature is preferably 0° C.-35° C.

The conditions and steps of the reaction described in method 2 may be conventional conditions and steps in the art. The following reaction conditions are particularly preferred in the present disclosure:

Step 1, the hydrolysis reaction conditions are any suitable reaction conditions commonly used in the art, such as alkaline hydrolysis or acid hydrolysis, and alkaline hydrolysis is for example sodium hydroxide hydrolysis or lithium hydroxide hydrolysis.

Step 2, the amino compound may be a primary or secondary amine; the organic solvent is preferably dichloromethane or DMF; the condensation reaction is carried out under any suitable reaction conditions commonly used in the art, such as EDCI/HOBT/DIPEA or HATU/DIPEA.

The present disclosure also provides a compound represented by formula 1C:

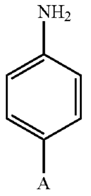

1C wherein, A is $C_3$-$C_{20}$ cycloalkyl substituted by one $R^1$, $R^1$ is —$NR^{1-3}R^{1-4}$ or —C(═O)$R^{1-5}$, and the $R^{1-3}$, $R^{1-4}$ and $R^{1-5}$ are defined as above.

In a certain scheme, the compound represented by formula 1C may be any of the following compounds:

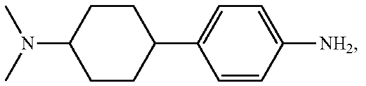

,

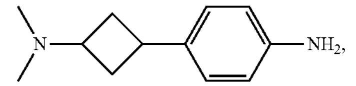

,

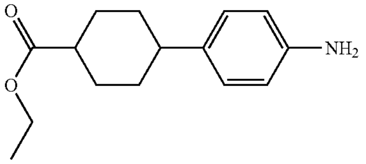

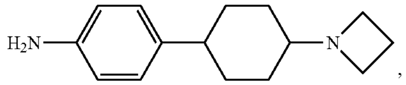

,

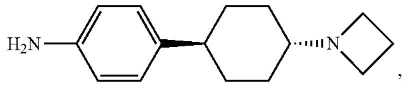

,

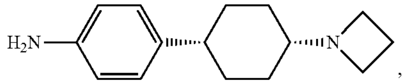

,

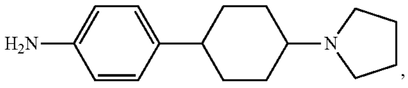

,

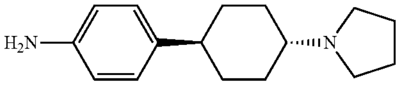

and

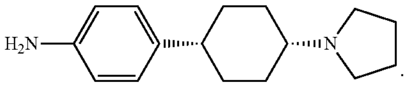

.

In a certain scheme, the compound represented by formula 1C may be any of the following compounds:

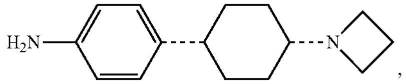

, its $^1$H NMR (400 MHz, $CDCl_3$) is δ 7.08-6.96 (m, 2H), 6.70-6.60 (m, 2H), 3.57 (s, 2H), 3.22 (t, J=7.0 Hz, 4H), 2.38 (tt, J=12.1, 3.2 Hz, 1H), 2.15-1.95 (m, 5H), 1.95-1.81 (m, 4H), 1.51-1.30 (m, 2H), 1.21-1.04 (m, 2H);

or,

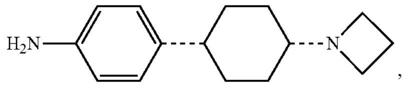

, its $^1$H NMR (400 MHz, MeOD) is δ 7.10-6.97 (m, 2H), 6.74-6.63 (m, 2H), 4.22-4.08 (t, J=8.0 Hz, 4H), 3.47-3.38 (m, 1H), 2.61-2.52 (m, 1H), 2.52-2.28 (m, 2H), 1.92-1.62 (m, 8H).

The present disclosure also provides a preparation method of the compound represented by formula 1C, which is any of the following methods:

method A: step I, protecting amino N of compound 1C1 in an organic solvent under alkaline condition to obtain compound 1C2; step II, a Suzuki reaction is carried out between compound 1C2 and compound 1C3 to obtain compound 1C4; step III, removing the ketal of compound 1C4 to obtain compound 1C5; step IV. a reductive amination reaction is carried out with compound 1C5 to obtain compound 1C6; step V, removing the amino protecting group PG of the compound 1C6 with a reducing agent and reducting the double bond simultaneously to obtain compound 1C;

Reaction formula 1

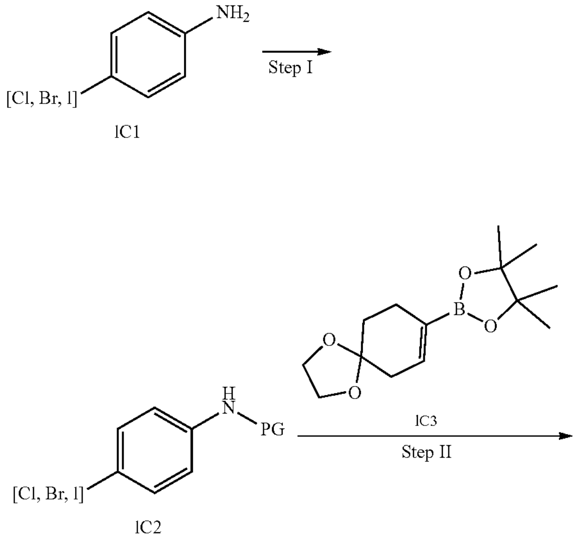

-continued

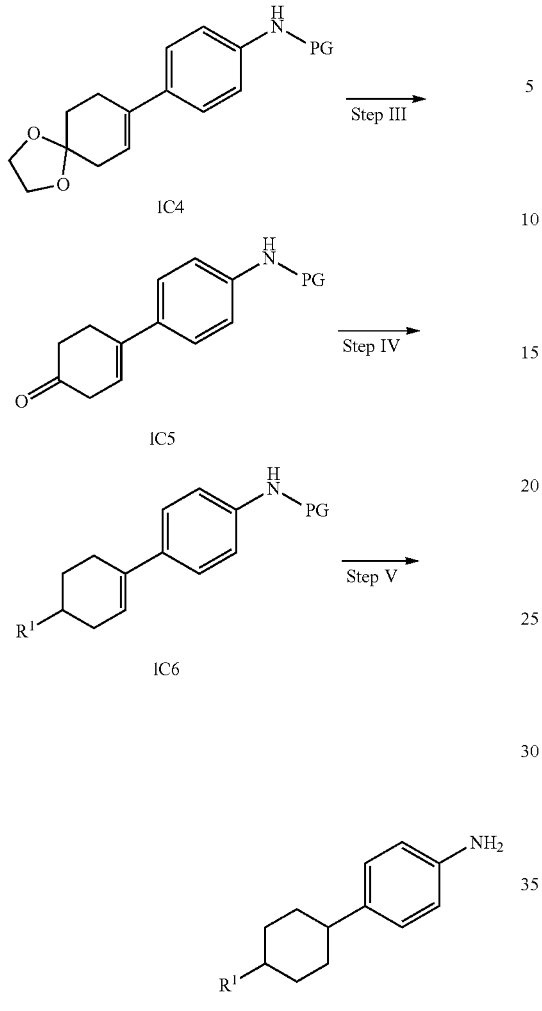

1C4

1C5

1C6

1C wherein, PG is an amino protecting group, R is $—NR^{1-3}R^{1-4}$, and $R^{1-3}$ and $R^{1-4}$ are defined as above;

method B, comprising the following steps: step I, a Suzuki reaction is carried out between compound 1C' and compound 1C2' to obtain compound 1C3'; step II, a reduction reaction is carried out with compound 1C' to obtain compound 1C;

Reaction formula 2

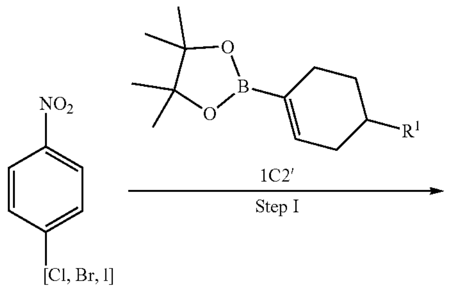

1C1′

-continued

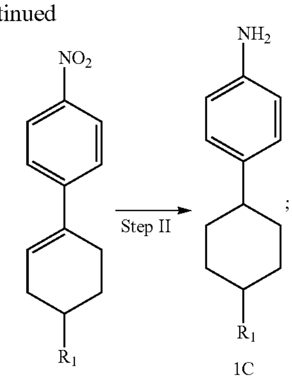

1C3′

1C wherein, $R^1$ is $—C(═O)R^{1-5}$, $R^{1-5}$ is defined as above;

method C, comprising the following steps: step I, a reductive amination reaction is carried out with compound 1C1" (ring A is oxo-$C_4$-$C_6$ cycloalkyl) to obtain compound 1C2" ($R^1$ is $—NR^{1-3}R^{1-4}$); step II, a Buchwald reaction is carried out between compound 1C2' and benzophenone imine to obtain compound 1C3' ($R^1$ is $—NR^{1-3}R^{1-4}$); step III, removing the diphenyl of compound 1C3" to obtain compound 1C;

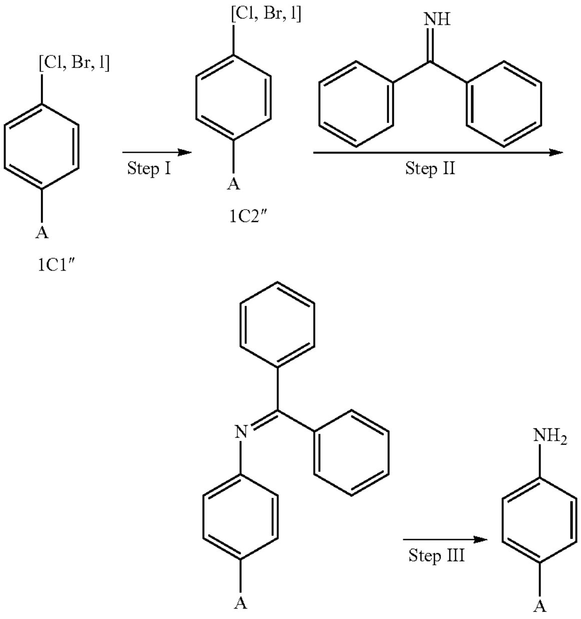

1C1″

1C2″

1C3″

1C wherein, A, $R^{1-3}$ and $R^{1-4}$ are defined as above.

The conditions and steps of the reaction described in method A may be conventional conditions and steps in the art. The following reaction conditions are particularly preferred in the present disclosure:

Step I, the amino protecting group PG may be any suitable amino protecting group commonly used in the art, preferably Cbz, which is intended to protect compound 1C1 from certain reactive groups (e.g., amino groups) on it when it is involved in the reaction. The compound 1C1 is preferably a bromide or an iodide.

Step II, the Suzuki reaction conditions are any suitable reaction conditions commonly used in the art. The Suzuki reaction conditions are preferably $Pd(Ph_3P)_4$ or $Pd(dppf)Cl_2$, potassium carbonate, 1,2-dimethoxyethane or dioxane.

Step III, the ketal removal conditions are any suitable reaction conditions commonly used in the art, the removal is preferably carried out using hydrochloric acid, and the reaction temperature is preferably 50° C.-100° C.

Step IV, the reductive amination reaction conditions are any suitable reaction conditions commonly used in the art, and the reducing agent is preferably sodium triacetoxyborohydride.

Step V, the conditions for removing the amino protection group PG with the reducing agent and simultaneously reducing the double bond can be the conventional conditions of the method in the art. The amino protecting group PG, such as benzyl or Cbz, preferably Cbz. The reducing agent is preferably palladium carbon/hydrogen.

The conditions and steps of the reaction described in method B may be conventional conditions and steps in the art. The following reaction conditions are particularly preferred in the present disclosure:

Step I, the Suzuki reaction conditions are any suitable reaction conditions commonly used in the art. The Suzuki reaction conditions are preferably $Pd(Ph_3P)_4$ or $Pd(dppf)Cl_2$, potassium carbonate, 1,2-dimethoxyethane or dioxane.

Step II, the reduction reaction conditions are any suitable reaction conditions commonly used in the art to reduce both nitro and double bonds, such as palladium carbon/hydrogen, palladium carbon/ammonium formate, palladium carbon/hydrazine hydrate.

The conditions and steps of the reaction described in method C may be conventional conditions and steps in the art. The following reaction conditions are particularly preferred in the present disclosure:

Step I, the reductive amination reaction conditions are any suitable reaction conditions commonly used in the art, and the reducing agent is preferably sodium triacetoxyborohydride.

Step II, the Buchwald reaction conditions are any suitable reaction conditions commonly used in the art. The Buchwald reaction conditions are preferably $Pd_2(dba)_3$/sodium tert-butoxide/Binap.

Step III. the reaction conditions for removing diphenyl are any suitable reaction conditions commonly used in the art, and the reaction conditions are preferably sodium acetate/hydroxylamine hydrochloride.

The present disclosure also provides an application of a substance X in the preparation of kinase inhibitors (such as WEE1 kinase);

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The present disclosure also provides an application of the substance X in the manufacture of a medicament;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The present disclosure also provides an application of the substance X in the manufacture of a medicament; the medicament is used for treating and/or preventing diseases related to WEE1 kinase;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The diseases related to WEE1 kinase such as cancer. The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

The present disclosure also provides an application of the substance X in the manufacture of a medicament; the medicament is used for treating and/or preventing cancer;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

The present disclosure also provides a method for treating and/or preventing diseases related to WEE1 kinase comprising administering a therapeutically effective amount of the substance X to a patient;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The diseases related to WEE1 kinase such as cancer. The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

The present disclosure also provides a method for treating and/or preventing cancer comprising administering a therapeutically effective amount of the substance X to a patient;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

The present disclosure also provides a pharmaceutical composition comprising the substance X and (one or more) pharmaceutical excipients;

the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The present disclosure also provides a combination comprising the substance X and an anticancer drug, the substance X is the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof.

The anticancer drugs may be a conventional anticancer drug in the art (but not substance X as described above), such as one or more of anticancer alkylating agents, anticancer metabolic antagonists, anticancer antibiotics, anticancer drugs derived from plant, anticancer platinum ligand compounds, anticancer camptothecin derivatives, anticancer tyrosine kinase inhibitors, monoclonal antibodies, interferons, biological response modifiers, mitoxantrone, L-asparaginase, procarbazine, dacarbazine, hydroxyurea, pentostatin, retinoic acid, alefacept, darbepoetin alfa, anastrozole, exemestane, bicalutamide, leuprolide, flutamide, fulvestrant, pegaptanib sodium, denileukin diftitox 2, aldesleukin, thyrotropina, arsenic trioxide, bortezomib, capecitabine and goserelin, for example, anticancer metabolic antagonists.

The anticancer alkylating agent may be a conventional anticancer alkylating agent in the art, such as one or more of mechlorethanmine N-oxide, cyclophosphamide, ifosfamide, melphalan, busulfan, dibromomannitol, carboquone, thiotepa, ranimustine, nimustine, temozolomide and carmustine.

The anticancer metabolic antagonist may be a conventional anticancer metabolic antagonist in the art, such as one or more of methotrexate, 6-mercaptopurine nucleoside, mercaptopurine, 5-fluorouracil, tegafur, doxifluridine, carmofur, cytarabine, cytarabine octadecyl sodium phosphate, enocitabine, S-1, gemcitabine, fludarabine and pemetrexed disodium, such as 5-fluorouracil.

The anticancer antibiotic may be a conventional anticancer antibiotic in the art, such as one or more of actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin.

The anticancer drug derived from plants may be a conventional anticancer drug derived from plants in the art, such as one or more of vincristine, vinblastine, vindesine, etoposide, sobuzoxane, docetaxel, paclitaxel and vinorelbine.

The anticancer platinum coordination compound may be a conventional anticancer platinum coordination compound in the art, such as one or more of cisplatin, carboplatin, nedaplatin and oxaliplatin.

The anticancer camptothecin derivative may be a conventional anticancer camptothecin derivative in the art, such as one or more of irinotecan, topotecan and camptothecin.

The anticancer tyrosine kinase inhibitor may be a conventional anticancer tyrosine kinase inhibitor in the art, such as one or more of gefitinib, imatinib and erlotinib.

The monoclonal antibody may be a conventional monoclonal antibody in the art, such as one or more of cetuximab, bevacizumab, rituximab, alemtuzumab and trastuzumab.

The interferon may be a conventional interferon in the art, such as one or more of interferon $\alpha$, interferon $\alpha$-2a, interferon $\alpha$-2b, interferon $\beta$, interferon $\gamma$-1a and interferon $\gamma$-n1.

The biological response regulator may be a conventional biological response regulator in the art, such as one or more of *coriolus versicolor* polysaccharide, lentinan, sizofiran, sapylin and ubenimex.

The components in the combination can be used simultaneously or separately (for example, sequentially); when the components in the combination are used simultaneously, the components in the combination can be uniformly mixed (e.g., the mixture of the components).

The components of the combination may be prepared as a single pharmaceutical composition for simultaneous use, or the components may be individually prepared as a single independent pharmaceutical composition (e.g., in kit form), which may be used simultaneously or separately (e.g., sequentially).

The present disclosure also provides an application of the above combination in the preparation of a medicament for preventing and/or treating cancer.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

In the application of the present disclosure, the above substance X and the above anticancer drugs can be administered simultaneously or separately (for example, sequentially).

The present disclosure also provides a method for treating and/or preventing cancer comprising administering a therapeutically effective amount of the above combination to a patient.

The anticancer drug can be as described above.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

The present disclosure also provides an application of the above substance X in the preparation of a medicament, the medicament in combination with an anticancer drug used for preventing and/or treating cancer.

The anticancer drug can be as described above.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

In the application of the present disclosure, the above substance X and the above anticancer drugs can be administered simultaneously or separately (for example, sequentially).

The present disclosure also provides an anticancer drug in the preparation of a medicament, the medicament in combination with the substance X used for preventing and/or treating cancer.

The anticancer drug can be as described above.

The cancers are for example brain cancer, head and neck cancer, esophageal cancer, thyroid cancer, small cell cancer, non-small cell cancer, breast cancer, lung cancer, stomach cancer, gallbladder-cholangiocarcinoma, liver cancer, pancreatic cancer, colon cancer, rectal cancer, ovarian cancer, choriocarcinoma, endometrial carcinoma, cervical cancer, renal pelvis-ureteral cancer, bladder cancer, prostate cancer, penile cancer, testicular cancer, embryonal carcinoma, nephroblastoma, skin cancer, malignant melanoma, neuroblastoma, osteosarcoma, ewing tumor, soft tissue tumor, acute leukemia, chronic lymphatic leukemia, chronic myeloid leukemia or Hodgkin's lymphoma, for example, breast cancer, lung cancer, pancreatic cancer, colon cancer, ovarian cancer, acute leukemia, chronic lymphatic leukemia, chronic myeloid leukemia, Hodgkin's lymphoma, for example, colon or ovarian cancer.

In the application of the present disclosure, the above substance X and the above anticancer drugs can be administered simultaneously or separately (for example, sequentially).

The present disclosure also provides a pharmaceutical composition comprising the above combination and (one or more) pharmaceutical excipients.

The pharmaceutical composition can be composed of the combination and the pharmaceutical excipients.

The present disclosure also provides a combination drug kit comprising a pharmaceutical composition A and a pharmaceutical composition B;

the pharmaceutical composition A comprises the above substance X, and (one or more) pharmaceutical excipients;

the pharmaceutical composition B comprises the anticancer drugs and one or more pharmaceutical excipients.

The anticancer drug can be as described above.

The combination drug kit can be composed of the pharmaceutical composition A and the pharmaceutical composition B.

The pharmaceutical composition A can be composed of the substance X, and (one or more) pharmaceutical excipients;

the pharmaceutical composition B can be composed of the anticancer drugs and one or more pharmaceutical excipients.

Each pharmaceutical composition in the combination drug kit can be used simultaneously or separately (for example, sequentially).

Unless otherwise specified, the following terms appearing in the present specification and claims have the following meanings:

The term "pharmaceutically acceptable" means that salts, solvents, excipients, etc. are generally nontoxic, safe and suitable for patient use. The "patient" is preferably a mammal, more preferably a human.

The term "pharmaceutically acceptable salt" refers to the salt prepared by the compound of the present disclosure and a relatively nontoxic and pharmaceutically acceptable acid or base. When the compound of the present disclosure contains a relatively acidic functional group, a base addition salt can be obtained by bringing the neutral form of the compound into contact with a sufficient amount of a pharmaceutically acceptable base in a pure solution or a suitable inert solvent. The pharmaceutically acceptable base addition salts include, but are not limited to, lithium salts, sodium salts, potassium salts, calcium salts, aluminum salts, magnesium salts, zinc salts, bismuth salts, ammonium salts, and diethanolamine salts. When the compound of the present disclosure contains a relatively basic functional group, an acid addition salt can be obtained by bringing the neutral form of the compound into contact with a sufficient amount of a pharmaceutically acceptable acid in a pure solution or a suitable inert solvent. The pharmaceutically acceptable acids include inorganic acids, the inorganic acids include but are not limited to hydrochloric acid, hydrobromic acid, hydroiodic acid, nitric acid, carbonic acid, phosphoric acid, phosphorous acid, sulfuric acid, etc. The pharmaceutically acceptable acids include organic acids, the organic acids including but not limited to: acetic acid, propionic acid, oxalic acid, isobutyric acid, maleic acid, malonic acid, benzoic acid, succinic acid, octanedioic acid, trans-butenedioic acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, hydrogen tartrate, ascorbic acid, gentianic acid, fumaric acid, gluconic acid, saccharic acid, formic acid, ethanesulfonic acid, pamoic acid (i.e., 4,4'-methylene-bis(3-hydroxy-2-naphthoic acid)), amino acid (e.g., glutamic acid, arginine), etc. When the compounds of the present disclosure contain relatively acidic and basic functional groups, they can be converted into base addition salts or acid addition salts. See Berge et al., "Pharmaceutical Salts", Journal of Pharmaceutical Science 66: 1-19 (1977) or Handbook of Pharmaceutical Salts: Properties, Selection, and Use (P. Heinrich Stahl and Camille G. Wermuth, ed., Wiley-VCH, 2002).

The term "solvate" refers to a substance formed by together a compound of the present disclosure with a stoichiometric or non-stoichiometric solvent. Solvent molecules in solvates can exist in the form of ordered or unordered arrangement. The solvents include but are not limited to: water, methanol, ethanol, etc.

The terms "pharmaceutically acceptable salts" and "solvates" in the terms "solvates of pharmaceutically acceptable salts", as described above, refer to compound of the present disclosure, 1. prepared with a relatively nontoxic, pharmaceutically acceptable acid or base, and 2. formed in combination with a stoichiometric or non-stoichiometric solvent. The "solvates of pharmaceutically acceptable salts" include but are not limited to hydrochloric acid monohydrate of the compound of the present disclosure.

The terms "compound", "pharmaceutically acceptable salt", "solvate" and "solvate of pharmaceutically acceptable salt" can exist in crystalline or amorphous form. The term "crystalline" means that the ions or molecules in it are arranged in a defined way in a three-dimensional space in a strictly periodic manner, and have a regular pattern of periodic recurrence at a certain distance apart; because of the above periodic arrangement, there can be a variety of crystalline forms, that is, the phenomenon of polycrystalline forms. The term "amorphous" refers to the disordered distribution of ions or molecules, that is, there is no periodic arrangement between ions and molecules.

The terms "compound", "pharmaceutically acceptable salt", "solvate" and "solvate of pharmaceutically acceptable salt" may exist in the form of a single stereoisomer or a mixture thereof (e.g. racemate), if stereoisomers exist. The term "stereoisomer" refers to cis-trans isomer or optical isomer. These stereoisomers can be separated, purified and enriched by asymmetric synthesis or chiral separation methods (including but not limited to thin layer chromatography, rotary chromatography, column chromatography, gas chromatography, high pressure liquid chromatography, etc.), and can also be obtained by chiral resolution by bonding (chemical bonding, etc.) or salting (physical bonding, etc.) with other chiral compounds. The term "single stereoisomer" means that one stereoisomer of a compound of the present disclosure is not less than 95% by mass relative to all stereoisomers of the compound.

The terms "compound", "pharmaceutically acceptable salt", "solvate" and "solvate of pharmaceutically acceptable salt" may exist in the form of single tautomer or a mixture thereof, preferably in the form in which the more stable tautomer is predominant.

The terms "compound", "pharmaceutically acceptable salt", "solvate" and "solvate of pharmaceutically acceptable salt" can exist in their natural abundance or unnatural abundance. Taking hydrogen atom as an example, its natural abundance form means that about 99.985% is protium and about 0.015% is deuterium; in the form of unnatural abundance, for example, about 95% of which is deuterium. That is, one or more atoms in the terms "compound", "pharmaceutically acceptable salt", "solvate" and "solvate of pharmaceutically acceptable salt" may be atoms that exist in unnatural abundance.

When an arbitrary variable (e.g. $R^{1-1-1}$) occurs many times in the definition of a compound, the definition of each position of the variable is independent of the definition of the rest, and their meanings are independent of each other and do not affect each other. Therefore, if a certain group is substituted by one, two or three $R^{1-1-1}$ groups, that is to say, the group may be substituted by up to three $R^{1-1-1}$ groups, the definition of $R^{1-1-1}$ at this position is independent from that of the $R^{1-1-1}$. In addition, the combination of substituents and/or variables is allowed only when the combination produces a stable compound.

The term "optionally substituted" means that it may or may not be substituted.

The term "halogen" refers to fluorine, chlorine, bromine or iodine.

The term "alkyl" refers to a saturated linear or branched monovalent hydrocarbon group having one to twelve carbon atoms (e.g. $C_1$-$C_6$ alkyl, e.g. $C_1$-$C_4$ alkyl). Examples of alkyl include, but are not limited to, methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, and 1-octyl.

The term "alkenyl" refers to a linear or branched monovalent hydrocarbon group having two to twelve carbon atoms with at least one unsaturated position, i.e., a carbon-carbon $sp^2$ double bond (e.g. $C_2$-$C_6$ alkenyl, e.g. $C_2$-$C_4$ alkenyl), and includes groups with "cis" and "trans" orientations or "E" and "Z" orientations. Examples include, but are not limited to, vinyl, allyl.

The term "alkynyl" refers to a linear or branched monovalent hydrocarbon group having two to twelve carbon atoms with at least one unsaturated position, i.e., a carbon-carbon sp triple bond (e.g. $C_2$-$C_6$ alkynyl, e.g. $C_2$-$C_4$ alkynyl). Examples include, but are not limited to, ethynyl and propynyl.

The term "cycloalkyl" refers to a saturated or partially unsaturated (containing one or two double bonds) non-aromatic cyclic hydrocarbon group (e.g. $C_3$-$C_6$ cycloalkyl) with three to twenty carbon atoms, including monocyclic cycloalkyl and polycyclic cycloalkyl. The cycloalkyl group contains 3 to 20 carbon atoms, preferably 3 to 12 carbon atoms, more preferably 3 to 6 carbon atoms.

Examples of monocyclic cycloalkyl include, but are not limited to, cyclopropyl, cyclobutyl, cyclopentyl, cyclohexyl, cycloheptyl, cyclooctyl, cyclononyl, cyclodecyl, cycloundecyl, cyclododecyl, 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

Polycyclic cycloalkyl are polycyclic (e.g., bicyclic and tricyclic) cycloalkyl structures, including spiro cycloalkyl, fused cycloalkyl and bridged cycloalkyl. Wherein, "spiro cycloalkyl" refers to a polycyclic group sharing one carbon atom (called spiro atom) between the single rings of 5 to 20 membered, which may contain one or more double bonds, but none of the rings has a fully conjugated 1 L electron system. Preferably 6 to 14 membered, more preferably 7 to 10 membered. According to the number of spiro cycloalkyl shared between rings, the spiro cycloalkyl is divided into monospiro cycloalkyl, bisspiro cycloalkyl or polyspiro cycloalkyl, preferably monospiro cycloalkyl and bisspiro cycloalkyl. More preferably 4 membered/4 membered, 4 membered/5 membered, 4 membered/6 membered, 5 membered/5 membered or 5 membered/6-membered monospiro cycloalkyl. Examples of spiro cycloalkyl include, but are not limited to:

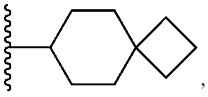, 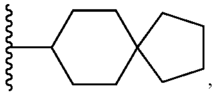, 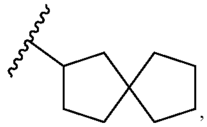, 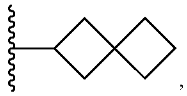, 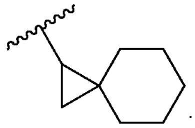.

Wherein, "fused cycloalkyl" refers to all-carbon polycyclic groups of 5 to 20 membered, each ring in the system sharing an adjacent pair of carbon atoms with other rings in the system, which may contain one or more double bonds, but none of the rings has a fully conjugated 7-electron system. Preferably 6 to 14 membered, more preferably 7 to 10 membered. According to the number of constituent rings, it can be divided into bicyclic, tricyclic, tetracyclic or polycyclic fused cycloalkyl, preferably bicyclic or tricyclic, more preferably 5-membered/5-membered or 5-membered/6-membered bicyclic cycloalkyl. Examples of fused cycloalkyl include, but are not limited to:

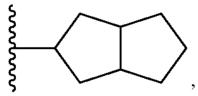, 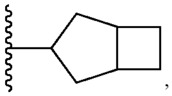, 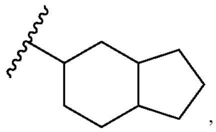, 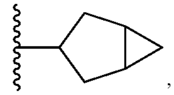, 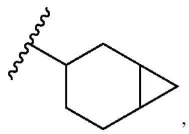, 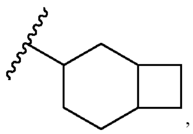, 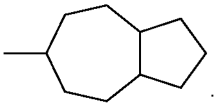.

"Bridged cycloalkyl" refers to all-carbon polycyclic group of 5 to 20 members, any two rings share two non-directly connected carbon atoms, which may contain one or more double bonds, but none of which has a completely conjugated π-electron system. Preferably 6 to 14 membered, more preferably 7 to 10 membered. According to the number of constituent rings, it can be divided into bicyclic, tricyclic, tetracyclic or polycyclic bridged cycloalkyl, preferably bicyclic, tricyclic or tetracyclic, more preferably bicyclic or tricyclic. Examples of bridged cycloalkyl include, but are not limited to:

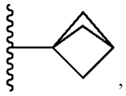, 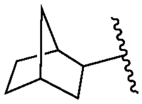, 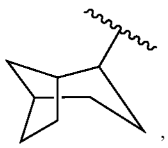, 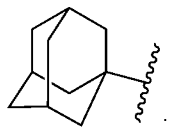.

The term "heterocycloalkyl" refers to a saturated carbocyclic group having 3 to 20 ring atoms, wherein at least one ring atom is a heteroatom independently selected from boron, silicon, oxygen, sulfur, selenium, nitrogen and phosphorus, and the remaining ring atoms are C. The group may be a carbon group or a heteroatom group (i.e. it may be C-linked or N-linked, as long as it is possible). Examples of heterocyclic groups include, but are not limited to, pyrrolidinyl, tetrahydrofuran, tetrahydrothiophene, tetrahydropyranyl, tetrahydrothiopyranyl, piperidinyl, morpholinyl, 4-thiomorpholinyl, thioalkyl and piperazinyl. Fused ring portion, spiro ring portion and bridge ring portion are also included in the scope of this definition. For example, the group derived from tetrahydropyrrole can be tetrahydropyrrol-1-yl (N-linked) or tetrahydropyrrol-3-yl (C-linked). For example a 3-7 membered monocyclic ring (1-6 carbon atoms and 1-3 heteroatoms selected from N, O, P, B, Si, S and Se, where N, B, P or Se is optionally substituted by one or more oxygen atoms to obtain groups like NO, BOH, PO, $PO_2$, SeO; N can be optionally quaternized; S atoms can be optionally substituted by one or more oxygen or nitrogen atoms to obtain a group like SO, $SO_2$, $S(=O)(=NR^a)$, $S(=NR^b)$ or $S(=NR^c)_2$, while $R^a$, $R^b$ and $R^c$ are independently cyano, $C_1$-$C_7$ alkyl, $C_3$-$C_{14}$ cycloalkyl, "$C_3$-$C_{14}$ heterocycloalkyl having 1-4 heteroatoms and one or more heteroatoms of boron, silicon, oxygen, sulfur, selenium, nitrogen and phosphorus", "$C_1$-$C_7$ heteroaryl having 1-4 heteroatoms and one or more heteroatoms of boron, silicon, oxygen, sulfur, selenium, nitrogen and phosphorus", $C_6$-$C_{10}$ aryl or $C_1$-$C_7$ alkoxy; meanwhile, the —$CH_2$— group may be optionally substituted by —C(=O)—, —C(=S)— or —$C(=NR^d)$—, $R^d$ is independently cyano, $C_1$-$C_7$ alkyl, $C_3$-$C_{14}$ cycloalkyl, "$C_3$-$C_{14}$ heterocycloalkyl having 1-4 heteroatoms and one or more heteroatoms of boron, silicon, oxygen, sulfur, selenium, nitrogen and phosphorus", "$C_1$-$C_7$ heteroaryl having 1-4 heteroatoms and one or more heteroatoms of boron, silicon, oxygen, sulfur, selenium, nitrogen and phosphorus", $C_6$-$C_{10}$ aryl or $C_1$-$C_7$ alkoxy; when the ring is a 3-membered ring, only one heteroatom is present in the ring), or, a bicyclic ring consisting of 7 to 10 atoms (4 to 9 carbon atoms and 1-3 heteroatoms selected from N, O, P, B, Si, S, wherein N, S, B or P is optionally substituted by one or more oxygen atoms to obtain groups like NO, BOH, SO, $SO_2$, PO, $PO_2$, SeO, while —$CH_2$— group may be optionally substituted by —C(=O)—). Depending on the structure, the heterocyclyl can be a monovalent group or a divalent group, i.e., a subheterocyclyl.

The term "aryl" refers to any stable monocyclic or bicyclic carbon ring with up to 10 atoms in each ring, wherein at least one of which is an aromatic ring. Examples of the above aryl units include phenyl, naphthyl, tetrahydronaphthyl, 2,3-dihydroindenyl, biphenyl, phenanthrenyl, anthryl or acenaphthyl. It will be understood that in the case where the aryl substituent is a bicyclic substituent and one of the rings is a non-aromatic ring the connection is made through the aromatic ring.

The term "heteroaryl" refers to a stable monocyclic or bicyclic ring with up to 7 atoms in each ring, wherein at least one ring is an aromatic ring and contains 1-4 heteroatoms selected from boron, silicon, oxygen, sulfur, selenium, nitrogen and phosphorus. Heteroaryl within this definition include, but are not limited to: acridinyl, carbazolyl, cinnolinyl, quinoxalinyl, pyrazolyl, indolyl, benzotriazolyl, furanyl, thienyl, benzothienyl, benzofuranyl, quinolyl, isoquinolyl, oxazolyl, isoxazolyl, indolyl, pyrazinyl, pyridazinyl, pyridyl, pyrimidinyl, pyrimidinyl, pyrrolyl, tetrahydroquinolyl. "Heteroaryl" should also be understood to include any N-oxide derivative of a nitrogen-containing heteroaryl. In the case wherein the heteroaryl substituent is a bicyclic substituent and one ring is a non-aromatic ring or does not contain heteroatoms, it can be understood that the connections are made through aromatic rings respectively. Heteroaromatic ring-fused aromatic ring and bicyclic heteroaromatic ring systems can be fused to form rings. Wherein, N, S, B, P or Se is optionally substituted by one or more oxygen atoms to obtain groups like NO, SO, $SO_2$, BOH, PO, $PO_2$, SeO, and the N atom can be quaternized. Heteroaryl can be attached to the main structure at any heteroatom or carbon atom to form stable compounds. Depending on the structure, heteroaryl can be monovalent groups or divalent groups, i.e., heteroarylene.

The term "alkoxy" refers to an alkyl linked by an oxygen bridge; the alkyl is defined as above.

The term "alkylthiol" refers to an alkyl linked by a sulfur bridge; the alkyl is defined as above.

The term "indeterminate of cis-trans conformation" refers to cis or trans.

The term "component" refers to each component of the combination of the present disclosure, i.e., the compound represented by formula I (or the compound represented by formula II), the pharmaceutically acceptable salt thereof, the solvate thereof, the solvate of the pharmaceutically acceptable salt thereof, the metabolite thereof or the prodrug thereof, or the anticancer drug.

The term "pharmaceutical excipients" refers to excipients and additives used in drug production and prescription formulation, and refers to all substances contained in pharmaceutical preparations except active ingredients. See the Pharmacopoeia of the People's Republic of China (2015 Edition) Part IV or Handbook of Pharmaceutical Excipients (Raymond C Rowe, 2009 Sixth Edition).

The term "treatment" refers to therapeutic therapy. When referring to a specific condition, treatment means (1) alleviating one or more biological manifestations of the disease or condition, (2) interfering with (a) one or more points in the biological cascade causing or contributing to the condition or (b) one or more biological manifestations of the condition, (3) ameliorating one or more symptoms, effects, or side effects associated with the condition or its treatment, or one or more symptoms, effects, or side effects, or (4) slowing the development of the condition or one or more biological manifestations of the condition.

The term "prevention" refers to a reduction in the risk of acquiring or developing diseases or disorders.

The term "therapeutically effective amount" refers to the amount of a compound that is sufficient to effectively treat the diseases or disorders described herein when administered to a patient. The "therapeutically effective amount" will vary according to the compound, the condition and its severity, and the age of the patient to be treated, but it can be adjusted by those skilled in the art as needed.

The term "patient" refers to any animal, preferably a mammal, preferably a human, to which the compound or composition is to be administered or has been administered according to an embodiment of the present disclosure. The term "mammal" includes any mammal. Examples of mammals include, but are not limited to, cattle, horses, sheep, pigs, cats, dogs, mice, rats, rabbits, guinea pigs, monkeys, humans, etc., with humans being the most preferred.

The term "active ingredient" refers to the active ingredient in the pharmaceutical composition or combination kit of the present disclosure, i.e., the compound represented by formula I (or the compound represented by formula II), the pharmaceutically acceptable salt thereof, the solvate thereof, the solvate of the pharmaceutically acceptable salt thereof, the metabolite thereof or the prodrug thereof, the anticancer drug, or a combination thereof.

On the basis of not violating the common sense in the field, the above preferred conditions can be arbitrarily combined to obtain the preferred embodiments of the present disclosure.

The reagents and raw materials used in the present disclosure are commercially available.

The positive progressive effect of the present disclosure is that: the compounds of the present disclosure have better inhibitory activity against WEE1 kinase and have better bioavailability.

The present disclosure will be further illustrated by way of embodiments below, but it is not limited to the scope of the embodiments. The experimental methods not specified in the specific conditions in the following embodiments are selected according to the conventional methods and conditions, or according to the commodity specifications.

The structures of all compounds of the present disclosure can be identified by nuclear magnetic resonance ($^1$HNMR) and/or mass spectrometry (MS).

$^1$H NMR chemical shift (6) was recorded in PPM ($10^{-6}$). NMR was performed by Bruker AVANCE-400 spectrometer.

LC-MS was determined by Agilent 1200HPLC/6120 mass spectrometer.

HPLC was determined by Agilent 1260 high performance liquid chromatograph. Specific conditions of HPLC: mobile phase A: water (0.1% formic acid), mobile phase B: acetonitrile; column time: 15 min; column type: Waters' Xselect, 5 μm, 4.6×250 mm.

The thin layer silica gel plate was Liangchen silicon source HSGF254 or Qingdao GF254 silica gel plate. Column chromatography generally uses Yantai Huanghai 200-300 mesh silica gel as carrier.

Embodiment 1

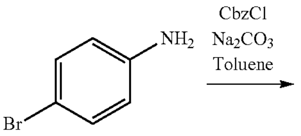

I-1-a

-continued

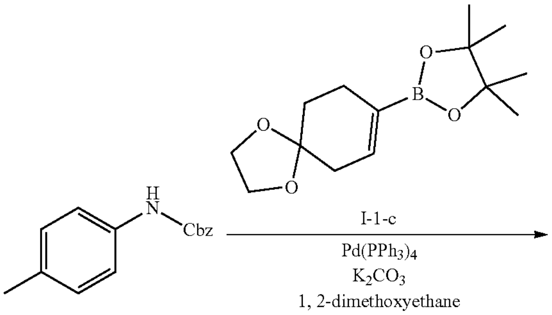

I-1-b

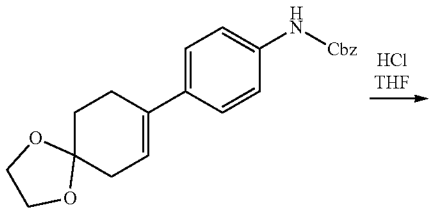

I-1-d

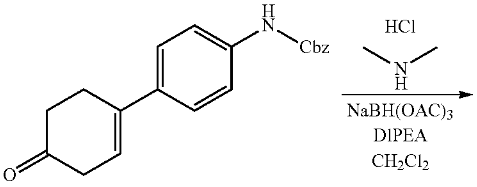

I-1-e

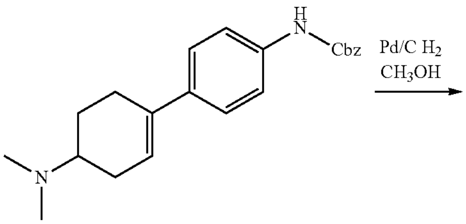

I-1-f

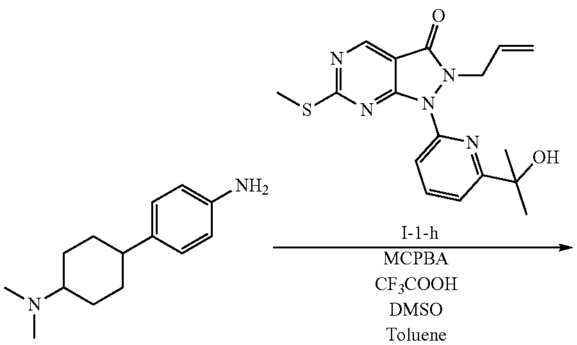

I-1-g

-continued

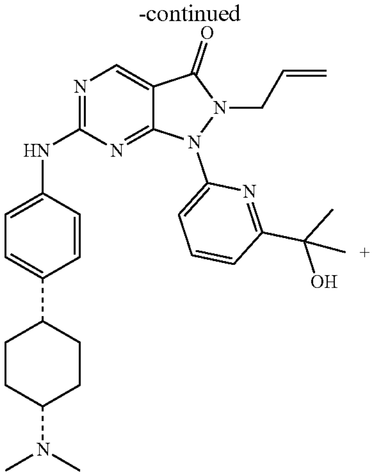

I-1-1

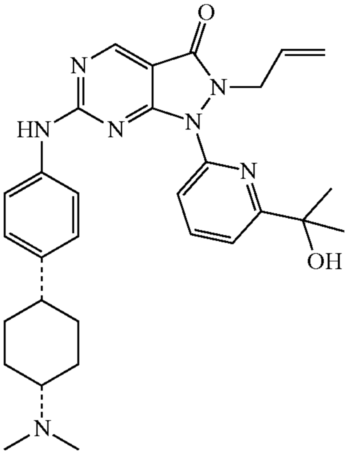

I-1-2

Step 1:

4-Bromoaniline (I-1-a) (58.1 mmol) was dissolved in toluene (250 mL); potassium carbonate (87.2 mmol) and benzyl chloroformate (87.2 mmol) were added to the reaction mixture, and the reaction mixture was stirred at room temperature for 16 hours. The reaction mixture was filtered, the filtrate was evaporated to dryness to obtain a crude product, and the crude product was washed with ethyl acetate to obtain the target compound benzyl (4-bromophenyl)carbamate (I-1-b)(15.2 g, 85.4%) as a gray solid. LC-MS: m/z: $(M+H)^+$=307.0.

Step 2:

Benzyl (4-bromophenyl)carbamate (16.0 mmol) (I-1-b) was dissolved in 1,2-dimethoxyethane (50 mL); and 4,4,5,5-tetramethyl-2-(1,4-dioxaspiro[4.5]dec-7-en-8-yl)-1,3,2-dioxaborolane (represented by formula I-1-c) (16.0 mmol), sodium carbonate (42.0 mmol) and tetrakis(triphenylphosphine)palladium (1.6 mmol) were added to the reaction mixture, the reaction mixture was heated to 80° C. and stirred for 16 hours. The reaction mixture was filtered, the filtrate was evaporated to dryness to obtain a crude product, and the crude product was purified by column chromatography (dichloromethane/methanol=100/0-95/5) to obtain the target compound benzyl (4-(1,4-dioxaspiro[4.5]dec-7-en-8-yl)phenyl)carbamate (I-1-d) (5.6 g, 94%) as a white solid. LC-MS: m/z: $(M+H)^+$=366.2.

Step 3:

Benzyl (4-(1,4-dioxaspiro[4.5]dec-7-en-8-yl)phenyl)carbamate (I-1-d) (15 mmol) was dissolved in tetrahydrofuran (15 mL). Hydrochloric acid (30.0 mL, 4N) was added to the reaction mixture, and the reaction mixture was stirred at 50° C. for 16 hours. The pH value of the reaction mixture was adjusted to 9 with potassium carbonate, then the mixture was extracted with dichloromethane, the organic phase was washed with saturated saline, dried over anhydrous sodium sulfate, filtered and evaporated to dryness to obtain the crude target compound benzyl (4'-oxo-2',3',4',5'-tetrahydro-[1,1'-biphenyl]-4-yl)carbamate (I-1-e) (4.0 g, 81%) as a yellow solid. LC-MS: m/z: $(M+H)^+$=322.1.

Step 4:

Benzyl (4'-oxo-2',3',4',5'-tetrahydro-[1,1'-biphenyl]-4-yl) carbamate (I-1-e) (12.0 mmol) was dissolved in dichloromethane (25 mL), dimethylamine hydrochloride (25.0 mmol) and diisopropylethylamine (25.0 mmol) were added to the reaction mixture, and the reaction mixture was stirred at room temperature for 2 hours, and sodium triacetoxyborohydride (37.0 mmol) was added to the reaction mixture, then the reaction mixture was stirred at room temperature for 16 hours. The pH value of the mixture was adjusted to 9 by adding saturated potassium carbonate aqueous solution, and the mixture was extracted with dichloromethane; then the organic phase was washed with saturated saline, dried over anhydrous sodium sulfate, filtered and evaporated to dryness to obtain a crude product, and the crude product was purified by column chromatography (dichloromethane/methanol=100/0-95/5) to obtain the target compound benzyl (4'-(dimethylamino)-2',3',4',5'-tetrahydro-[1,1'-biphenyl]-4-yl) carbamate (I-1-f) (3.5 g, 80%) as a yellow solid. LC-MS: m/z: $(M+H)^+$=351.2.

Step 5:

Benzyl (4'-(dimethylamino)-2',3',4',5'-tetrahydro-[1,1'-biphenyl]-4-yl)carbamate (I-1-f) (10.0 mmol) was dissolved in methanol (20 mL), palladium carbon (0.35 g) was added thereto, and the reaction mixture was stirred under hydrogen at room temperature for 16 hours. The reaction mixture was filtered, and the filtrate was evaporated to dryness to obtain a crude product, the crude product was washed with ethyl acetate and filtered, and the filter cake was the target compound 4-(4-(dimethylamino)cyclohexyl)aniline (I-1-g) (1.20 g, 55%) as a white solid. LC-MS: m/z: $(M+H)^+$=219.2.

Step 6:

2-(1,1-Difluoroallyl)-1-(6-(2-hydroxypropan-2-yl)pyridin-2-yl)-6-((4-(4-methylpiperazin-1-yl)phenyl)amino)-1,2-dihydro-3H-pyrazolo[3,4-d]pyrimidin-3-one (represented by formula I-1-h) (150 mg, 0.42 mmol) was dissolved in toluene (20 mL), 3-chlorophenoxyformic acid (105 mg, 0.47 mmol) was added thereto, and the reaction mixture was stirred at room temperature for 0.5 hours, then the reaction mixture was evaporated to dryness, the obtained sulfoxide intermediate was dissolved in dimethyl sulfoxide (10 mL); 4-(4-methylpiperazin-1-yl)aniline (120 mg, 0.55 mmol) and trifluoroacetic acid (0.2 mL) were added thereto, and the reaction mixture was heated to 60° C. and stirred for 24 hours. The pH value of the reaction mixture was adjusted to 9 with saturated sodium carbonate solution, water (50 mL) and dichloromethane (50 mL) were added thereto, the phases were separated, and the organic phase was washed with saturated saline, dried over anhydrous sodium sulfate, filtered, evaporated to dryness, prepared and purified in liquid phase to obtain compound I-1-1 and compound I-1-2. Compound I-1-1: HPLC retention time (RT)=10.55 min (HPLC conditions: gradient elution, 5% mobile phase B→50% mobile phase B), the yield of the compound was 56% (110 mg) as a white solid: $^1$H NMR (400 MHz, MeOD) δ 8.85 (s, 1H), 8.46 (s, 2H), 7.99 (t, J=7.9 Hz, 1H), 7.79 (d, J=8.0 Hz, 1H), 7.65 (dd, J=16.6, 8.1 Hz, 3H), 7.22 (d, J=8.6 Hz, 2H), 5.73 (ddt, J=16.3, 10.2, 6.1 Hz, 1H), 5.05 (dd, J=10.3, 1.1 Hz, 1H), 4.93 (dd, J=17.1, 1.3 Hz, 1H), 4.82 (d, J=6.1 Hz, 2H), 2.90 (s, 6H), 2.60 (d, J=8.4 Hz, 1H), 2.21 (s, 2H), 2.10 (d, J=10.6 Hz, 2H), 1.70 (d, J=11.4 Hz, 4H), 1.59 (s, 6H). LC-MS: m/z: $(M+H)^+$=528.3. Compound I-1-2: HPLC retention time (RT)=10.78 min (HPLC conditions: gradient elution, 5% mobile phase B→50% mobile phase B), the yield of the compound was 72% (160 mg) as a white solid: $^1$H NMR (400 MHz, $CDCl_3$) δ 8.86 (s, 1H), 8.54 (s, 1H), 7.95 (t, J=7.9 Hz, 1H), 7.75 (d, J=8.0 Hz, 1H), 7.59 (d, J=8.5 Hz, 2H), 7.43 (d, J=7.6 Hz, 1H), 7.32 (d, J=8.5 Hz, 2H), 5.72 (ddt, J=16.5, 10.3, 6.2 Hz, 1H), 5.06 (d, J=10.2 Hz, 1H), 4.95 (dd, J=17.1, 1.0 Hz, 1H), 4.75 (d, J=6.1 Hz, 2H), 3.05 (m, 1H), 2.93 (m, 1H), 2.68 (s, 6H), 2.32 (m, 2H), 1.84 (m, 6H), 1.60 (s, 6H). LC-MS: m/z: $(M+H)^+$=528.3.

Embodiment 3

1-3

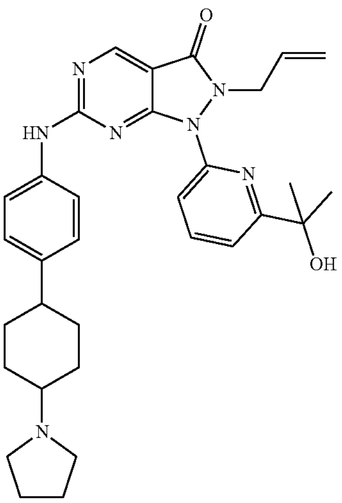

1-3-1

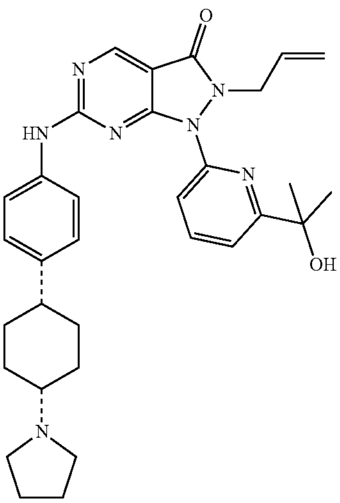

-continued

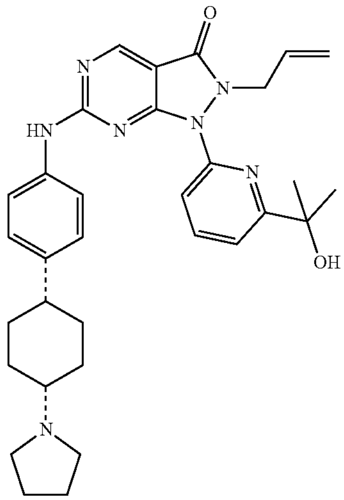

I-3-2

Compound (I-3-1) and compound (I-3-2) can be synthesized by the same method as in embodiment 1 using cyclopentane as a raw material. The details were as follows:

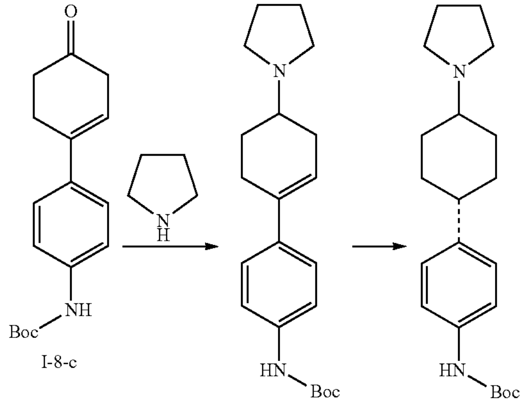

I-8-c

I-3-a

I-3-1-b

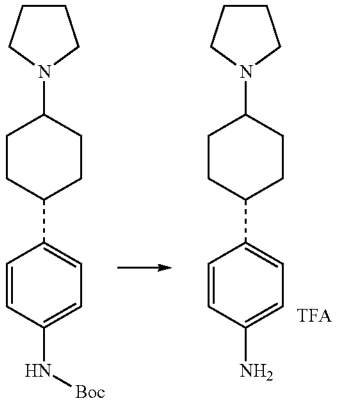

I-3-2-b

I-3-2-c

-continued

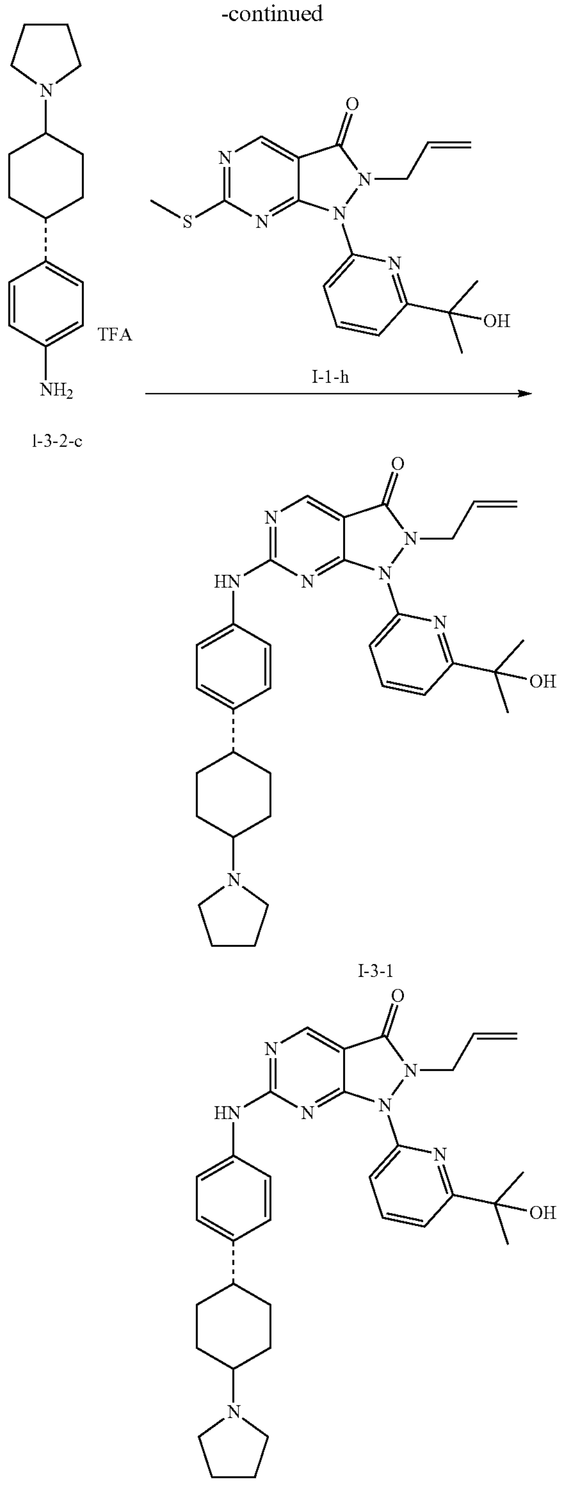

I-3-2-c

I-1-h

I-3-1

I-3-2

Step 1:

Sodium borohydride acetate (0.85 g, 4 mmol) was added to a mixture of tert-butyl (4'-oxo-2',3',4',5'-tetrahydro-[1,1'-biphenyl]-4-yl)carbamate (0.46 g, 1.6 mmol) (I-8-c) and tetrahydropyrrole (0.28 g, 3.9 mmol) in 20 mL of dichloromethane, and the mixture was stirred overnight at room temperature; the reaction mixture was washed with saturated sodium carbonate aqueous solution (20 mL), water (2*10 mL) and saturated saline sequentially; the organic phase was dried over anhydrous sodium sulfate, and the residue was mixed with silica gel and passed through a column {7M ammonia methanol: (dichloromethane:ethyl acetate=12:2)=0-15%} to obtain compound I-3-a, 200 mg of white solid. The yield was 40%. LC-MS: m/z: $(M+H)^+$=343.

Step 2:

Tert-butyl (4'-(pyrrolidin-1-yl)-2',3',4',5'-tetrahydro-[1,1'-biphenyl]-4-yl)carbamate (300 mg, 0.87 mmol) (I-3-a) and 10% palladium carbon (100 mg) were added to 30 mL of methanol, the reaction flask was ventilated three times with a hydrogen balloon, and the reaction mixture was stirred overnight at room temperature in a hydrogen atmosphere. The reaction mixture was filtered and evaporated to dryness to obtain a crude product, which was separated by thin layer chromatography silica gel plate {7M ammonia methanol: (dichloromethane:ethyl acetate=9:3)=1:12} to obtain compound I-3-2-b, 70 mg of white solid (Rf=0.7), and compound I-3-1-b, 90 mg of white solid (Rf=0.5). The total yield was 52%. LC-MS: m/z: $(M+H)^+$=345.

Step 3:

Tert-butyl (4-(4-(pyrrolidin-1-yl)cyclohexyl)phenyl)carbamate (I-3-2-b) (Rf=0.7) (70 mg, 0.2 mmol) was added to 2 mL of dichloromethane, then 2 mL of trifluoroacetic acid was added thereto, and the mixture was stirred at room temperature for 2 hours. After the reaction mixture was concentrated, a brown oil (I-3-2-c) was obtained, which was directly used for the next step. LC-MS: m/z: $(M+H)^+$=245.

Tert-butyl (4-(4-(pyrrolidin-1-yl)cyclohexyl)phenyl)carbamate (I-3-1-b) (Rf=0.5) (70 mg, 0.2 mmol) was added to 2 mL of dichloromethane, then 2 mL of trifluoroacetic acid was added thereto, and the mixture was stirred at room temperature for 2 hours. After the reaction mixture was concentrated, a brown oil (I-3-1-c) was obtained, which was directly used for the next step. LC-MS: m/z: $(M+H)^+$=245.

Step 4:

m-Chloroperoxybenzoic acid (66 mg, 0.326 mmol) was added to a solution of 2-allyl-1-(6-(2-hydroxypropan-2-yl) pyridin-2-yl)-6-(methylthio)-1,2-dihydro-3H-pyrazolo[3,4-d]pyrimidin-3-one (I-1-h) (90 mg, 0.25 mmol) in 10 mL of toluene, and the obtained mixture was stirred at room temperature for 1 hour. The above reaction mixture was concentrated, and then trifluoroacetate of 4-(4-(azetidin-1-yl) cyclohexyl)aniline (I-3-1-c) (0.26 mmol), 0.15 mL of trifluoroacetic acid and 3 mL of dimethyl sulfoxide were added thereto, and the mixture was stirred at 60° C. overnight. 2 ML of saturated sodium carbonate aqueous solution and 10 mL of water were added to the above reaction mixture, and the mixture was extracted three times with dichloromethane (3*10 mL); then the organic phase was combined, washed with 5 mL of water and 5 mL of saturated sodium chloride solution, respectively, dried over anhydrous sodium sulfate, and concentrated to obtain a crude product; the crude product was separated by thin layer chromatography plate {7M ammonia methanol: (dichloromethane: ethyl acetate=5:1)=1:12} to obtain compound I-3-1, 40 mg of white solid (Rf=0.4), the yield was 28%. Compound 1-3-1: HPLC retention time (RT)=11.01 min (HPLC conditions: mobile phase A was water (containing 0.1% HCOOH), mobile phase B was acetonitrile; gradient elution: 5% mobile phase B→50% mobile phase B), $^1$H NMR (400 MHz, $CDCl_3$) δ 8.87 (s, 1H), 7.90 (t, J=7.9 Hz, 1H), 7.78 (d, J=8.0 Hz, 1H), 7.53 (d, J=8.5 Hz, 2H), 7.39 (dd, J=7.6, 0.5 Hz, 1H), 7.20 (d, J=8.5 Hz, 2H), 5.72 (ddt, J=16.4, 10.2, 6.2 Hz, 1H), 5.06 (dd, J=10.2, 1.0 Hz, 1H), 4.95 (dd, J=17.1, 1.2 Hz, 1H), 4.76 (d, J=6.2 Hz, 2H), 4.04 (s, 1H), 2.66 (m, 4H), 2.58-2.47 (m, 1H), 2.16 (m, 4H), 1.96 (m, 2H), 1.87-1.78 (m, 4H), 1.60 (s, 6H), 1.58-1.39 (m, 4H). LC-MS: m/z: $(M+H)^+$=554.

m-Chloroperoxybenzoic acid (60 mg, 0.296 mmol) was added to a solution of 2-allyl-1-(6-(2-hydroxypropan-2-yl) pyridin-2-yl)-6-(methylthio)-1,2-dihydro-3H-pyrazolo[3,4-d]pyrimidin-3-one (I-1-h) (80 mg, 0.22 mmol) in 10 mL of toluene, and the obtained mixture was stirred at room temperature for 1 hour. The above reaction mixture was concentrated, and then trifluoroacetate of 4-(4-(azetidin-1-yl) cyclohexyl)aniline (I-3-2-c) (0.2 mmol), 0.15 mL of trifluoroacetic acid and 3 mL of dimethyl sulfoxide were added thereto, and the mixture was stirred at 60° C. overnight. 2 ML of saturated sodium carbonate aqueous solution and 10 mL of water were added to the above reaction mixture, and the mixture was extracted three times with dichloromethane (3*10 mL); then the organic phase was combined, washed with 5 mL of water and 5 mL of saturated sodium chloride solution, respectively, dried over anhydrous sodium sulfate, and concentrated to obtain a crude product; the crude product was separated by thin layer chromatography plate {7M ammonia methanol: (dichloromethane: ethyl acetate=5:1)=1:12} to obtain compound I-3-2, 50 mg of white solid (Rf=0.6), the yield was 40%. Compound 1-3-2: HPLC retention time (RT)=11.20 min (HPLC conditions: mobile phase A was water (containing 0.1% HCOOH), mobile phase B was acetonitrile; gradient elution: 5% mobile phase B→50% mobile phase B), $^1$H NMR (400 MHz, $CDCl_3$) δ 8.87 (s, 1H), 7.92 (t, J=7.9 Hz, 1H), 7.80 (d, J=8.0 Hz, 1H), 7.52 (d, J=8.5 Hz, 2H), 7.38 (d, J=7.6 Hz, 1H), 7.29 (t, J=4.2 Hz, 2H), 5.79-5.66 (m, 1H), 5.06 (dd, J=10.2, 1.0 Hz, 1H), 4.96 (dd, J=17.1, 1.2 Hz, 1H), 4.77 (d, J=6.2 Hz, 2H), 4.02 (s, 1H), 2.70-2.50 (m, 5H), 2.26 (s, 1H), 1.98 (m, 4H), 1.82 (s, 4H), 1.69-1.56 (m, 10H). LC-MS: m/z: $(M+H)^+$=554.

Embodiment 4

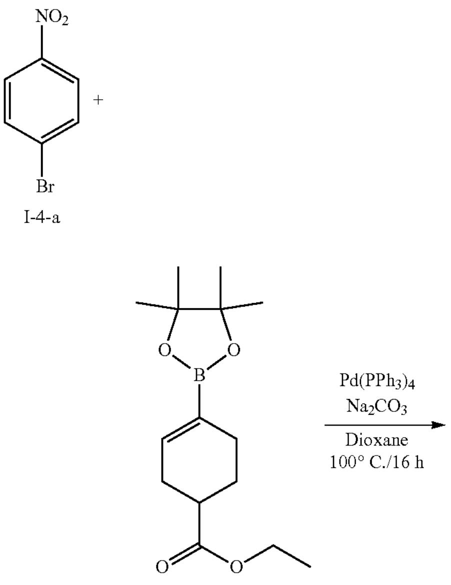

I-4-a

I-4-b

-continued

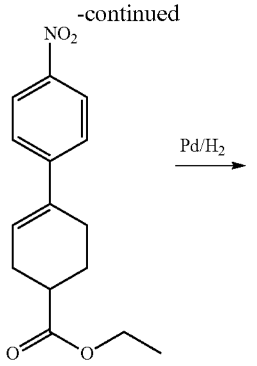

I-4-c

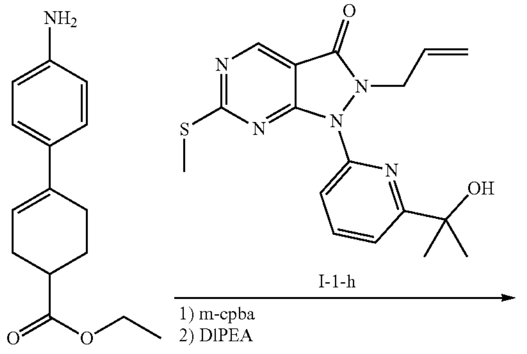

I-1-h

I-4-d

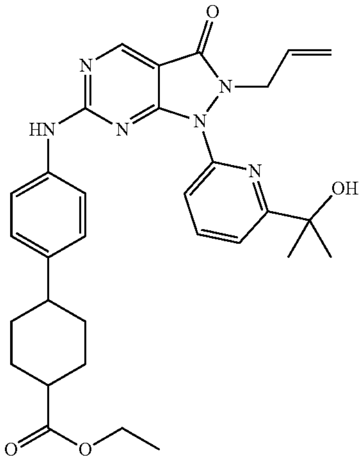

I-4

Step 1:

1-Bromo-4-nitrobenzene (I-4-a) (692 mg, 3.43 mmol), ethyl 4-(4,4,5,5-tetramethyl-1,3,2-dioxaborolan-2-yl)cyclohex-3-ene-1-carboxylate (I-4-b) (800 mg, 2.85 mmol), tetrakis(triphenylphosphine)palladium (330 mg, 0.286 mmol), triphenylphosphine (75 mg, 0.286 mmol) and potassium carbonate (789 mg, 5.71 mmol) were dissolved in 1,4-dioxane (20 mL), the mixture was heated to 90° C. under the protection of argon and stirred for about 16 hours. Then the reaction mixture was concentrated and purified by column chromatography (silica gel, petroleum ether/ethyl acetate=100% to 90%) to obtain 450 mg of the compound represented by formula I-4-c as a white solid. Yield: 47%. $^1$H NMR (400 MHz, $CDCl_3$) δ 8.23-8.16 (m, 2H), 7.57-7.49 (m, 2H), 6.33 (dd, J=5.1, 2.8 Hz, 1H), 4.26-4.15 (m, 2H), 2.72-2.61 (m, 1H), 2.59-2.51 (m, 4H), 2.24 (ddd, J=9.3, 8.0, 3.9 Hz, 1H), 1.90 (dddd, J=13.1, 11.0, 8.8, 6.7 Hz, 1H), 1.31 (dd, J=9.2, 5.1 Hz, 3H).

Step 2:

Ethyl 4-(4-nitrophenyl)cyclohex-3-ene-1-carboxylate (I-4-c) (450 mg, 1.63 mmol) was dissolved in methanol (10 mL), palladium/carbon catalyst (45 mg, 10%) was added thereto, and the mixture was stirred at room temperature for about 2 days under hydrogen atmosphere, filtered, the filtrate was concentrated and purified by column chromatography (silica gel, petroleum ether/ethyl acetate=100% to 90%) to obtain 280 mg of the compound represented by formula I-4-d as a white solid. Yield: 69%. LC-MS: m/z: $(M+H)^+$=248.4.

Step 3:

2-Allyl-1-[6-(1-hydroxy-1-methyl-ethyl)-2-pyridyl]-6-methylthiopyrazolo[3,4-d]pyrimidin-3-one (I-1-h) (428 mg, 1.20 mmol) was dissolved in toluene (20 mL), m-chloroperoxybenzoic acid (259 mg, 1.5 mmol) was added thereto, the mixture was stirred at room temperature for about 1 hour, then ethyl 4-(4-aminophenyl)cyclohexane carboxylate (247 mg, 1.0 mmol) and DIPEA (258 mg, 2.0 mmol) were added thereto, and the mixture was heated to 90° C. and stirred for about 16 hours. The reaction mixture was concentrated and purified by column chromatography (silica gel, dichloromethane/methanol=100% to 90%), preparative high performance liquid phase, and thin layer chromatography ($DCM/CH_3OH/NH_3$ $CH_3OH$=10/1/0.15) to obtain 440 mg of the compound represented by formula I-4 as a white solid, yield: 79%. $^1$H NMR (400 MHz, $CDCl_3$) δ 8.87 (d, J=2.1 Hz, 1H), 7.91 (td, J=7.9, 1.5 Hz, 1H), 7.78 (d, J=8.0 Hz, 1H), 7.54 (t, J=7.9 Hz, 2H), 7.39 (d, J=7.7 Hz, 1H), 7.21 (d, J=8.5 Hz, 2H), 5.72 (ddt, J=16.4, 10.2, 6.2 Hz, 1H), 5.07 (dd, J=10.2, 1.1 Hz, 1H), 4.96 (dd, J=17.1, 1.2 Hz, 1H), 4.77 (d, J=6.2 Hz, 2H), 4.25-4.10 (m, 2H), 3.95 (s, 1H), 2.73 (s, 1H), 2.56 (dt, J=15.5, 10.8 Hz, 1H), 2.28 (d, J=7.9 Hz, 1H), 2.14 (d, J=10.6 Hz, 1H), 2.05-1.97 (m, 1H), 1.78 (dd, J=19.0, 8.5 Hz, 1H), 1.67 (dt, J=10.1, 6.1 Hz, 3H), 1.61 (s, 6H), 1.59-1.44 (m, 1H), 1.34-1.26 (m, 3H). LC-MS: m/z: $(M+H)^+$=557.4.

Embodiment 5

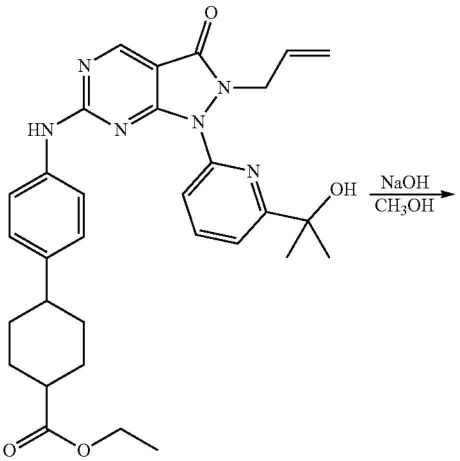

I-4

-continued

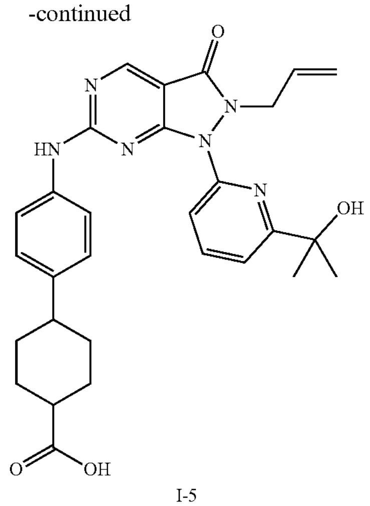

I-5

4-[4-[[2-Allyl-1-[6-(1-hydroxy-1-methyl-ethyl)-2-pyridyl]-3-oxo-pyrazolo[3,4-d]pyrimidin-6-ethyl[amino] phenyl]cyclohexane carboxylate (I-4) (420 mg, 0.75 mmol) was dissolved in methanol (20 mL), 2N sodium hydroxide aqueous solution (10 mL) was added, the mixture was stirred at room temperature for about 3 days, concentrated to remove methanol, extracted with dichloromethane, then the organic layer was discarded, and the pH value was adjusted to 4 by adding 1N hydrochloric acid aqueous solution to the aqueous layer, then the the aqueous layer was extracted with dichloromethane; and the organic layer was dried over anhydrous sodium sulfate, concentrated, purified by column chromatography (silica gel, dichloromethane/methanol=100% to 95%) to obtain 256 mg of the compound represented by formula I-5 as a white solid, yield: 64%. $^1$H NMR (400 MHz, MeOD) δ 8.84 (d, J=1.4 Hz, 1H), 8.00 (td, J=7.9, 4.0 Hz, 1H), 7.83-7.76 (m, 1H), 7.67 (dd, J=7.7, 0.7 Hz, 1H), 7.60 (dd, J=8.4, 5.7 Hz, 2H), 7.19 (dd, J=13.2, 8.6 Hz, 2H), 5.73 (ddd, J=17.0, 6.1, 4.1 Hz, 1H), 5.08-5.03 (m, 1H), 4.95 (d, J=1.3 Hz, 1H), 4.86-4.79 (m, 2H), 2.72 (s, 1H), 2.58 (s, 1H), 2.27 (d, J=6.7 Hz, 1H), 2.13 (d, J=10.0 Hz, 1H), 1.96 (d, J=10.2 Hz, 1H), 1.80-1.66 (m, 4H), 1.64-1.52 (m, 7H). LC-MS: m/z: $(M+H)^+$=529.3.

Embodiment 6

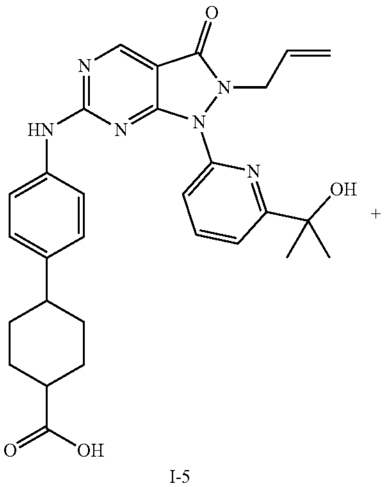

I-5

-continued

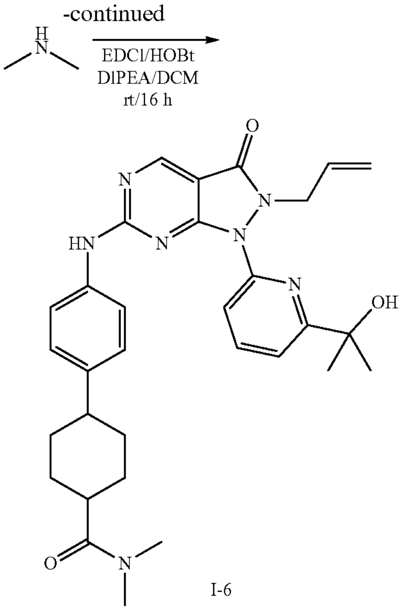

I-6

40 mg (0.076 mmol) of 4-(4-((2-allyl-1-(6-(2-hydroxypropan-2-yl)pyridin-2-yl)-3-oxo-2,3-dihydro-1H-pyrazolo [3,4-d]pyrimidin-6-yl)amino)phenyl)cyclohexane-1-carboxylic acid (I-5) was dissolved in 5 mL of dichloromethane, and 9 mg (0.11 mol) of dimethylamine hydrochloride, 17 mg (0.11 mmol) of EDCI, 15 mg (0.11 mmol) of HOBt and 19 mg (0.15 mmol) of DIPEA were added thereto, and the mixture was stirred at room temperature for about 16 hours, and then purified by thin layer chromatography (DCM/CH3OH=100/10) to obtain 15 mg of a light yellow solid (I-6), the yield was 35%. $^1$H NMR (400 MHz, $CDCl_3$) δ 8.86 (d, J=4.2 Hz, 1H), 7.97-7.88 (m, 1H), 7.79 (d, J=8.0 Hz, 1H), 7.53 (dd, J=12.3, 8.5 Hz, 2H), 7.39 (d, J=7.6 Hz, 1H), 7.28-7.15 (m, 2H), 5.80-5.65 (m, 1H), 5.06 (d, J=10.0 Hz, 1H), 4.95 (d, J=17.1 Hz, 1H), 4.77 (d, J=6.0 Hz, 2H), 3.10 (d, J=12.1 Hz, 3H), 2.98 (s, 3H), 2.67-2.57 (m, 1H), 2.14 (dd, J=20.9, 10.3 Hz, 1H), 2.06-1.97 (m, 2H), 1.92 (d, J=14.0 Hz, 1H), 1.78-1.66 (m, 4H), 1.61 (s, 6H), 1.49 (dd, J=22.8, 12.2 Hz, 1H). LC-MS: m/z: $(M+H)^+$=556.3.

Embodiment 7

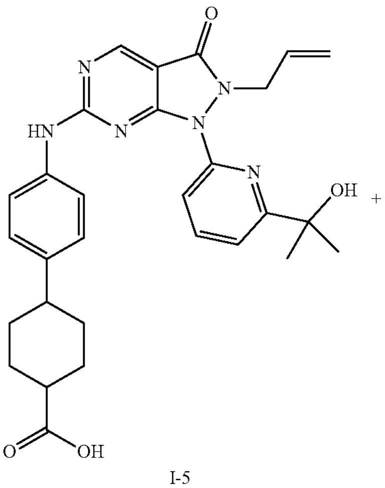

I-5

-continued

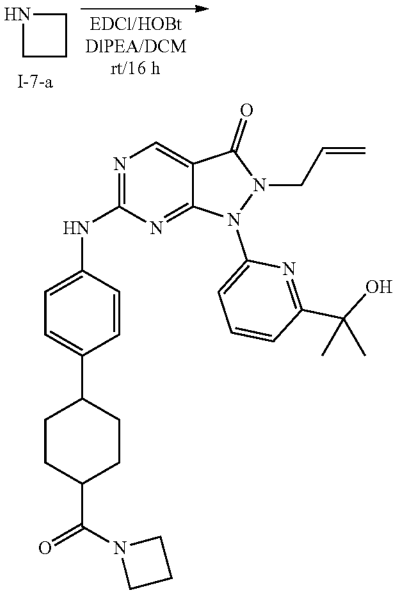

I-7-a

I-7

40 mg (0.076 mmol) of 4-(4-((2-allyl-1-(6-(2-hydroxy-propan-2-yl)pyridin-2-yl)-3-oxo-2,3-dihydro-1H-pyrazolo[3,4-d]pyrimidin-6-yl)amino)phenyl)cyclohexane-1-carboxylic acid (I-5) was dissolved in 5 mL of dichloromethane, and 9 mg (0.11 mol) of azetidine hydrochloride (I-7-a), 17 mg (0.11 mmol) of EDCI, 15 mg (0.11 mmol) of HOBt and 19 mg (0.15 mmol) of DIPEA were added thereto, and the mixture was stirred at room temperature for about 16 hours, and then purified by thin layer chromatography (DCM/CH3OH=100/10) to obtain 15 mg of a light yellow solid (I-7), the yield was 35%. $^1$H NMR (400 MHz, $CDCl_3$) δ 8.85 (d, J=4.7 Hz, 1H), 7.91 (dt, J=10.7, 7.9 Hz, 1H), 7.78 (d, J=7.8 Hz, 1H), 7.53 (dd, J=12.0, 8.5 Hz, 2H), 7.39 (dd, J=7.6, 2.4 Hz, 1H), 7.22 (dd, J=19.5, 8.5 Hz, 2H), 5.71 (ddt, J=16.4, 10.2, 6.2 Hz, 1H), 5.06 (d, J=10.2 Hz, 1H), 4.95 (d, J=17.1 Hz, 1H), 4.77 (d, J=6.1 Hz, 2H), 4.21 (dd, J=16.4, 8.6 Hz, 2H), 4.10-4.02 (m, 2H), 2.63-2.52 (m, 2H), 2.35-2.20 (m, 2H), 2.15-2.07 (m, 1H), 2.00 (dd, J=13.4, 3.0 Hz, 2H), 1.92-1.83 (m, 1H), 1.79-1.63 (m, 4H), 1.60 (s, 6H), 1.48 (ddd, J=24.7, 12.5, 2.5 Hz, 1H). LC-MS: m/z: $(M+H)^+$=568.4.

Embodiment 8

I-8

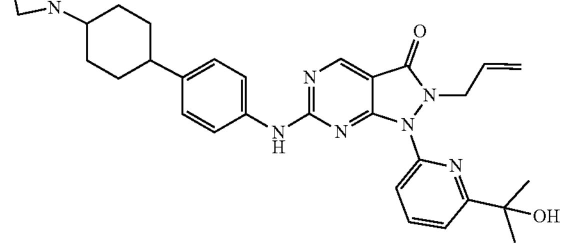

-continued

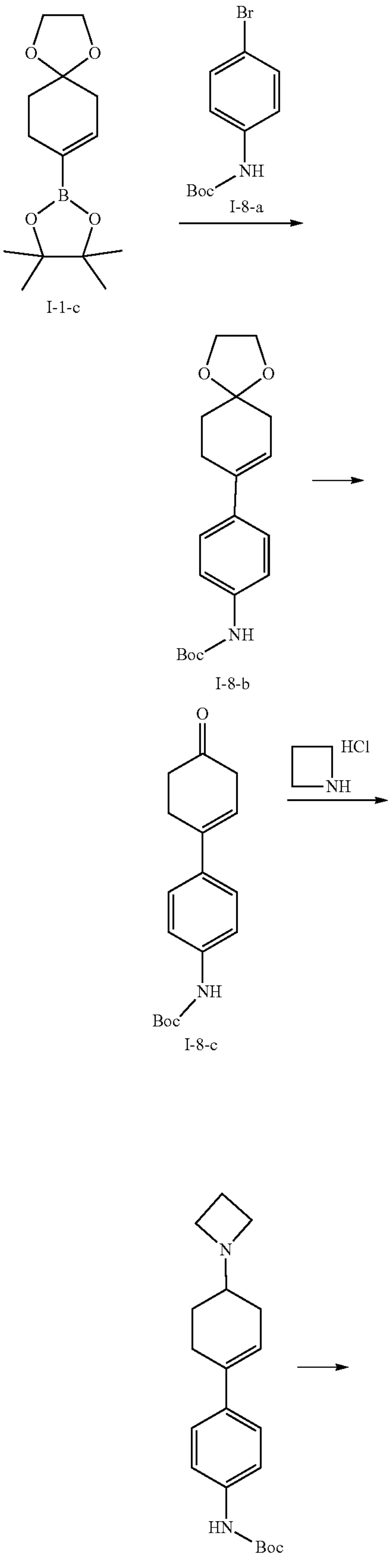

I-1-c

I-8-a

I-8-b

I-8-c

I-8-d

-continued

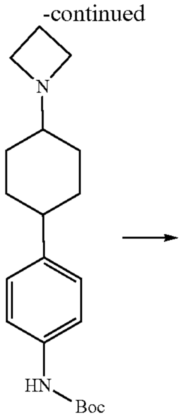

I-8-e

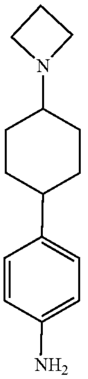

I-8-f

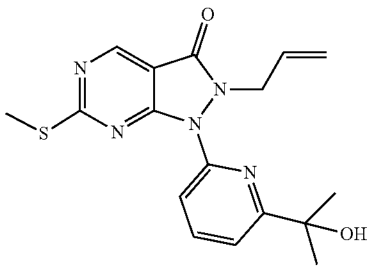

I-1-h

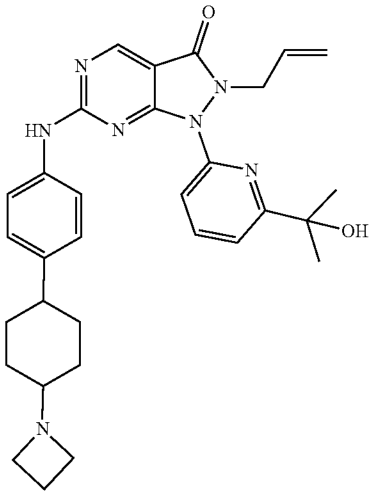

I-8

Step 1:

4,4,5,5-Tetramethyl-2-(1,4-dioxaspiro[4.5]dec-7-en-8-yl)-1,3,2-dioxaborolane (I-1-c) (19 g, 71.4 mmol), tert-butyl (4-bromophenyl)carbamate (I-8-a) (18.4 g, 67.6 mmol), 2 mol/L sodium carbonate aqueous solution (75 mL) and Pd(dppf)$Cl_2$ (3.3 g, 4.5 mmol) were added to 250 mL of 1,4-dioxane, and the reaction flask was ventilated with a nitrogen balloon for three times, and the mixture was stirred at 98° C. overnight. The reaction mixture was filtered and concentrated, and the aqueous phase was extracted with ethyl acetate (2*100 mL), the combined organic phase was washed with saturated saline, dried over anhydrous sodium sulfate and concentrated to obtain a crude product, which was purified by column (ethyl acetate:petroleum ether=0-40%) to obtain 19 g of a brown solid (I-8-b). The yield was 84.8%. LC-MS: m/z: $(M-56+H)^+$=276.

Step 2:

1.38 Mol/L hydrochloric acid (160 mL) was added to a solution of tert-butyl (4-(1,4-dioxaspiro[4.5]dec-7-en-8-yl)phenyl)carbamate (I-8-b) (16 g, 48 mmol) in 100 mL of tetrahydrofuran, and the mixture was stirred at room temperature overnight. Then the mixture was extracted with ethyl acetate (2*150 mL), the combined organic phase was washed three times with saturated saline, and the organic phase was dried over anhydrous sodium sulfate and concentrated to obtain 13.5 g of a yellow-brown solid (I-8-c), which was directly used for the next step. The yield was 97%. LC-MS: m/z: $(M-56+H)^+$=232.

Step 3:

N,N'-diisopropylethylamine (12 mL, 69 mmol) and sodium borohydride acetate (14 g, 71 mmol) were added to a mixture of tert-butyl (4'-oxo-2',3',4',5'-tetrahydro-[1,1'-biphenyl]-4-yl)carbamate (I-8-c) (10 g, 34.8 mmol) and azetidine hydrochloride (3 g, 32 mmol) in 100 mL of dichloromethane, and the mixture was stirred at room temperature overnight; then the solvent was evaporated, and 100 mL of dichloromethane was added thereto, and the mixture was washed with saturated sodium carbonate aqueous solution (20 mL), water (2*30 mL) and saturated saline sequentially; then the organic phase was dried over anhydrous sodium sulfate and then mixed with silica gel and passed through the column {7M ammonia methanol:(dichloromethane:ethyl acetate=15:1)=0-15%} to obtain 7.3 g of white solid (I-8-d). The yield was 64%. LC-MS: m/z: $(M+H)^+$=329.

Step 4:

Tert-butyl (4'-(azetidin-1-yl)-2',3',4',5'-tetrahydro-[1,1'-biphenyl]-4-yl)carbamate (I-8-d) (7.3 g, 22 mmol) and 10% palladium carbon (200 mg) were added to 150 mL of methanol, the reaction flask was ventilated three times with a hydrogen balloon, and the reaction mixture was stirred overnight at room temperature in a hydrogen atmosphere. The reaction mixture was filtered and evaporated to dryness to obtain a crude product, the crude product was washed with ethyl acetate and filtered, and the filter cake was 4.1 g of compound I-8-e (Rf=0.4) as a white solid. The total yield was 85%. LC-MS: m/z: $(M+H)^+$=331.

Step 5:

Tert-butyl (4-(4-(azetidin-1-yl)cyclohexyl)phenyl)carbamate (3 g, 9 mmol) (represented by formula I-8-e) was added to 20 mL of dichloromethane, then 20 mL of trifluoroacetic acid was added thereto, and the mixture was stirred at room temperature for 2 hours. After the reaction mixture was concentrated, 10 mL of water and 20 mL of saturated sodium carbonate solution were added thereto, and the formed solid was filtered, washed with water and drained to obtain 1.8 g of compound I-8-f as a brown solid, which was directly used in the next step. The yield was 86%. $^1H$ NMR (400 MHz, $CDCl_3$) δ 7.08-6.96 (m, 2H), 6.70-6.60 (m, 2H), 3.57 (s, 2H), 3.22 (t, J=7.0 Hz, 4H), 2.38 (tt, J=12.1, 3.2 Hz, 1H), 2.15-1.95 (m, 5H), 1.95-1.81 (m, 4H), 1.51-1.30 (m, 2H), 1.21-1.04 (m, 2H). LC-MS: m/z: $(M+H)^+$=231.

Step 6:

m-Chloroperoxybenzoic acid (1.33 g, 6.57 mmol) was added to a solution of 2-allyl-1-(6-(2-hydroxypropan-2-yl)pyridin-2-yl)-6-(methylthio)-1,2-dihydro-3H-pyrazolo[3,4-d]pyrimidin-3-one (1.86 g, 5.2 mmol) (represented by I-1-h) in 60 mL of toluene, and the obtained mixture was stirred at room temperature for 1 hour. The above reaction mixture was concentrated, and then 4-(4-(azetidin-1-yl)cyclohexyl) aniline (1.2 g, 5.2 mmol) (represented by I-8-f), 0.8 mL of trifluoroacetic acid and 20 mL of dimethyl sulfoxide were added thereto, and the mixture was stirred at 60° C. overnight. 20 ML of saturated sodium carbonate aqueous solution and 50 mL of water were added to the above reaction mixture, and the mixture was extracted three times with dichloromethane (3*150 mL); then the organic phase was combined, washed with 50 mL of water and 30 mL of saturated sodium chloride solution, respectively, dried over anhydrous sodium sulfate, and concentrated to obtain a crude product; the crude product was separated by thin layer chromatography plate {7M ammonia methanol: (dichloromethane:ethyl acetate=5:1)=1:12} to obtain compound I-8, 1.88 g of a white solid, the yield was 67%. $^{1}$H NMR (400 MHz, $CDCl_3$) δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H). LC-MS: m/z: $(M+H)^+$ =540.4.

Embodiment 8-1

The product of embodiment 8 (compound I-8) was detected by HPLC (conditions: mobile phase A was water (containing HCOOH 0.1%), mobile phase B was acetonitrile; gradient elution: 5% mobile phase B→50% mobile phase B) with the only retention time: HPLC retention time (RT)=10.78 min. Therefore, its cyclohexyl part was cis or trans, i.e., it was

I-8-1

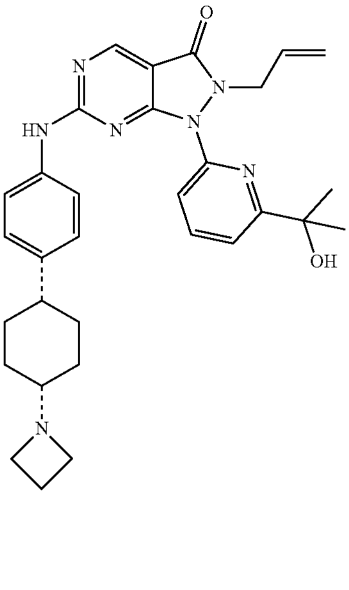

,

⋰ refers to cis or trans.

The reaction route was as follows:

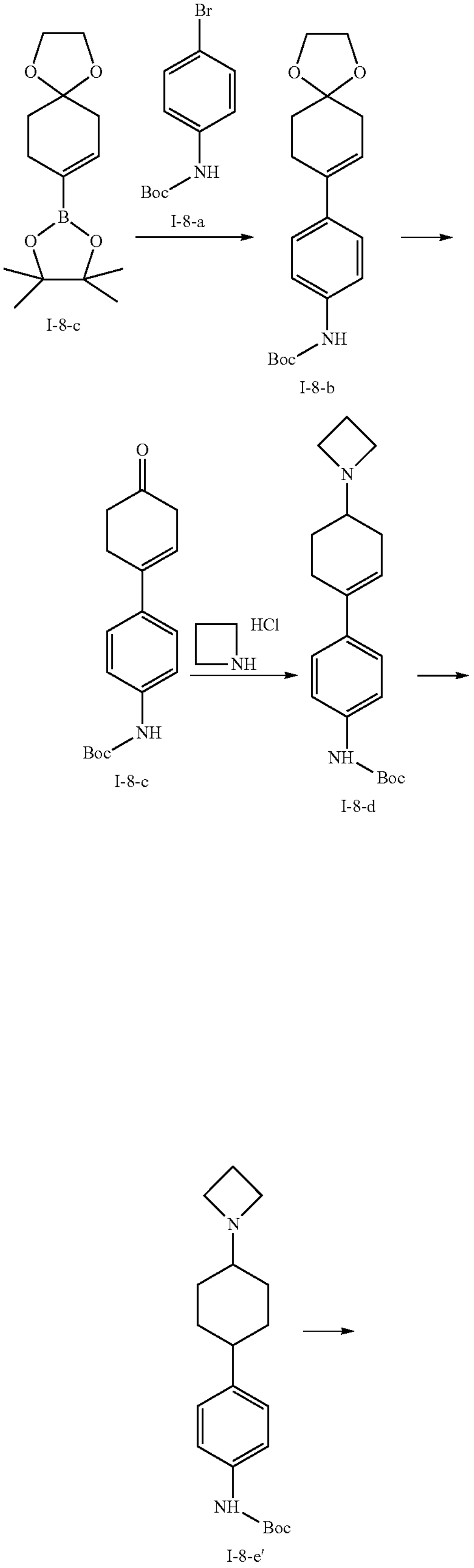

-continued

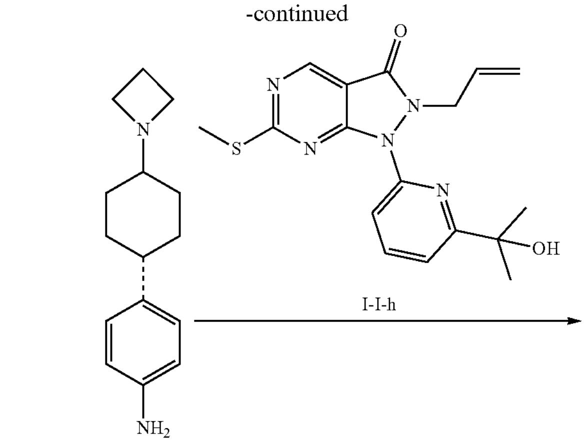

I-8-f'

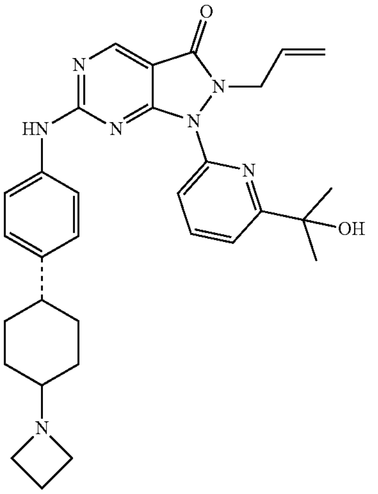

I-8-1

Embodiment 8-2

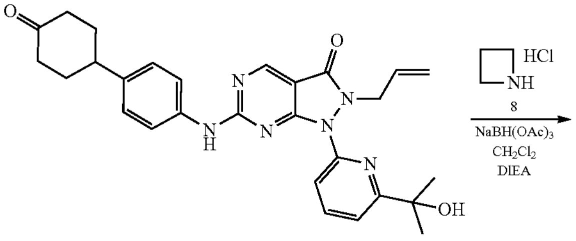

I-19-d

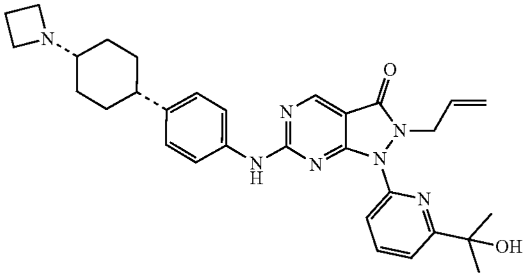

+

I-8-1

-continued

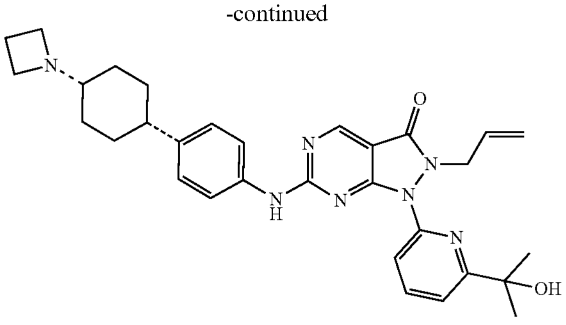

I-8-2

2-Allyl-1-(6-(2-hydroxypropan)pyridin-2-yl)-6-((4-(4-oxocyclohexyl)phenyl)amino)-1,2-dihydro-3H-pyrazolo[3,4-d]pyrimidin-3-one (I-19-d) (19.0 mmol) was dissolved in dichloromethane (500 mL), and azetidine hydrochloride (21.0 mmol), N-ethyl-N-isopropyl-2-amine (38.0 mmol) and sodium triacetoxyborohydride (57 mmol) were added to the reaction mixture, and the reaction mixture was stirred at 30° C. for 16 hours. Water (300 mL) and potassium carbonate were added to the reaction mixture, the pH value was adjusted to 9, and the mixture was extracted with dichloromethane; the organic phase was washed with saturated saline, dried over anhydrous magnesium sulfate, filtered, and the filtrate was evaporated to dryness to obtain a crude product, and the crude product was purified by column chromatography (dichloromethane/methanol=0/100-5/95) to obtain target compound I-8-1 (1.8 g, 24.7%) and target compound I-8-2 (4.7 g, 65.3%), both of which were white solids.

Compound I-8-1: HPLC: retention time (RT)=10.78 min (HPLC conditions: mobile phase A was water (containing HCOOH 0.1%), mobile phase B was acetonitrile; gradient elution: 5% mobile phase B→50% mobile phase B), $^1$H NMR (400 MHz, $CDCl_3$) δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H). LC-MS: m/z: $(M+H)^+$=540.4.

Compound I-8-2: HPLC: retention time (RT)=11.00 min (HPLC conditions: mobile phase A was water (containing HCOOH 0.1%), mobile phase B was acetonitrile; gradient elution: 5% mobile phase B→50% mobile phase B), $^1$H NMR (400 MHz, $CDCl_3$) δ8.87 (s, 1H), 7.92 (d, J=7.8 Hz, 1H), 7.80 (d, J=8.0 Hz, 1H), 7.52 (d, J=8.4 Hz, 2H), 7.39 (d, J=7.6 Hz, 1H), 7.29-7.25 (m, 2H), 5.82-5.63 (m, 1H), 5.12-4.91 (m, 2H), 4.78 (d, J=6.2 Hz, 2H), 4.01 (s, 1H), 3.17 (s, 4H), 2.53 (s, 1H), 2.33 (s, 1H), 2.06 (d, J=4.4 Hz, 2H), 1.89 (d, J=11.6 Hz, 2H), 1.75 (d, J=14.1 Hz, 2H), 1.59 (d, J=17.2 Hz, 8H), 1.46 (t, J=13.1 Hz, 2H). LC-MS: 540.0$[M+1]^+$.

It can be seen that there was a big difference between the cis- and trans-configuration hydrogen spectrum data, which was enough to distinguish them.

Embodiment 8-3

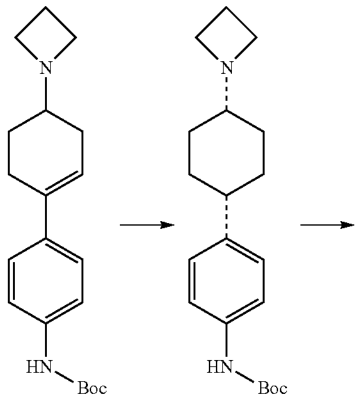

I-8-d I-8-e''

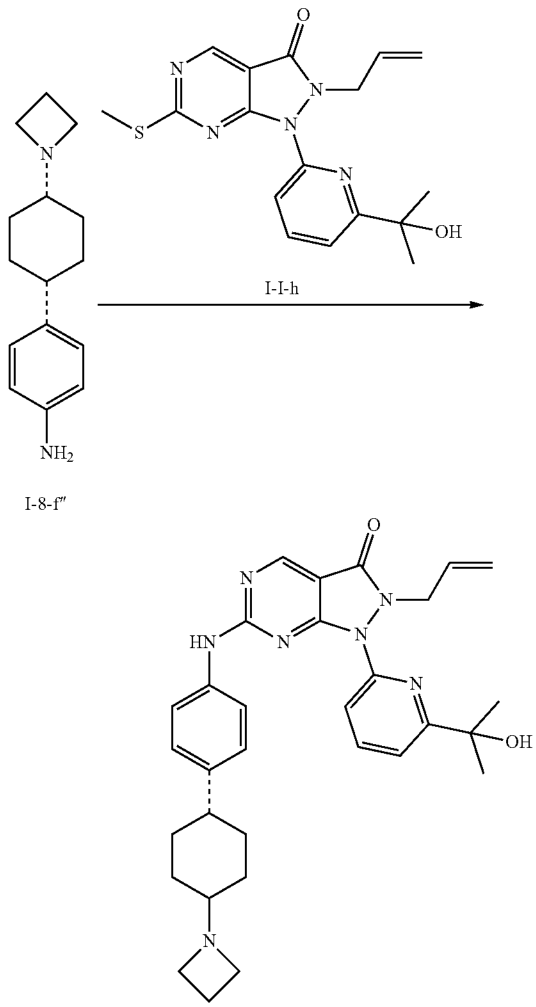

I-8-f''

I-I-h

I-8-2

Step 1:

Tert-butyl (4'-(azetidin-1-yl)-2',3',4',5'-tetrahydro-[1,1'-biphenyl]-4-yl)carbamate (I-8-d) (7.3 g, 22 mmol) and 10% palladium carbon (200 mg) were added to 150 mL of methanol, the reaction flask was ventilated three times with a hydrogen balloon, and the reaction mixture was stirred overnight at room temperature in a hydrogen atmosphere. The reaction mixture was filtered and evaporated to dryness to obtain a crude product, which was mixed with silica gel and passed through the column {7 M ammonia methanol: (dichloromethane:ethyl acetate=12:3)=0-15%} to obtain 2.1 g of compound I-8-e" (Rf=0.6) as a white solid and 4.1 g of compound I-8-e' as a white solid (Rf=0.4). The total yield was 85%. LC-MS: m/z: $(M+H)^+$=331.

Step 2:

Tert-butyl (4-(4-(azetidin-1-yl)cyclohexyl)phenyl)carbamate (2 g, 9 mmol) (represented by formula I-8-e") was added to 20 mL of dichloromethane, then 20 mL of trifluoroacetic acid was added thereto, and the mixture was stirred at room temperature for 2 hours. After the reaction mixture was concentrated, 10 mL of water and 20 mL of saturated sodium carbonate solution were added thereto, and the formed solid was filtered, washed with water and drained to obtain 1.2 g of compound I-8-f" as a brown solid, which was directly used in the next step. The yield was 86%. $^1$H NMR (400 MHz, MeOD) δ 7.10-6.97 (m, 2H), 6.74-6.63 (m, 2H), 4.22-4.08 (t, J=8.0 Hz, 4H), 3.47-3.38 (m, 1H), 2.61-2.52 (m, 1H), 2.52-2.28 (m, 2H), 1.92-1.62 (m, 8H). LC-MS: m/z: $(M+H)^+$=231.

Step 3:

m-Chloroperoxybenzoic acid (1.33 g, 6.57 mmol) was added to a solution of 2-allyl-1-(6-(2-hydroxypropan-2-yl)pyridin-2-yl)-6-(methylthio)-1,2-dihydro-3H-pyrazolo[3,4-d]pyrimidin-3-one (1.86 g, 5.2 mmol) (represented by I-1-h) in 60 mL of toluene, and the obtained mixture was stirred at room temperature for 1 hour. The above reaction mixture was concentrated, and then 4-(4-(azetidin-1-yl)cyclohexyl)aniline (1.2 g, 5.2 mmol) (represented by I-8-f"), 0.8 mL of trifluoroacetic acid and 20 mL of dimethyl sulfoxide were added thereto, and the mixture was stirred at 60° C. overnight. 20 ML of saturated sodium carbonate aqueous solution and 50 mL of water were added to the above reaction mixture, and the mixture was extracted three times with dichloromethane (3*150 mL); then the organic phase was combined, washed with 50 mL of water and 30 mL of saturated sodium chloride solution, respectively, dried over anhydrous sodium sulfate, and concentrated to obtain a crude product; the crude product was separated by thin layer chromatography plate {7M ammonia methanol: (dichloromethane:ethyl acetate=5:1)=1:12} to obtain compound I-8-2, 1.88 g of a white solid, the yield was 67%. $^1$H NMR (400 MHz, $CDCl_3$) δ8.87 (s, 1H), 7.92 (d, J=7.8 Hz, 1H), 7.80 (d, J=8.0 Hz, 1H), 7.52 (d, J=8.4 Hz, 2H), 7.39 (d, J=7.6 Hz, 1H), 7.29-7.25 (m, 2H), 5.82-5.63 (m, 1H), 5.12-4.91 (m, 2H), 4.78 (d, J=6.2 Hz, 2H), 4.01 (s, 1H), 3.17 (s, 4H), 2.53 (s, 1H), 2.33 (s, 1H), 2.06 (d, J=4.4 Hz, 2H), 1.89 (d, J=11.6 Hz, 2H), 1.75 (d, J=14.1 Hz, 2H), 1.59 (d, J=17.2 Hz, 8H), 1.46 (t, J=13.1 Hz, 2H). LC-MS: m/z: $(M+H)^+$=540.

Embodiment 15

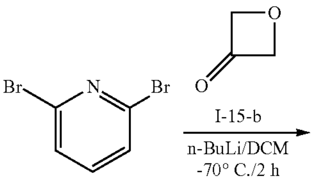

I-15-a

-continued

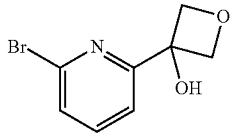

+

I-15-c

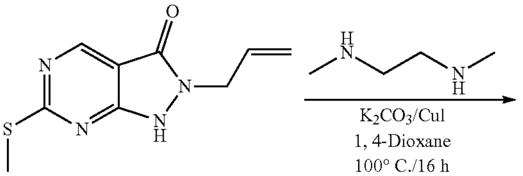

I-15-d

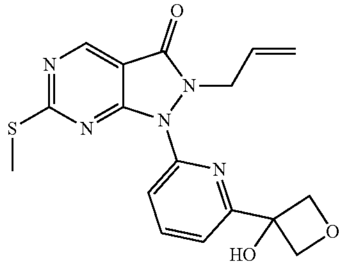

+

I-15-e

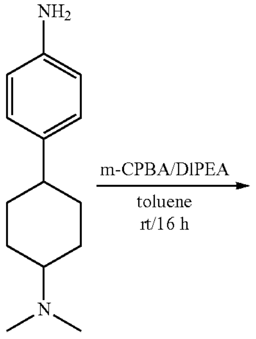

I-1-f

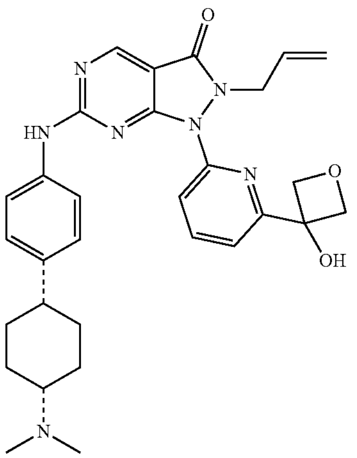

+

I-15-1

-continued

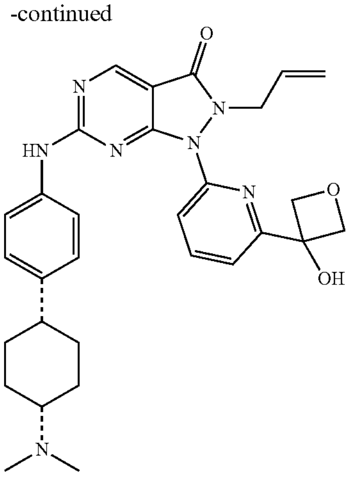

I-15-2

Step 1:

1 g (4.22 mmol) of 2,6-dibromopyridine (I-15-a) was dissolved in 30 mL of dichloromethane, the mixture was cooled to −78° C., and 1.86 mL (4.64 mmol, 2M solution of dioxane) of n-butyllithium solution was slowly added dropwise, after the mixture was stirred for about 15 min, and 0.3 g (4.22 mmol) of oxetan-3-one (represented by formula I-15-b) was added thereto, the stirring was continued for about 1 hour; and the mixture was quenched with saturated ammonium chloride aqueous solution, and then extracted with dichloromethane, the organic layer was dried over anhydrous sodium sulfate, concentrated, and purified by column chromatography (petroleum ether/ethyl acetate=100% to 50%) to obtain 660 mg of 3-(6-bromo-2-pyridyl)oxetan-3-ol (I-15-c) as a white solid, the yield was 68%. LC-MS: m/z: $(M+H)^+$=230.1.

Step 2:

106 mg (0.48 mmol) of 2-allyl-6-methylthio-1H-pyrazolo[3,4-d]pyrimidin-3-one (I-15-d) and 100 mg (0.43 mmol) of 3-(6-bromo-2-pyridyl)oxetan-3-ol (I-15-c) were dissolved into 10 mL of 1,4-dioxane, and then 90 mg (0.65 mmol) of potassium carbonate, 83 mg (0.43 mmol) of cuprous iodide and 77 mg (0.87 mmol) of N1,N2-dimethylethyl-1,2-diamine were added thereto, and the mixture was heated to 100° C. under the protection of argon and stirred overnight. The residue was concentrated and purified by silica gel column chromatography (UV, dichloromethane/methanol=100% to 10%) to obtain 140 mg of 2-allyl-1-[6-(3-hydroxyoxetan-3-yl)-2-pyridinyl]-6-methylthiopyrazolo[3,4-d]pyrimidin-3-one (I-15-e) as a brown oil, the yield was 86%. LC-MS: m/z: $(M+H)^+$=372.1.

Step 3:

549 mg (1.478 mmol) of 2-allyl-1-[6-(3-hydroxyoxetan-3-yl)-2-pyridinyl]-6-methylthiopyrazolo[3,4-d]pyrimidin-3-one (represented by I-15-e) was dissolved in 30 mL of toluene, 397 mg (1.7714 mmol) of 3-chloroperoxybenzoic acid was added thereto, and the mixture was stirred at room temperature for about 1 hour, then 354 mg (1.622 mmol) of 4-(4-(dimethylamino)cyclohexyl)aniline (I-1-f) and 381 mg (2.9480 mmol) of DIPEA were added thereto, and the reaction mixture was concentrated and purified by thin layer chromatography (dichloromethane/methanol/methanol solution of ammonia=25/1/0.15) to obtain compound I-15-1 and compound I-15-2. Compound I-15-1: HPLC retention time (RT)=7.02 min (HPLC conditions: gradient elution, 5% mobile phase B→95% mobile phase B), the yield of the compound was 10% (80 mg) as a white solid; $^{1}$H NMR (400 MHz, MeOD) δ 8.84 (s, 1H), 8.04 (t, J=7.9 Hz, 1H), 7.92 (d, J=8.1 Hz, 1H), 7.67 (d, J=7.6 Hz, 1H), 7.60 (d, J=8.6 Hz, 2H), 7.21 (d, J=8.6 Hz, 2H), 5.78 (ddt, J=16.3, 10.3, 6.1 Hz, 1H), 5.12-5.05 (m, 3H), 4.98 (dd, J=17.1, 1.3 Hz, 1H), 4.89 (d, J=6.1 Hz, 2H), 4.84 (s, 2H), 3.68 (s, 2H), 2.97-2.86 (m, 1H), 2.66 (s, 6H), 2.60-2.50 (m, 1H), 2.15 (d, J=8.6 Hz, 2H), 2.04 (d, J=9.0 Hz, 2H), 1.66-1.54 (m, 4H). LC-MS: m/z: $(M+H)^+$=542.4. Compound I-15-2: HPLC retention time (RT)=7.16 min (HPLC conditions: gradient elution, 5% mobile phase B→95% mobile phase B), the yield of the compound was 20% (160 mg) as a white solid: $^{1}$H NMR (400 MHz, MeOD) δ 8.83 (s, 1H), 8.04 (t, J=7.9 Hz, 1H), 7.92 (d, J=8.0 Hz, 1H), 7.67-7.62 (m, 1H), 7.59 (d, J=8.6 Hz, 2H), 7.29 (d, J=8.5 Hz, 2H), 5.76 (ddt, J=16.3, 10.2, 6.1 Hz, 1H), 5.10-5.02 (m, 3H), 4.96 (dd, J=17.1, 1.3 Hz, 1H), 4.87 (d, J=6.8 Hz, 2H), 4.82 (d, J=6.8 Hz, 2H), 2.73 (d, J=4.2 Hz, 1H), 2.29 (d, J=21.9 Hz, 7H), 2.04-1.90 (m, 4H), 1.66 (dd, J=15.6, 6.1 Hz, 4H). LC-MS: m/z: $(M+H)^+$=542.3.

Embodiment 19

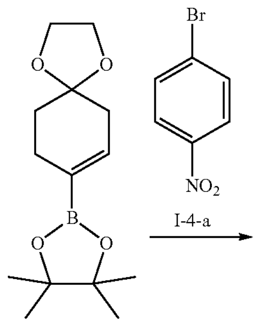

I-4-a

I-1-c

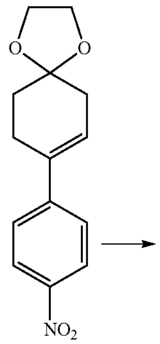

I-19-a

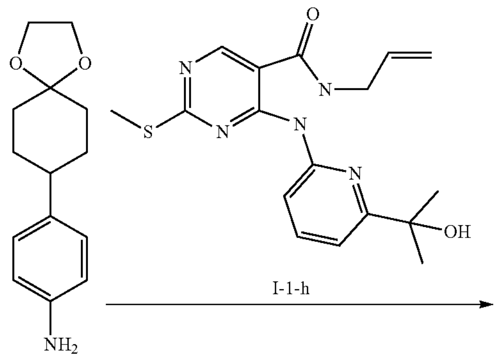

I-1-h

I-19-b

-continued

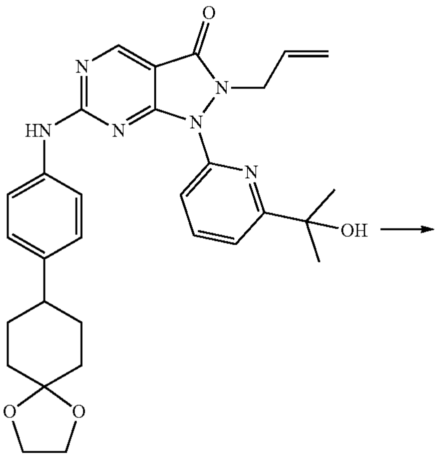

I-19-c

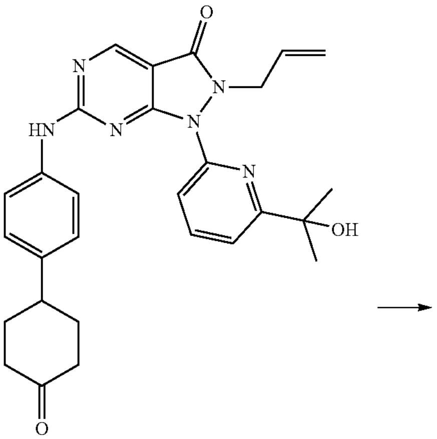

I-19-d

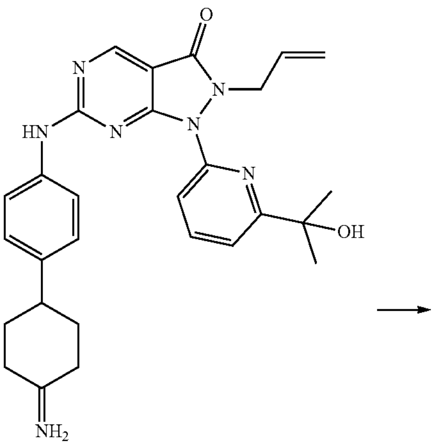

I-19-e

-continued

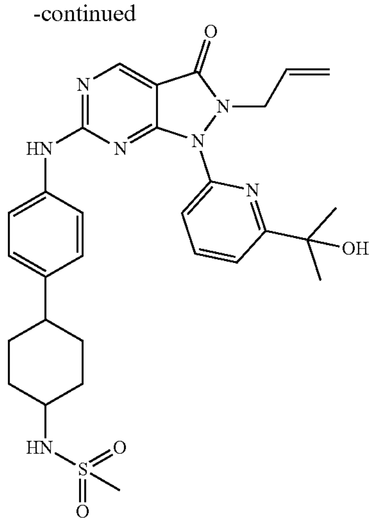

I-19

Step 1:

4,4,5,5-Tetramethyl-2-(1,4-dioxaspiro[4.5]dec-7-en-8-yl)-1,3,2-dioxaborolane (0.8 g, 3 mmol) (represented by formula I-1-c), 1-bromo-4-nitrobenzene (0.606 g, 3 mmol) (I-4-a), 1 mol/L sodium carbonate aqueous solution (6 mL) and $Pd(PPh_3)_2Cl_2$ (106 mg, 0.15 mmol) were added to 30 mL of 1,4-dioxane, and the reaction flask was ventilated three times with a nitrogen balloon, and the mixture was stirred at 95° C. overnight. The reaction mixture was filtered and concentrated, and the aqueous phase was extracted with ethyl acetate (2×30 mL), the combined organic phase was washed with saturated saline, dried over anhydrous sodium sulfate and concentrated to obtain a crude product, which was purified by column (ethyl acetate:petroleum ether=0-30%) to obtain 0.73 g of 8-(4-nitrophenyl)-1,4-dioxaspiro[4.5]dec-7-ene (I-19-a) as a brown solid, the yield was 90%. $^1$H NMR (400 MHz, CDCl3) δ 8.24-8.14 (m, 2H), 7.60-7.50 (m, 2H), 6.21 (td, J=4.0, 2.0 Hz, 1H), 4.06 (s, 4H), 2.71 (ddd, J=6.5, 4.2, 1.7 Hz, 2H), 2.59-2.49 (m, 2H), 1.97 (t, J=6.5 Hz, 2H). LC-MS: m/z: $(M+H)^+$=262.3.

Step 2:

8-(4-Nitrophenyl)-1,4-dioxaspiro[4.5]dec-7-ene (I-19-a) and 10% palladium carbon (100 mg) were added to 50 mL of dichloromethane, the reaction flask was ventilated three times with a hydrogen balloon, and the reaction mixture was stirred at room temperature for 4 hours in a hydrogen atmosphere. The reaction mixture was filtered and evaporated to dryness to obtain 560 mg of 4-(1,4-dioxaspiro[4.5]decan-8-yl)aniline (I-19-b) as a brown solid, which was directly used in the next step, the yield was 96%. LC-MS: m/z: $(M+H)^+$=234.3.

Step 3:

m-Chloroperoxybenzoic acid (55 mg, 0.246 mmol) was added to a solution of 2-allyl-1-(6-(2-hydroxypropan-2-yl)pyridin-2-yl)-6-(methylthio)-1,2-dihydro-3H-pyrazolo[3,4-d]pyrimidin-3-one (72 mg, 0.2 mmol) (I-1-h) in 15 mL of toluene, and the obtained mixture was stirred at room temperature for 1 hour. The above reaction mixture was concentrated, and then 4-(1,4-dioxaspiro[4.5]decan-8-yl)aniline (I-19-b), 0.15 mL of trifluoroacetic acid and 3 mL of dimethyl sulfoxide were added thereto, and the mixture was stirred at 60° C. overnight. 10 ML of saturated sodium carbonate aqueous solution and 25 mL of water were added to the above reaction mixture, and the mixture was extracted three times with dichloromethane (3×20 mL); then the organic phase was combined, washed with 10 mL of water and 10 mL of saturated sodium chloride solution, respectively, dried over anhydrous sodium sulfate, and concentrated to obtain a crude product; the crude product was separated by thin layer chromatography plate {7M ammonia methanol: (dichloromethane:ethyl acetate=5:1)=1:12} to obtain 60 mg of 6-((4-(1,4-dioxaspiro[4.5]decan-8-yl)phenyl)amino)-2-allyl-1-(6-(2-hydroxypropan-2-yl)pyridin-2-yl)-1,2-dihydro-3H-pyrazolo[3,4-d]pyrimidin-3-one (represented by I-19-c) as a white solid, the yield was 54%. LC-MS: m/z: $(M+H)^+$=543.3.

Step 4:

6-((4-(1,4-Dioxaspiro[4.5]decan-8-yl)phenyl)amino)-2-allyl-1-(6-(2-hydroxypropan-2-yl)pyridin-2-yl)-1,2-dihydro-3H-pyrazolo[3,4-d]pyrimidin-3-one (represented by I-19-c) was added to a mixed solution consisting of 3 mL of tetrahydrofuran and 3 mL of 2 mol/L hydrochloric acid, and the mixture was stirred at room temperature overnight. The pH of the reaction mixture was adjusted to about 10 with sodium bicarbonate, extracted with dichloromethane (2×20 mL), and the crude product was concentrated after the organic phase was dried over anhydrous sodium sulfate. The obtained crude product was separated by thin layer chromatography plate with methanol:(dichloromethane:ethyl acetate=9:3)=1:12 to obtain 50 mg of 2-allyl-1-(6-(2-hydroxypropan-2-yl)pyridin-2-yl)-6-((4-(4-oxocyclohexyl)phenyl)amino)-1,2-dihydro-3H-pyrazolo[3,4-d]pyrimidin-3-one (I-19-d) as a white solid, the yield was 90%. LC-MS: m/z: $(M+H)^+$=499.3.

Step 5:

2-Allyl-1-(6-(2-hydroxypropan-2-yl)pyridin-2-yl)-6-((4-(4-oxocyclohexyl)phenyl)amino)-1,2-dihydro-3H-pyrazolo[3,4-d]pyrimidin-3-one (50 mg, 0.1 mmol) (I-19-d) and ammonium acetate (77 mg, 1 mmol) were added to 10 mL of methanol, the mixture was stirred at room temperature for 10 min, then sodium cyanoborohydride (30 mg, 0.5 mmol) was added thereto, and the mixture was stirred overnight at room temperature. After the reaction mixture was concentrated, 20 mL of dichloromethane was added thereto, and the mixture was washed with 10 mL of 1 mol/L sodium carbonate solution and 5 mL of water sequentially. The organic phase was dried over anhydrous sodium sulfate, and the obtained crude product was concentrated and directly used in the next step. 40 Mg of white solid (I-19-e), the yield was 80%. LC-MS: m/z: $(M+H)^+$=500.3.

Step 6:

2-Allyl-6-((4-(4-aminocyclohexyl)phenyl)amino)-1-(6-(2-hydroxypropan-2-yl)pyridin-2-yl)-1,2-dihydro-3H-pyrazolo[3,4-d]pyrimidin-3-one (35 mg, 0.07 mmol) (I-19-e) and N,N-diisopropylethylamine (0.02 mL) were added to 10 mL of dichloromethane, then methanesulfonyl chloride (9 mg, 0.078 mmol) was added thereto, and the mixture was stirred overnight at room temperature. The reaction mixture was concentrated and then prepared by high performance liquid phase to obtain 9 mg of N-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)cyclohexyl)methanesulfonamide (I-19) as a white solid, the yield was 22%. $^1$H NMR (400 MHz, $CDCl_3$) δ 8.88 (s, 1H), 7.91 (t, J=7.9 Hz, 1H), 7.77 (d, J=7.9 Hz, 1H), 7.56 (d, J=8.5 Hz, 2H), 7.40 (d, J=7.4 Hz, 1H), 7.19 (d, J=8.5 Hz, 2H), 5.78-5.66 (m, 1H), 5.07 (dd, J=10.2, 1.0 Hz, 1H), 4.96 (dd, J=17.1, 1.2 Hz, 1H), 4.77 (d, J=6.2 Hz, 2H), 4.42 (d, J=7.6 Hz, 1H), 3.49-3.35 (m, 1H), 3.04 (s, 3H), 2.57-2.46 (m, 1H), 2.29-2.17 (m, 2H), 2.05-1.96 (m, 8H), 1.56-1.65 (m, 2H), 1.41-1.50 (m, 2H). LC-MS: m/z: $(M+H)^+$=578.3.

Embodiment 20

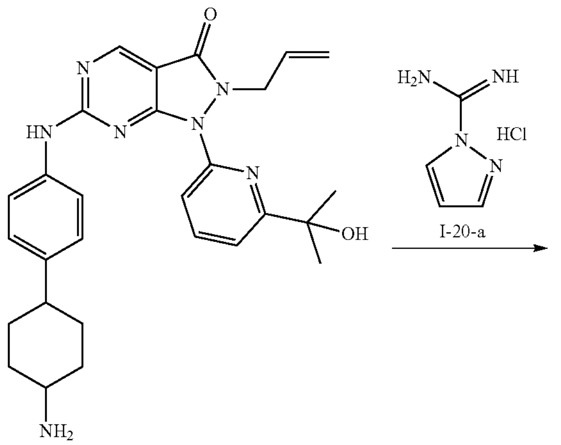

I-19-c

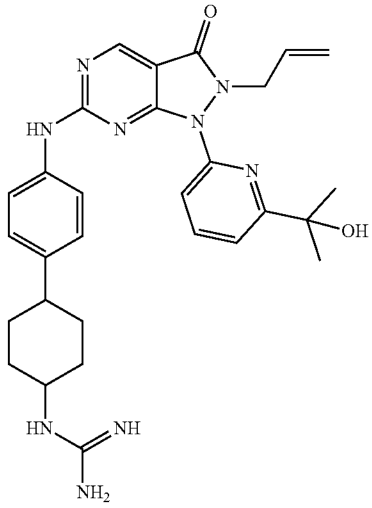

I-20

2-Allyl-6-((4-(4-aminocyclohexyl)phenyl)amino)-1-(6-(2-hydroxypropan-2-yl)pyridin-2-yl)-1,2-dihydro-3H-pyrazolo[3,4-d]pyrimidin-3-one (120 mg, 0.24 mmol) (compound represented by I-19-c), 1H-pyrazole-carboximidamide hydrochloride (45 mg, 0.31 mmol) and N,N-diisopropylethylamine (0.2 mL) were added to 5 mL of N,N-dimethylformamide, the mixture was stirred at 65° C. overnight. The reaction mixture was concentrated and separated by thin layer chromatography plate (7M ammonia methanol:dichloromethane=1:8) to obtain 30 mg of white solid (compound represented by I-20), the yield was 23%. LC-MS: m/z: $(M+H)^+$=542. $^1$H NMR (400 MHz, MeOD) δ 8.84 (s, 1H), 8.02 (m, 1H), 7.80 (m, 1H), 7.72-7.58 (m, 3H), 7.25 (m, 2H), 5.73 (ddt, J=16.5, 10.3, 6.1 Hz, 1H), 5.05 (dd, J=10.2, 1.0 Hz, 1H), 4.95 (d, 1H), 4.83 (d, J=6.1 Hz, 2H), 3.54-3.42 (m, 1H), 2.59 (m, 1H), 2.14 (m, 1H), 1.98 (m, 2H), 1.83 (m, 1H), 1.68 (m, 2H), 1.60 (s, 6H), 1.50 (m, 2H).

Embodiment 23

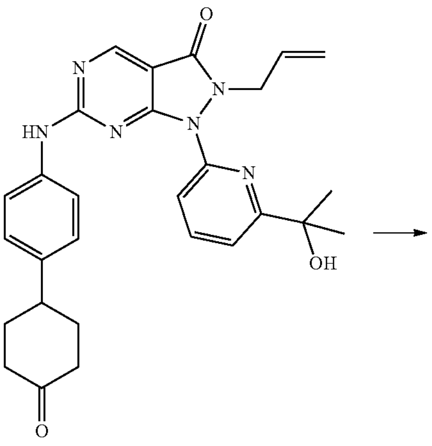

I-19-d

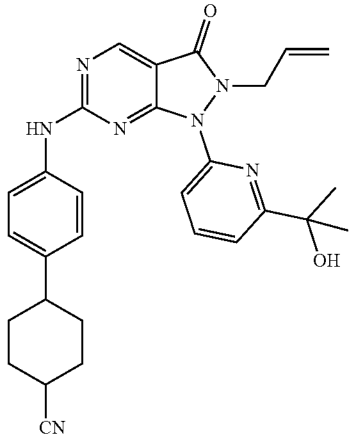

I-23

Potassium tert-butoxide (2 equiv., 0.2006 mmol) was dissolved in dry dimethyl sulfoxide (1 mL, 100 mass %), and then a solution of tosylmethyl isocyanide (1.5 equiv., 0.1504 mmol) in dry dimethyl sulfoxide (1 mL) was added thereto at room temperature. Compound (I-19-d) (50 mg, 0.1003 mmol) was dissolved in dry methanol (0.5 mL), the solution was added to the above reaction mixture, and then the reaction was stirred at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/methanol system, methanol concentration from 0% to 10%, 12 column volumes) to obtain compound (I-23): (15 mg, 0.02943 mmol), the yield was 29.35%, yellow solid. $^1$H NMR (400 MHz, DMSO) δ 10.28 (s, 1H), 8.88 (d, J=1.8 Hz, 1H), 8.09-7.97 (m, 1H), 7.75 (d, J=8.4 Hz, 1H), 7.66 (dd, J=20.6, 8.5 Hz, 3H), 7.19 (dd, J=11.1, 8.7 Hz, 2H), 5.74-5.61 (m, 1H), 5.00 (d, J=10.2 Hz, 1H), 4.82 (d, J=17.1 Hz, 1H), 4.69 (d, J=5.5 Hz, 2H), 3.23 (s, 1H), 2.74 (t, J=12.1 Hz, 1H), 2.53 (s, 1H), 2.12 (d, J=10.1 Hz, 1H), 1.98 (d, J=13.2 Hz, 1H), 1.82 (d, J=13.2 Hz, 2H), 1.77-1.57 (m, 3H), 1.49 (d, J=18.2 Hz, 6H). LC-MS: m/z: $(M+H)^+$=510.2.

Embodiment 31

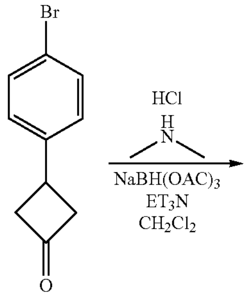

I-31-a

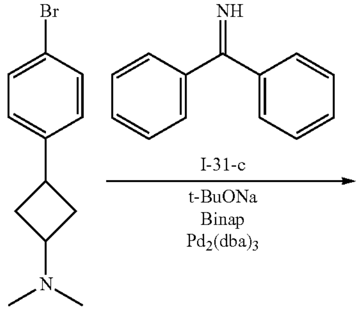

I-31-b

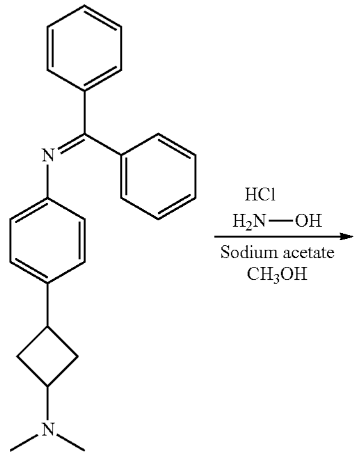

I-31-d

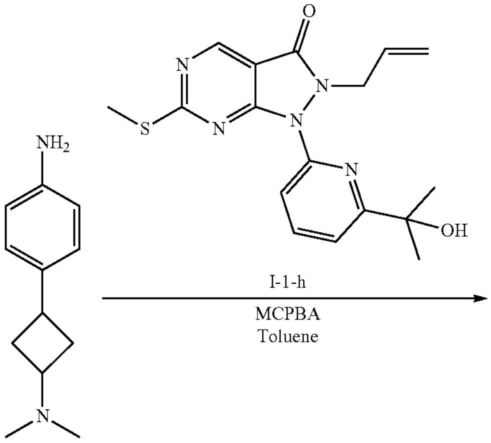

I-31-e

-continued

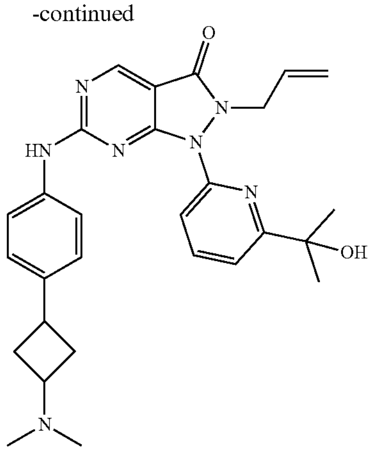

I-31

Step 1:

3-(4-Bromophenyl)cyclobutanone (I-31-a) (4.40 mmol) was dissolved in dichloromethane (10 mL); triethylamine (8.9 mmol), dimethylamine hydrochloride (8.9 mmol) and sodium triacetoxyborohydride (8.9 mmol) were added to the reaction mixture, and the reaction mixture was stirred at room temperature for 16 hours. The pH value of the reaction mixture was adjusted to 9 with potassium carbonate aqueous solution, the mixture was extracted with dichloromethane, the organic phase was washed with saturated saline, dried over anhydrous sodium sulfate, filtered, and the filtrate was evaporated to dryness to obtain 1.1 g of the crude target compound 3-(4-bromophenyl)-N,N-dimethylcyclobutylamine (represented by I-31-b) as a colorless oil, the yield was 97%. LC-MS: m/z: $(M+H)^+$=255.4.

Step 2:

3-(4-Bromophenyl)-N,N-dimethylcyclobutylamine (I-31-b) (4.30 mmol) was dissolved in toluene (20 mL); and diphenylmethylamine (I-31-c) (4.8 mmol), sodium tert-butoxide (6.9 mmol), 1,1'-binaphthyl-2,2'-bis(diphenylphosphine) (0.43 mmol) and tris(dibenzylideneacetone)dipalladium (0.13 mmol) were added to the reaction mixture, then the reaction was heated to 90° C. and stirred for 16 hours under the protection of nitrogen. The reaction mixture was cooled to room temperature, and concentrated to obtain a crude product, and the crude product was purified by column chromatography (dichloromethane/methanol=100/0-95/5) to obtain 1.5 g of target compound 3-(4-((diphenylmethylene)amino)phenyl)-N,N-dimethylcyclobutanamine (I-31-d) as a colorless oil, the yield was 98%. LC-MS: m/z: $(M+H)^+$ =355.3.

Step 3:

4-(3-Dimethylamino)cyclobutyl)aniline (I-31-d) (4.2 mmol) was dissolved in methanol (20 mL), sodium acetate (13.0 mmol) and hydroxylamine hydrochloride (8.5 mmol) were added to the reaction mixture, and the reaction mixture was stirred at 50° C. for 16 hours. The reaction mixture was evaporated to dryness to obtain a crude product, and the crude product was purified by column chromatography (dichloromethane/methanol=100/0-95/5) to obtain 0.75 g of the target compound 4-(3-dimethylamino)cyclobutyl) aniline (I-31-e), the yield was 93%. LC-MS: m/z: $(M+H)^+$=191.3.

Step 4:

2-Allyl-1-(7-hydroxy-7-methyl-6,7-dihydro-5H-cyclopenta[b]pyridin-2-yl)-6-(methylthio)-1,2-dihydro-3H-pyrazolo[3,4-d]pyrimidin-3-one (I-1-h) (0.65 mmol) was dissolved in toluene (20 mL), and 3-chloroperoxybenzoic acid (0.62 mmol) was added thereto, and the reaction mixture was stirred for 0.5 hours at room temperature. 4-(3-Dimethylamino)cyclobutyl)aniline (I-31-e)(0.67 mmol) was added to the reaction mixture, and the reaction mixture was stirred at room temperature for 16 hours. The reaction mixture was evaporated to dryness to obtain a crude product, the crude product was slurried with ethyl acetate and dichloromethane to obtain 92 mg of target compound 2-allyl-6-((4-(3-(dimethylamino)cyclobutyl)phenyl)amino)-1-(6-(2-hydroxypropan-2-yl)pyridin-2-yl)-1,2-dihydro-3H-pyrazolo[3,4-d]pyrimidin-3-one (I-31) as a white solid, the yield was 32.9%. $^1$H NMR (400 MHz, DMSO) δ 10.27 (s, 1H), 8.89 (s, 1H), 8.12 (s, 1H), 7.74 (dd, J=22.6, 8.3 Hz, 3H), 7.64 (d, J=7.3 Hz, 1H), 7.37 (d, J=8.5 Hz, 2H), 5.76-5.61 (m, 1H), 5.34 (s, 1H), 5.01 (dd, J=10.3, 1.2 Hz, 1H), 4.84 (d, J=17.1 Hz, 1H), 4.70 (d, J=5.7 Hz, 2H), 3.62 (s, 1H), 3.12 (s, 1H), 2.71-2.58 (m, 8H), 2.38 (d, J=9.2 Hz, 2H), 1.47 (s, 6H), 1.32-1.24 (m, 1H). LC-MS: m/z: $(M+H)^+$=500.3.

Embodiment 32

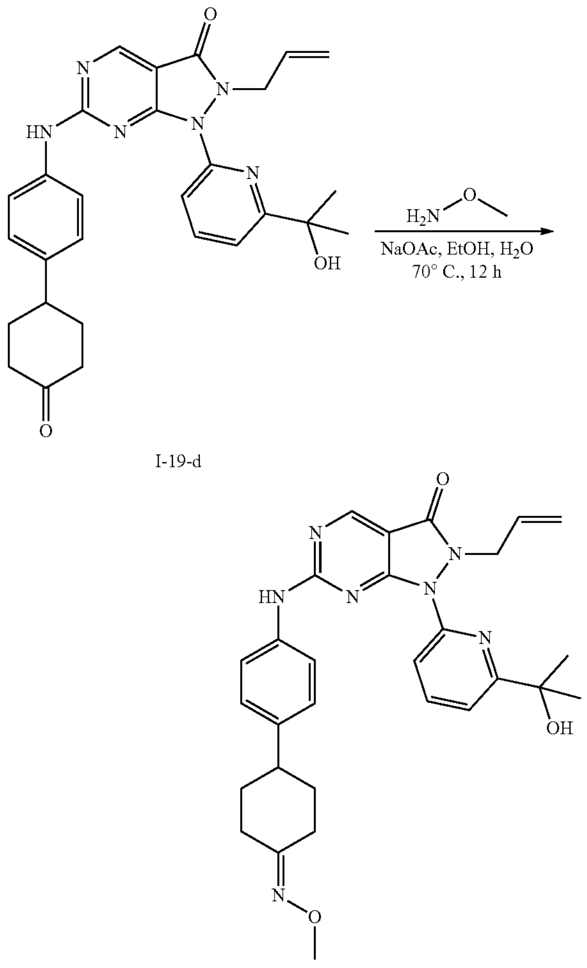

I-19-d

I-32

Compound (I-19-d) (80 mg, 0.1604 mmol, 100 mass %) was dissolved in ethanol (4 mL, 100 mass %), then water (2 mL, 100 mass %) and hydroxylamine hydrochloride (3 equiv., 0.4813 mmol, 100 mass %) were added at room temperature, and the reaction was stirred at 70° C. for 12 hours. The reaction was quenched with aq. $NaHCO_3$ and extracted with ethyl acetate (2×20 mL), the organic phase was washed with saline (1×20 mL), dried over $Na_2SO_4$, filtered and concentrated to obtain a crude product. The crude product was washed with 2 mL of methanol and filtered to obtain compound (I-32) (60 mg, 0.1137 mmol), the yield was 70.88%, white solid. $^1$H NMR (400 MHz, DMSO) δ 10.26 (s, 1H), 8.88 (s, 1H), 8.07 (t, J=7.8 Hz, 1H), 7.76 (d, J=8.0 Hz, 1H), 7.65 (dd, J=14.5, 7.9 Hz, 2H), 7.22 (d, J=8.5 Hz, 2H), 5.74-5.60 (m, 1H), 5.35 (s, 1H), 5.00 (d, J=10.3 Hz, 1H), 4.83 (d, J=17.1 Hz, 1H), 4.69 (d, J=5.6 Hz, 2H), 3.74 (s, 3H), 3.24-3.15 (m, 1H), 2.77 (t, J=12.0 Hz, 1H), 2.37 (d, J=14.0 Hz, 1H), 2.25 (td, J=13.4, 4.6 Hz, 1H), 1.99-1.84 (m, 3H), 1.67-1.50 (m, 2H), 1.49 (d, J=14.0 Hz, 6H). LC-MS: m/z: $(M+H)^+$=528.

Embodiment 33

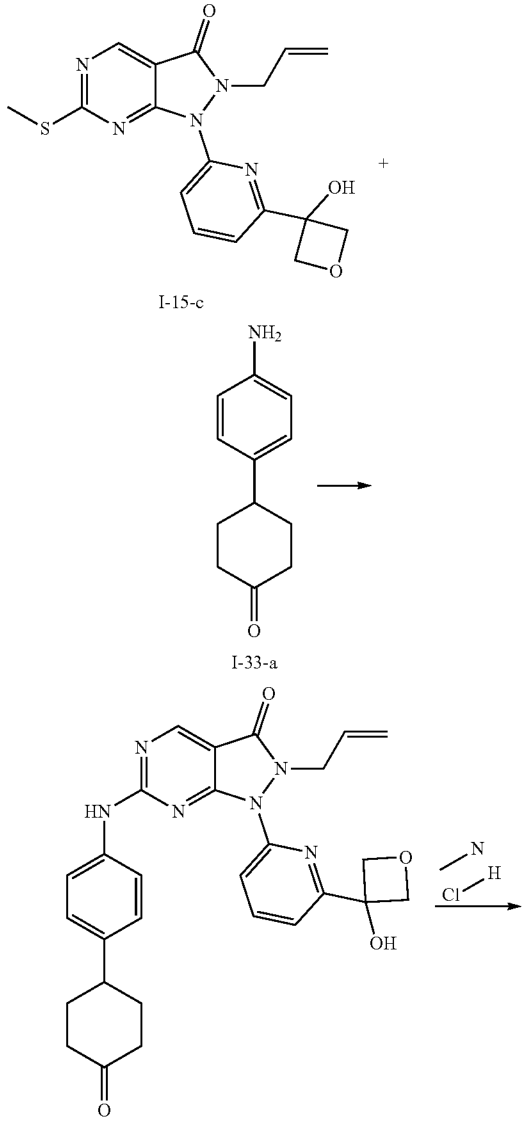

I-15-c

I-33-a

I-33-b

-continued

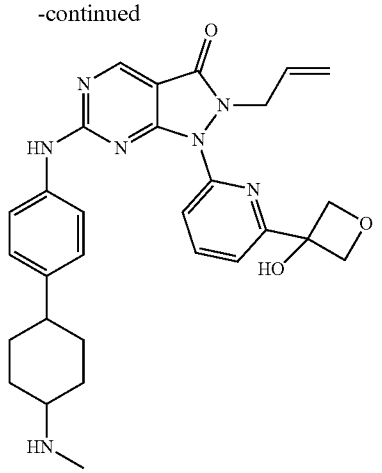

I-33

Step 1:

Compound (I-15-c) (400 mg, 1.077 mmol) was dissolved in toluene (20 mL), then m-CPBA (1.2 equiv., 1.292 mmol, 77 mass %) was added thereto at room temperature, and the reaction was stirred for 2 hours at room temperature. Compound (I-33-a) (1.2 equiv., 1.292 mmol) and DIPEA (2 equiv., 2.154 mmol) were added to the above reaction mixture sequentially, and the reaction was continued with stirring at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: ethyl acetate/dichloromethane system, ethyl acetate concentration from 0% to 10%, 24 column volumes) to obtain compound (I-33-b): (120 mg, 0.2341 mmol), the yield was 21.74%, yellow solid. $^1$H NMR (400 MHz, DMSO) δ 8.91 (d, J=2.4 Hz, 1H), 8.11 (t, J=7.9 Hz, 1H), 7.89 (d, J=8.3 Hz, 1H), 7.68 (d, J=8.2 Hz, 2H), 7.57 (d, J=7.7 Hz, 1H), 7.28 (d, J=8.6 Hz, 2H), 5.72 (ddd, J=23.0, 10.3, 5.9 Hz, 1H), 5.02 (dd, J=10.3, 1.3 Hz, 1H), 4.95-4.89 (m, 2H), 4.87 (d, J=1.4 Hz, 1H), 4.75 (d, J=5.8 Hz, 1H), 4.70 (t, J=6.2 Hz, 2H), 3.04 (t, J=11.9 Hz, 1H), 2.67-2.53 (m, 2H), 2.30 (t, J=15.0 Hz, 2H), 2.08 (d, J=10.0 Hz, 2H), 1.96-1.81 (m, 2H).

Step 2:

Compound (I-33-b) (100 mg, 0.1951 mmol) was dissolved in methanol (3 mL); and DIPEA (5 equiv., 0.9754 mmol) was added thereto, and the reaction was stirred for 5 min at room temperature. Then, $Na(OAc)_3BH$ (3 equiv., 0.5853 mmol) was added, and the reaction was continued with stirring at room temperature for 12 hours. The reaction was quenched with aq. $NaHCO_3$, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/methanol (1% ammonia methanol) system, methanol concentration from 0% to 10%, 12 column volumes) to obtain compound (I-33): (80 mg, 0.15 mmol), the yield was 77.3%, white solid. $^1$H NMR (400 MHz, MeOD) δ 8.86 (s, 0H), 8.11-8.01 (m, 1H), 7.94 (d, J=7.9 Hz, 2H), 7.67 (d, J=7.6 Hz, 2H), 7.62 (d, J=8.6 Hz, 2H), 7.28 (d, J=8.5 Hz, 2H), 5.83-5.74 (m, 1H), 5.09 (dd, J=7.9, 4.4 Hz, 3H), 4.98 (dd, J=17.1, 1.3 Hz, 2H), 4.85 (d, J=6.7 Hz, 2H), 2.87 (s, 1H), 2.64 (s, 1H), 2.47 (s, 3H), 1.97-1.67 (m, 8H). LC-MS: m/z: $(M+H)^+$=529.2.

Embodiment 34

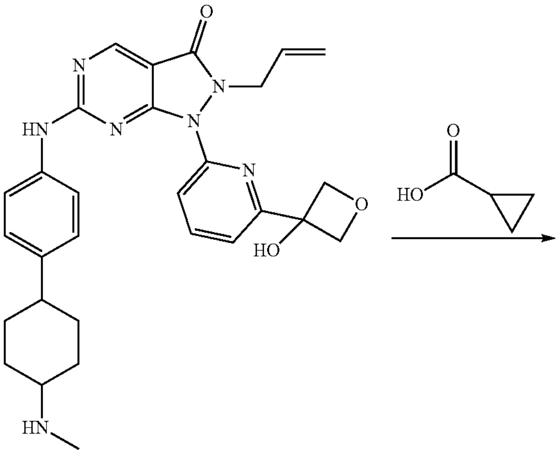

I-33

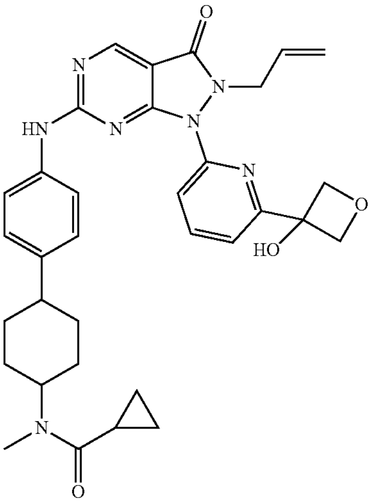

I-34

Compound (I-33) (40 mg, 0.07582 mmol), cyclopropylacetic acid (1.1 eq., 73 mg) were dissolved in dichloromethane (2 mL), then DIPEA (2 equiv., 0.1516 mmol) and HATU (1 equiv., 0.07582 mmol) were added sequentially, and the reaction was stirred for 6 hours at room temperature. The reaction was quenched with water, and extracted with dichloromethane (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/methanol system, methanol concentration from 0% to 10%, 12 column volumes) to obtain compound (I-34): (10 mg, 0.01679 mmol), the yield was 22.14%, yellow solid. $^1$H NMR (400 MHz, MeOD) δ 8.87 (d, J=6.6 Hz, 1H), 8.06 (t, J=7.9 Hz, 1H), 7.95 (d, J=7.9 Hz, 1H), 7.68 (dd, J=7.8, 5.4 Hz, 2H), 7.61 (d, J=8.6 Hz, 1H), 7.41 (d, J=8.4 Hz, 1H), 7.24 (t, J=8.7 Hz, 1H), 5.84-5.72 (m, 1H), 5.09 (d, J=6.2 Hz, 2H), 5.07 (d, J=1.3 Hz, 1H), 5.02-4.94 (m, 2H), 4.90 (s, 2H), 4.84 (d, J=6.7 Hz, 2H), 3.15 (d, J=2.6 Hz, 1H), 3.08 (s, 1H), 2.95 (s, 1H), 2.71 (s, 1H), 2.43 (s, 1H), 1.93-2.03 (m, 3H), 1.76 (s, 2H), 1.51 (s, 1H), 1.31 (d, J=4.3 Hz, 3H), 0.89 (dd, J=20.1, 9.0 Hz, 4H). LC-MS: m/z: $(M+H)^+$=596.2.

Embodiment 35

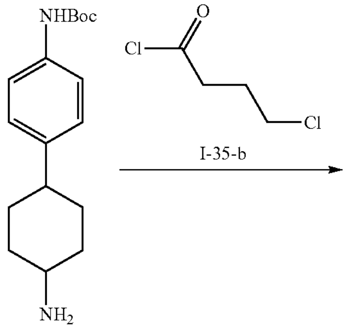

I-35-a

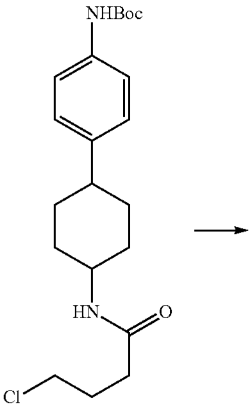

I-35c

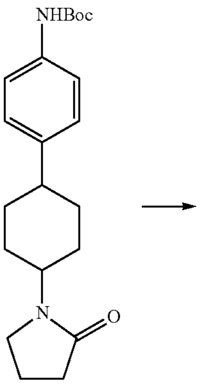

I-35-d

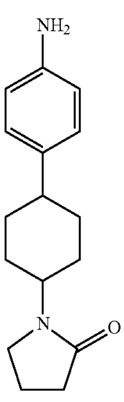

I-35-e

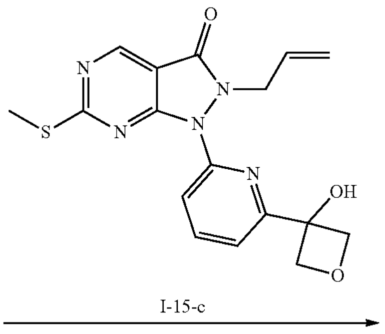

-continued

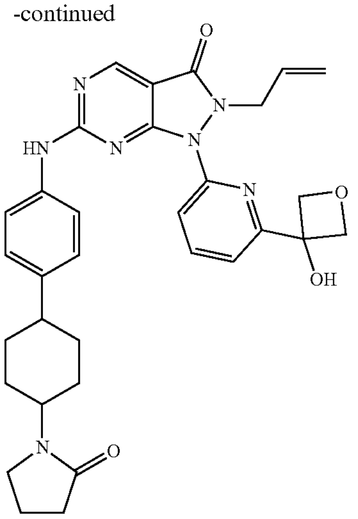

I-35

Step 1:

Compound (I-35-a) (100 mg, 0.3444 mmol) was dissolved in tetrahydrofuran (5 mL), and TEA (5 equiv., 1.722 mmol) and compound (I-35-b) (2 equiv., 0.6887 mmol) were added, and the reaction was stirred for 8 hours at room temperature. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: petroleum ether/ethyl acetate system, ethyl acetate concentration from 10% to 60%, 12 column volumes) to obtain compound (I-35-c): (100 mg, 0.2532 mmol), the yield was 73.54%, white solid. LC-MS: m/z: $(M+H-tBu)^+$=339.1.

Step 2:

Compound (I-35-c) (200 mg, 0.5065 mmol) was dissolved in tetrahydrofuran (5 mL), then sodium hydride (2 equiv., 1.013 mmol, 60 mass %) was added thereto, and the reaction was stirred for 2 hours at 50° C. The reaction was quenched with water, and extracted with ethyl acetate (2×20 mL), the the organic phase was washed with saline (1×20 mL), dried over $Na_2SO_4$, filtered and concentrated to obtain compound (I-35-d): (180 mg, 0.502 mmol), the yield was 99.14%, white solid. $^1H$ NMR (400 MHz, MeOD) δ7.31 (dt, J=11.6, 8.5 Hz, 3H), 7.15 (d, J=8.5 Hz, 1H), 4.07-3.92 (m, 1H), 3.47 (dt, J=29.5, 7.2 Hz, 2H), 2.39 (dt, J=16.3, 8.1 Hz, 2H), 2.22 (d, J=10.1 Hz, 1H), 2.03 (s, 4H), 1.84-1.57 (m, 6H), 1.53 (d, J=2.8 Hz, 9H). LC-MS: m/z: $(M+H)^+$=359.1.

Step 3:

Compound (I-35-d) (180 mg, 0.669 mmol) was dissolved in dichloromethane (4 mL), then trifluoroacetic acid (1 mL) was added thereto, and the reaction was stirred for 12 hours at room temperature. After the reaction mixture was concentrated, aq. $NaHCO_3$ was added thereto, and the mixture was extracted with ethyl acetate (2×20 mL); the organic phase was washed with saline (1×20 mL), dried over $Na_2SO_4$, filtered and concentrated to obtain compound (I-35-e): (120 mg, 0.464 mmol), the yield was 100%, yellow solid. LC-MS: m/z: $(M+H)^+$=259.1.

Step 4:

Compound (I-15-c) (100 mg, 0.2693 mmol) was dissolved in toluene (2 mL), then m-CPBA (1.2 equiv., 0.3231 mmol, 77 mass %) was added thereto at room temperature, and the reaction was stirred for 2 hours at room temperature. Compound (I-35-e) (1.2 equiv., 0.3231 mmol) and DIPEA (2 equiv., 0.5385 mmol) were added to the above reaction mixture at room temperature sequentially, and the reaction was continued with stirring at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/tetrahydrofuran system, tetrahydrofuran concentration from 0% to 30%, 12 column volumes) to obtain compound (I-35): (40 mg, 0.06876 mmol), the yield was 25.54%, white solid. $^1H$ NMR (400 MHz, $CDCl_3$) δ 8.87-8.79 (m, 1H), 8.14-8.07 (m, 1H), 8.04-7.96 (m, 1H), 7.89-7.80 (m, 1H), 7.61-7.50 (m, 2H), 7.38-7.32 (m, 1H), 7.25-7.19 (m, 1H), 7.01 (t, J=3.4 Hz, 1H), 5.72 (ddd, J=16.6, 11.1, 8.6 Hz, 1H), 5.17-5.09 (m, 2H), 5.04-4.98 (m, 1H), 4.98-4.92 (m, 1H), 4.87-4.77 (m, 2H), 4.73-4.64 (m, 2H), 4.20-4.06 (m, 1H), 3.47-3.38 (m, 1H), 3.38-3.29 (m, 1H), 3.05-2.98 (m, 1H), 2.49-2.35 (m, 2H), 2.27-2.17 (m, 1H), 2.07-1.86 (m, 4H), 1.75-1.60 (m, 3H). LC-MS: m/z: $(M+H)^+$=582.2.

Embodiment 36

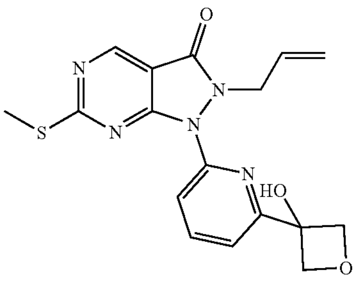

I-15-c

+

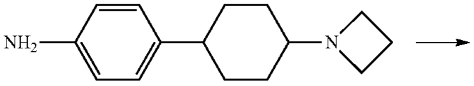

I-36-a

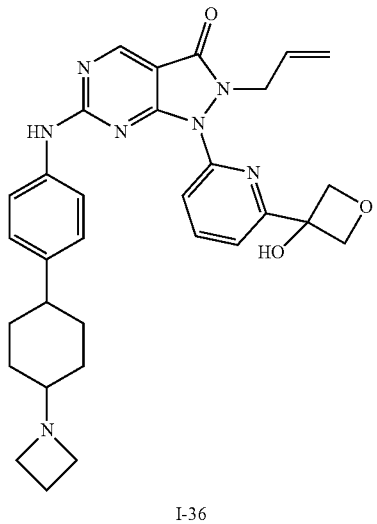 [SMILES: C=CCn1c(=O)c2cnc(Nc3ccc(C4CCC(N5CCC5)CC4)cc3)nc2n1-c1cccc(C2(O)COC2)n1 ; "I-36-2"]

I-36

-continued

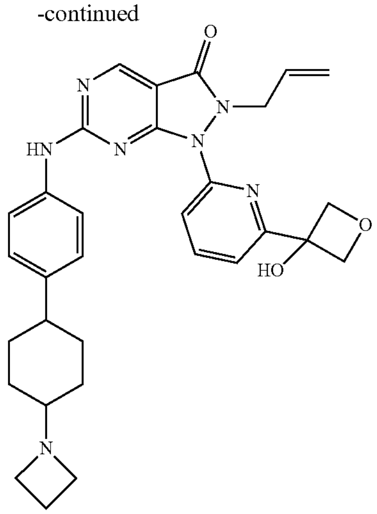

I-36-1

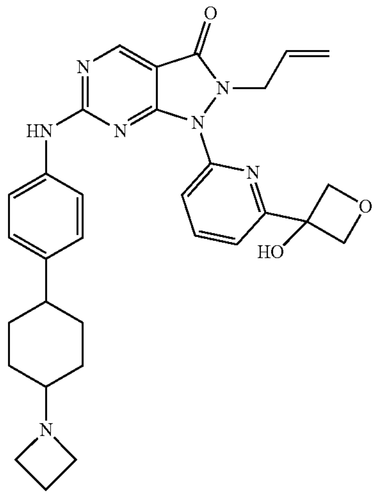

I-36-2

2-Allyl-1-(6-(3-hydroxyoxetan-3-yl)pyridin-2-yl)-6-(methylthio)-1,2-dihydro-3H-pyrazolo[3,4-d]pyrimidin-3-one (represented by formula 1-15-c) (200 mg, 0.538 mmol) was dissolved in 5 mL of toluene, and 3-chloroperoxybenzoic acid (140 mg, 0.69 mmol) was added thereto, and the reaction mixture was stirred at 20° C. for 2 hours. The reaction mixture was concentrated to dryness under reduced pressure. The obtained solid was dissolved in 5 mL of DMSO, and trifluoroacetic acid (20 mg, 0.2 mmol) and 4-(4-(azetidin-1-yl)cyclohexyl)aniline (represented by formula I-36-a) (140 mg, 0.64 mmol) were added, and the reaction mixture was stirred at 65° C. for 16 hours. The reaction was quenched with water and then extracted with dichloromethane (30 mL*3), the organic layer was dried over anhydrous sodium sulfate, concentrated and purified by column chromatography (methanol/dichloromethane/ethyl acetate=0.5:10:4 to 1:10:4) to obtain a yellow solid (I-36-2) (22 mg, 7.4%) and a yellow solid (I-36-1) (64 mg, 21.4%). Compound I-36-1: HPLC retention time (RT)=7.14 min (HPLC conditions: mobile phase A was water (containing HCOOH 0.1%), mobile phase B was acetonitrile; gradient elution: 5% mobile phase B→95% mobile phase B), $^1H$ NMR (400 MHz, $CDCl_3$) δ8.88 (d, J=2.6 Hz, 1H), 8.09 (dd, J=15.0, 7.8 Hz, 1H), 7.99-7.83 (m, 2H), 7.54 (t, J=9.5 Hz, 2H), 7.39 (d, J=8.7 Hz, 1H), 7.21 (d, J=8.5 Hz, 1H), 5.74

(dq, J=10.5, 5.9 Hz, 1H), 5.12 (t, J=8.8 Hz, 3H), 4.99 (d, J=17.1 Hz, 1H), 4.80 (d, J=6.3 Hz, 2H), 4.67 (d, J=6.0 Hz, 2H), 3.39-3.24 (m, 4H), 2.60-2.34 (m, 3H), 2.14 (dt, J=14.0, 6.8 Hz, 3H), 1.96 (d, J=10.8 Hz, 4H), 1.55-1.37 (m, 2H), 1.27-1.12 (m, 2H); LC-MS: m/z: $(M+H)^+$=554.1. Compound I-36-2: HPLC retention time (RT)=7.15 min (HPLC conditions: mobile phase A was water (containing HCOOH 0.1%), mobile phase B was acetonitrile; gradient elution: 5% mobile phase B→95% mobile phase B), $^1$H NMR (400 MHz, MeOD) δ8.86 (s, 1H), 8.02 (dt, J=24.0, 7.9 Hz, 3H), 7.64 (dd, J=27.1, 8.1 Hz, 3H), 7.27 (t, J=8.6 Hz, 2H), 7.01-6.91 (m, 3H), 6.72-6.64 (m, 3H), 5.79 (ddd, J=16.3, 11.2, 6.1 Hz, 1H), 5.10-5.05 (m, 2H), 4.85 (d, J=6.8 Hz, 2H), 2.57 (d, J=10.7 Hz, 1H), 2.48-2.28 (m, 3H), 2.23-2.06 (m, 3H), 1.98-1.71 (m, 6H), 1.58 (dd, J=23.2, 12.9 Hz, 3H), 1.44 (ddd, J=16.1, 13.2, 3.5 Hz, 2H), 1.19-1.00 (m, 2H); LC-MS: m/z: $(M+H)^+$=554.1.

Embodiment 37

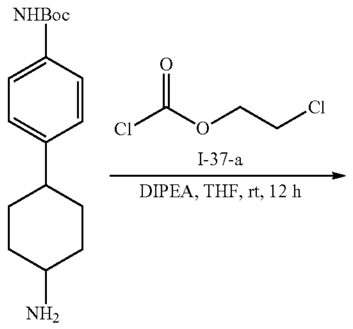

I-35-a

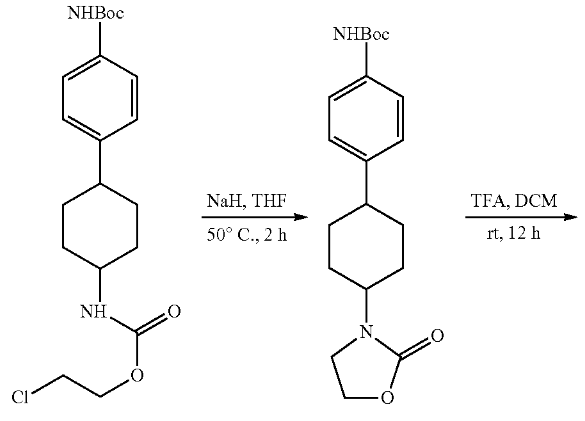

I-37-b

I-37-c

-continued

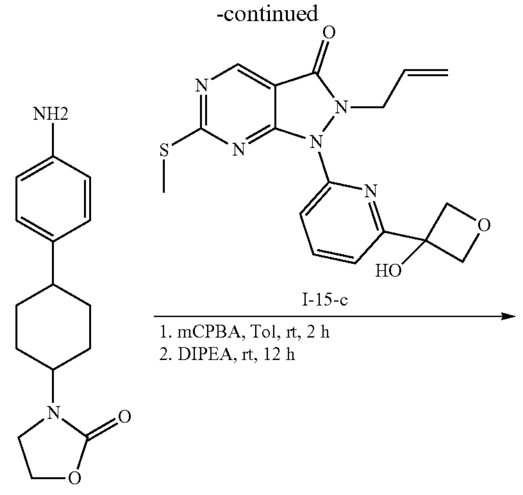

I-37-d

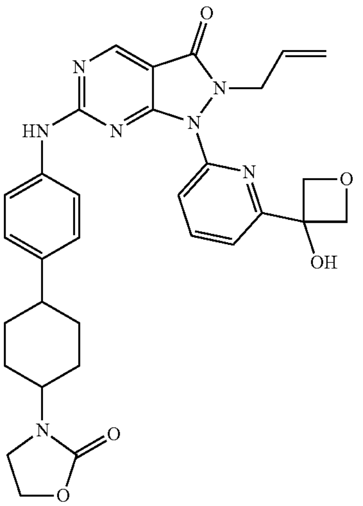

I-37

Step 1:

Compound (I-35-a) (150 mg, 0.5165 mmol) was dissolved in tetrahydrofuran (6 mL), and DIPEA (5 equiv., 2.583 mmol) and compound (I-35-a) (3 equiv., 1.550 mmol) were added thereto, and the reaction was stirred for 12 hours at room temperature. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: petroleum ether/ethyl acetate system, ethyl acetate concentration from 0% to 40%, 12 column volumes) to obtain compound (I-37-b): (120 mg, 0.3023 mmol), the yield was 58.53%, white solid. $^1$H NMR (400 MHz, MeOD) δ 7.38-7.27 (m, 2H), 7.24-7.18 (m, 1H), 7.18-7.09 (m, 1H), 4.38-4.23 (m, 2H), 3.83-3.67 (m, 2H), 2.63 (td, J=14.1, 6.0 Hz, 1H), 2.52-2.37 (m, 1H), 2.31 (s, 1H), 2.25-2.13 (m, 1H), 2.00-1.84 (m, 3H), 1.82-1.63 (m, 3H), 1.53 (s, 9H).

Step 2:

Compound (I-37-b) (120 mg, 0.30 mmol) was dissolved in tetrahydrofuran (5 mL), then sodium hydride (2 equiv., 0.607 mmol, 60 mass %) was added thereto, and the reaction was stirred for 2 hours at 50° C. The reaction was quenched with water, and extracted with ethyl acetate (2×20 mL), the the organic phase was washed with saline (1×20 mL), dried over $Na_2SO_4$, filtered and concentrated to obtain compound (I-37-c): (80 mg, 0.22 mmol), the yield was 73.4%, white solid. $^1$H NMR (400 MHz, MeOD) δ7.31 (dt, J=18.7, 8.6 Hz, 3H), 7.15 (d, J=8.5 Hz, 1H), 4.42-4.26 (m, 2H), 3.66 (ddd, J=16.1, 12.2, 5.9 Hz, 2H), 2.50 (s, 1H), 2.15 (dd, J=17.3, 6.4 Hz, 2H), 1.99-1.79 (m, 4H), 1.77-1.61 (m, 3H), 1.53 (d, J=1.7 Hz, 9H). LC-MS: m/z: $(M+H)^+$=305.1.

Step 3:

Compound (I-37-c) (80 mg, 0.22 mmol) was dissolved in dichloromethane (2 mL), then trifluoroacetic acid (1 mL) was added thereto, and the reaction was stirred for 12 hours at room temperature. The reaction mixture was concentrated, then aq. $NaHCO_3$ was added thereto, and the mixture was extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: petroleum ether/ethyl acetate system, ethyl acetate concentration from 0% to 50%, 12 column volumes) to obtain compound (I-37-d): (60 mg, 0.2305 mmol), the yield was 100%, yellow solid. $^1$H NMR (400 MHz, MeOD) δ 7.11 (d, J=8.1 Hz, 1H), 7.00 (d, J=8.3 Hz, 1H), 6.78-6.66 (m, 2H), 4.40-4.29 (m, 2H), 3.70-3.57 (m, 4H), 2.10 (d, J=17.5 Hz, 1H), 1.97-1.81 (m, 4H), 1.72-1.57 (m, 3H). LC-MS: m/z: $(M+H)^+$=261.1.

Step 4:

Compound (I-15-c) (60 mg, 0.1616 mmol) was dissolved in toluene (2 mL), then m-CPBA (1.2 equiv., 0.1939 mmol, 77 mass %) was added thereto at room temperature, and the reaction was stirred for 2 hours at room temperature. Compound (I-37-d) (1.4 equiv., 0.2262 mmol) and DIPEA (2 equiv., 0.3231 mmol) were added to the above reaction mixture at room temperature sequentially, and the reaction was continued with stirring at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/tetrahydrofuran system, tetrahydrofuran concentration from 0% to 50%, 12 column volumes) to obtain compound (I-37): (15 mg, 0.02570 mmol), the yield was 15.91%, yellow solid. $^1$H NMR (400 MHz, $CDCl_3$) δ8.77 (s, 1H), 8.16-8.07 (m, 1H), 8.03 (d, J=7.6 Hz, 1H), 7.83-7.75 (m, 1H), 7.56 (dd, J=12.6, 6.1 Hz, 2H), 7.33 (d, J=8.5 Hz, 1H), 7.21 (d, J=8.5 Hz, 1H), 5.72 (dd, J=17.0, 10.3 Hz, 1H), 5.13 (dd, J=9.1, 6.1 Hz, 2H), 4.96 (d, J=17.0 Hz, 2H), 4.81 (d, J=7.2 Hz, 2H), 4.69 (d, J=6.2 Hz, 2H), 4.41-4.28 (m, 2H), 3.86 (s, 1H), 3.77 (t, J=6.6 Hz, 1H), 3.63-3.50 (m, 2H), 2.98 (m, 1H), 2.15 (m, 1H), 1.97 (dd, J=18.9, 9.6 Hz, 2H), 1.78 (d, J=5.0 Hz, 2H), 1.65 (d, J=8.7 Hz, 2H). LC-MS: m/z: $(M+H)^+$=584.1.

Embodiment 38

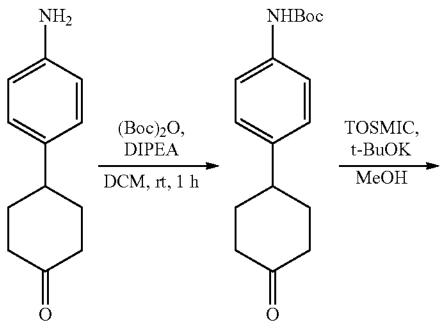

I-33-a

I-38-a

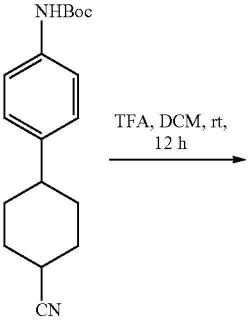

I-38-b

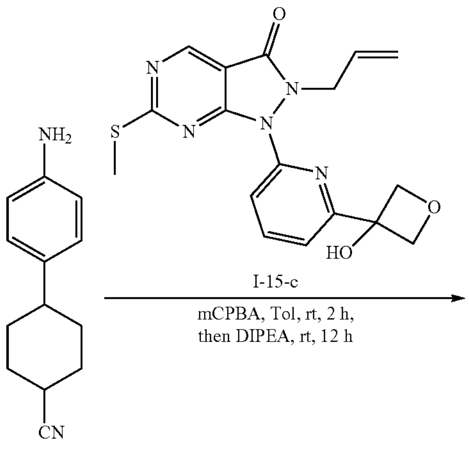

I-15-c

I-38-c

-continued

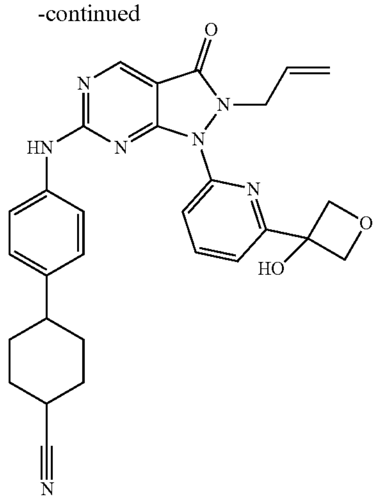

I-38

Step 1:

Compound (I-33-a) (150 mg, 0.79260 mmol) was dissolved in dichloromethane (2 mL), and then $(Boc)_2O$ (1.2 equiv., 0.95112 mmol) and DIPEA (2 equiv., 1.5852 mmol) were added thereto, and the reaction was stirred at room temperature for 12 hours. The reaction was quenched with water and extracted with dichloromethane (2×20 mL), the organic phase was washed with saline (1×20 mL), dried over $Na_2SO_4$, filtered and concentrated to obtain compound (I-38-a): (250 mg, 0.8639 mmol), the yield was 100.0%, yellow solid. $^1$H NMR (400 MHz, DMSO) δ 9.25 (s, 1H), 7.37 (d, J=8.4 Hz, 2H), 7.17 (d, J=8.6 Hz, 2H), 2.98 (ddd, J=12.0, 8.7, 3.3 Hz, 1H), 2.65-2.52 (m, 2H), 2.25 (dd, J=12.5, 2.0 Hz, 2H), 2.11-1.97 (m, 2H), 1.83 (ddd, J=25.9, 13.2, 4.0 Hz, 2H), 1.47 (s, 9H).

Step 2:

Potassium tert-butoxide (3 equiv., 1.866 mmol) was dissolved in dry tetrahydrofuran (1 mL), and then a solution of tosylmethyl isocyanide (1.5 equiv., 0.933 mmol) in dry tetrahydrofuran (1 mL) was added thereto at room temperature. Compound (I-38-a) (180 mg, 0.6220 mmol) was dissolved in dry methanol (0.5 mL), the solution was added to the above reaction mixture, and then the reaction was stirred at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/methanol system, methanol concentration from 0% to 10%, 12 column volumes) to obtain compound (I-38-b): (60 mg, 0.1997 mmol), the yield was 32.11%, yellow solid. LC-MS: m/z: $(M+H)^+$=244.7.

Step 3:

Compound (I-38-b) (50 mg, 0.16 mmol) was dissolved in dichloromethane (2 mL), then trifluoroacetic acid (1 mL) was added thereto, and the reaction was stirred for 12 hours at room temperature. After the reaction mixture was concentrated, aq. $NaHCO_3$ was added thereto, and the mixture was extracted with ethyl acetate (2×20 mL); the organic phase was washed with saline (1×20 mL), dried over $Na_2SO_4$, filtered and concentrated to obtain compound (I-38-c): (50 mg, 0.159 mmol), the yield was 96%, yellow solid. LC-MS: m/z: $(M+H)^+$=201.1.

Step 4:

Compound (I-15-c) (50 mg, 0.1346 mmol) was dissolved in toluene (2 mL), then m-CPBA (1.2 equiv., 0.1616 mmol, 77 mass %) was added thereto at room temperature, and the reaction was stirred for 2 hours at room temperature. Compound (I-38-c) (50 mg, 0.1346 mmol) and DIPEA (2 equiv., 0.2693 mmol) were added to the above reaction mixture at room temperature sequentially, and the reaction was continued with stirring at room temperature for 12 hours. The reaction was quenched with water, and extracted with ethyl acetate (2×20 mL), the the organic phase was washed with saline (1×20 mL), dried over $Na_2SO_4$, filtered and concentrated to obtain a crude product. The crude product was refined by normal phase silica gel column (elution conditions: dichloromethane/tetrahydrofuran system, tetrahydrofuran concentration from 0% to 30%, 12 column volumes) to obtain compound (I-38): (10 mg, 0.01910 mmol), the yield was 14.19%, white solid. $^1$H NMR (400 MHz, $CDCl_3$) δ 8.69 (s, 1H), 8.18 (d, J=8.0 Hz, 1H), 8.10 (dd, J=17.9, 7.6 Hz, 1H), 7.81-7.72 (m, 1H), 7.63-7.49 (m, 2H), 7.25 (d, J=8.4 Hz, 1H), 7.19 (d, J=8.3 Hz, 1H), 5.70 (d, J=6.8 Hz, 1H), 5.15 (d, J=10.1 Hz, 1H), 5.14-5.07 (m, 1H), 4.95 (d, J=16.6 Hz, 1H), 4.83 (t, J=6.7 Hz, 2H), 4.71 (s, 2H), 2.54 (dd, J=24.9, 12.6 Hz, 2H), 2.30 (d, J=11.2 Hz, 1H), 2.18 (d, J=13.5 Hz, 1H), 2.02 (d, J=12.9 Hz, 1H), 1.96-1.80 (m, 2H), 1.78 (d, J=16.1 Hz, 1H), 1.49 (dd, J=26.4, 11.2 Hz, 2H). LC-MS: m/z: $(M+H)^+$=524.1.

Embodiment 40

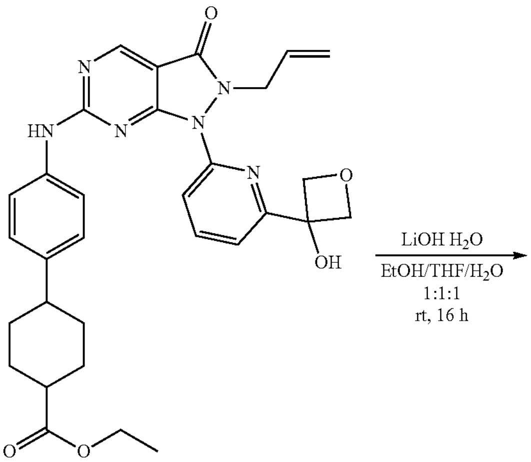

I-39

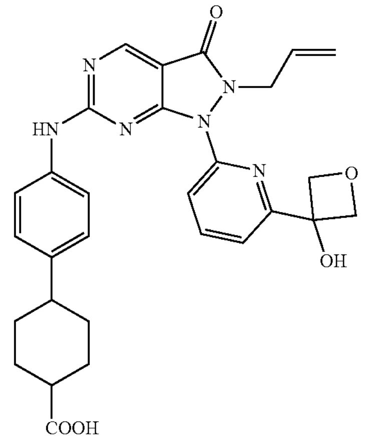

I-40

Compound (I-39) (70 mg, 0.12 mmol) was dissolved in a mixture of ethanol (2 mL), tetrahydrofuran (2 mL) and water (2 mL), then lithium hydroxide monohydrate (15 mg, 0.36 mmol) was added thereto, and the reaction mixture was concentrated after stirring at room temperature for 16 hours; the reaction mixture was purified by thin layer chromatography (dichloromethane: ammonia methanol (7 M): ethyl acetate=7:1:1) to obtain a white solid (I-40) (40 mg, 60%). $^{1}$H NMR (400 MHz, Methanol-$d_4$) δ 8.84 (s, 1H), 8.05 (t, J=7.9 Hz, 1H), 7.92 (d, J=8.1 Hz, 1H), 7.66 (dd, J=7.6, 0.9 Hz, 1H), 7.63-7.53 (m, 2H), 7.22-7.14 (m, 2H), 5.84-5.74 (m, 1H), 5.10-5.07 (m, 2H), 5.06 (q, J=1.3 Hz, 1H), 4.98 (dq, J=17.0, 1.4 Hz, 1H), 4.89 (dt, J=6.1, 1.4 Hz, 2H), 2.71 (d, J=6.9 Hz, 1H), 2.59 (s, 1H), 2.24 (dd, J=16.4, 7.8 Hz, 2H), 2.04 (d, J=8.5 Hz, 1H), 1.73 (td, J=10.9, 6.8 Hz, 6H). LC-MS: m/z: [M+1]+=543.0.

Embodiment 41

I-41

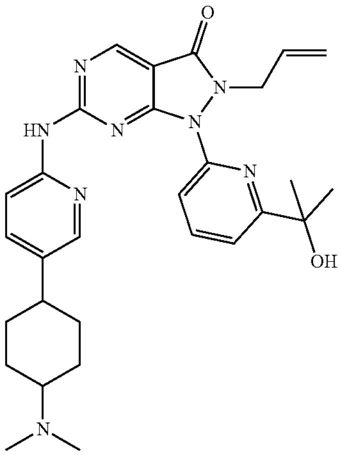

I-41-1

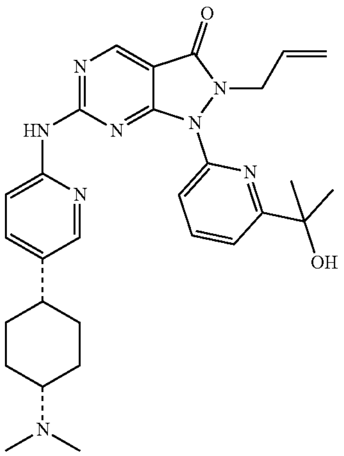

-continued

I-41-2

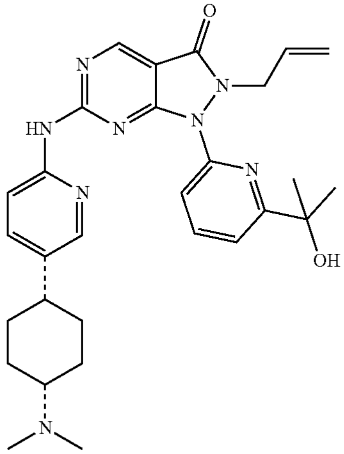

Compound (I-41-1) and compound (I-41-2) can be synthesized by the same method as in embodiment 1 using 5-bromo-2-nitropyridine as raw material. Compound 1-41-1: HPLC retention time (RT)=6.17 min (HPLC conditions: mobile phase A was water (containing HCOOH 0.1%), mobile phase B was acetonitrile; gradient elution: 5% mobile phase B→95% mobile phase B), $^{1}$H NMR (400 MHz, Chloroform-d) δ 9.00 (s, 1H), 8.30 (d, J=8.6 Hz, 1H), 8.22 (d, J=2.4 Hz, 1H), 7.96 (t, J=7.9 Hz, 1H), 7.73 (dd, J=8.1, 0.8 Hz, 1H), 7.55 (dd, J=8.7, 2.4 Hz, 1H), 7.44 (dd, J=7.7, 0.8 Hz, 1H), 5.77-5.66 (m, 1H), 5.12-5.05 (m, 1H), 4.97 (dq, J=17.0, 1.4 Hz, 1H), 4.76 (dt, J=6.3, 1.3 Hz, 2H), 2.70 (s, 1H), 2.56 (s, 6H), 2.23 (q, J=9.5 Hz, 4H), 2.11-2.01 (m, 4H), 1.58 (t, J=10.3 Hz, 6H). LC-MS: m/z: $[M+1]^+$ =529.1. Compound 1-41-2: HPLC retention time (RT)=6.28 min (HPLC conditions: mobile phase A was water (containing HCOOH 0.1%), mobile phase B was acetonitrile; gradient elution: 5% mobile phase B→95% mobile phase B), $^{1}$H NMR (400 MHz, Chloroform-d) δ8.99 (s, 1H), 8.54 (s, 1H), 8.32 (d, J=8.7 Hz, 1H), 8.26 (d, J=2.4 Hz, 1H), 8.10 (t, J=7.7 Hz, 1H), 7.92 (s, 1H), 7.78 (dd, J=8.1, 0.8 Hz, 1H), 7.47-7.41 (m, 1H), 5.79-5.71 (m, 1H), 5.08 (dq, J=10.1, 1.2 Hz, 1H), 4.97 (dq, J=17.0, 1.3 Hz, 1H), 4.77 (dt, J=6.2, 1.4 Hz, 2H), 3.99 (s, 1H), 2.75 (d, J=11.0 Hz, 1H), 2.52 (s, 6H), 2.32-2.18 (m, 1H), 2.09 (d, J=14.4 Hz, 4H), 1.31 (d, J=22.8 Hz, 4H). LC-MS: m/z: $[M+1]^+$=529.1.

With reference to the above embodiments, the compounds shown in Table 1 were prepared, and their structural characteristics were as follows:

TABLE 1

| List of compounds | | | |
|---|---|---|---|
| Compound | Structure | Characterization data | Method |
| I-2 | 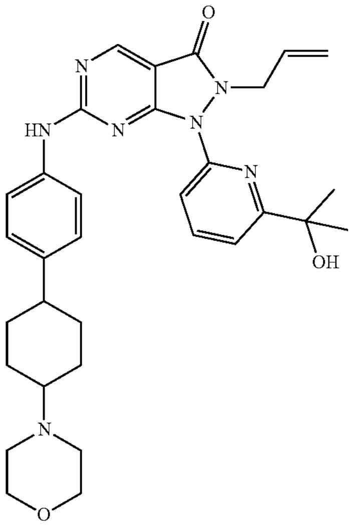<br>I-2 | $^1$H NMR (400 MHz, MeOD) δ 8.85 (s, 1H), 8.00 (t, J = 7.9 Hz, 1H), 7.80 (d, J = 8.1 Hz, 1H), 7.68 (d, J = 7.7 Hz, 1H), 7.62 (d, J = 8.6 Hz, 2H), 7.28 (d, J = 8.6 Hz, 2H), 5.78-5.68 (m, 1H), 5.06 (d, J = 10.3 Hz, 1H), 4.95 (s, 1H), 4.82 (s, 2H), 3.82-3.76 (m, 1H), 2.81 (s, 1H), 2.71 (s, 3H), 2.49 (s, 1H), 2.08 (d, J = 10.9 Hz, 3H), 1.94 (d, J = 15.0 Hz, 3H), 1.72 (s, 4H), 1.59 (d, J = 7.0 Hz, 6H). LC-MS: m/z: $(M + H)^+$ = 570.3. | I-1 |
| I-8 | 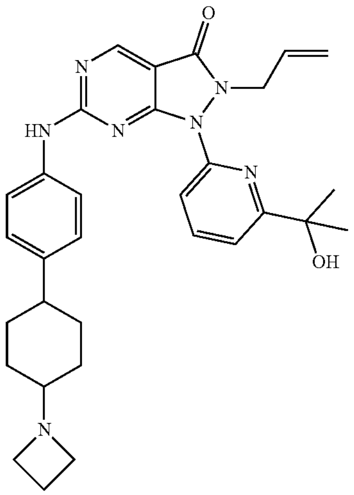<br>I-8 | $^1$H NMR (400 MHz, $CDCl_3$) δ 8.86 (s, 1H), 7.93-7.85 (m, 1H), 7.78 (d, J = 7.8 Hz, 1H), 7.52 (d, J = 8.5 Hz, 2H), 7.39 (dd, J = 7.6, 0.7 Hz, 1H), 7.19 (d, J = 8.5 Hz, 2H), 5.71 (ddt, J = 16.4, 10.2, 6.2 Hz, 1H), 5.05 (dd, J = 10.2, 1.1 Hz, 1H), 4.94 (dd, J = 17.1, 1.3 Hz, 1H), 4.77 (d, J = 6.2 Hz, 2H), 4.11 (d, J = 8.9 Hz, 1H), 3.24 (t, J = 7.0 Hz, 4H), 2.52-2.43 (m, 1H), 2.14-2.00 (m, 3H), 1.92 (d, J = 11.2 Hz, 4H), 1.60 (s, 6H), 1.45 (dt, J = 14.9, 7.5 Hz, 2H) 1.23-1.08 (m, 2H). LC-MS: m/z: $(M + H)^+$ = 540.4. | I-1 See embodiment 8 for details |

TABLE 1-continued

| List of compounds | | | |
|---|---|---|---|
| Compound | Structure | Characterization data | Method |
| I-8-1 | 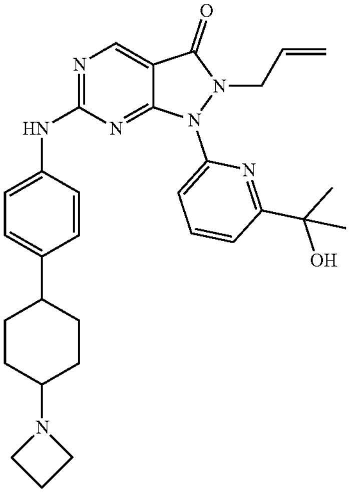 I-8-1 | $^1$H NMR (400 MHz, $CDCl_3$) δ 8.86 (s, 1H), 7.93-7.85 (m, 1H), 7.78 (d, J = 7.8 Hz, 1H), 7.52 (d, J = 8.5 Hz, 2H), 7.39 (dd, J = 7.6, 0.7 Hz, 1H), 7.19 (d, J = 8.5 Hz, 2H), 5.71 (ddt, J = 16.4, 10.2, 6.2 Hz, 1H), 5.05 (dd, J = 10.2, 1.1 Hz, 1H), 4.94 (dd, J = 17.1, 1.3 Hz, 1H), 4.77 (d, J = 6.2 Hz, 2H), 4.11 (d, J = 8.9 Hz, 1H), 3.24 (t, J = 7.0 Hz, 4H), 2.52-2.43 (m, 1H), 2.14-2.00 (m, 3H), 1.92 (d, J = 11.2 Hz, 4H), 1.60 (s, 6H), 1.45 (dt, J = 14.9, 7.5 Hz, 2H) 1.23-1.08 (m, 2H). LC-MS: m/z: $(M + H)^+$ = 540.4. After testing, its retention time was unique: HPLC retention time (RT) = 10.78 min (HPLC conditions: mobile phase A was water (containing HCOOH 0.1%), mobile phase B was acetonitrile; gradient elution: 5% mobile phase B→50% mobile phase B). Therefore, its cyclohexyl moiety was cis or trans. This can be further corroborated by together embodiment 8-2. | I-1 See embodiment 8-1 for details |
| I-8-2 | 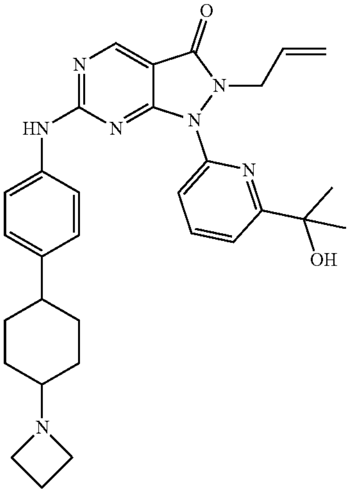 I-8-2 | $^1$H NMR (400 MHz, $CDCl_3$) δ 8.87 (s, 1H), 7.92 (d, J = 7.8 Hz, 1H), 7.80 (d, J = 8.0 Hz, 1H), 7.52 (d, J = 8.4 Hz, 2H), 7.39 (d, J = 7.6 Hz, 1H), 7.29-7.25 (m, 2H), 5.82-5.63 (m, 1H), 5.12-4.91 (m, 2H), 4.78 (d, J = 6.2 Hz, 2H), 4.01 (s, 1H), 3.17 (s, 4H), 2.53 (s, 1H), 2.33 (s, 1H), 2.06 (d, J = 4.4 Hz, 2H), 1.89 (d, J = 11.6 Hz, 2H), 1.75 (d, J = 14.1 Hz, 2H), 1.59 (d, J = 17.2 Hz, 8H), 1.46 (t, J = 13.1 Hz, 2H). LC-MS: 540.0 $[M + H]^+$. HPLC retention time (RT) = 10.997 min (HPLC conditions: mobile phase A was water (containing HCOOH 0.1%), mobile phase B was acetonitrile; gradient elution: 5% mobile phase B→50% mobile phase B). | See embodiment 8-2 or embodiment 8-3 |
| I-17 | 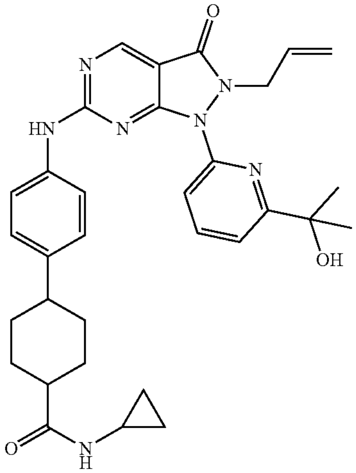 I-17 | $^1$H NMR (400 MHz, $CDCl_3$) δ 8.84 (d, J = 3.7 Hz, 1H), 7.94 (dd, J = 14.8, 6.9 Hz, 1H), 7.76 (d, J = 7.9 Hz, 1H), 7.58-7.50 (m, 2H), 7.42 (dd, J = 7.5, 4.1 Hz, 1H), 7.22 (dd, J = 15.8, 8.5 Hz, 2H), 5.71 (dd, J = 11.5, 5.4 Hz, 2H), 5.07 (d, J = 10.2 Hz, 1H), 4.95 (d, J = 17.1 Hz, 1H), 4.77 (d, J = 6.1 Hz, 2H), 2.82-2.72 (m, 1H), 2.60 (s, 1H), 2.12-2.01 (m, 3H), 1.92 (d, J = 12.5 Hz, 1H), 1.81-1.67 (m, 3H), 1.62 (s, 6H), 1.54-1.43 (m, 1H), 0.93-0.78 (m, 3H), 0.52 (s, 2H). LC-MS: m/z: $(M + H)^+$ = 568.4. | I-7 |

TABLE 1-continued

| List of compounds | | | |
|---|---|---|---|
| Compound | Structure | Characterization data | Method |
| I-39 | 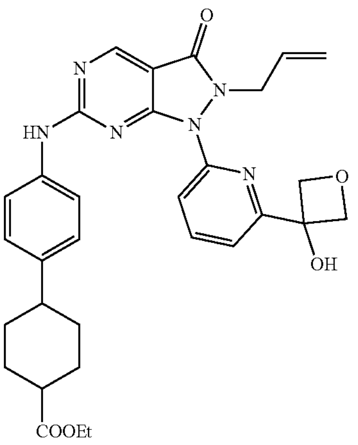 I-39 | $^1$H NMR (400 MHz, Methanol-$d_4$) δ 8.85 (d, J = 1.1 Hz, 1H), 8.05 (td, J = 7.9, 4.8 Hz, 1H), 7.96-7.86 (m, 1H), 7.67 (d, J = 7.6 Hz, 1H), 7.59 (ddd, J = 9.2, 4.6, 2.3 Hz, 2H), 7.25-7.19 (m, 1H), 7.19-7.11 (m, 1H), 5.78 (ddt, J = 16.5, 10.1, 6.1 Hz, 1H), 5.12-5.07 (m, 2H), 5.06 (t, J = 1.3 Hz, 1H), 4.98 (dd, J = 17.0, 1.4 Hz, 1H), 4.90 (d, J = 1.4 Hz, 2H), 4.25-4.19 (m, 1H), 4.14 (dd, J = 14.1, 7.1 Hz, 1H), 2.34-2.12 (m, 2H), 2.07 (dd, J = 17.0, 4.1 Hz, 1H), 1.99-1.82 (m, 1H), 1.74-1.65 (m, 2H), 1.65-1.53 (m, 2H) 1.31 (d, J = 4.2 Hz, 3H) 1.29-1.25 (m, 2H). LC-MS: m/z: $[M + H]^+$ = 571.1. | I-4 |

Effect Embodiment 1

I. Inhibitory Effect of Compound on WEE1 Kinase In Vitro

Test Method:

The tested compounds were screened on WEE1 kinase with ATP concentration of $K_m$ by ELISA. Compounds were screened on WEE1 kinase to evaluate the kinase inhibitory activity of the tested compounds. In the detection process, the initial concentration of the tested compounds was all selected as 100 nM, and each compound was selected with 6 gradient dilution concentrations, the gradient dilution ratio was 4-fold, and two replicate wells were detected for each concentration, MK1775 was used as the standard control.

WEE1, purchased from CarnaBiosciences, Inc., Item No. 05-177; dimethyl sulfoxide, purchased from Sigma-Aldrich, Item No. D8418; ATP, purchased from Sigma-Aldrich, Item No. A7699; DTT solution, purchased from Sigma-Aldrich, Item No. 43816; protein tyrosine kinase (PTK) substrate (poly-Glu-Tyr), purchased from Sigma-Aldrich, Item No. P4476; P-Tyr (PY99), purchased from Santa Cruz, Item No. sc-7020; Anti-mouse IgG HRP-linked Antibody, purchased from Santa Cruz, Item No. 7076S; TMB liquid Substrate System, purchased from Sigma-Aldrich, Item No. T0440; Costar Stripwell Microplate No Lid 1×8 Flat Bottom, Certified High Binding, purchased from Sigma-Aldrich, Item No. 42592; 96-well compound plate, purchased from Thermo Scientific, Item No. 267245.

Test Steps:

1. Coating substrate: 1) An appropriate volume of substrate storage solution protein tyrosine kinase (PTK) substrate (poly-Glu-Tyr) was taken, diluted 10 times with PBS, and the concentration was diluted from 250 mg/mL to 25 mg/mL. The mixture was added to a high adsorption 96-well plate at 125 µL per well. The plate was placed in an incubator at 37° C. for overnight coating. 2) After 24 hours, the 96-well plate was taken out, the liquid in the 96-well plate was poured out, cleaned with washing buffer for 3 times, and the incubator at 37° C. was inverted and dried for 2 hours.
2. Compound preparation and transfer: 1) compound dilution: 10 mM of the test compound storage solution was taken, the compound in 96-well compound plate was diluted with DMSO in multiple steps to obtain the initial concentration of 100× compound as the first concentration, and then DMSO was used for 4-fold gradient dilution, for a total of 6 concentrations; after that, 2 µL of the gradient dilution solution was added to 48 µL of 1× reaction buffer respectively to prepare 4× compound; 2) 4× compounds were transferred: 10 µL of 4× compounds from the 96-well compound plate configured in the previous step were transferred into the dried high adsorption 96-well plate; 10 µL of the following liquids were added to the compound-free control wells and ATP-control wells: 2 µL of DMSO was added to 48 µL of 1× reaction buffer.
3. Enzyme reaction stage: 1) WEE1 kinase and ATP were prepared into 2× enzyme solution and 4×ATP solution respectively with 1× reaction buffer. In this screening, the final concentration of WEE1 kinase was: 0.15 ng/µL and the final concentration of ATP was: 12 M; 2) 20 µL of enzyme solution of 2 was added to the high adsorption 96-well plate; 3) 10 µL of 4×ATP solution was added to the high adsorption 96-well plate and 10 µL of 1× reaction buffer was added to the ATP-control group; 4) the plate was placed in HERAEUS Multifuge X1R centrifuge at 2000 rpm for 20 s and then placed at room temperature and reacted for 60 min.
4. Reaction termination stage: 1) the reaction mixture in the plate was poured out, 200 µL of washing buffer was added to each well, and washed for 5 times; the primary antibody P-Tyr (PY99) (dilution ratio 1:2000) was added, 100 µL per well, at room temperature for 30 min. 2) The primary antibody in the plate was poured out, 200 μL of washing buffer was added to each well, and washed for 5 times; the second antibody Anti-mouse IgG HRP-linked Antibody (dilution ratio 1:2000) was added, 100 μL per well, at room temperature for 30 min. 3) The secondary antibody in the plate was poured out, washed 5 times with washing buffer, and TMB was added, 100 μL per well, and colored for 10-30 min, depending on the color depth. The reaction was terminated with 1N sulfuric acid before reading.

5. Detection and data processing: 1) The light absorption at 450 nM was read on ThermoScientific MultiScan GO, and the background was read at 650 nM at the same time. 2) Graphpad Prism 5.0 was used to fit Log(inhibitor) vs. response-Variable slope (four parameters) curves to the data, and the corresponding $IC_{50}$ (half maximal inhibitory concentration) was calculated.

II. The Data of the Test Result.

The structure of the control samples used in the tests was shown in Table 2.

TABLE 2

Structure of control sample

| Control sample number | Chemical structure |
|---|---|
| Control 1 (AZD1775/MK1775) | 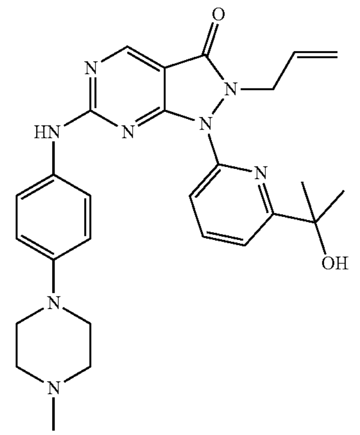 [SMILES: C=CCn1c(=O)c2cnc(Nc3ccc(N4CCN(C)CC4)cc3)nc2n1-c1cccc(C(C)(C)O)n1] |
| Control 2 (WO 2019/096322 Al Patent Compound) | 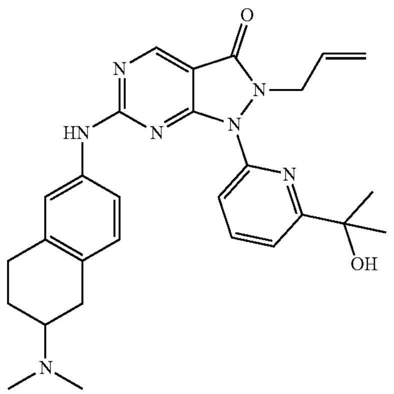 [SMILES: C=CCn1c(=O)c2cnc(Nc3ccc4c(c3)CCC(N(C)C)C4)nc2n1-c1cccc(C(C)(C)O)n1] |

The test results were detailed in Table 3.

TABLE 3

Test results of WEEE 1 enzyme inhibitory activity and cell inhibitory activity

| Compound number | WEE1 $IC_{50}$, nM | Compound number | WEE1 $IC_{50}$, nM |
|---|---|---|---|
| Control 1 | 2.57 | Control 2 | 1.98 |
| I-1-1 | 1.90 | I-1-2 | 2.08 |
| I-2 | 2.57 | I-3-1 | 0.35 |
| I-3-2 | 0.66 | I-5 | 7.15 |
| I-6 | 6.76 | I-7 | 6.53 |
| I-8 | 1.52 | I-8-1 | 1.52 |
| I-8-2 | 3.52 | I-15-1 | 1.52 |
| I-15-2 | 1.68 | I-17 | 4.05 |
| I-19 | 3.89 | I-20 | 3.45 |
| I-23 | 0.71 | I-31 | 2.05 |
| I-32 | 7.39 | I-33 | 4.22 |
| I-34 | 3.30 | I-36-2 | 2.92 |
| I-37 | 1.99 | I-38 | 1.68 |
| I-39 | 2.08 | I-40 | 4.58 |
| I-41-1 | 2.11 | I-41-2 | 2.74 |

Conclusion: As shown in Table 3, the compounds of the present disclosure have a good inhibitory effect on Weel kinase.

Effect Embodiment 2 Bioavailability Test In Vivo in Mice

I. Experimental Animals and Test Products

1. Experimental Animal

| Species | Strain | Certificate number | Weight (g) | Number (pcs) |
|---|---|---|---|---|
| Mice | ICR | 20180006002806 | 20 | 60 |

All the above were provided by Shanghai Sino-British SIPPR Lab. Animal Ltd.

2. Preparation of Test Products 2.1 Preparation of Mother Liquor 404.6 μL of DMSO was added to the compound powder of the present disclosure until the compound was completely dissolved, and 50 mg/mL mother liquor was prepared in a clarified state.

2.2 Preparation of Administration Solution

The compound of the present disclosure: 24 μL of mother liquor was accurately measured, diluted to 4 mL according to the ratio of 0.9% normal saline:PEG400=8:2, the preparation concentration was 0.3 mg/mL, the solution was in a clarified state, and it was used as intravenous administration solution. In addition, 80 μL mother liquor was accurately measured, and 0.5% CMC-Na was added to 8 mL to grind it into a uniform suspension with a concentration of 0.5 mg/mL, which was used as intragastric administration solution.

II. Animal Experiments

Intravenous group: 24 ICR mice, 20±2 g, were given the intravenous administration solution of the compound of the present disclosure by intravenous injection, with the volume of 10 mL/kg, with the dose of 3 mg/kg, the blood was taken from the fundus venous plexus of mice, 2, 5, 15, 30, 60, 90, 120, 240, 360, 480, 600 and 1440 minutes before and after administration.

Intragastric group: 24 ICR mice, 20±2 g, were given the intragastric administration solution of the compound of the present disclosure by intragastric injection, with the volume of 20 mL/kg, with the dose of 10 mg/kg, the blood was taken from the fundus venous plexus of mice, 5, 15, 30, 60, 90, 120, 240, 360, 480, 600 and 1440 minutes before and after administration.

Blood sample was centrifuged at 8000 rpm for 5 min, and the plasma was stored in a centrifuge tube at −20° C. for later use.

III. Treatment of Plasma Samples

1. Preparation of Standard Curve

The concentration range of standard working solution was 60, 20, 6, 2, 0.6, 0.2, 0.1, 0.04 μg/mL.

47.5 μL of blank mouse plasma was taken and 2.5 μL of standard curve working solution was added to prepare samples with a series of concentrations of 3, 1, 0.3, 0.1, 0.03, 0.01, 0.005, 0.002 and 0.001 g/mL; the samples were vortexed evenly, and 300 μL of acetonitrile containing internal standard (Propranolol, 25 ng/mL) was added to precipitate protein, the samples were vortexed for 10 min, 6000 g, 4° C., centrifuged for 10 min, and the supernatant was injected into a 96-well plate.

2. Treatment of QC Sample

The concentration range of QC working solution: Low: 0.06 μg/mL; Middle: 1.6 μg/mL; High: 48 μg/mL.

47.5 μL of blank mouse plasma was taken and 2.5 μL of QC working solution was added to prepare samples with a series of concentrations of 2.4, 0.08, 0.003 μg/mL; the samples were vortexed evenly, and 300 μL of acetonitrile containing internal standard (Propranolol, 25 ng/mL) was added to precipitate protein, the samples were vortexed for 10 min, 6000 g, 4° C., centrifuged for 10 min, and the supernatant was injected into a 96-well plate.

3. Treatment of Plasma Samples

300 μL of acetonitrile containing internal standard (Propranolol, 25 ng/mL) was added to 50 μL of plasma samples to precipitate protein, vortexed for 10 min, 6000 g, 4° C., centrifuged for 10 min; the supernatant before intravenous injection for 1 hour was taken, diluted 10 times with acetonitrile containing internal standard, the rest supernatant was kept undiluted, centrifuged for 10 min again at 6000 g, 4° C., and the supernatant was taken and then injected into a 96-well plate.

IV. Experimental Results of Bioavailability in Mice

1. Test Parameters

Dose; peak concentration: $C_{max}$; peak time: $T_{max}$; area under the drug-time curve from $AUC_{last}$ 0 to time t; half-life: $T_{1/2}$; mean retention time: MRT; clearance: Cl; apparent distribution volume: $V_z$; steady-state distributed volume: $V_{ss}$; absolute bioavailability: F.

2. Pharmacokinetics Data of Mice

The pharmacokinetic parameters of the compound in mice after intravenous injection or intragastric administration were shown in Table 4 and Table 5 below.

TABLE 4

Pharmacokinetic parameters of compounds in mice

| | | Control 1 (MK1775) | | Control 2 | | I-1-1 | | I-8 | |
|---|---|---|---|---|---|---|---|---|---|
| | | iv | po | iv | po | iv | po | iv | po |
| Dose | mg/kg | 3 | 10 | 3 | 10 | 3 | 10 | 3 | 10 |
| $C_{max}$ | ng/mL | 773.8 ± 53.79 | 205.2 ± 124.5 | 646.4 ± 76.85 | 27.79 ± 4.76 | 700.8 ± 142.5 | 245.2 ± 220.3 | 644.0 ± 132.2 | 58.08 ± 7.09 |
| $T_{max}$ | h | 0.05 ± 0.03 | 0.33 ± 0.14 | 0.03 | 1.67 ± 2.02 | 0.03 | 2.50 ± 1.32 | 0.03 | 1.67 ± 0.29 |
| $AUC_{last}$ | (h) * (ng/mL) | 273.1 ± 21.34 | 151.7 ± 62.14 | 261.52 ± 26.93 | 80.15 ± 9.62 | 372.5 ± 24.38 | 528.6 ± 331.1 | 317.5 ± 34.41 | 637.9 ± 302.3 |
| $T_{1/2}$ | h | 0.65 ± 0.03 | 3.10 ± 0.22 | 1.37 ± 0.33 | 2.51 ± 1.85 | 4.31 ± 1.51 | 3.10 ± 9.02 | 1.22 ± 0.10 | 1.57 ± 0.39 |
| MRT | h | 0.42 ± 0.02 | 4.33 ± 0.28 | 0.86 ± 0.16 | 3.78 ± 1.56 | 1.75 ± 0.46 | 4.33 ± 9.02 | 1.11 ± 0.08 | 3.47 ± 1.22 |
| Cl | L/kg * h | 10.99 ± 0.87 | / | 11.3 ± 1.20 | / | 7.74 ± 0.36 | / | 9.29 ± 0.85 | / |
| Vz | L/kg | 10.31 ± 1.12 | / | 22.2 ± 3.29 | / | 48.52 ± 18.38 | / | 16.33 ± 2.48 | / |
| Vss | L/kg | 4.58 ± 0.44 | / | 9.69 ± 0.96 | / | 13.61 ± 3.95 | / | 10.32 ± 0.86 | / |
| F | % | | 16.67 | | 9.19 | | 42.57 | | 60.27 |

TABLE 5

Pharmacokinetic parameters of compounds in mice

| | | I-8-1 | |
|---|---|---|---|
| | | iv | po |
| Dose | mg/kg | 3 | 10 |
| $C_{max}$ | ng/mL | 644.0 ± 132.2 | 58.08 ± 7.09 |
| $T_{max}$ | h | 0.03 | 1.67 ± 0.29 |
| $AUC_{last}$ | (h)*(ng/mL) | 317.5 ± 34.41 | 637.9 ± 302.3 |
| $T_{1/2}$ | h | 1.22 ± 0.10 | 1.57 ± 0.39 |
| MRT | h | 1.11 ± 0.08 | 3.47 ± 1.22 |
| Cl | L/kg*h | 9.29 ± 0.85 | / |
| Vz | L/kg | 16.33 ± 2.48 | / |
| Vss | L/kg | 10.32 ± 0.86 | / |
| F | % | | 60.27 |

Conclusion: The compound of the present disclosure can significantly improve the pharmacokinetics of mice.

Effect Embodiment 3 Bioavailability Test In Vivo in Cynomolgus Monkey

I. Experimental Animals and Subjects

Twelve male Non-Naïve cynomolgus monkeys were purchased from GuangxiGuidong Primate Development Experiment Co. LTD.

| Grouping | Subjects | Number Male | Dose (mg/kg) | Administration concentration (mg/mL) | Administration volume (mL/kg) | Administration mode | Sample collection |
|---|---|---|---|---|---|---|---|
| 1 | I-8-1 | 3 | 3 | 1.5 | 2 | IV | Plasma |
| 2 | | 3 | 20 | 4 | 5 | PO* | Plasma |
| 3 | AZD1775 | 3 | 3 | 1.5 | 2 | IV | Plasma |
| 4 | | 3 | 20 | 4 | 5 | PO* | Plasma |

Note:
*indicates the oral fasting, the food was withdrawn from 16:00-17:00 p.m. the day before the administration, and the food was added about 4 hours after the administration in the morning of the administration.

II. Preparation of Subjects

The test product was prepared with free alkali concentration, and the purity was not converted.

IV. Animal Experiments

1. Dose and Mode of Administration

Before administration, all animals were fasted overnight (approximately 12 hours) and fed as required and administered according to the table below.

| Grouping | Gender | Subjects | Weight (kg) | Subjects Dose (mg/kg) | Subjects Solution concentration* (mg/ml) | Administration volume (mL/kg) | Dose (mL) | Route of administration |
|---|---|---|---|---|---|---|---|---|
| 1 | M | I-8-1 | 2.30 | 3 | 1.5 | 2 | 4.6 | IV |
| 1 | M | I-8-1 | 2.30 | 3 | 1.5 | 2 | 4.6 | IV |
| 1 | M | I-8-1 | 2.45 | 3 | 1.5 | 2 | 5.0 | IV |
| 2 | M | I-8-1 | 2.50 | 20 | 4 | 5 | 13 | PO |
| 2 | M | I-8-1 | 2.85 | 20 | 4 | 5 | 14 | PO |
| 2 | M | I-8-1 | 2.45 | 20 | 4 | 5 | 12 | PO |
| 3 | M | AZD1775 | 2.35 | 3 | 1.5 | 2 | 4.8 | IV |
| 3 | M | AZD1775 | 2.55 | 3 | 1.5 | 2 | 5.2 | IV |
| 3 | M | AZD1775 | 2.35 | 3 | 1.5 | 2 | 4.8 | IV |
| 4 | M | AZD1775 | 2.20 | 20 | 4 | 5 | 11 | PO |
| 4 | M | AZD1775 | 2.30 | 20 | 4 | 5 | 12 | PO |
| 4 | M | AZD1775 | 2.50 | 20 | 4 | 5 | 13 | PO |

*Drug concentration was calculated according to free base.
**All animals were fasted overnight before administration (withdrawn at 16:00-17:00 pm approximately the day before administration) and fed 4 hours after administration on the morning of the day of administration.

III. Preparation of Administration Solution

I. Preparation of I-8-1:

54.31 mg of I-8-1 was accurately weighed, and 1.08 mL of DMSO was added, then the mixture was vortexed for 1 min, sonicated for 15 min, and then diluted to 36 mL according to the ratio of 10% HP-β-cyclodextrin (prepared by normal saline): PEG=8:2, vortexed for 1 min. A colorless clarified administration solution (the pH value was about 7) at a concentration of 1.5 mg/mL was prepared for intravenous administration to Group 1.

300.9 mg of I-8-1 was accurately weighed, and 75 mL of 0.5% CMC-Na was added, the mixture was fully ground and stirred for 5 min. A white suspension (the pH value was about 7) at a concentration of 4 mg/mL was prepared for oral administration to Group 2.

2. Preparation of AZD1775:

54.05 mg of AZD1775 was accurately weighed, and 1.08 mL of DMSO was added, then he mixture was vortexed for 1 min, sonicated for 15 min, and then diluted to 36 mL according to the ratio of 10%-D-cyclodextrin (prepared by normal saline): PEG=8:2, vortexed for 1 min. A yellow clarified administration solution (the pH value was about 7) at a concentration of 1.5 mg/mL was prepared for intravenous administration to Group 3.

300.7 mg of AZD1775 was accurately weighed, and 75 mL of 0.5% CMC-Na was added, the mixture was fully ground and stirred for 5 min. A yellow suspension (the pH value was about 7) at a concentration of 4 mg/mL was prepared for oral administration to Group 4.

2. Collection and Treatment of Plasma Samples

Intravenous group: before administration (0 h), 0.033 h, 0.083 h, 0.25 h, 0.5 h, 1 h, 1.5 h, 2 h, 4 h, 6 h, 8 h, 12 h, 24 h after administration.

Oral group: before administration (0 h), 0.083 h, 0.25 h, 0.5 h, 1.5 h, 1 h, 2 h, 4 h, 6 h, 8 h, 12 h, 24 h after administration.

Blood samples were collected by puncture through lower limb vein or other suitable blood vessels at 1 mL/time point (3 mL of blood samples were collected from each animal before administration), anticoagulated with heparin sodium, and placed on ice after collection. Plasma was separated at 2200 g/min, 10 min, 2-8° C., plasma samples were stored in a −80° C. refrigerator before being transferred to the client. Plasma samples are stored in dry ice and transferred to the client. The final treatment of the sample will be recorded in the experimental record.

V. Treatment of Plasma Samples

I. Preparation of Standard Curve

The concentration range of standard working solution was 60, 20, 6, 2, 0.6, 0.2, 0.1, 0.04, 0.02 μg/mL.

47.5 μL of blank cynomolgus monkey plasma was taken and 2.5 μL of standard curve working solution was added to prepare samples with a series of concentrations of 3, 1, 0.3, 0.1, 0.03, 0.01, 0.005, 0.002 and 0.001 g/mL; the samples were vortexed evenly, and 300 μL of acetonitrile containing internal standard (Propranolol, 25 ng/mL) was added to precipitate protein, the samples were vortexed at 6000 g, centrifuged for 10 min. 80 μL of supernatant was injected into a 96-well plate.

2. Treatment of QC Sample

The concentration range of QC working fluid: Low: 0.06 μg/mL; Middle: 1.6 μg/mL; High: 48 g/mL.

47.5 μL of blank cynomolgus monkey plasma was taken and 2.5 μL of standard curve working solution was added to prepare samples with a series of concentrations of 2.4, 0.08 and 0.003 μg/mL; the samples were vortexed evenly, and 300 μL of acetonitrile containing internal standard (Propranolol, 25 ng/mL) was added, the samples were vortexed at 6000 g, centrifuged for 10 min. 80 μL of supernatant was injected into a 96-well plate.

3. Treatment of Plasma Samples

300 μL of acetonitrile was added to 50 μL of plasma samples containing internal standard (Propranolol, 25 ng/mL) to precipitate protein, vortexed for 10 min, centrifuged at 6000 g for 10 min, after I-8-1&AZD1775 intravenous injection group was diluted 10 times with internal standard acetonitrile (Propranolol, 25 ng/mL) at the time point before 1 hour, the remaining supernatant was not diluted, centrifuged again at 6000 g at 4° C. for 10 min, and the supernatant was taken and injected into a 96 well plate.

VI. Experimental Results of Bioavailability in Cynomolgus Monkeys

1. Test Parameters

Dose; peak concentration: $C_{max}$; peak time: $T_{max}$; area under the drug-time curve from $AUC_{last}$ 0 to time t; half-life: $T_{1/2}$; mean retention time: MRT; clearance: Cl; apparent distribution volume: $V_z$; steady-state distributed volume: $V_{ss}$; absolute bioavailability: F.

2. Pharmacokinetics Data

The pharmacokinetic parameters of the compound in cynomolgus monkeys after intravenous injection or intragastric administration were shown in Table 6 below.

TABLE 6

Pharmacokinetic parameters of compounds in cynomolgus monkeys

| Parameters | | AZD1775-iv | AZD1775-po | I-8-1-iv | I-8-1-po |
|---|---|---|---|---|---|
| Dose | mg/kg | 3 | 20 | 3 | 20 |
| $C_{max}$ | ng/mL | 1202 ± 134.2 | 1627. ± 243.7 | 838.4 ± 190.0 | 720.8 ± 260.4 |
| $T_{max}$ | h | 2.69 ± 4.60 | 2.00 | 0.03 | 4.50 ± 2.60 |
| $AUC_{last}$ | (h)*(ng/mL) | 4494 ± 1719 | 8155 ± 818.2 | 957.6 ± 126.3 | 6548 ± 3043 |
| $AUC_{extra}$ | (h)*(ng/mL) | 47.62 ± 58.18 | 8.46 ± 1.91 | 16.11 ± 9.34 | 187.03 ± 166.00 |
| AUCtot | (h)*(ng/mL) | 4542 ± 1777 | 8163 ± 819.7 | 973.8 ± 131.4 | 6735 ± 3201 |
| thalf | h | 2.78 ± 0.26 | 2.03 ± 1.22 | 2.05 ± 1.24 | 3.71 ± 0.72 |
| MRT | h | 6.53 ± 2.51 | 3.58 ± 0.07 | 3.17 ± 0.82 | 7.91 ± 2.00 |
| Clearance | L/h/kg | 0.72 ± 0.23 | / | 3.12 ± 0.43 | / |
| Vz | L/kg | 2.84 ± 0.76 | / | 8.78 ± 4.22 | / |
| Vss | L/kg | 4.33 ± 0.74 | / | 9.67 ± 1.32 | / |
| BA | % | | 27.22 | | 102.56 |

Conclusion: The compound of the present disclosure can significantly improve the pharmacokinetics of cynomolgus monkeys.

Although the specific embodiments of the present disclosure have been described above, those skilled in the art should understand that these are only examples, various changes or modifications can be made to these embodiments without departing from the principle and essence of the present invention. Therefore, the protection scope of the present disclosure is defined by the appended claims.

What is claimed is:

1. A pyrazolone-fused pyrimidine compound represented by formula II, a pharmaceutically acceptable salt thereof, a solvate thereof, a solvate of the pharmaceutically acceptable salt thereof, a metabolite thereof or a prodrug thereof:

II

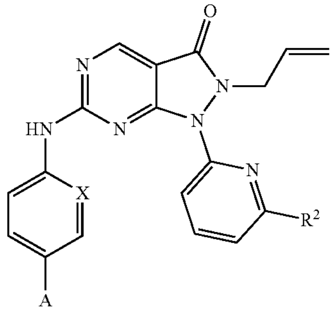

wherein, A is $C_3$-$C_{20}$ cycloalkyl substituted by one or two $R^1$;

X is CH or N;

$R^1$ is independently halogen, —$OR^{1-1}$, —$SR^{1-2}$, —CN, —$NR^{1-3}R^{1-4}$, —C(═O)$R^{1-5}$, —C(═$NR^{1-6}$)$R^{1-7}$, ═N—O—$R^{1-9}$ or "$C_2$-$C_7$ alkenyl, $C_2$-$C_8$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-8}$;

$R^{1-1}$ is independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-1-1}$;

$R^{1-1-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-1-1-1}$"; $R^{1-1-1-1}$ is independently $C_1$-$C_7$ alkyl or $C_3$-$C_{14}$ cycloalkyl;

$R^{1-2}$ is independently hydrogen or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-2-1}$;

$R^{1-2-1}$ is independently hydrogen, halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-2-1-1}$"; $R^{1-2-1-1}$ is independently $C_1$-$C_7$ alkyl or $C_3$-$C_{14}$ cycloalkyl;

$R^{1-3}$ and $R^{1-4}$ are independently hydrogen, —S(═O)$_2$ $R^{1-3-1}$, —C(O)$R^{1-3-2}$, —C(═$NR^{1-3-3}$)$NR^{1-3-5}R^{1-3-6}$, S(═O)$_2$$NR^{1-3-7}R^{1-3-8}$, —C(═O)$NR^{1-3-9}R^{1-3-10}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

or, $R^{1-3}$ and $R^{1-4}$ together with a nitrogen atom they are attached to form a $C_3$-$C_{14}$ heterocycloalkyl optionally substituted by one, two or three $R^{1-3-12}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-3}$)—; $R^{1-3-13}$ is independently $C_1$-$C_7$ alkyl or $C_3$-$C_{14}$ cycloalkyl;

$R^{1-3-1}$ and $R^{1-3-2}$ are independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$; $R^{1-3-1-1}$ is independently $C_1$-$C_7$ alkyl or $C_3$-$C_{14}$ cycloalkyl;

$R^{1-3-3}$ is independently hydrogen, —CN, $C_1$-$C_7$ alkyl, $C_2$-$C_7$ alkenyl, $C_2$-$C_7$ alkynyl or $C_3$-$C_{14}$ cycloalkyl;

$R^{1-3-5}$, $R^{1-3-6}$, $R^{1-3-7}$, $R^{1-3-8}$, $R^{1-3-9}$ and $R^{1-3-10}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-3-5}$ and $R^{1-3-6}$ together with a nitrogen atom they are attached to form a $C_3$-$C_{14}$ heterocycloalkyl optionally substituted by one, two or three $R^{1-3-5-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-5-2}$)—; $R^{1-3-5-1}$ is independently $C_1$-$C_7$ alkyl or $C_3$-$C_{14}$ cycloalkyl; $R^{1-3-5-2}$ is independently $C_1$-$C_7$ alkyl or $C_3$-$C_{14}$ cycloalkyl;

or, $R^{1-3-7}$ and $R^{1-3-8}$ together with a nitrogen atom they are attached to form a $C_3$-$C_{14}$ heterocycloalkyl optionally substituted by one, two or three $R^{1-3-7-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-7-2}$)—; $R^{1-3-7-1}$ is independently $C_1$-$C_7$ alkyl or $C_3$-$C_{14}$ cycloalkyl; $R^{1-3-7-2}$ is independently $C_1$-$C_7$ alkyl or $C_3$-$C_{14}$ cycloalkyl;

or, $R^{1-3-9}$ and $R^{1-3-10}$ together with a nitrogen atom they are attached to form a $C_3$-$C_{14}$ heterocycloalkyl optionally substituted by one, two or three $R^{1-3-9-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-9-2}$)—; $R^{1-3-9-1}$ is independently $C_1$-$C_7$ alkyl or $C_3$-$C_{14}$ cycloalkyl; $R^{1-3-9-2}$ is independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-3-12}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-12-1}$"; $R^{1-3-12-1}$ is independently $C_1$-$C_7$ alkyl or $C_3$-$C_{14}$ cycloalkyl;

$R^{1-5}$ is independently hydrogen, —N$R^{1-5-1}R^{1-5-2}$, —O$R^{1-5-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-5-1}$ and $R^{1-5-2}$ together with a nitrogen atom they are attached to form a $C_3$-$C_{14}$ heterocycloalkyl optionally substituted by one, two or three $R^{1-5-1-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-5-1-2}$)—; $R^{1-5-1-1}$ is independently $C_1$-$C_7$ alkyl or $C_3$-$C_{14}$ cycloalkyl; $R^{1-5-1-2}$ is independently $C_1$-$C_7$ alkyl or $C_3$-$C_{14}$ cycloalkyl;

$R^{1-5-3}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-6-1}$;

$R^{1-6-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-6-1-1}$"; $R^{1-6-1-1}$ is independently $C_1$-$C_7$ alkyl or $C_3$-$C_{14}$ cycloalkyl;

$R^{1-7}$ is independently hydrogen, —O$R^{1-7-1}$, —N$R^{1-7-2}$ $R^{1-7-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-7-4}$;

$R^{1-7-1}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-7-2}$ and $R^{1-7-3}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-7-2}$ and $R^{1-7-3}$ together with a nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-7-2-2}$)—; $R^{1-7-2-1}$ is independently $C_1$-$C_7$ alkyl or $C_3$-$C_{14}$ cycloalkyl; $R^{1-7-2-2}$ is independently $C_1$-$C_7$ alkyl or $C_3$-$C_{14}$ cycloalkyl;

$R^{1-7-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-7-4-1}$"; $R^{1-7-4-1}$ is independently $C_1$-$C_7$ alkyl or $C_3$-$C_{14}$ cycloalkyl;

$R^{1-8}$ is independently oxo, halogen, —OH, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^{1-9}$ is independently hydrogen or $C_1$-$C_7$ alkyl;

$R^2$ is —O$R^{2-1}$, cyano, carboxyl; or "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-1}$ is $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{2-2}$ is independently halogen, hydroxyl, amino, $C_1$-$C_7$ alkyl, $C_1$-$C_7$ alkoxy, $C_3$-$C_{14}$ cycloalkyl or $C_3$-$C_{14}$ heterocycloalkyl;

the $C_3$-$C_{14}$ heterocycloalkyl, and $C_1$-$C_7$ heteroaryl independently have 1, 2, 3, or 4 heteroatoms selected from one or more of boron, silicon, oxygen, sulfur, selenium, nitrogen and phosphorus.

2. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, the compound is a pyrazolone-fused pyrimidine compound represented by formula I:

I

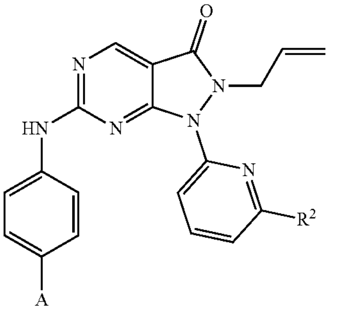

wherein, A is $C_3$-$C_{20}$ cycloalkyl substituted by one or two $R^1$;

$R^1$ is independently halogen, —$OR^{1-1}$, —$SR^{1-2}$, —CN, —$NR^{1-3}R^{1-4}$, —C(═O)$R^{1-5}$, —C(═$NR^{1-6}$)$R^{1-7}$ or "$C_2$-$C_7$ alkenyl, $C_2$-$C_8$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-8}$;

$R^{1-1}$ is independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-1-1}$;

$R^{1-1-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-1-1-1}$"; $R^{1-1-1-1}$ is independently $C_1$-$C_7$ alkyl or $C_3$-$C_{14}$ cycloalkyl;

$R^{1-2}$ is independently hydrogen, or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-2-1}$;

$R^{1-2-1}$ is independently hydrogen, halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-2-1-1}$"; $R^{1-2-}$-1 is independently $C_1$-$C_7$ alkyl or $C_3$-$C_{14}$ cycloalkyl;

$R^{1-3}$ and $R^{1-4}$ are independently hydrogen, —S(═O)$_2$ $R^{1-3-1}$, —C(O)$R^{1-3-2}$, —C(═$NR^{1-3-3}$)$NR^{1-3-5}R^{1-3-6}$, S(═O)$_2$$NR^{1-3-7}R^{1-3-8}$, —C(═O)$NR^{1-319}R^{1-3-0}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

or, $R^{1-3}$ and $R^{1-4}$ together with a nitrogen atom they are attached to form a $C_3$-$C_{14}$ heterocycloalkyl optionally substituted by one, two or three $R^{1-3-12}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-13}$)—; $R^{1-3-13}$ is independently $C_1$-$C_7$ alkyl or $C_3$-$C_{14}$ cycloalkyl;

$R^{1-3-1}$ and $R^{1-3-2}$ are independently "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$;

$R^{1-3-1-1}$ is independently $C_1$-$C_7$ alkyl or $C_3$-$C_{14}$ cycloalkyl;

$R^{1-3-3}$ is independently hydrogen, —CN, $C_1$-$C_7$ alkyl, $C_2$-$C_7$ alkenyl, $C_2$-$C_7$ alkynyl or $C_3$-$C_{14}$ cycloalkyl;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-3-5}$ and $R^{1-3-6}$ together with a nitrogen atom they are attached to form a $C_3$-$C_{14}$ heterocycloalkyl optionally substituted by one, two or three $R^{1-3-5-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-5-2}$)—; $R^{1-3-5-1}$ is independently $C_1$-$C_7$ alkyl or $C_3$-$C_{14}$ cycloalkyl; $R^{1-3-5-2}$ is independently $C_1$-$C_7$ alkyl or $C_3$-$C_{14}$ cycloalkyl;

or, $R^{1-3-7}$ and $R^{1-3-8}$ together with a nitrogen atom they are attached to form a $C_3$-$C_{14}$ heterocycloalkyl optionally substituted by one, two or three $R^{1-3-7-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-7-2}$)—; $R^{1-3-7-1}$ is independently $C_1$-$C_7$ alkyl or $C_3$-$C_{14}$ cycloalkyl; $R^{1-3-7-2}$ is independently $C_1$-$C_7$ alkyl or $C_3$-$C_{14}$ cycloalkyl;

or, $R^{1-3-9}$ and $R^{1-3-10}$ together with a nitrogen atom they are attached to form a $C_3$-$C_{14}$ heterocycloalkyl optionally substituted by one, two or three $R^{1-3-9-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-3-9-2}$)—; $R^{1-3-9-1}$ is independently $C_1$-$C_7$ alkyl or $C_3$-$C_{14}$ cycloalkyl; $R^{1-3-9-2}$ is independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-3-12}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-12-1}$"; $R^{1-3-12-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl, $C_2$-$C_7$ alkenyl, $C_2$-$C_7$ alkynyl or $C_3$-$C_{14}$ cycloalkyl;

or, $R^{1-5-1}$ and $R^{1-5-2}$ together with a nitrogen atom they are attached to form a $C_3$-$C_{14}$ heterocycloalkyl optionally substituted by one, two or three $R^{1-5-1-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-5-1-2}$)—; $R^{1-5-1-1}$ is independently $C_1$-$C_7$ alkyl or $C_3$-$C_{14}$ cycloalkyl; $R^{1-5-1-2}$ is independently $C_1$-$C_7$ alkyl or $C_3$-$C_{14}$ cycloalkyl;

$R^{1-5-3}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-6-1}$;

$R^{1-6-1}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-6-1-1}$"; $R^{1-6-1-1}$ is independently $C_1$-$C_7$ alkyl or $C_3$-$C_{14}$ cycloalkyl;

$R^{1-7}$ is independently hydrogen, —$OR^{1-7-1}$, —$NR^{1-7-2}R^{1-7-3}$ or "$C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-7-4}$;

$R^{1-7-1}$ is independently hydrogen, $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-7-2}$ and $R^{1-7-3}$ are independently $C_1$-$C_7$ alkyl, $C_2$-$C_7$ alkenyl, $C_2$-$C_7$ alkynyl or $C_3$-$C_{14}$ cycloalkyl;

or, $R^{1-7-2}$ and $R^{1-7-3}$ together with a nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom, sulfinyl, sulfonyl, carbonyl, vinylidene or —N($R^{1-7-2-2}$)—; $R^{1-7-2-1}$ is independently $C_1$-$C_7$ alkyl or $C_3$-$C_{14}$ cycloalkyl; $R^{1-7-2-2}$ is independently $C_1$-$C_7$ alkyl or $C_3$-$C_{14}$ cycloalkyl;

$R^{1-7-4}$ is independently halogen, hydroxyl, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-7-4-1}$"; $R^{1-7-4-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^2$ is —$OR^{2-1}$, cyano, carboxyl; or "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-1}$ is $C_1$-$C_7$ alkyl, $C_2$-$C_7$ alkenyl, $C_2$-$C_7$ alkynyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{2-2}$ is independently halogen, hydroxyl, amino, $C_1$-$C_7$ alkyl, $C_1$-$C_7$ alkoxy, $C_3$-$C_{14}$ cycloalkyl or $C_3$-$C_{14}$ heterocycloalkyl;

the $C_3$-$C_{14}$ heterocycloalkyl, and $C_1$-$C_7$ heteroaryl have 1, 2, 3 or 4 heteroatoms independently selected from one or more of boron, silicon, oxygen, sulfur, selenium, nitrogen and phosphorus.

3. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, when A is $C_3$-$C_{20}$ cycloalkyl substituted by one or two $R^1$, the $C_3$-$C_{20}$ cycloalkyl is $C_3$-$C_{20}$ monocyclic cycloalkyl, $C_3$-$C_{20}$ spiro cycloalkyl, $C_3$-$C_{20}$ fused cycloalkyl or $C_3$-$C_{20}$ bridged cycloalkyl;

or, when A is $C_3$-$C_{20}$ cycloalkyl substituted by one or two $R^1$, the $C_3$-$C_{20}$ cycloalkyl is $C_3$-$C_{20}$ saturated cycloalkyl;

or, when $R^1$ is independently $C_3$-$C_{14}$ heterocycloalkyl, the $C_3$-$C_{14}$ heterocycloalkyl is $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl;

or, when $R^1$ is independently $C_3$-$C_{14}$ heterocycloalkyl, the heteroatom of the $C_3$-$C_{14}$ heterocycloalkyl is not substituted;

or, when $R^1$ is independently $C_3$-$C_{14}$ heterocycloalkyl, the methylene in the $C_3$-$C_{14}$ heterocycloalkyl is not substituted;

or, when $R^1$ is independently $C_3$-$C_{14}$ heterocycloalkyl substituted by one $R^{1-8}$, the $C_3$-$C_{14}$ heterocycloalkyl is $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl;

or, when $R^1$ is independently $C_3$-$C_{14}$ heterocycloalkyl substituted by one $R^{1-8}$, the heteroatom of the $C_3$-$C_{14}$ heterocycloalkyl is not substituted except $R^{1-8}$;

or, when $R^1$ is independently $C_3$-$C_{14}$ heterocycloalkyl substituted by one $R^{1-8}$, the methylene in the $C_3$-$C_{14}$ heterocycloalkyl is not substituted;

or, when $R^{1-3}$ and $R^{1-4}$ are independently $C_1$-$C_7$ alkyl, the $C_1$-$C_7$ alkyl is $C_1$-$C_3$ alkyl;

or, when $R^{1-3-1}$ is independently $C_1$-$C_7$ alkyl, the $C_1$-$C_7$ alkyl is $C_1$-$C_3$ alkyl;

or, when $R^{1-3-2}$ is independently $C_3$-$C_{14}$ cycloalkyl, the $C_3$-$C_{14}$ cycloalkyl is $C_3$-$C_{14}$ monocyclic cycloalkyl, $C_3$-$C_{14}$ spiro cycloalkyl, $C_3$-$C_{14}$ fused cycloalkyl or $C_3$-$C_{14}$ bridged cycloalkyl;

or, when $R^{1-3-2}$ is $C_3$-$C_{14}$ cycloalkyl, the $C_3$-$C_{14}$ cycloalkyl is $C_3$-$C_{14}$ saturated cycloalkyl;

or, when $R^{1-5}$ is independently $C_3$-$C_{14}$ heterocycloalkyl, the $C_3$-$C_{14}$ heterocycloalkyl is $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl;

or, when $R^{1-5}$ is independently $C_3$-$C_{14}$ heterocycloalkyl, the heteroatom of the $C_3$-$C_{14}$ heterocycloalkyl is not substituted;

or, when $R^{1-5}$ is independently $C_3$-$C_{14}$ heterocycloalkyl, the methylene in the $C_3$-$C_{14}$ heterocycloalkyl is not substituted;

or, when $R^{1-5-1}$ and $R^{1-5-2}$ are independently $C_1$-$C_7$ alkyl, the $C_1$-$C_7$ alkyl is $C_1$-$C_3$ alkyl;

or, when $R^{1-5-1}$ and $R^{1-5-2}$ are independently $C_3$-$C_{14}$ cycloalkyl, the $C_3$-$C_{14}$ cycloalkyl is $C_3$-$C_{14}$ monocyclic cycloalkyl, $C_3$-$C_{14}$ spiro cycloalkyl, $C_3$-$C_{14}$ fused cycloalkyl or $C_3$-$C_{14}$ bridged cycloalkyl;

or, when $R^{1-5-1}$ and $R^{1-5-2}$ are independently $C_3$-$C_{14}$ cycloalkyl, the $C_3$-$C_{14}$ cycloalkyl is $C_3$-$C_{14}$ saturated cycloalkyl;

or, when $R^{1-5-3}$ is independently $C_1$-$C_7$ alkyl, the $C_1$-$C_7$ alkyl is $C_1$-$C_3$ alkyl;

or, when $R^{1-9}$ is independently $C_1$-$C_7$ alkyl, the $C_1$-$C_7$ alkyl is $C_1$-$C_3$ alkyl;

or, when $R^2$ is $C_2$-$C_7$ alkyl optionally substituted by one, two or three $R^{2-2}$, the $C_2$-$C_7$ alkyl is $C_2$-$C_4$ alkyl;

or, when $R^2$ is $C_3$-$C_{14}$ heterocycloalkyl optionally substituted by one, two or three $R^{2-2}$, the $C_3$-$C_{14}$ heterocycloalkyl is $C_3$-$C_{14}$ monocyclic heterocycloalkyl, $C_3$-$C_{14}$ spiro heterocycloalkyl, $C_3$-$C_{14}$ fused heterocycloalkyl or $C_3$-$C_{14}$ bridged heterocycloalkyl;

or, when $R^2$ is $C_3$-$C_{14}$ heterocycloalkyl optionally substituted by one, two or three $R^{2-2}$, the heteroatom of the $C_3$-$C_{14}$ heterocycloalkyl is not substituted except $R^{2-2}$;

or, when $R^2$ is $C_3$-$C_{14}$ heterocycloalkyl optionally substituted by one, two or three $R^{2-2}$, the methylene in the $C_3$-$C_{14}$ heterocycloalkyl is not substituted;

or, a ratio of each isomer in the pyrazolone-fused pyrimidine compound represented by formula II is equal;

or, the atoms in the pyrazolone-fused pyrimidine compound represented by formula II, the pharmaceutically acceptable salt thereof, the solvate thereof, the solvate of the pharmaceutically acceptable salt thereof, the metabolite thereof or the prodrug thereof all exist in their natural abundance.

4. The pyrazolone-fused pyrimidine compound represented by formula II according to claim 3, the pharmaceutically acceptable salt thereof, the solvate thereof, the solvate of the pharmaceutically acceptable salt thereof, the metabolite thereof or the prodrug thereof, wherein, when A is $C_3$-$C_{20}$ cycloalkyl substituted by one or two $R^1$, the $C_3$-$C_{20}$ cycloalkyl is $C_3$-$C_{20}$ monocyclic cycloalkyl, $C_3$-$C_{20}$ monocyclic cycloalkyl is $C_3$-$C_6$ monocyclic cycloalkyl;

or, when A is $C_3$-$C_{20}$ cycloalkyl substituted by one or two $R^1$, the $C_3$-$C_{20}$ cycloalkyl is $C_3$-$C_{20}$ bridged cycloalkyl; the $C_3$-$C_{20}$ bridged cycloalkyl is $C_5$-$C_8$ bridged cycloalkyl;

or, when $R^1$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is "$C_3$-$C_9$ monocyclic heterocycloalkyl having one or two heteroatoms selected from one or two of N, O and S";

or, when $R^1$ is independently $C_3$-$C_{14}$ heterocycloalkyl substituted by one $R^{1-8}$, the $C_3$-$C_{14}$ heterocycloalkyl is $C_3$-$C_{14}$ monocyclic heterocycloalkyl; the $C_3$-$C_{14}$ monocyclic heterocycloalkyl is the "$C_3$-$C_9$ monocyclic heterocycloalkyl having one or two heteroatoms selected from one or two of N, O and S";

or, when $R^{1-3}$ and $R^{1-4}$ are independently $C_1$-$C_7$ alkyl, the $C_1$-$C_7$ alkyl is methyl, ethyl, n-propyl or isopropyl;

or, when $R^{1-3-1}$ is independently $C_1$-$C_7$ alkyl, the $C_1$-$C_7$ alkyl is methyl, ethyl, n-propyl or isopropyl;

or, when $R^{1-3-2}$ is independently $C_3$-$C_{14}$ cycloalkyl, the $C_3$-$C_{14}$ cycloalkyl is $C_3$-$C_{14}$ monocyclic cycloalkyl; the $C_3$-$C_{14}$ monocyclic cycloalkyl is $C_3$-$C_6$ monocyclic cycloalkyl;

or, when $R^{1-5}$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is "$C_3$-$C_9$ monocyclic heterocycloalkyl having one or two heteroatoms selected from one or two of N, O and S";

or, when $R^{1-5-1}$ and $R^{1-5-2}$ are independently $C_1$-$C_7$ alkyl, the $C_1$-$C_7$ alkyl is methyl, ethyl, n-propyl or isopropyl;

or, when $R^{1-5-1}$ and $R^{1-5-2}$ are independently $C_3$-$C_{14}$ cycloalkyl, the $C_3$-$C_{14}$ cycloalkyl is $C_3$-$C_{14}$ monocyclic cycloalkyl; the $C_3$-$C_{14}$ monocyclic cycloalkyl is $C_3$-$C_6$ monocyclic cycloalkyl;

or, when $R^{1-5-3}$ is independently $C_1$-$C_7$ alkyl, the $C_1$-$C_7$ alkyl is methyl, ethyl, n-propyl or isopropyl;

or, when $R^2$ is $C_2$-$C_7$ alkyl optionally substituted by one, two or three $R^{2-2}$, the $C_2$-$C_7$ alkyl is ethyl, n-propyl, isopropyl, n-butyl, isobutyl, sec-butyl or tert-butyl;

or, when $R^2$ is independently $C_3$-$C_{14}$ heterocycloalkyl substituted by one, two or three $R^{22}$, the $C_3$-$C_{14}$ heterocycloalkyl is $C_3$-$C_{14}$ monocyclic heterocycloalkyl; the $C_3$-$C_{14}$ monocyclic heterocycloalkyl is "$C_3$-$C_9$ monocyclic heterocycloalkyl having one or two heteroatoms selected from one or two of N, O and S";

or, a ratio of each isomer in the pyrazolone-fused pyrimidine compound represented by formula I is equal;

or, the atoms in the pyrazolone-fused pyrimidine compound represented by formula I, the pharmaceutically acceptable salt thereof, the solvate thereof, the solvate of the pharmaceutically acceptable salt thereof, the metabolite thereof or the prodrug thereof all exist in their natural abundance.

5. The pyrazolone-fused pyrimidine compound represented by formula II according to claim 4, the pharmaceutically acceptable salt thereof, the solvate thereof, the solvate of the pharmaceutically acceptable salt thereof, the metabolite thereof or the prodrug thereof, wherein, when A is $C_3$-$C_{20}$ cycloalkyl substituted by one or two $R^1$, the $C_3$-$C_{20}$ cycloalkyl is $C_3$-$C_{20}$ monocyclic cycloalkyl, the $C_3$-$C_{20}$ monocyclic cycloalkyl is cyclopropyl, cyclobutyl, cyclopentyl or cyclohexyl;

or, when A is $C_3$-$C_{20}$ cycloalkyl substituted by one or two $R^1$, the $C_3$-$C_{20}$ cycloalkyl is $C_3$-$C_{20}$ bridged cycloalkyl; the $C_3$-$C_{20}$ bridged cycloalkyl is

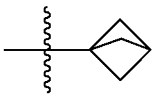 or 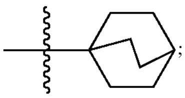;

or, when $R^1$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is

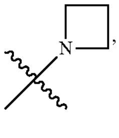, 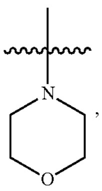, 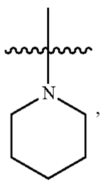, 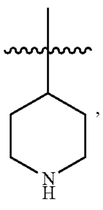, or

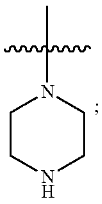;

or, when $R^1$ is independently $C_3$-$C_{14}$ heterocycloalkyl substituted by one $R^{1-8}$, the $C_3$-$C_{14}$ heterocycloalkyl substituted by one $R^{1-8}$ is

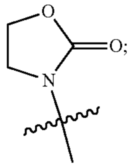 [SMILES: *N1CCOC1=O]

or, when $R^{1-3-2}$ is $C_3$-$C_{14}$ cycloalkyl, the $C_3$-$C_{14}$ cycloalkyl is $C_3$-$C_{14}$ monocyclic cycloalkyl; the $C_3$-$C_{14}$ monocyclic cycloalkyl is cyclopropyl, cyclobutyl, cyclopentyl or cyclohexyl;

or, when $R^{1-5}$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is

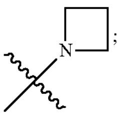 [SMILES: *N1CCC1]

or, when $R^{1-5-1}$ and $R^{1-5-2}$ are independently $C_3$-$C_{14}$ cycloalkyl, the $C_3$-$C_{14}$ cycloalkyl is $C_3$-$C_{14}$ monocyclic cycloalkyl; the $C_3$-$C_{14}$ monocyclic cycloalkyl is cyclopropyl, cyclobutyl, cyclopentyl or cyclohexyl;

or, when $R^2$ is $C_3$-$C_{14}$ heterocycloalkyl optionally substituted by one, two or three $R^{2-2}$, the $C_3$-$C_{14}$ heterocycloalkyl is $C_3$-$C_{14}$ monocyclic heterocycloalkyl; the $C_3$-$C_{14}$ monocyclic heterocycloalkyl is oxetan-3-yl.

6. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, when A is $C_3$-$C_{20}$ cycloalkyl substituted by one $R^1$, the A is

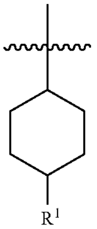 or 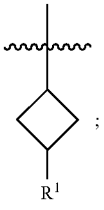 ;

or, when $R^1$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is

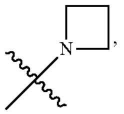 [SMILES: *N1CCC1], 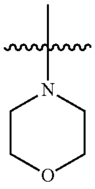, 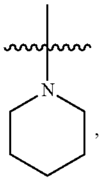, 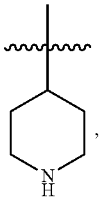, or

-continued

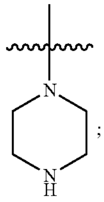

or, when $R^{1-5}$ is independently $C_3$-$C_{14}$ heterocycloalkyl, the $C_3$-$C_{14}$ heterocycloalkyl is $C_3$-$C_{14}$ monocyclic heterocycloalkyl; the $C_3$-$C_{14}$ monocyclic heterocycloalkyl is

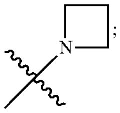

or, when $R^2$ is $C_2$-$C_7$ alkyl substituted by one $R^{2-2}$, $R^{2-2}$ is hydroxyl; the $C_2$-$C_7$ alkyl substituted by one $R^{2-2}$ is

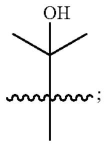 [SMILES: *C(C)(C)O]

or, when $R^2$ is $C_3$-$C_{14}$ heterocycloalkyl substituted by one $R^{2-2}$, $R^{2-2}$ is halogen or hydroxyl; the $C_3$-$C_{14}$ heterocycloalkyl substituted by one $R^{2-2}$ is

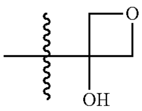 or 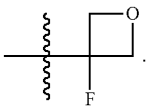.

7. The pyrazolone-fused pyrimidine compound represented by formula II according to claim 6, the pharmaceutically acceptable salt thereof, the solvate thereof, the solvate of the pharmaceutically acceptable salt thereof, the metabolite thereof or the prodrug thereof, wherein, when A is $C_3$-$C_{20}$ cycloalkyl substituted by one $R^1$; the A is

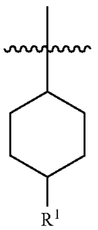 or 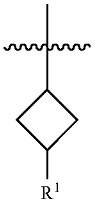, 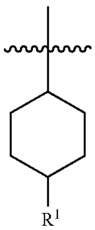 is 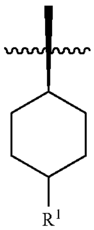 and/or

-continued

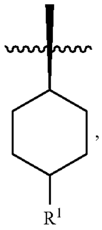, 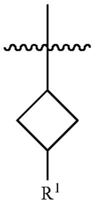 is 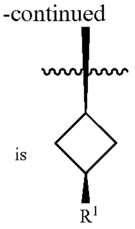 and/or 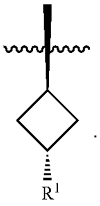.

8. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, A is $C_3$-$C_{20}$ cycloalkyl substituted by one $R^1$;

or, X is N;

or, $R^1$ is independently cyano, halogen, —$NR^{1-3}R^{1-4}$, —C(═O)$R^{1-5}$, —C(═$NR^{1-6}$)$R^{1-7}$, ═N—O—$R^{1-9}$, $C_1$-$C_7$ heteroaryl or "$C_3$-$C_{14}$ heterocycloalkyl" optionally substituted by one $R^{1-8}$;

or, $R^{1-3}$ and $R^{1-4}$ are independently hydrogen, —S(═O)$_2R^{1-3-1}$, —C(═O)$R^{1-3-2}$, —C(═$NR^{1-3-3}$)$NR^{1-3-5}R^{1-3-6}$, or $C_1$-$C_7$ alkyl; $R^{1-3-1}$ and $R^{1-3-2}$ are independently $C_1$-$C_7$ alkyl or $C_3$-$C_{14}$ cycloalkyl; $R^{1-3-3}$ is hydrogen; $R^{1-3-5}$ and $R^{1-3-6}$ are hydrogen;

or, $R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

or, $R^{1-8}$ is independently oxo;

or, $R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$; $R^{2-2}$ is independently halogen or hydroxyl.

9. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, A is $C_3$-$C_{20}$ cycloalkyl substituted by one $R^1$;

or, $R^1$ is independently cyano, halogen, —$NR^{1-3}R^{1-4}$, —C(═O)$R^{1-5}$, —C(═$NR^{1-6}$)$R^{1-7}$, $C_1$-$C_7$ heteroaryl or $C_3$-$C_{14}$ heterocycloalkyl;

or, $R^{1-3}$ and $R^{1-4}$ are independently hydrogen, —S(═O)$_2R^{1-3-1}$ or $C_1$-$C_7$ alkyl; $R^{1-3-1}$ is independently $C_1$-$C_7$ alkyl;

or, $R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

or, $R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$; $R^{2-2}$ is independently halogen or hydroxyl.

10. The pyrazolone-fused pyrimidine compound represented by formula II according to claim 9, the pharmaceutically acceptable salt thereof, the solvate thereof, the solvate of the pharmaceutically acceptable salt thereof, the metabolite thereof or the prodrug thereof, wherein, $R^1$ is independently —$NR^{1-3}R^{1-4}$, —C(═O)$R^{1-5}$ or $C_3$-$C_{14}$ heterocycloalkyl;

or, $R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen;

or, $R^2$ is "$C_2$-$C_7$ alkyl or $C_3$-$C_{14}$ heterocycloalkyl substituted by one $R^{2-2}$"; $R^{2-2}$ is halogen or hydroxyl.

11. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, the pyrazolone-fused pyrimidine compound represented by formula II is a compound of any one of scheme (1), scheme (2), scheme (3), scheme (4), scheme (5), scheme (6), scheme (7), scheme (8) or scheme (9):

scheme (1):

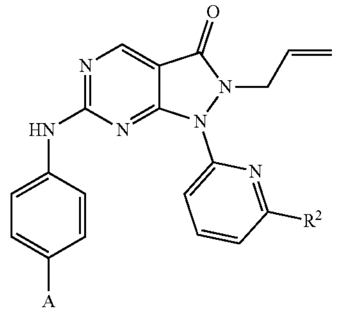

I

A is

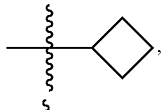, 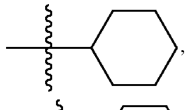,

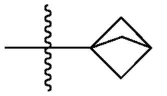 or 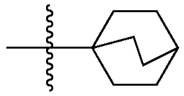

substituted by one or two $R^1$;

$R^1$ is independently halogen, —CN, —$NR^{1-3}R^{1-4}$, —C(═O)$R^{1-5}$, —C(═$NR^{1-6}$)$R^{1-7}$ or "$C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, —S(═O)$_2NR^{1-3-7}R^{1-3-8}$, —C(═O)$NR^{1-3-9}R^{1-3-10}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

$R^{1-3-1}$ and $R^{1-3-2}$ are independently "$C_1$-$C_7$ alkyl, $C_3$-$C_{14}$ cycloalkyl, $C_3$-$C_{14}$ heterocycloalkyl or $C_6$-$C_{10}$ aryl" optionally substituted by one or two $R^{1-3-1-1}$; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with a nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom;

$R^{1-7-2-1}$ is independently $C_1$-$C_7$ alkyl or $C_3$-$C_{14}$ cycloalkyl;

$R^{1-8}$ is independently halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-2}$ is independently halogen or hydroxyl;

the $C_3$-$C_{14}$ heterocycloalkyl, and $C_1$-$C_7$ heteroaryl have 1, 2, 3, or 4 heteroatoms independently selected from one or more of boron, silicon, oxygen, sulfur, selenium, nitrogen and phosphorus;

scheme (2):

I

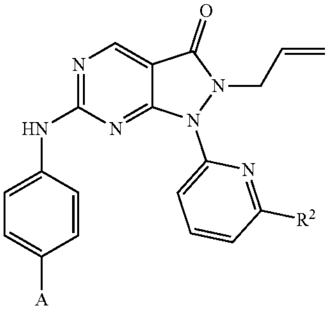

A is $C_3$-$C_{20}$ cycloalkyl substituted by one or two $R^1$;

$R^1$ is independently cyano, halogen, —$NR^{1-3}R^{1-4}$, —C(=O)$R^{1-5}$, —C(=$NR^{1-6}$)$R^{1-7}$, $C_1$-$C_7$ heteroaryl or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is halogen or hydroxyl;

scheme (3):

I

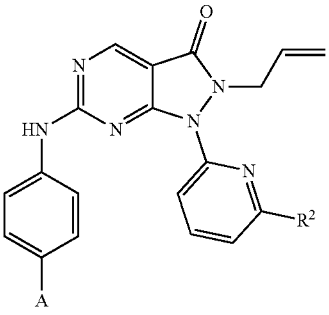

A is $C_3$-$C_{20}$ cycloalkyl substituted by one $R^1$;

$R^1$ is —$NR^{1-3}R^{1-4}$, —C(=O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl;

scheme (4):

I

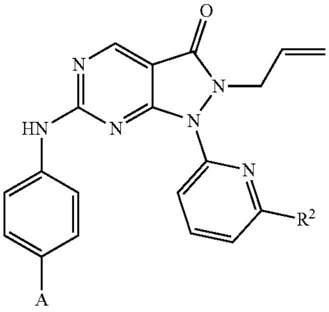

A is $C_3$-$C_{20}$ cycloalkyl substituted by one $R^1$;

$R^1$ is —$NR^{1-3}R^{1-4}$, —C(=O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen;

$R^2$ is "$C_2$-$C_7$ alkyl or $C_3$-$C_{14}$ heterocycloalkyl substituted by one $R^{2-2}$"; $R^{2-2}$ is hydroxyl;

scheme (5):

I

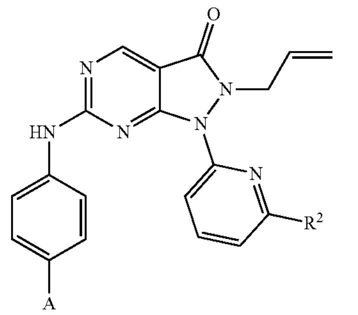

A is

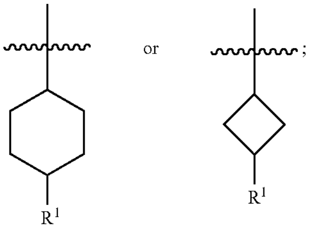

$R^1$ is —$NR^{1-3}R^{1-4}$, —C(=O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl;

scheme (6):

I

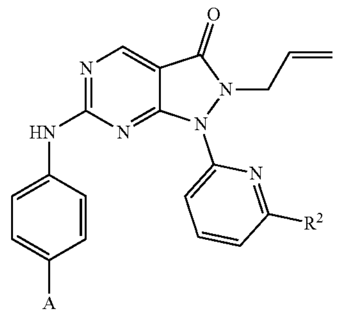

A is

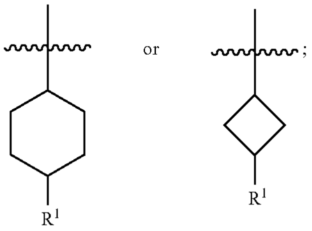

$R^1$ is —$NR^{1-3}R^{1-4}$, —C(=O)$R^{1-5}$ or $C_3$-$C_{14}$ heterocycloalkyl;

$R^{1-3}$ and $R^{1-4}$ are independently hydrogen, —S(=O)$_2$ $R^{1-3-1}$ or $C_1$-$C_7$ alkyl; $R^{1-3-1}$ is independently $C_1$-$C_7$ alkyl;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^2$ is

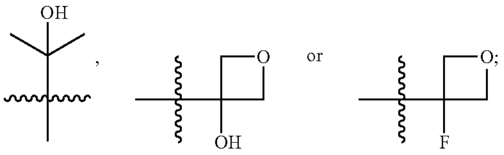

scheme (7):

A is

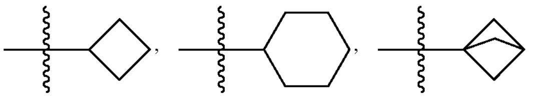

or

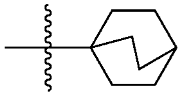

substituted by one or two $R^1$;

X is CH or N;

$R^1$ is independently halogen, —CN, —$NR^{1-3}R^{1-4}$, —C(=O)$R^{1-5}$, —C(=$NR^{1-6}$)$R^{1-7}$, =N—O—$R^{1-9}$ or "$C_3$-$C_{14}$ cycloalkyl, $C_3$-$C_{14}$ heterocycloalkyl, $C_6$-$C_{10}$ aryl, or $C_1$-$C_7$ heteroaryl" optionally substituted by one, two or three $R^{1-8}$;

$R^{1-3}$ and $R^{1-4}$ are independently hydrogen, —S(=O)$_2$ $R^{1-3-1}$, —C(=O)$R^{1-3-2}$, —C(=$NR^{1-3-3}$)$NR^{1-3-5}R^{1-3-6}$, —S(=O)$_2$$NR^{1-3-7}R^{1-3-8}$, —C(=O)$NR^{1-3-9}R^{1-3-10}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-3-11}$;

$R^{1-3-1}$ and $R^{1-3-2}$ are independently "$C_1$-$C_7$ alkyl, $C_3$-$C_{14}$ cycloalkyl, $C_3$-$C_{14}$ heterocycloalkyl or $C_6$-$C_{10}$ aryl optionally substituted" by one or two $R^{1-3-1-1}$; $R^{1-3-1-1}$ is independently $C_1$-$C_7$ alkyl;

$R^{1-3-3}$ is independently hydrogen;

$R^{1-3-5}$, $R^{1-3-6}$, $R^{1-3-7}$, $R^{1-3-8}$, $R^{1-3-9}$ and $R^{1-3-10}$ are independently hydrogen, $C_1$-$C_7$ alkyl or $C_3$-$C_{14}$ cycloalkyl;

$R^{1-3-11}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-3-11-1}$"; $R^{1-3-11-1}$ is independently $C_1$-$C_7$ alkyl or $C_3$-$C_{14}$ cycloalkyl;

$R^{1-5}$ is independently hydrogen, —$NR^{1-5-1}R^{1-5-2}$, —$OR^{1-5-3}$ or "$C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl" optionally substituted by one, two or three $R^{1-5-4}$;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen, $C_1$-$C_7$ alkyl, $C_3$-$C_{14}$ cycloalkyl, $C_3$-$C_{14}$ heterocycloalkyl, $C_6$-$C_{10}$ aryl or $C_1$-$C_7$ heteroaryl;

$R^{1-5-4}$ is independently halogen, hydroxyl, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-5-4-1}$"; $R^{1-5-4-1}$ is independently $C_1$-$C_7$ alkyl or $C_3$-$C_{14}$ cycloalkyl;

$R^{1-6}$ is independently hydrogen, —CN, —OH;

$R^{1-7}$ is independently hydrogen, —$NR^{1-7-2}R^{1-7-3}$;

$R^{1-7-2}$ and $R^{1-7-3}$ are independently $C_1$-$C_7$ alkyl or $C_3$-$C_{14}$ cycloalkyl;

or, $R^{1-7-2}$ and $R^{1-7-3}$ together with a nitrogen atom they are attached to form a $C_3$-$C_{14}$ heterocycloalkyl optionally substituted by one, two or three $R^{1-7-2-1}$; one or more methylenes in the $C_3$-$C_{14}$ heterocycloalkyl are optionally and independently substituted by oxygen atom, sulfur atom; $R^{1-7-2-1}$ is independently $C_1$-$C_7$ alkyl or $C_3$-$C_{14}$ cycloalkyl;

$R^{1-8}$ is independently oxo, halogen, —OH, amino, mercapto, cyano, $C_1$-$C_7$ alkyl, $C_1$-$C_7$ alkoxy, $C_1$-$C_7$ alkylthio, $C_3$-$C_{14}$ cycloalkyl, $C_3$-$C_{14}$ heterocycloalkyl, $C_6$-$C_{10}$ aryl, $C_1$-$C_7$ heteroaryl or "amino substituted by one or two $R^{1-8-1}$"; $R^{1-8-1}$ is independently $C_1$-$C_7$ alkyl or $C_3$-$C_{14}$ cycloalkyl;

$R^{1-9}$ is independently hydrogen or $C_1$-$C_7$ alkyl;

$R^2$ is "$C_2$-$C_7$ alkyl, $C_3$-$C_{14}$ cycloalkyl or $C_3$-$C_{14}$ heterocycloalkyl" optionally substituted by one, two or three $R^{2-2}$;

$R^{2-2}$ is independently halogen or hydroxyl;

the $C_3$-$C_{14}$ heterocycloalkyl, and $C_1$-$C_7$ heteroaryl have 1, 2, 3 or 4 heteroatoms independently selected from one or more of boron, silicon, oxygen, sulfur, selenium, nitrogen and phosphorus;

scheme (8):

A is $C_3$-$C_{20}$ cycloalkyl substituted by one or two $R^1$;

X is CH or N;

$R^1$ is independently cyano, halogen, —$NR^{1-3}R^{1-4}$, —C(═O)$R^{1-5}$, —C(═$NR^{1-6}$)$R^{1-7}$, ═N—O—$R^{1-9}$, $C_1$-$C_7$ heteroaryl or "$C_3$-$C_{14}$ heterocycloalkyl" optionally substituted by one $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is independently —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is halogen or hydroxyl;

scheme (9):

A is $C_3$-$C_{20}$ cycloalkyl substituted by one $R^1$;

X is CH or N;

$R^1$ is —CN, —$NR^{1-3}R^{1-4}$, —C(═O)$R^{1-5}$, ═N—O—$R^{1-9}$ or "$C_3$-$C_{14}$ heterocycloalkyl" optionally substituted by one $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl;

$R^{1-5-1}$ and $R^{1-5-2}$ are independently hydrogen, $C_1$-$C_7$ alkyl or $C_3$-$C_{14}$ cycloalkyl;

$R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl;

scheme (10):

A is $C_3$-$C_{20}$ cycloalkyl substituted by one $R^1$;

X is CH or N;

$R^1$ is —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl;

$R^{1-5-1}$ and $R^{1-5-2}$ are independently hydrogen, $C_1$-$C_7$ alkyl or $C_3$-$C_{14}$ cycloalkyl;

$R^{1-5-3}$ is hydrogen;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl;

scheme (11):

A is

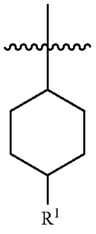

or

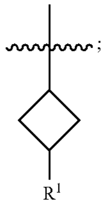

;

X is CH or N;

$R^1$ is —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$;

$R^{1-3}$ and $R^{1-4}$ are independently hydrogen, —S(═O)$_2$ $R^{1-3-1}$, —C(O)$R^{1-3-2}$, —C(═$NR^{1-3-3}$)$NR^{1-3-5}R^{1-3-6}$, or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is —$NR^{1-5-1}R^{1-5-2}$, —$OR^{1-5-3}$ or $C_3$-$C_{14}$ heterocycloalkyl; $R^{1-5-1}$ and $R^{1-5-2}$ are independently hydrogen, $C_1$-$C_7$ alkyl or $C_3$-$C_{14}$ cycloalkyl; $R^{1-5-3}$ is hydrogen or $C_1$-$C_7$ alkyl;

$R^{1-8}$ is independently oxo;

$R^{1-9}$ is independently hydrogen or $C_1$-$C_7$ alkyl;

$R^2$ is "$C_2$-$C_7$ alkyl or $C_3$-$C_{14}$ heterocycloalkyl substituted by one $R^{2-2}$"; $R^{2-2}$ is hydroxyl;

scheme (12):

A is

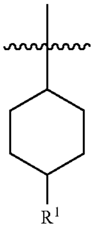

or

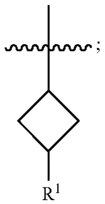

X is CH or N;

$R^1$ is independently —CN, —$NR^{1-3}R^{1-4}$, —C(═O)$R^{1-5}$, ═N—O—$R^{1-9}$, or "$C_3$-$C_{14}$ heterocycloalkyl" optionally substituted by one $R^{1-8}$;

$R^{1-3}$ and $R^{1-4}$ are independently hydrogen, —S(═O)$_2$ $R^{1-3-1}$, —C(═O)$R^{1-3-2}$, —C(═$NR^{1-3-3}$)$NR^{1-3-5}R^{1-3-6}$, or $C_1$-$C_7$ alkyl;

$R^{1-3-1}$ and $R^{1-3-2}$ are independently $C_1$-$C_7$ alkyl, or $C_3$-$C_{14}$ cycloalkyl;

$R^{1-3-3}$ is hydrogen;

$R^{1-3-5}$ and $R^{1-3-6}$ are hydrogen;

$R^{1-5}$ is independently —$NR^{1-5-1}R^{1-5-2}$, —$OR^{1-5-3}$, or $C_3$-$C_{14}$ heterocycloalkyl;

$R^{1-5-1}$ and $R^{1-5-2}$ are independently hydrogen, $C_1$-$C_7$ alkyl, or $C_3$-$C_{14}$ cycloalkyl;

$R^{1-5-3}$ is independently hydrogen or $C_1$-$C_7$ alkyl;

$R^{1-8}$ is independently oxo;

$R^{1-9}$ is independently hydrogen or $C_1$-$C_7$ alkyl;

$R^2$ is

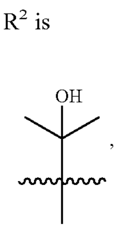

,

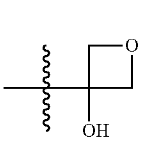

or

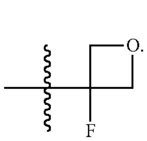

12. The pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof, wherein, the pyrazolone-fused pyrimidine compound represented by formula II is a compound selected from scheme A, scheme B, scheme C, scheme D, scheme E, scheme F, and scheme G:

scheme A:

I-1

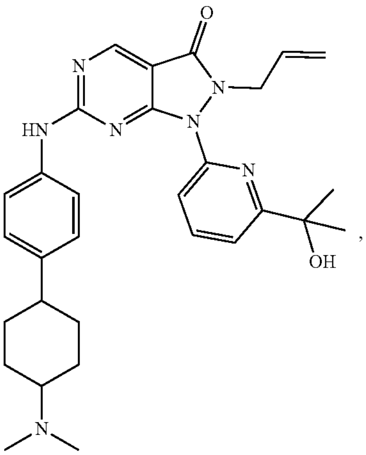

I-2

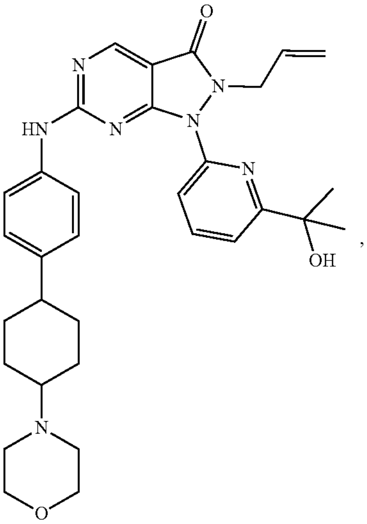

I-3

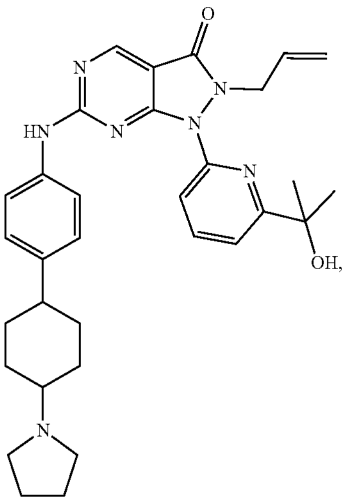

-continued
I-4
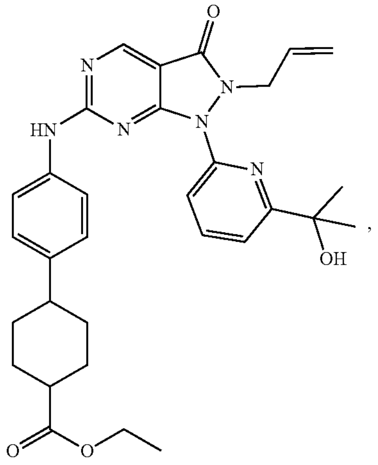
I-5
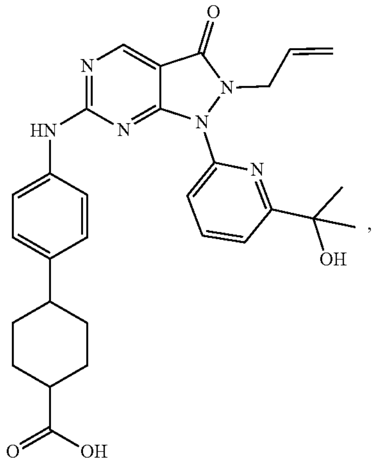
I-6
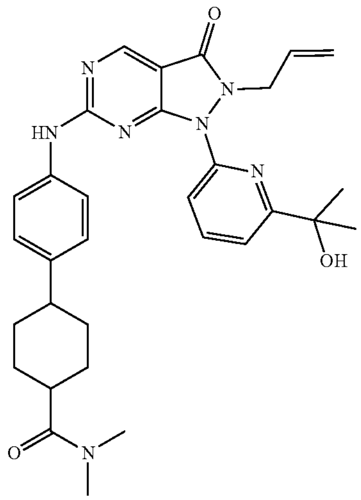
-continued
I-7
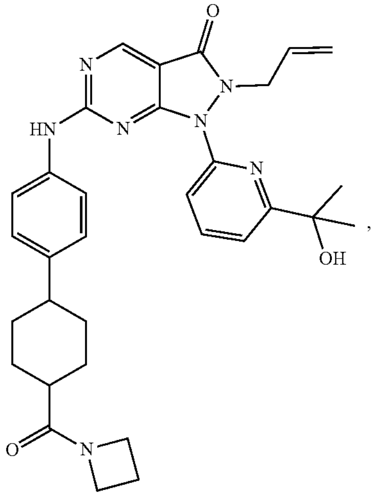
I-8
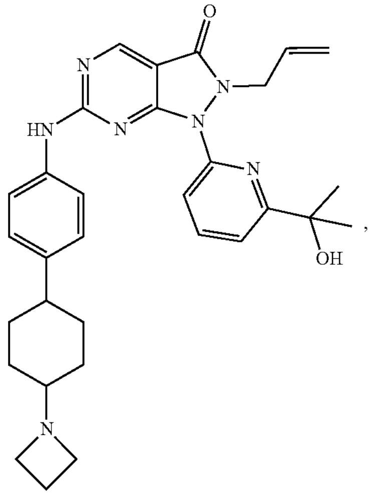
I-9
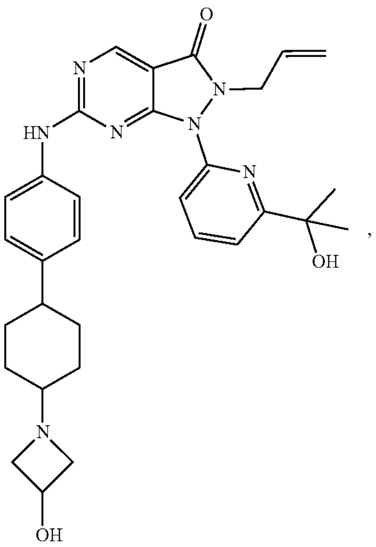

-continued
I-10
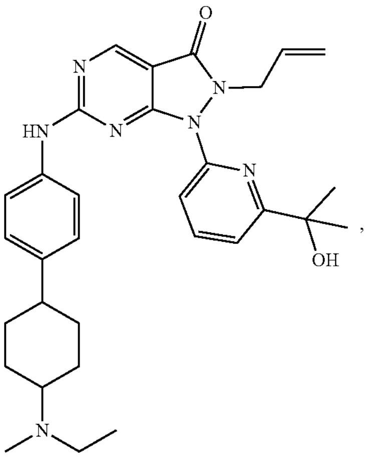
I-11
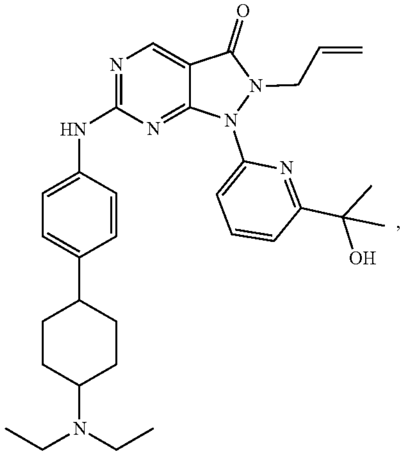
I-12
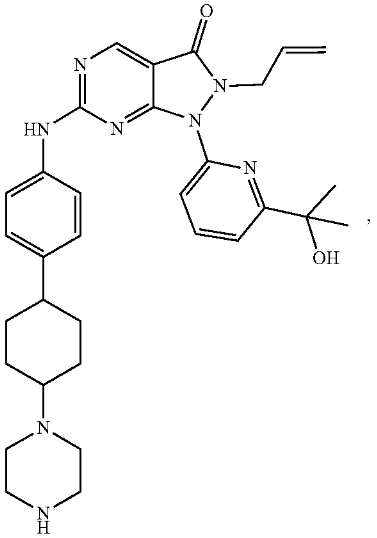
-continued
I-13
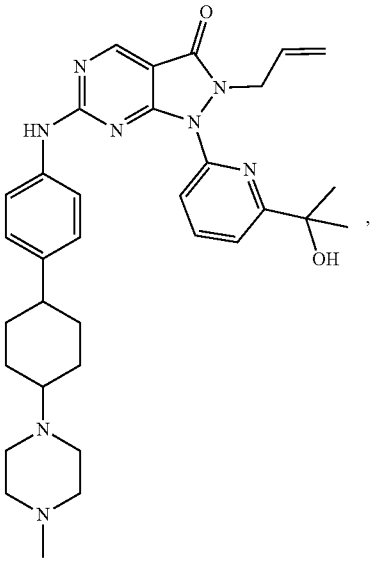
I-14
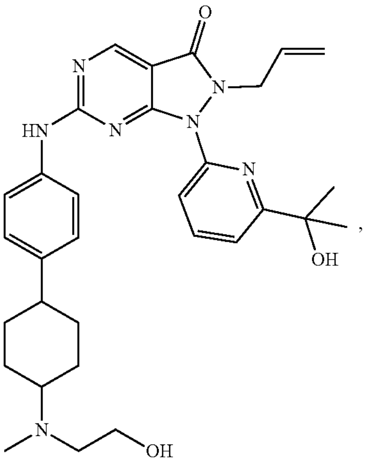
I-15
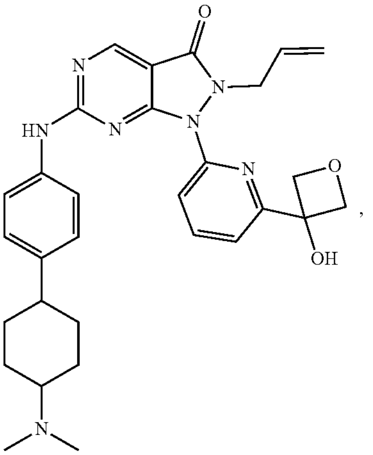

-continued
I-16
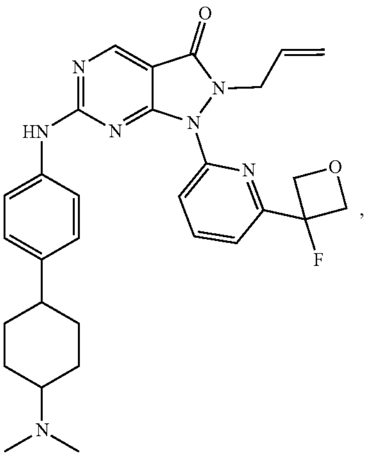
I-17
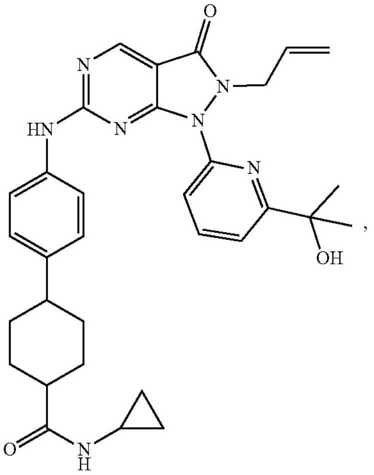
I-18
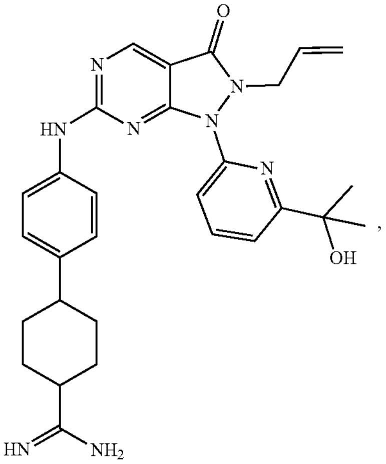
-continued
I-19
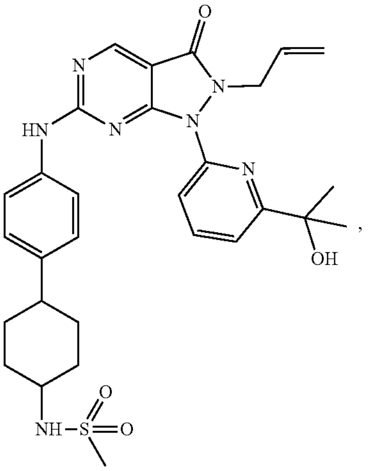
I-20
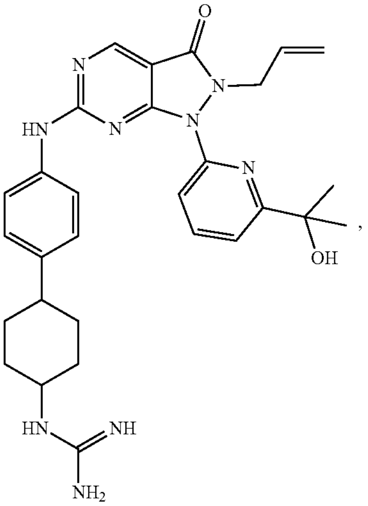
I-21
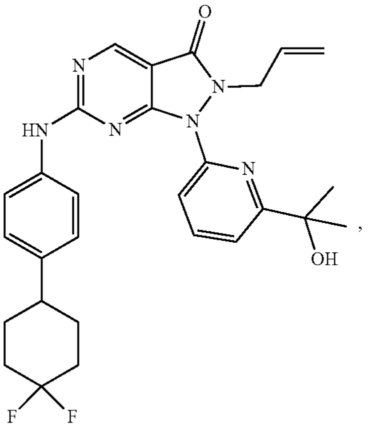

-continued
I-22
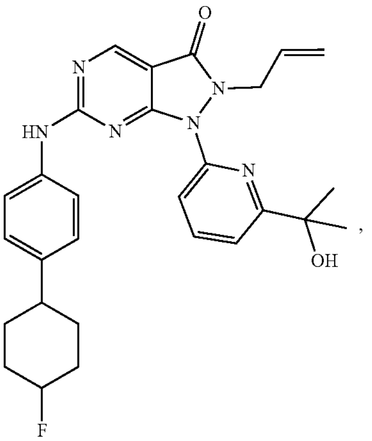
I-23
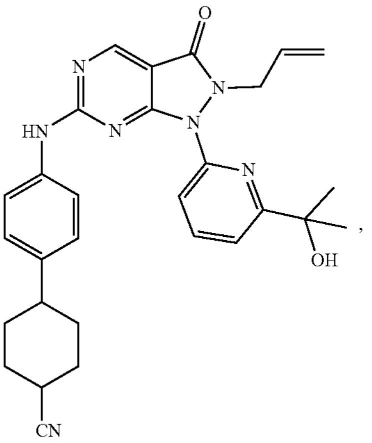
I-24
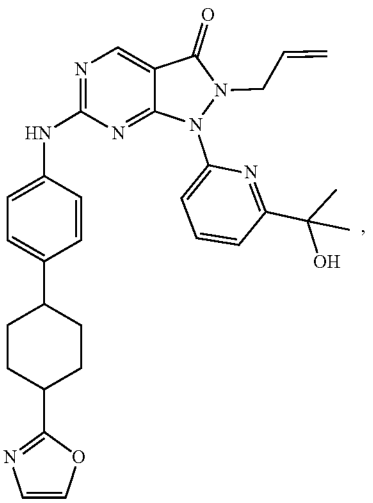
-continued
I-25
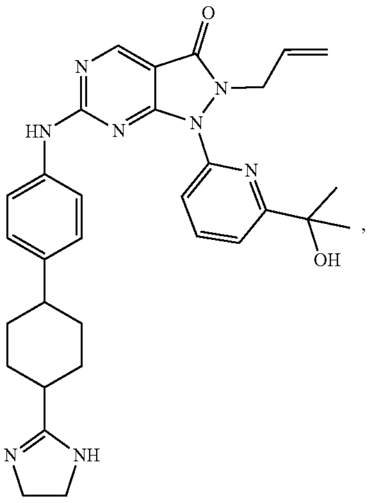
I-26
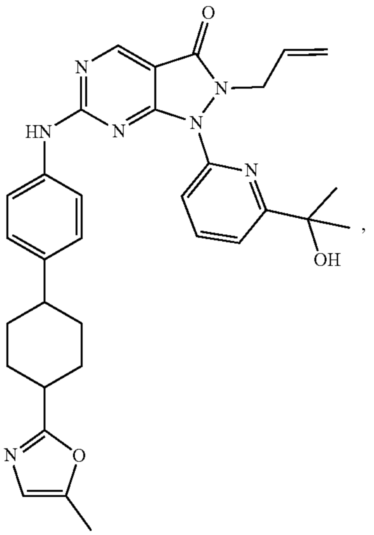
I-27
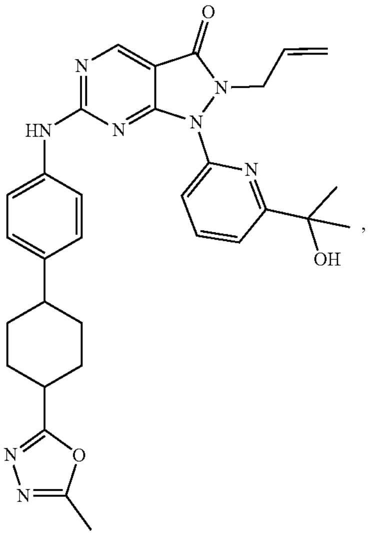

-continued
I-28
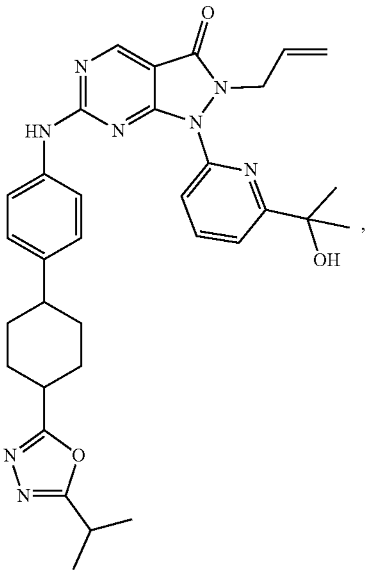
I-29
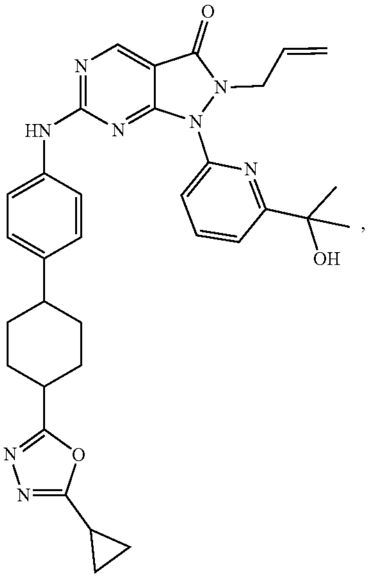
-continued
I-30
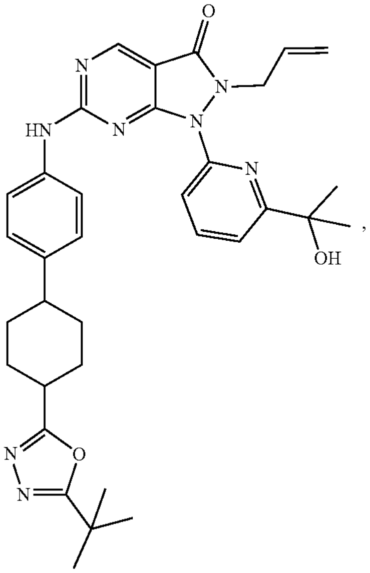
I-31
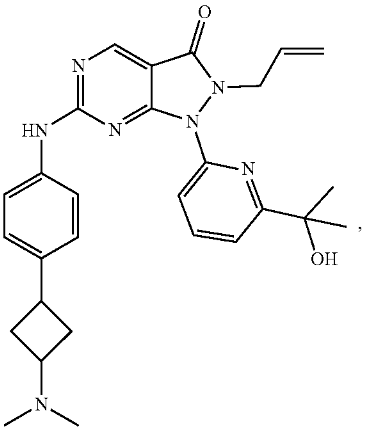
I-32
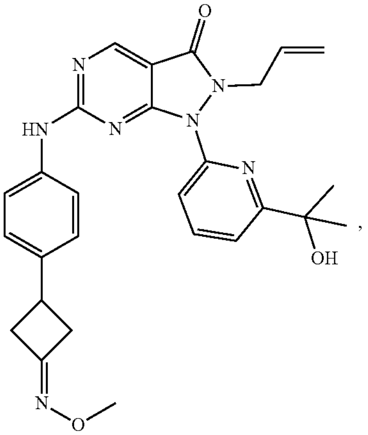

-continued
I-33
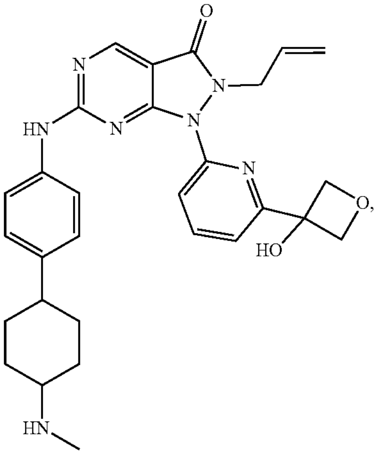
I-34
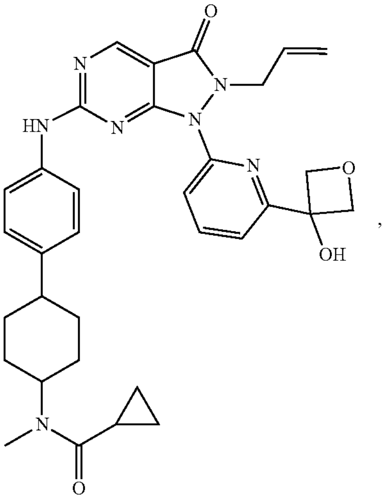
I-35
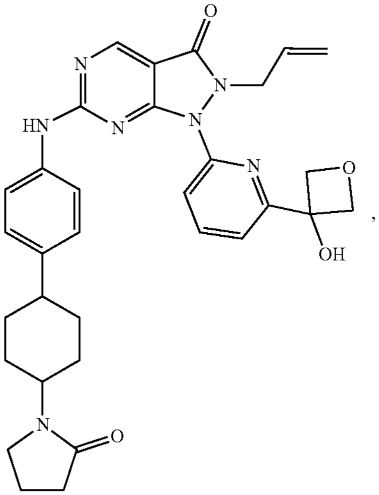
-continued
I-36
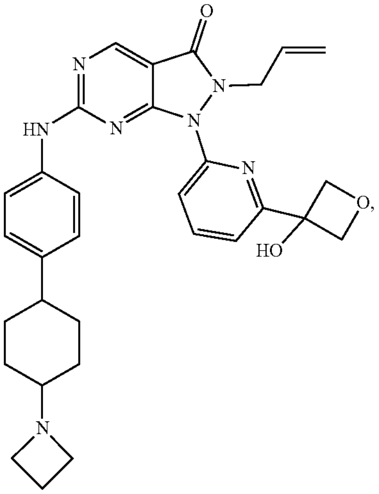
I-37
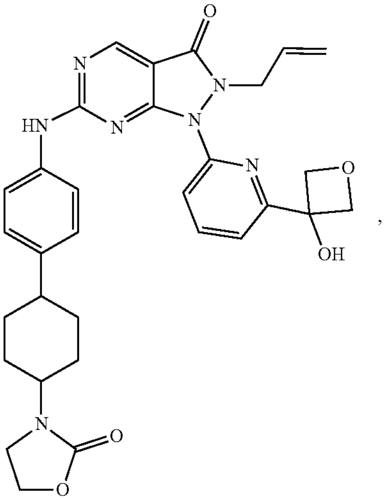
I-38
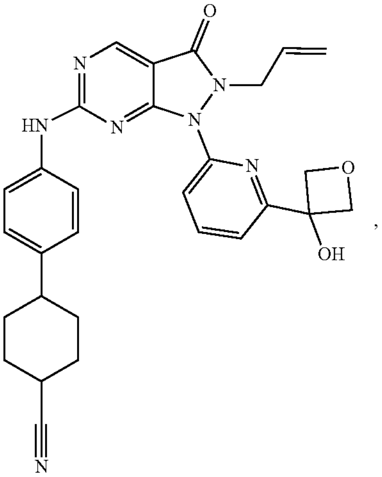

-continued
I-39
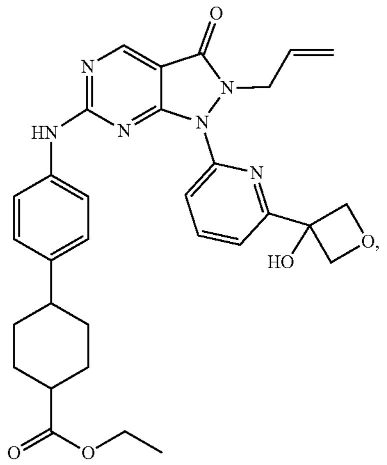
I-40
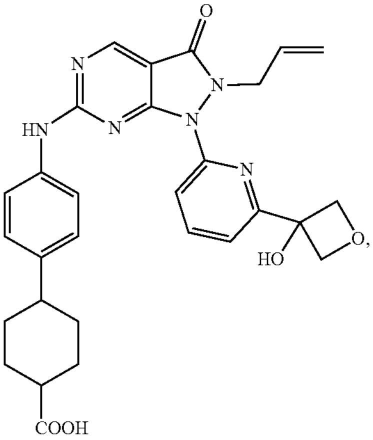
and
I-41
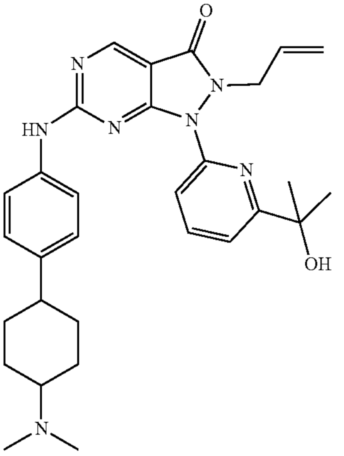
;
scheme B:
I-2
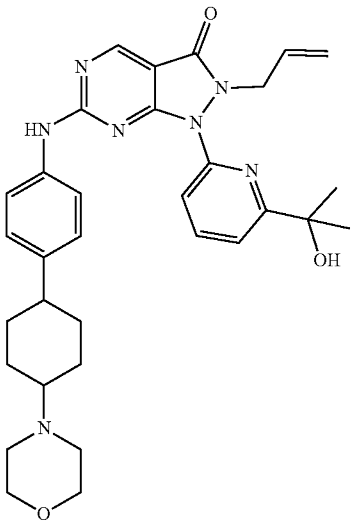
its $^{1}$H NMR (400 MHz, MeOD) is δ 8.85 (s, 1H), 8.00 (t, J=7.9 Hz, 1H), 7.80 (d, J=8.1 Hz, 1H), 7.68 (d, J=7.7 Hz, 1H), 7.62 (d, J=8.6 Hz, 2H), 7.28 (d, J=8.6 Hz, 2H), 5.78-5.68 (m, 1H), 5.06 (d, J=10.3 Hz, 1H), 4.95 (s, 1H), 4.82 (s, 2H), 3.82-3.76 (m, 1H), 2.81 (s, 1H), 2.71 (s, 3H), 2.49 (s, 1H), 2.08 (d, J=10.9 Hz, 3H), 1.94 (d, J=15.0 Hz, 3H), 1.72 (s, 4H), 1.59 (d, J=7.0 Hz, 6H);
I-4
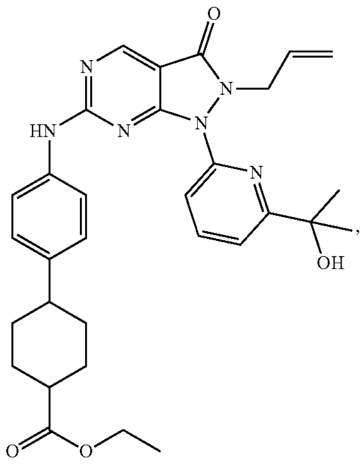
its $^{1}$H NMR (400 MHz, $CDCl_3$) is δ 8.87 (d, J=2.1 Hz, 1H), 7.91 (td, J=7.9, 1.5 Hz, 1H), 7.78 (d, J=8.0 Hz, 1H), 7.54 (t, J=7.9 Hz, 2H), 7.39 (d, J=7.7 Hz, 1H), 7.21 (d, J=8.5 Hz, 2H), 5.72 (ddt, J=16.4, 10.2, 6.2 Hz, 1H), 5.07 (dd, J=10.2, 1.1 Hz, 1H), 4.96 (dd, J=17.1, 1.2 Hz, 1H), 4.77 (d, J=6.2 Hz, 2H), 4.25-4.10 (m, 2H), 3.95 (s, 1H), 2.73 (s, 1H), 2.56 (dt, J=15.5, 10.8 Hz, 1H), 2.28 (d, J=7.9 Hz, 1H), 2.14 (d, J=10.6 Hz, 1H), 2.05-1.97 (m, 1H), 1.78 (dd, J=19.0, 8.5 Hz, 1H), 1.67 (dt, J=10.1, 6.1 Hz, 3H), 1.61 (s, 6H), 1.59-1.44 (m, 1H), 1.34-1.26 (m, 3H);

I-5

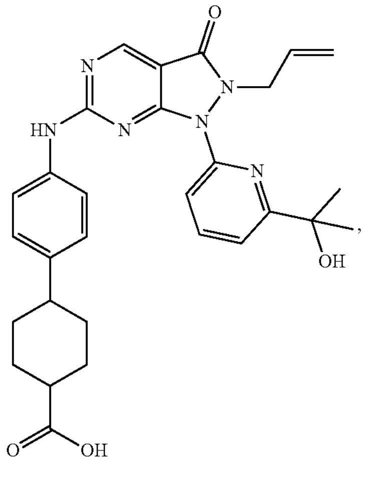

its H NMR (400 MHz, MeOD) is δ 8.84 (d, J=1.4 Hz, 1H), 8.00 (td, J=7.9, 4.0 Hz, 1H), 7.83-7.76 (m, 1H), 7.67 (dd, J=7.7, 0.7 Hz, 1H), 7.60 (dd, J=8.4, 5.7 Hz, 2H), 7.19 (dd, J=13.2, 8.6 Hz, 2H), 5.73 (ddd, J=17.0, 6.1, 4.1 Hz, 1H), 5.08-5.03 (m, 1H), 4.95 (d, J=1.3 Hz, 1H), 4.86-4.79 (m, 2H), 2.72 (s, 1H), 2.58 (s, 1H), 2.27 (d, J=6.7 Hz, 1H), 2.13 (d, J=10.0 Hz, 1H), 1.96 (d, J=10.2 Hz, 1H), 1.80-1.66 (m, 4H), 1.64-1.52 (m, 7H);

I-6

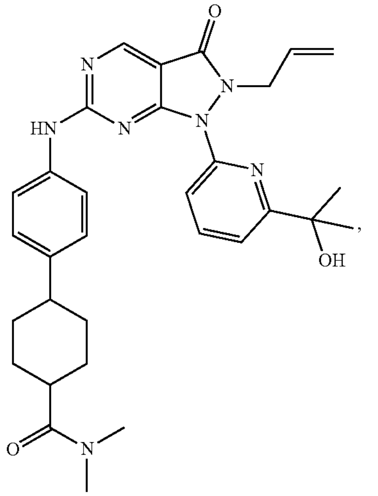

its $^1$H NMR (400 MHz, $CDCl_3$) is δ 8.86 (d, J=4.2 Hz, 1H), 7.97-7.88 (m, 1H), 7.79 (d, J=8.0 Hz, 1H), 7.53 (dd, J=12.3, 8.5 Hz, 2H), 7.39 (d, J=7.6 Hz, 1H), 7.28-7.15 (m, 2H), 5.80-5.65 (m, 1H), 5.06 (d, J=10.0 Hz, 1H), 4.95 (d, J=17.1 Hz, 1H), 4.77 (d, J=6.0 Hz, 2H), 3.10 (d, J=12.1 Hz, 3H), 2.98 (s, 3H), 2.67-2.57 (m, 1H), 2.14 (dd, J=20.9, 10.3 Hz, 1H), 2.06-1.97 (m, 2H), 1.92 (d, J=14.0 Hz, 1H), 1.78-1.66 (m, 4H), 1.61 (s, 6H), 1.49 (dd, J=22.8, 12.2 Hz, 1H);

I-7

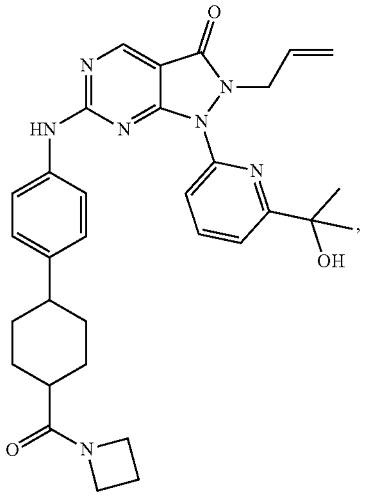

its $^1$H NMR (400 MHz, $CDCl_3$) is δ 8.85 (d, J=4.7 Hz, 1H), 7.91 (dt, J=10.7, 7.9 Hz, 1H), 7.78 (d, J=7.8 Hz, 1H), 7.53 (dd, J=12.0, 8.5 Hz, 2H), 7.39 (dd, J=7.6, 2.4 Hz, 1H), 7.22 (dd, J=19.5, 8.5 Hz, 2H), 5.71 (ddt, J=16.4, 10.2, 6.2 Hz, 1H), 5.06 (d, J=10.2 Hz, 1H), 4.95 (d, J=17.1 Hz, 1H), 4.77 (d, J=6.1 Hz, 2H), 4.21 (dd, J=16.4, 8.6 Hz, 2H), 4.10-4.02 (m, 2H), 2.63-2.52 (m, 2H), 2.35-2.20 (m, 2H), 2.15-2.07 (m, 1H), 2.00 (dd, J=13.4, 3.0 Hz, 2H), 1.92-1.83 (m, 1H), 1.79-1.63 (m, 4H), 1.60 (s, 6H), 1.48 (ddd, J=24.7, 12.5, 2.5 Hz, 1H);

I-8

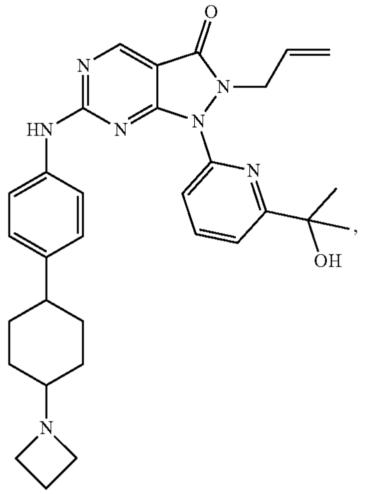

its $^1$H NMR (400 MHz, $CDCl_3$) is δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H);

I-17

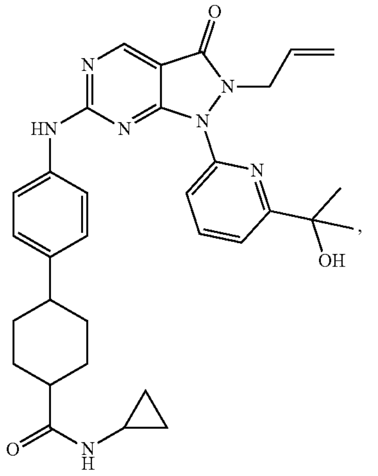

its ¹H NMR (400 MHz, $CDCl_3$) is δ 8.84 (d, J=3.7 Hz, 1H), 7.94 (dd, J=14.8, 6.9 Hz, 1H), 7.76 (d, J=7.9 Hz, 1H), 7.58-7.50 (m, 2H), 7.42 (dd, J=7.5, 4.1 Hz, 1H), 7.22 (dd, J=15.8, 8.5 Hz, 2H), 5.71 (dd, J=11.5, 5.4 Hz, 2H), 5.07 (d, J=10.2 Hz, 1H), 4.95 (d, J=17.1 Hz, 1H), 4.77 (d, J=6.1 Hz, 2H), 2.82-2.72 (m, 1H), 2.60 (s, 1H), 2.12-2.01 (m, 3H), 1.92 (d, J=12.5 Hz, 1H), 1.81-1.67 (m, 3H), 1.62 (s, 6H), 1.54-1.43 (m, 1H), 0.93-0.78 (m, 3H), 0.52 (s, 2H);

I-19

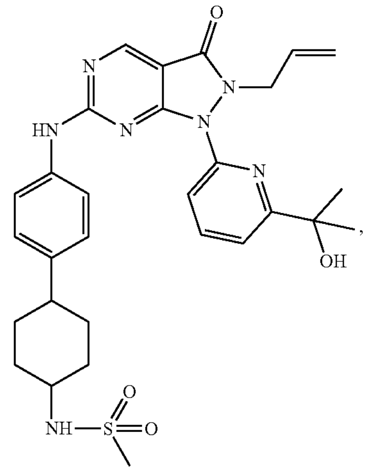

its ¹H NMR (400 MHz, $CDCl_3$) is δ 8.88 (s, 1H), 7.91 (t, J=7.9 Hz, 1H), 7.77 (d, J=7.9 Hz, 1H), 7.56 (d, J=8.5 Hz, 2H), 7.40 (d, J=7.4 Hz, 1H), 7.19 (d, J=8.5 Hz, 2H), 5.78-5.66 (m, 1H), 5.07 (dd, J=10.2, 1.0 Hz, 1H), 4.96 (dd, J=17.1, 1.2 Hz, 1H), 4.77 (d, J=6.2 Hz, 2H), 4.42 (d, J=7.6 Hz, 1H), 3.49-3.35 (m, 1H), 3.04 (s, 3H), 2.57-2.46 (m, 1H), 2.29-2.17 (m, 2H), 2.05-1.96 (m, 8H), 1.56-1.65 (m, 2H), 1.41-1.50 (m, 2H);

I-20

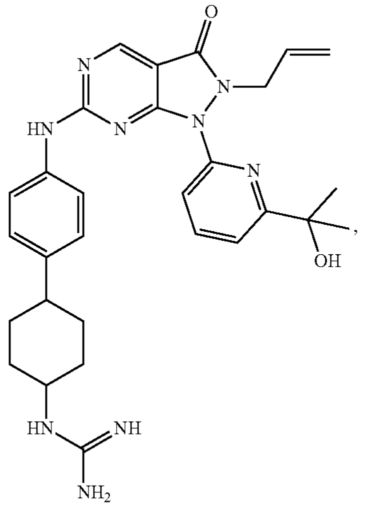

its ¹H NMR (400 MHz, MeOD) is δ 8.84 (s, 1H), 8.02 (m, 1H), 7.80 (m, 1H), 7.72-7.58 (m, 3H), 7.25 (m, 2H), 5.73 (ddt, J=16.5, 10.3, 6.1 Hz, 1H), 5.05 (dd, J=10.2, 1.0 Hz, 1H), 4.95 (d, 1H), 4.83 (d, J=6.1 Hz, 2H), 3.54-3.42 (m, 1H), 2.59 (m, 1H), 2.14 (m, 1H), 1.98 (m, 2H), 1.83 (m, 1H), 1.68 (m, 2H), 1.60 (s, 6H), 1.50 (m, 2H);

I-23

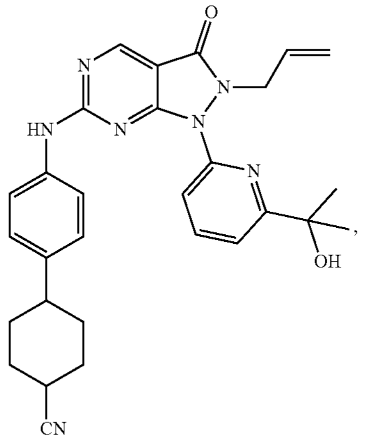

its ¹H NMR (400 MHz, DMSO) is δ 10.28 (s, 1H), 8.88 (d, J=1.8 Hz, 1H), 8.09-7.97 (m, 1H), 7.75 (d, J=8.4 Hz, 1H), 7.66 (dd, J=20.6, 8.5 Hz, 3H), 7.19 (dd, J=11.1, 8.7 Hz, 2H), 5.74-5.61 (m, 1H), 5.00 (d, J=10.2 Hz, 1H), 4.82 (d, J=17.1 Hz, 1H), 4.69 (d, J=5.5 Hz, 2H), 3.23 (s, 1H), 2.74 (t, J=12.1 Hz, 1H), 2.53 (s, 1H), 2.12 (d, J=10.1 Hz, 1H), 1.98 (d, J=13.2 Hz, 1H), 1.82 (d, J=13.2 Hz, 2H), 1.77-1.57 (m, 3H), 1.49 (d, J=18.2 Hz, 6H);

I-31

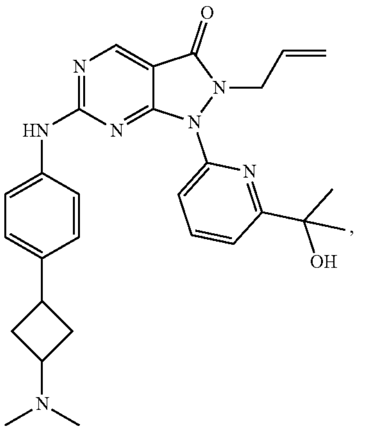

its $^1H$ NMR (400 MHz, DMSO) is δ 10.27 (s, 1H), 8.89 (s, 1H), 8.12 (s, 1H), 7.74 (dd, J=22.6, 8.3 Hz, 3H), 7.64 (d, J=7.3 Hz, 1H), 7.37 (d, J=8.5 Hz, 2H), 5.76-5.61 (m, 1H), 5.34 (s, 1H), 5.01 (dd, J=10.3, 1.2 Hz, 1H), 4.84 (d, J=17.1 Hz, 1H), 4.70 (d, J=5.7 Hz, 2H), 3.62 (s, 1H), 3.12 (s, 1H), 2.71-2.58 (m, 8H), 2.38 (d, J=9.2 Hz, 2H), 1.47 (s, 6H), 1.32-1.24 (m, 1H);

I-32

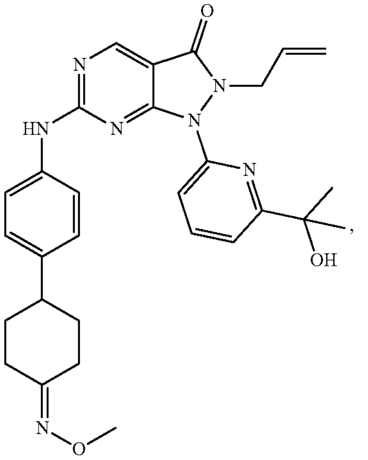

its $^1H$ NMR (400 MHz, DMSO) is δ 10.26 (s, 1H), 8.88 (s, 1H), 8.07 (t, J=7.8 Hz, 1H), 7.76 (d, J=8.0 Hz, 1H), 7.65 (dd, J=14.5, 7.9 Hz, 2H), 7.22 (d, J=8.5 Hz, 2H), 5.74-5.60 (m, 1H), 5.35 (s, 1H), 5.00 (d, J=10.3 Hz, 1H), 4.83 (d, J=17.1 Hz, 1H), 4.69 (d, J=5.6 Hz, 2H), 3.74 (s, 3H), 3.24-3.15 (m, 1H), 2.77 (t, J=12.0 Hz, 1H), 2.37 (d, J=14.0 Hz, 1H), 2.25 (td, J=13.4, 4.6 Hz, 1H), 1.99-1.84 (m, 3H), 1.67-1.50 (m, 2H), 1.49 (d, J=14.0 Hz, 6H);

I-33

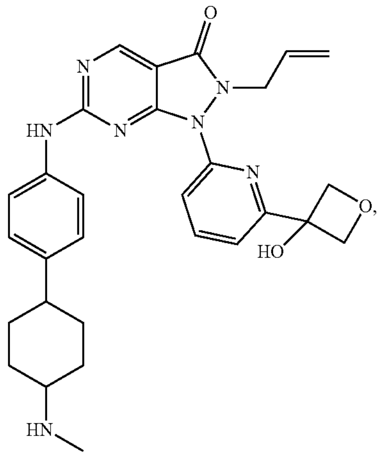

its $^1H$ NMR (400 MHz, MeOD) is δ 8.86 (s, OH), 8.11-8.01 (m, 1H), 7.94 (d, J=7.9 Hz, 2H), 7.67 (d, J=7.6 Hz, 2H), 7.62 (d, J=8.6 Hz, 2H), 7.28 (d, J=8.5 Hz, 2H), 5.83-5.74 (m, 1H), 5.09 (dd, J=7.9, 4.4 Hz, 3H), 4.98 (dd, J=17.1, 1.3 Hz, 2H), 4.85 (d, J=6.7 Hz, 2H), 2.87 (s, 1H), 2.64 (s, 1H), 2.47 (s, 3H), 1.97-1.67 (m, 8H);

I-34

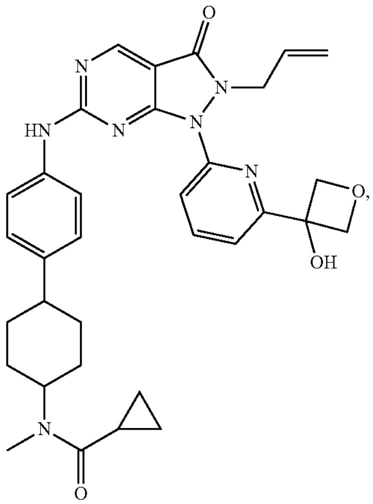

its $^1H$ NMR (400 MHz, MeOD) is δ 8.87 (d, J=6.6 Hz, 1H), 8.06 (t, J=7.9 Hz, 1H), 7.95 (d, J=7.9 Hz, 1H), 7.68 (dd, J=7.8, 5.4 Hz, 2H), 7.61 (d, J=8.6 Hz, 1H), 7.41 (d, J=8.4 Hz, 1H), 7.24 (t, J=8.7 Hz, 1H), 5.84-5.72 (m, 1H), 5.09 (d, J=6.2 Hz, 2H), 5.07 (d, J=1.3 Hz, 1H), 5.02-4.94 (m, 2H), 4.90 (s, 2H), 4.84 (d, J=6.7 Hz, 2H), 3.15 (d, J=2.6 Hz, 1H), 3.08 (s, 1H), 2.95 (s, 1H), 2.71 (s, 1H), 2.43 (s, 1H), 1.93-2.03 (m, 3H), 1.76 (s, 2H), 1.51 (s, 1H), 1.31 (d, J=4.3 Hz, 3H), 0.89 (dd, J=20.1, 9.0 Hz, 4H);

I-35

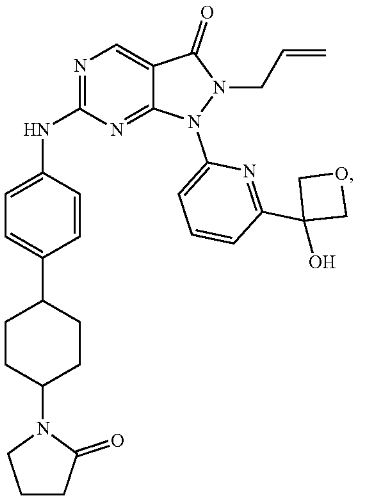

its $^1H$ NMR (400 MHz, $CDCl_3$) is δ 8.87-8.79 (m, 1H), 8.14-8.07 (m, 1H), 8.04-7.96 (m, 1H), 7.89-7.80 (m, 1H), 7.61-7.50 (m, 2H), 7.38-7.32 (m, 1H), 7.25-7.19 (m, 1H), 7.01 (t, J=3.4 Hz, 1H), 5.72 (ddd, J=16.6, 11.1, 8.6 Hz, 1H), 5.17-5.09 (m, 2H), 5.04-4.98 (m, 1H), 4.98-4.92 (m, 1H), 4.87-4.77 (m, 2H), 4.73-4.64 (m, 2H), 4.20-4.06 (m, 1H), 3.47-3.38 (m, 1H), 3.38-3.29 (m, 1H), 3.05-2.98 (m, 1H), 2.49-2.35 (m, 2H), 2.27-2.17 (m, 1H), 2.07-1.86 (m, 4H), 1.75-1.60 (m, 3H);

I-37

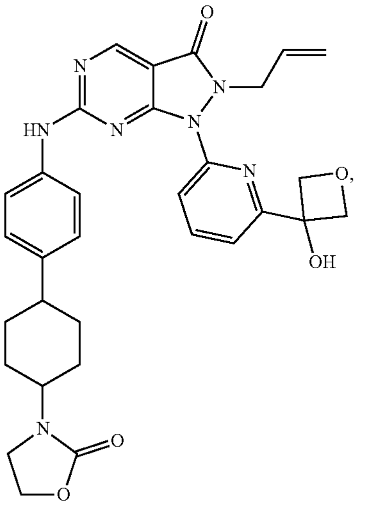

its $^1H$ NMR (400 MHz, $CDCl_3$) is δ 8.77 (s, 1H), 8.16-8.07 (m, 1H), 8.03 (d, J=7.6 Hz, 1H), 7.83-7.75 (m, 1H), 7.56 (dd, J=12.6, 6.1 Hz, 2H), 7.33 (d, J=8.5 Hz, 1H), 7.21 (d, J=8.5 Hz, 1H), 5.72 (dd, J=17.0, 10.3 Hz, 1H), 5.13 (dd, J=9.1, 6.1 Hz, 2H), 4.96 (d, J=17.0 Hz, 2H), 4.81 (d, J=7.2 Hz, 2H), 4.69 (d, J=6.2 Hz, 2H), 4.41-4.28 (m, 2H), 3.86 (s, 1H), 3.77 (t, J=6.6 Hz, 1H), 3.63-3.50 (m, 2H), 2.98 (m, 1H), 2.15 (m, 1H), 1.97 (dd, J=18.9, 9.6 Hz, 2H), 1.78 (d, J=5.0 Hz, 2H), 1.65 (d, J=8.7 Hz, 2H);

I-38

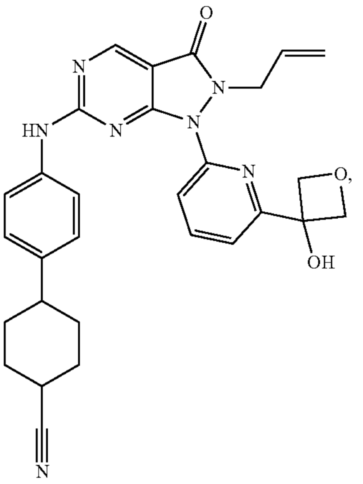

its $^1H$ NMR (400 MHz, $CDCl_3$) is δ 8.69 (s, 1H), 8.18 (d, J=8.0 Hz, 1H), 8.10 (dd, J=17.9, 7.6 Hz, 1H), 7.81-7.72 (m, 1H), 7.63-7.49 (m, 2H), 7.25 (d, J=8.4 Hz, 1H), 7.19 (d, J=8.3 Hz, 1H), 5.70 (d, J=6.8 Hz, 1H), 5.15 (d, J=10.1 Hz, 1H), 5.14-5.07 (m, 1H), 4.95 (d, J=16.6 Hz, 1H), 4.83 (t, J=6.7 Hz, 2H), 4.71 (s, 2H), 2.54 (dd, J=24.9, 12.6 Hz, 2H), 2.30 (d, J=11.2 Hz, 1H), 2.18 (d, J=13.5 Hz, 1H), 2.02 (d, J=12.9 Hz, 1H), 1.96-1.80 (m, 2H), 1.78 (d, J=16.1 Hz, 1H), 1.49 (dd, J=26.4, 11.2 Hz, 2H);

I-39

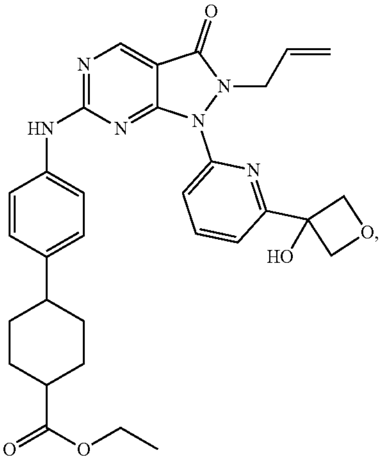

its $^1H$ NMR (400 MHz, Methanol-$d_4$) is δ 8.85 (d, J=1.1 Hz, 1H), 8.05 (td, J=7.9, 4.8 Hz, 1H), 7.96-7.86 (m, 1H), 7.67 (d, J=7.6 Hz, 1H), 7.59 (ddd, J=9.2, 4.6, 2.3 Hz, 2H), 7.25-7.19 (m, 1H), 7.19-7.11 (m, 1H), 5.78 (ddt, J=16.5, 10.1, 6.1 Hz, 1H), 5.12-5.07 (m, 2H), 5.06 (t, J=1.3 Hz, 1H), 4.98 (dd, J=17.0, 1.4 Hz, 1H), 4.90 (d, J=1.4 Hz, 2H), 4.25-4.19 (m, 1H), 4.14 (dd, J=14.1, 7.1 Hz, 1H), 2.34-2.12 (m, 2H), 2.07 (dd, J=17.0, 4.1 Hz, 1H), 1.99-1.82 (m, 1H), 1.74-1.65 (m, 2H), 1.65-1.53 (m, 2H), 1.31 (d, J=4.2 Hz, 3H), 1.29-1.25 (m, 2H);

I-40
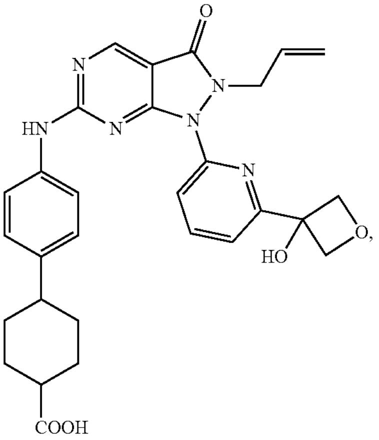
its $^{1}$H NMR (400 MHz, Methanol-$d_4$) is δ 8.84 (s, 1H), 8.05 (t, J=7.9 Hz, 1H), 7.92 (d, J=8.1 Hz, 1H), 7.66 (dd, J=7.6, 0.9 Hz, 1H), 7.63-7.53 (m, 2H), 7.22-7.14 (m, 2H), 5.84-5.74 (m, 1H), 5.10-5.07 (m, 2H), 5.06 (q, J=1.3 Hz, 1H), 4.98 (dq, J=17.0, 1.4 Hz, 1H), 4.89 (dt, J=6.1, 1.4 Hz, 2H), 2.71 (d, J=6.9 Hz, 1H), 2.59 (s, 1H), 2.24 (dd, J=16.4, 7.8 Hz, 2H), 2.04 (d, J=8.5 Hz, 1H), 1.73 (td, J=10.9, 6.8 Hz, 6H);
scheme C:
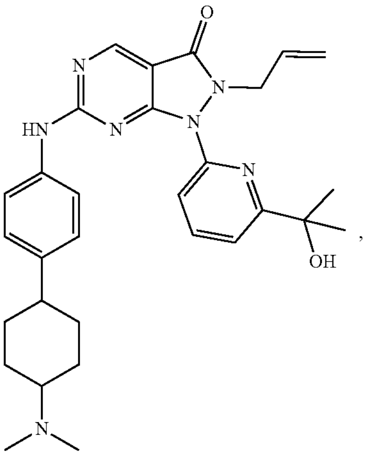
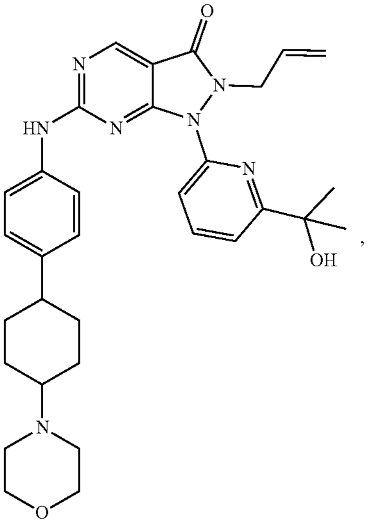
-continued
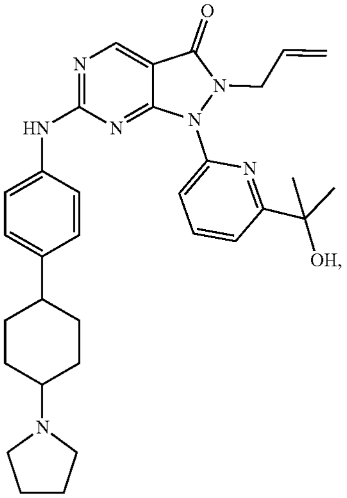
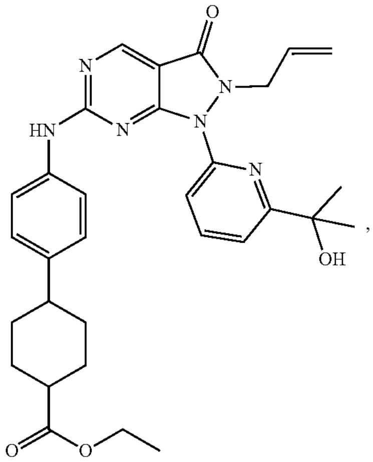
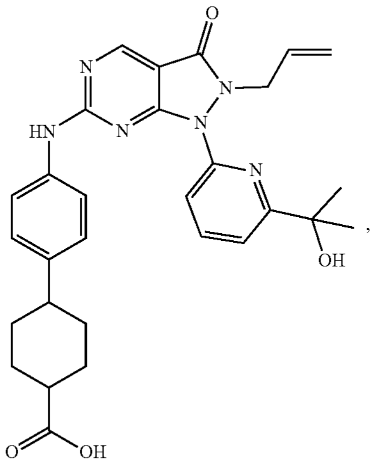

-continued
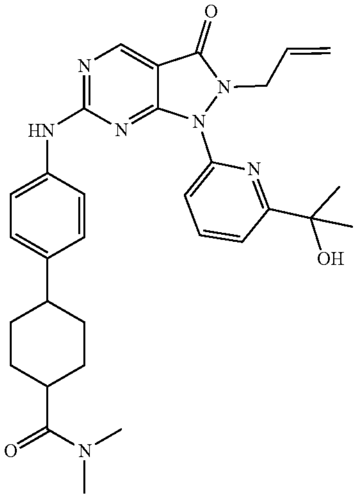
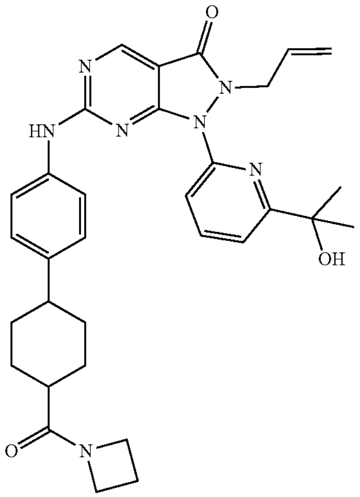
,
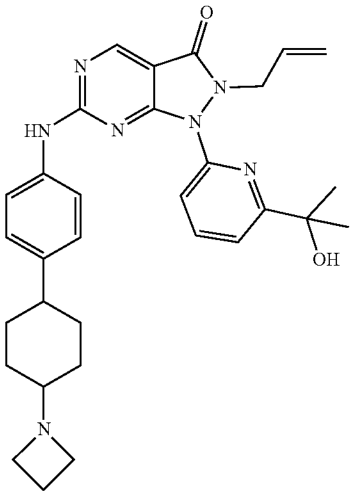
,
-continued
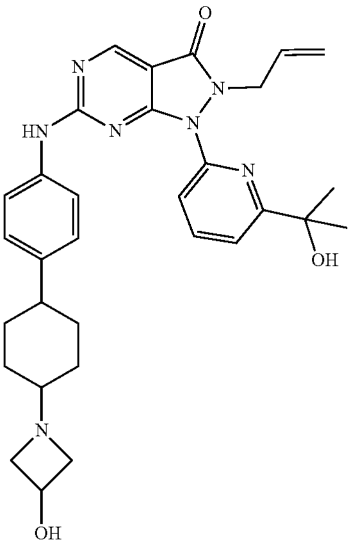
,
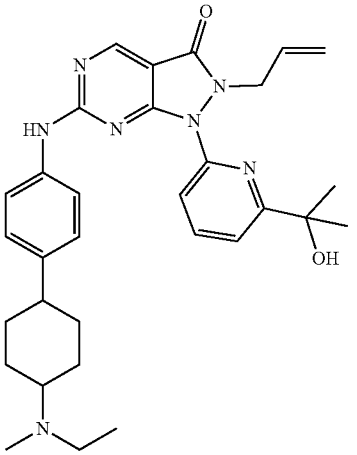
,
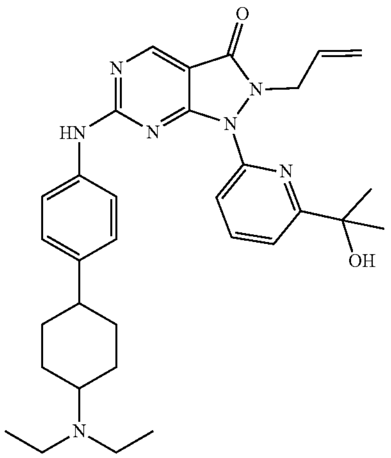
, -continued
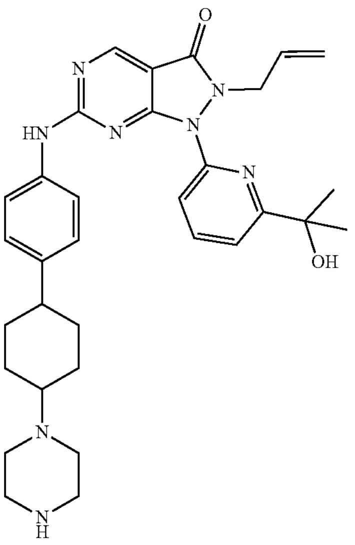
,
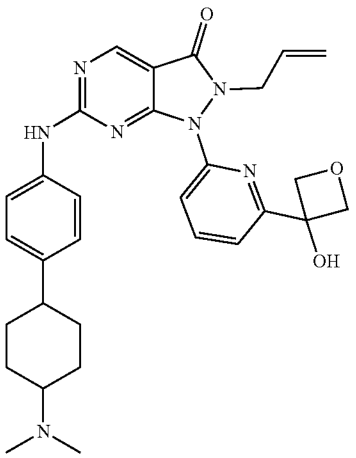
,
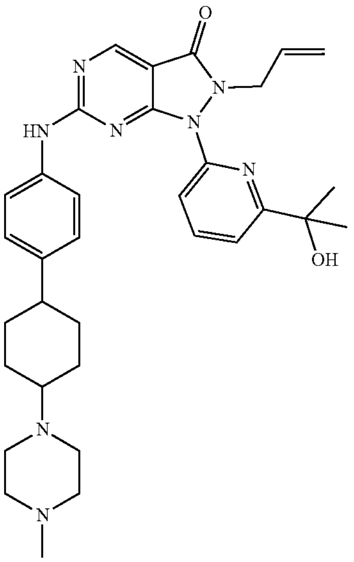
,
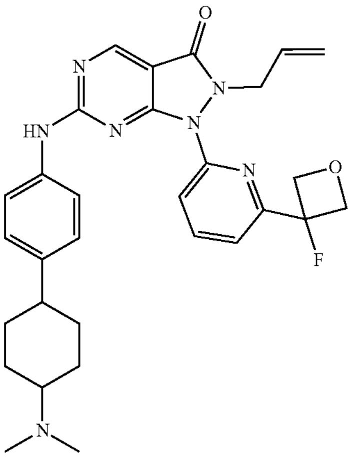
,
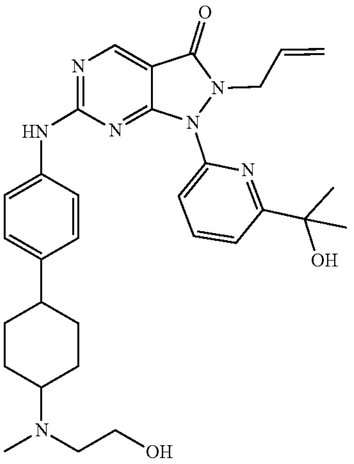
,
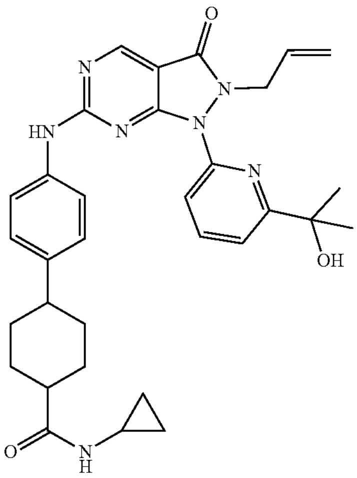
, -continued
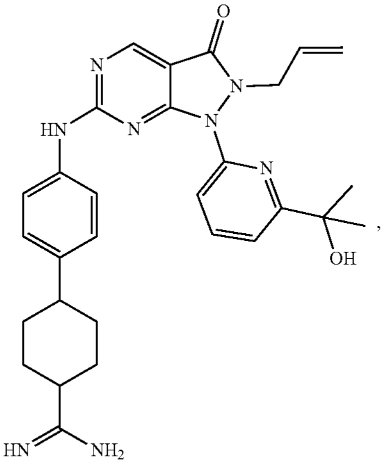
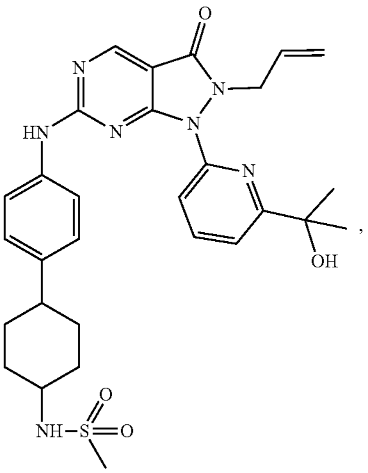
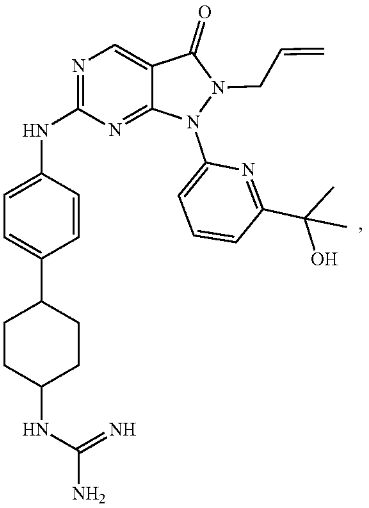
-continued
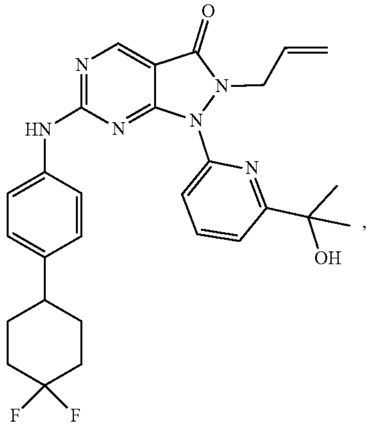
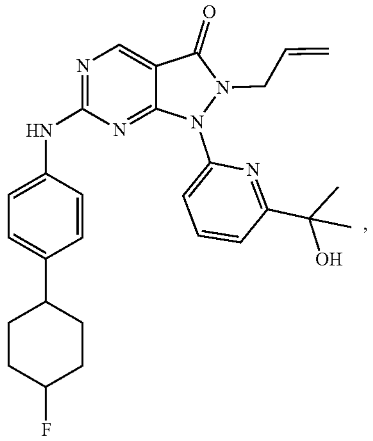
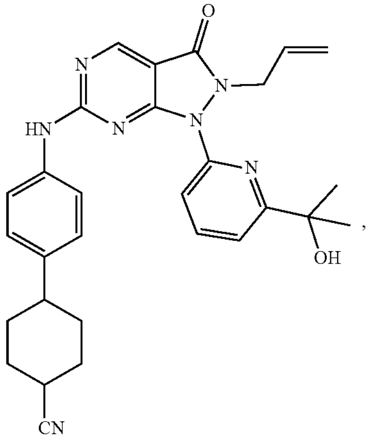

-continued
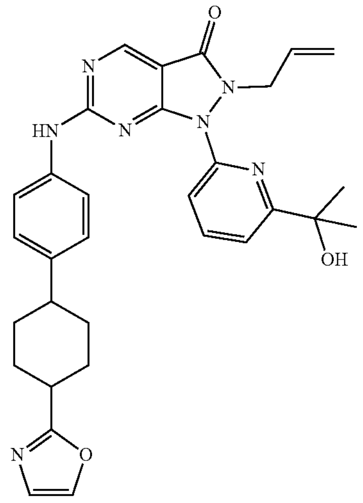
,
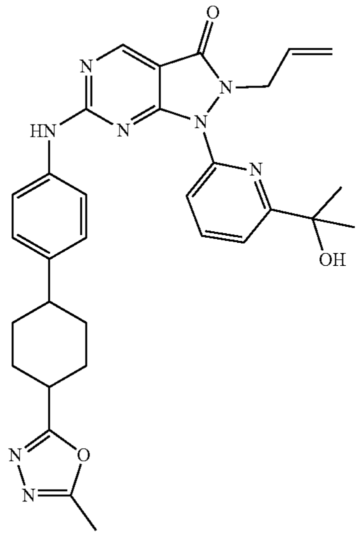
,
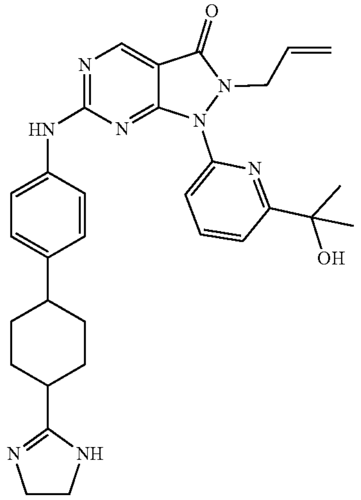
,
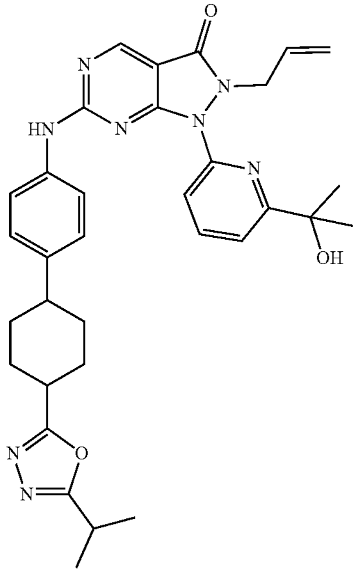
,
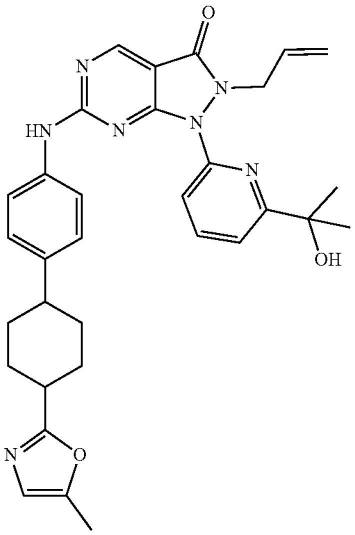
,
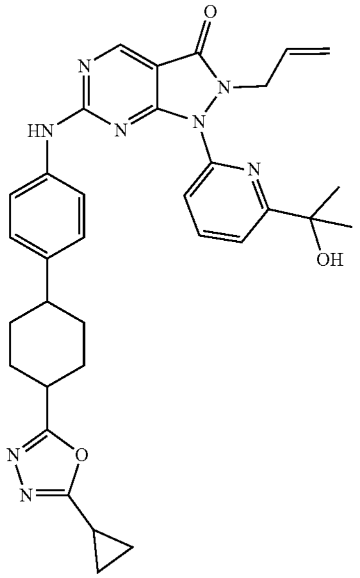
, -continued
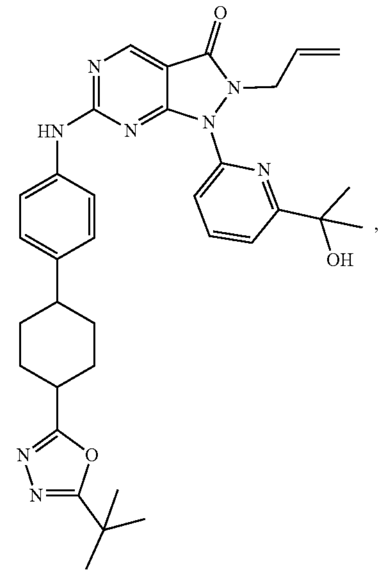
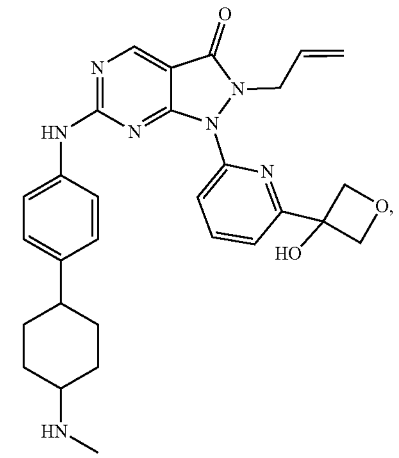
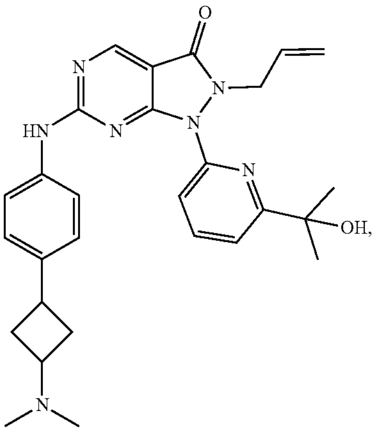
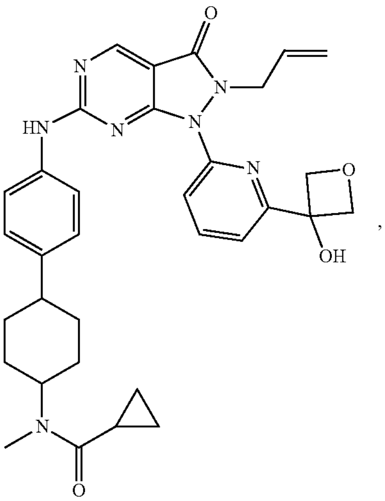
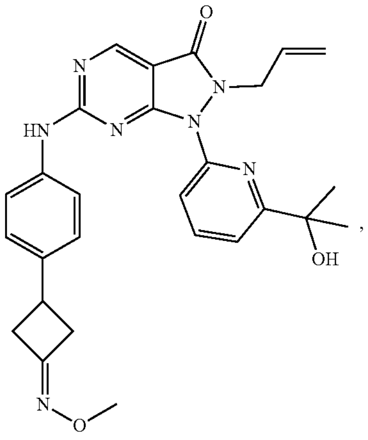
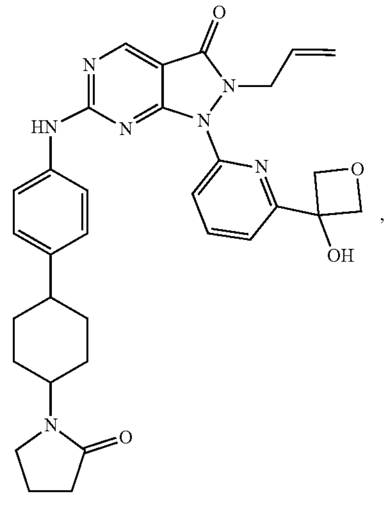

-continued
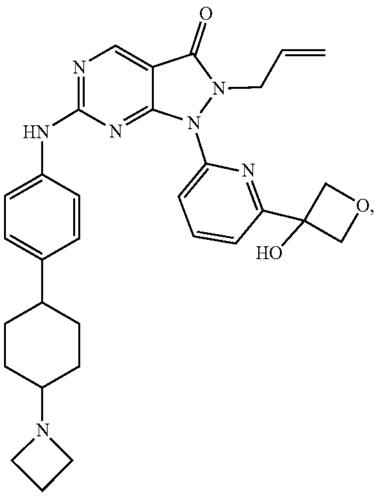
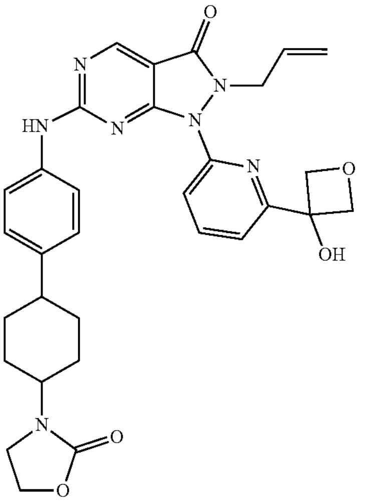
,
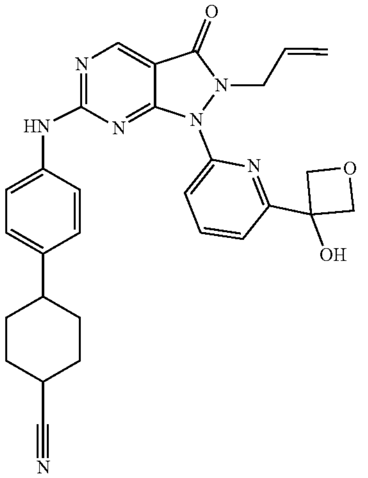
,
-continued
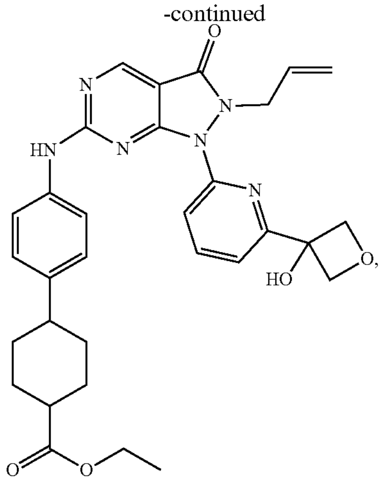
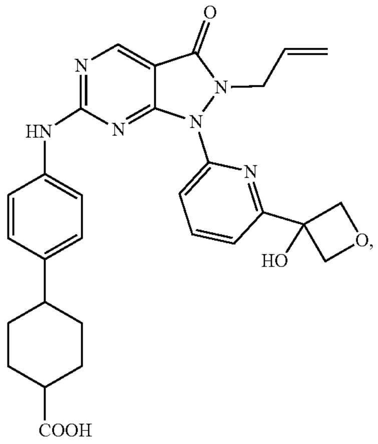
and
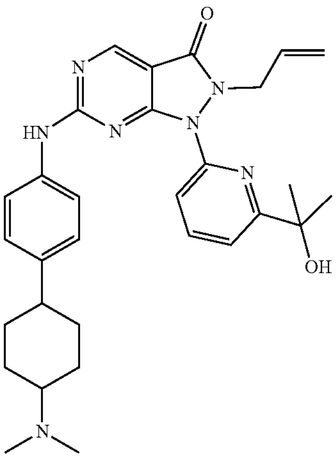
;

scheme D:

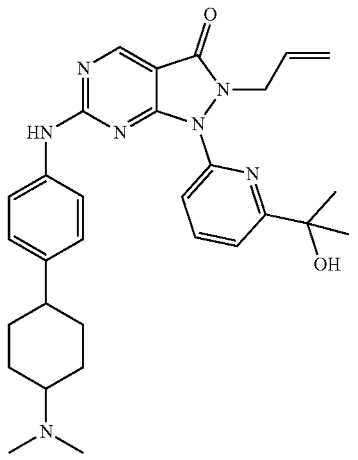 [SMILES: C=CCn1c(=O)c2cnc(Nc3ccc(C4CCC(N(C)C)CC4)cc3)nc2n1-c1cccc(C(C)(C)O)n1]

(I-1-1), its $^1$H NMR (400 MHz, MeOD) is δ 8.85 (s, 1H), 8.46 (s, 2H), 7.99 (t, J=7.9 Hz, 1H), 7.79 (d, J=8.0 Hz, 1H), 7.65 (dd, J=16.6, 8.1 Hz, 3H), 7.22 (d, J=8.6 Hz, 2H), 5.73 (ddt, J=16.3, 10.2, 6.1 Hz, 1H), 5.05 (dd, J=10.3, 1.1 Hz, 1H), 4.93 (dd, J=17.1, 1.3 Hz, 1H), 4.82 (d, J=6.1 Hz, 2H), 2.90 (s, 6H), 2.60 (d, J=8.4 Hz, 1H), 2.21 (s, 2H), 2.10 (d, J=10.6 Hz, 2H), 1.70 (d, J=11.4 Hz, 4H), 1.59 (s, 6H);

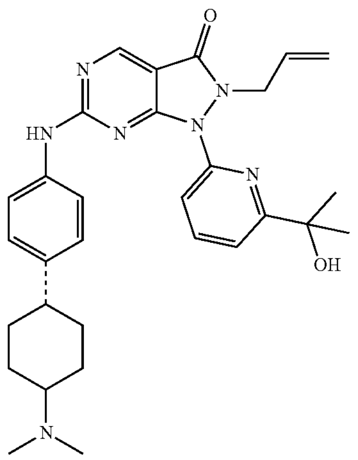

(I-1-2), its $^1$H NMR (400 MHz, $CDCl_3$) is δ 8.86 (s, 1H), 8.54 (s, 1H), 7.95 (t, J=7.9 Hz, 1H), 7.75 (d, J=8.0 Hz, 1H), 7.59 (d, J=8.5 Hz, 2H), 7.43 (d, J=7.6 Hz, 1H), 7.32 (d, J=8.5 Hz, 2H), 5.72 (ddt, J=16.5, 10.3, 6.2 Hz, 1H), 5.06 (d, J=10.2 Hz, 1H), 4.95 (dd, J=17.1, 1.0 Hz, 1H), 4.75 (d, J=6.1 Hz, 2H), 3.05 (m, 1H), 2.93 (m, 1H), 2.68 (s, 6H), 2.32 (m, 2H), 1.84 (m, 6H), 1.60 (s, 6H);

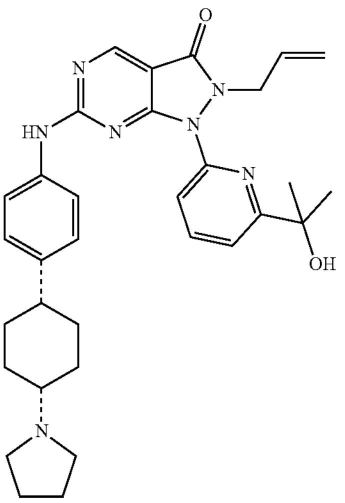

(I-3-1), its $^1$H NMR (400 MHz, $CDCl_3$) is δ 8.87 (s, 1H), 7.90 (t, J=7.9 Hz, 1H), 7.78 (d, J=8.0 Hz, 1H), 7.53 (d, J=8.5 Hz, 2H), 7.39 (dd, J=7.6, 0.5 Hz, 1H), 7.20 (d, J=8.5 Hz, 2H), 5.72 (ddt, J=16.4, 10.2, 6.2 Hz, 1H), 5.06 (dd, J=10.2, 1.0 Hz, 1H), 4.95 (dd, J=17.1, 1.2 Hz, 1H), 4.76 (d, J=6.2 Hz, 2H), 4.04 (s, 1H), 2.66 (m, 4H), 2.58-2.47 (m, 1H), 2.16 (m, 4H), 1.96 (m, 2H), 1.87-1.78 (m, 4H), 1.60 (s, 6H), 1.58-1.39 (m, 4H);

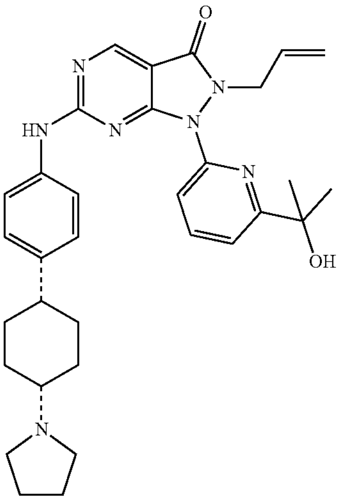

(I-3-2), its $^1$H NMR (400 MHz, $CDCl_3$) is δ 8.87 (s, 1H), 7.92 (t, J=7.9 Hz, 1H), 7.80 (d, J=8.0 Hz, 1H), 7.52 (d, J=8.5 Hz, 2H), 7.38 (d, J=7.6 Hz, 1H), 7.29 (t, J=4.2 Hz, 2H), 5.79-5.66 (m, 1H), 5.06 (dd, J=10.2, 1.0 Hz, 1H), 4.96 (dd, J=17.1, 1.2 Hz, 1H), 4.77 (d, J=6.2 Hz, 2H), 4.02 (s, 1H), 2.70-2.50 (m, 5H), 2.26 (s, 1H), 1.98 (m, 4H), 1.82 (s, 4H), 1.69-1.56 (m, 10H);

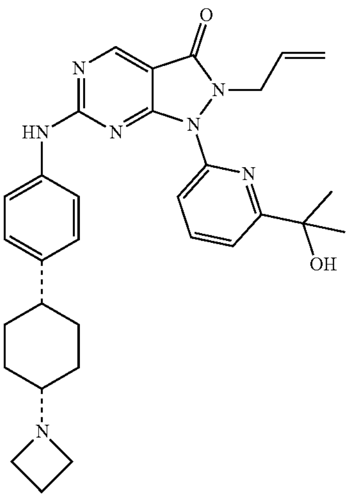

(I-8-1), its $^1$H NMR (400 MHz, $CDCl_3$) is δ 8.86 (s, 1H), 7.93-7.85 (m, 1H), 7.78 (d, J=7.8 Hz, 1H), 7.52 (d, J=8.5 Hz, 2H), 7.39 (dd, J=7.6, 0.7 Hz, 1H), 7.19 (d, J=8.5 Hz, 2H), 5.71 (ddt, J=16.4, 10.2, 6.2 Hz, 1H), 5.05 (dd, J=10.2, 1.1 Hz, 1H), 4.94 (dd, J=17.1, 1.3 Hz, 1H), 4.77 (d, J=6.2 Hz, 2H), 4.11 (d, J=8.9 Hz, 1H), 3.24 (t, J=7.0 Hz, 4H), 2.52-2.43 (m, 1H), 2.14-2.00 (m, 3H), 1.92 (d, J=11.2 Hz, 4H), 1.60 (s, 6H), 1.45 (dt, J=14.9, 7.5 Hz, 2H), 1.23-1.08 (m, 2H);

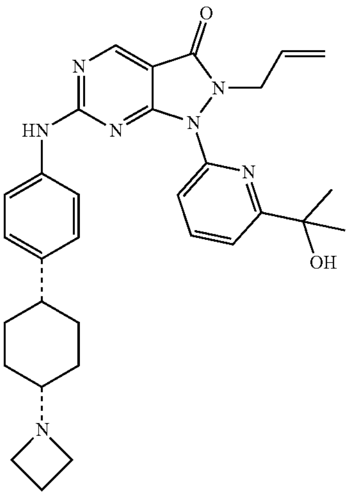

(I-8-2), its $^1$H NMR (400 MHz, $CDCl_3$) is δ8.87 (s, 1H), 7.92 (d, J=7.8 Hz, 1H), 7.80 (d, J=8.0 Hz, 1H), 7.52 (d, J=8.4 Hz, 2H), 7.39 (d, J=7.6 Hz, 1H), 7.29-7.25 (m, 2H), 5.82-5.63 (m, 1H), 5.12-4.91 (m, 2H), 4.78 (d, J=6.2 Hz, 2H), 4.01 (s, 1H), 3.17 (s, 4H), 2.53 (s, 1H), 2.33 (s, 1H), 2.06 (d, J=4.4 Hz, 2H), 1.89 (d, J=11.6 Hz, 2H), 1.75 (d, J=14.1 Hz, 2H), 1.59 (d, J=17.2 Hz, 8H), 1.46 (t, J=13.1 Hz, 2H);

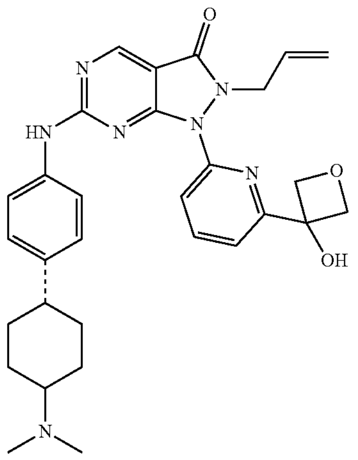

(I-15-1), its $^1$H NMR (400 MHz, MeOD) is δ 8.84 (s, 1H), 8.04 (t, J=7.9 Hz, 1H), 7.92 (d, J=8.1 Hz, 1H), 7.67 (d, J=7.6 Hz, 1H), 7.60 (d, J=8.6 Hz, 2H), 7.21 (d, J=8.6 Hz, 2H), 5.78 (ddt, J=16.3, 10.3, 6.1 Hz, 1H), 5.12-5.05 (m, 3H), 4.98 (dd, J=17.1, 1.3 Hz, 1H), 4.89 (d, J=6.1 Hz, 2H), 4.84 (s, 2H), 3.68 (s, 2H), 2.97-2.86 (m, 1H), 2.66 (s, 6H), 2.60-2.50 (m, 1H), 2.15 (d, J=8.6 Hz, 2H), 2.04 (d, J=9.0 Hz, 2H), 1.66-1.54 (m, 4H);

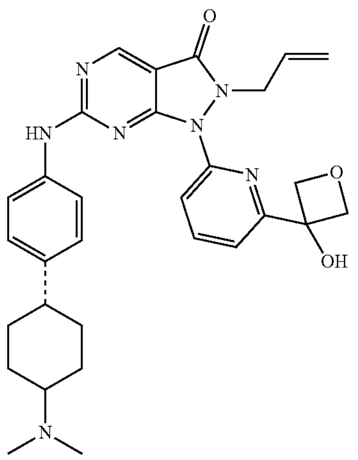

(I-15-2), its $^1$H NMR (400 MHz, MeOD) is δ 8.83 (s, 1H), 8.04 (t, J=7.9 Hz, 1H), 7.92 (d, J=8.0 Hz, 1H), 7.67-7.62 (m, 1H), 7.59 (d, J=8.6 Hz, 2H), 7.29 (d, J=8.5 Hz, 2H), 5.76 (ddt, J=16.3, 10.2, 6.1 Hz, 1H), 5.10-5.02 (m, 3H), 4.96 (dd, J=17.1, 1.3 Hz, 1H), 4.87 (d, J=6.8 Hz, 2H), 4.82 (d, J=6.8 Hz, 2H), 2.73 (d, J=4.2 Hz, 1H), 2.29 (d, J=21.9 Hz, 7H), 2.04-1.90 (m, 4H), 1.66 (dd, J=15.6, 6.1 Hz, 4H);

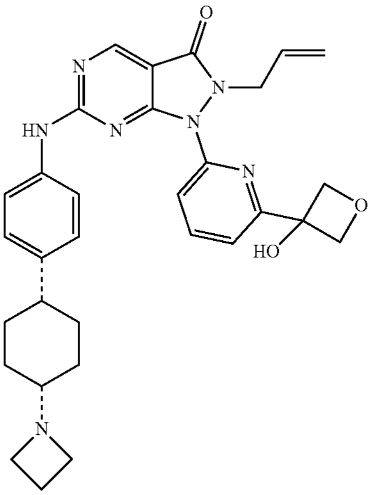

(I-36-1), its $^1$H NMR (400 MHz, $CDCl_3$) is δ 8.88 (d, J=2.6 Hz, 1H), 8.09 (dd, J=15.0, 7.8 Hz, 1H), 7.99-7.83 (m, 2H), 7.54 (t, J=9.5 Hz, 2H), 7.39 (d, J=8.7 Hz, 1H), 7.21 (d, J=8.5 Hz, 1H), 5.74 (dq, J=10.5, 5.9 Hz, 1H), 5.12 (t, J=8.8 Hz, 3H), 4.99 (d, J=17.1 Hz, 1H), 4.80 (d, J=6.3 Hz, 2H), 4.67 (d, J=6.0 Hz, 2H), 3.39-3.24 (m, 4H), 2.60-2.34 (m, 3H), 2.14 (dt, J=14.0, 6.8 Hz, 3H), 1.96 (d, J=10.8 Hz, 4H), 1.55-1.37 (m, 2H), 1.27-1.12 (m, 2H);

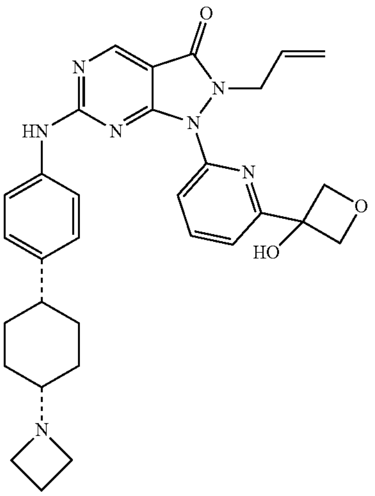

(I-36-2), its $^1$H NMR (400 MHz, MeOD) is δ 8.86 (s, 1H), 8.02 (dt, J=24.0, 7.9 Hz, 3H), 7.64 (dd, J=27.1, 8.1 Hz, 3H), 7.27 (t, J=8.6 Hz, 2H), 7.01-6.91 (m, 3H), 6.72-6.64 (m, 3H), 5.79 (ddd, J=16.3, 11.2, 6.1 Hz, 1H), 5.10-5.05 (m, 2H), 4.85 (d, J=6.8 Hz, 2H), 2.57 (d, J=10.7 Hz, 1H), 2.48-2.28 (m, 3H), 2.23-2.06 (m, 3H), 1.98-1.71 (m, 6H), 1.58 (dd, J=23.2, 12.9 Hz, 3H), 1.44 (ddd, J=16.1, 13.2, 3.5 Hz, 2H), 1.19-1.00 (m, 2H);

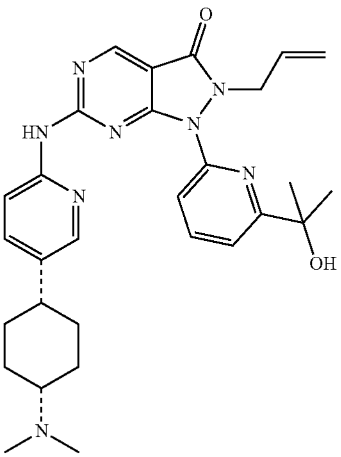

(I-41-1), its $^1$H NMR (400 MHz, Chloroform-d) is δ 9.00 (s, 1H), 8.30 (d, J=8.6 Hz, 1H), 8.22 (d, J=2.4 Hz, 1H), 7.96 (t, J=7.9 Hz, 1H), 7.73 (dd, J=8.1, 0.8 Hz, 1H), 7.55 (dd, J=8.7, 2.4 Hz, 1H), 7.44 (dd, J=7.7, 0.8 Hz, 1H), 5.77-5.66 (m, 1H), 5.12-5.05 (m, 1H), 4.97 (dq, J=17.0, 1.4 Hz, 1H), 4.76 (dt, J=6.3, 1.3 Hz, 2H), 2.70 (s, 1H), 2.56 (s, 6H), 2.23 (q, J=9.5 Hz, 4H), 2.11-2.01 (m, 4H), 1.58 (t, J=10.3 Hz, 6H);

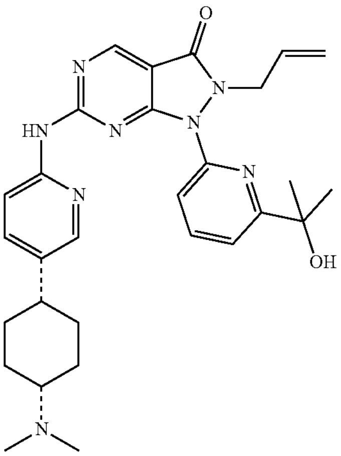

(I-41-2), its $^1$H NMR (400 MHz, Chloroform-d) is δ8.99 (s, 1H), 8.54 (s, 1H), 8.32 (d, J=8.7 Hz, 1H), 8.26 (d, J=2.4 Hz, 1H), 8.10 (t, J=7.7 Hz, 1H), 7.92 (s, 1H), 7.78 (dd, J=8.1, 0.8 Hz, 1H), 7.47-7.41 (m, 1H), 5.79-5.71 (m, 1H), 5.08 (dq, J=10.1, 1.2 Hz, 1H), 4.97 (dq, J=17.0, 1.3 Hz, 1H), 4.77 (dt, J=6.2, 1.4 Hz, 2H), 3.99 (s, 1H), 2.75 (d, J=11.0 Hz, 1H), 2.52 (s, 6H), 2.32-2.18 (m, 1H), 2.09 (d, J=14.4 Hz, 4H), 1.31 (d, J=22.8 Hz, 4H);

wherein, means an uncertain cis-trans conformation;

scheme E:

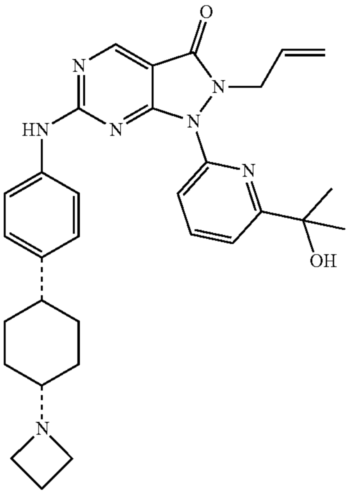

(I-8-1), its $^1$H NMR (400 MHz, $CDCl_3$) has a peak of 1.23-1.08;

wherein, means an uncertain cis-trans conformation;

scheme F:

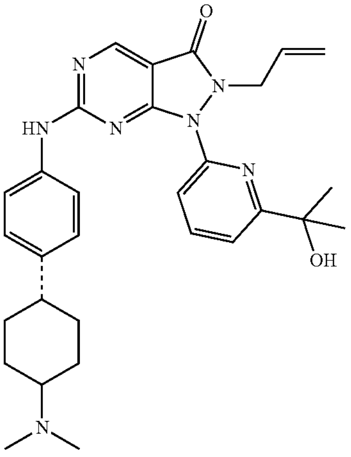

(I-1-1) with a retention time of 10.55 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

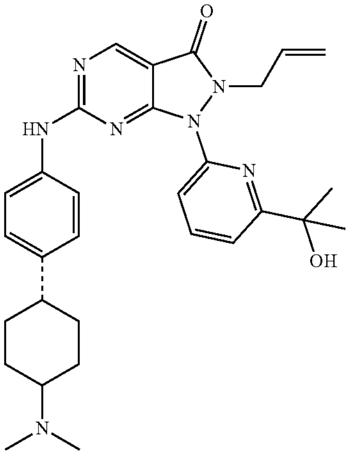

(I-1-2) with a retention time of 10.78 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

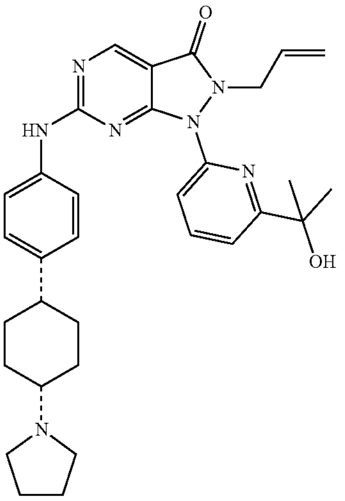

(I-3-1) with a retention time of 11.01 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

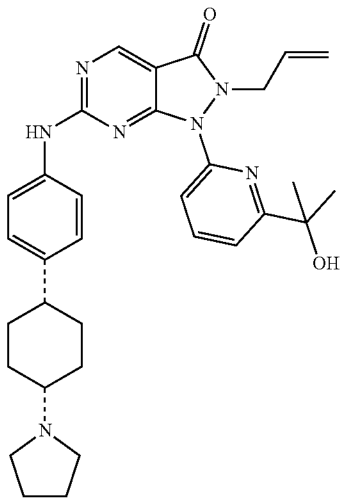 [SMILES: C=CCn1c(=O)c2cnc(Nc3ccc([C@H]4CC[C@@H](N5CCCC5)CC4)cc3)nc2n1-c1cccc(C(C)(C)O)n1]

(I-3-2) with a retention time of 11.20 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

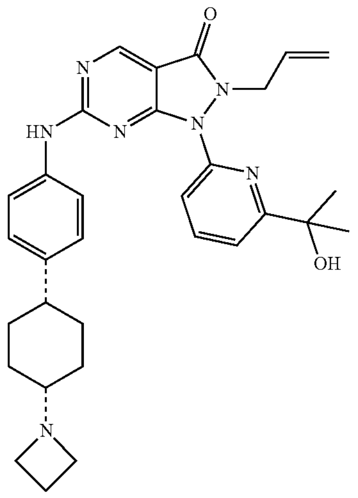

(I-8-1) with a retention time of 10.78 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

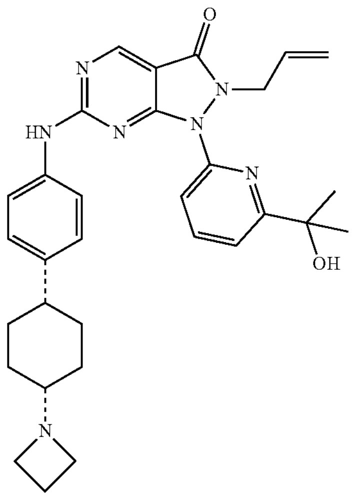

(I-8-2) with a retention time of 11.00 min under the following conditions: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→50% mobile phase B;

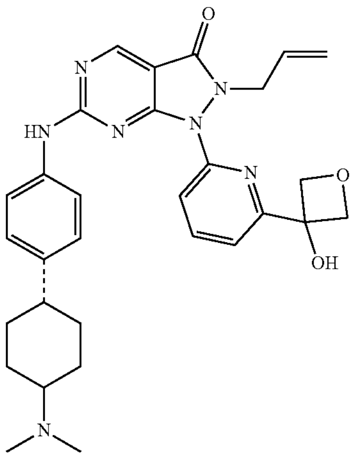

(I-15-1) with a retention time of 7.02 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

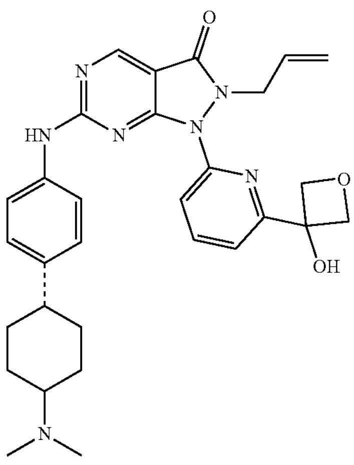

(I-15-2) with a retention time of 7.16 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

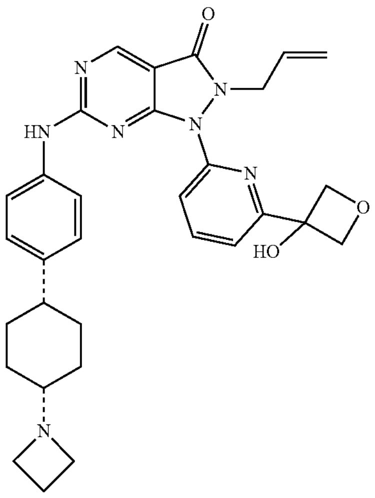

(I-36-1) with a retention time of 7.14 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

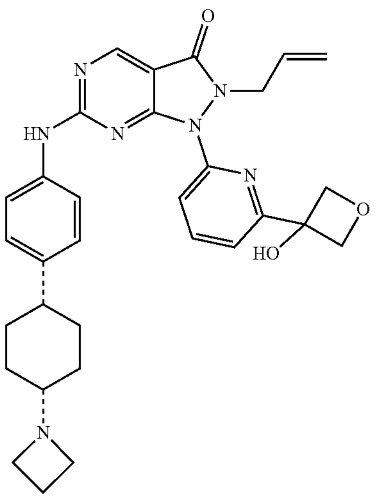 [SMILES: C=CCn1c(=O)c2cnc(Nc3ccc([C@H]4CC[C@@H](N5CCC5)CC4)cc3)nc2n1-c1cccc(C2(O)COC2)n1]

(I-36-2) with a retention time of 7.15 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

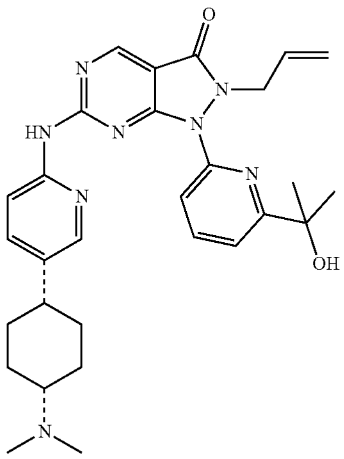 [SMILES: C=CCn1c(=O)c2cnc(Nc3ccc([C@H]4CC[C@@H](N(C)C)CC4)cn3)nc2n1-c1cccc(C(C)(C)O)n1]

(I-41-1) with a retention time of 6.17 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;

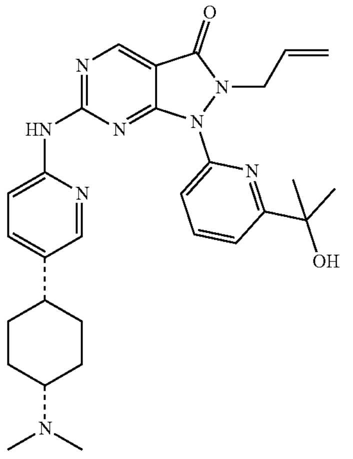
(I-41-2) with a retention time of 6.28 min under conditions comprising: Agilent 1260 high performance liquid chromatograph; mobile phase A: water (0.1% formic acid), mobile phase B: acetonitrile; column time: 15 min; column type: Waters' Xselect, 5 μm, 4.6×250 mm; gradient elution, 5% mobile phase B→95% mobile phase B;
wherein, means that the cis-trans conformation is uncertain;
scheme G:
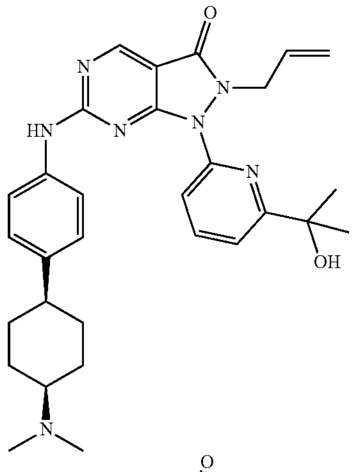
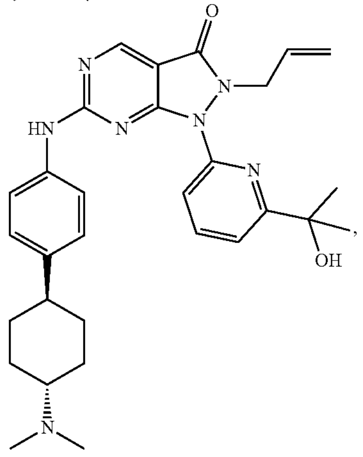
-continued
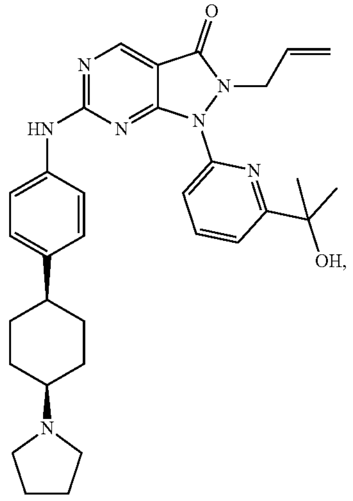
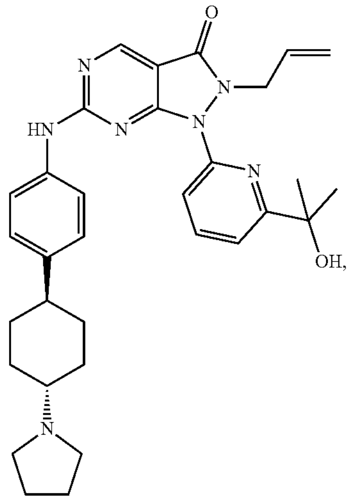
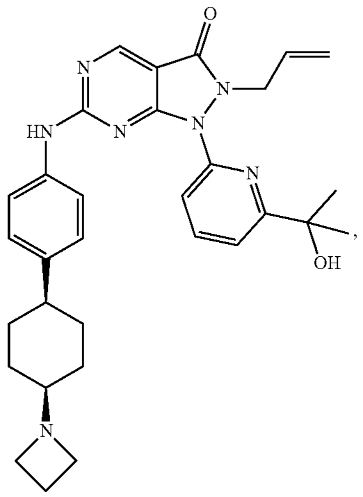

-continued
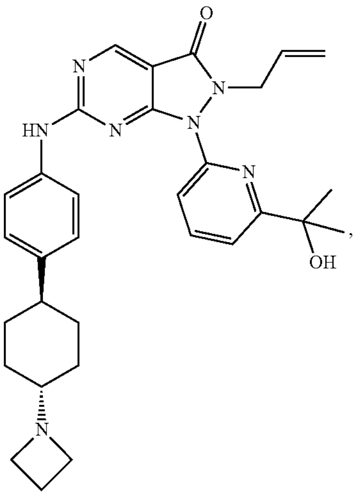
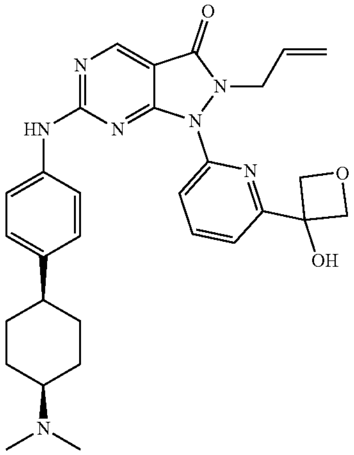
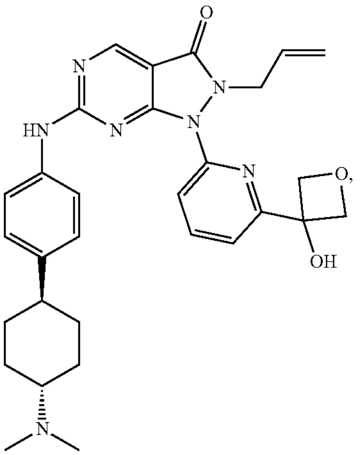
-continued
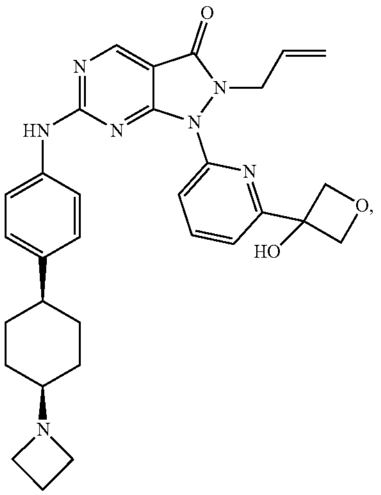
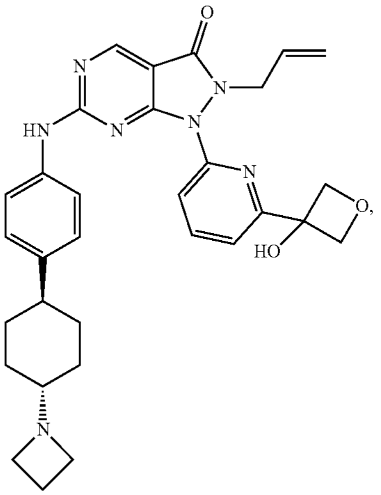
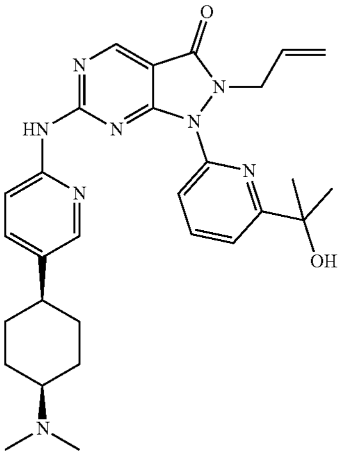
and -continued

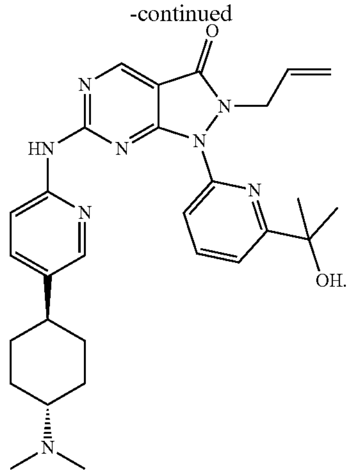

13. A preparation method of the pyrazolone-fused pyrimidine compound represented by formula II according to claim 1, the method is method 1 or method 2:

method 1, comprising: step I, oxidizing compound II-1A by an oxidant in an organic solvent to obtain compound II-1B; and step II, reacting compound II-1B with compound II-1C in an organic solvent and under alkaline conditions to obtain compound II;

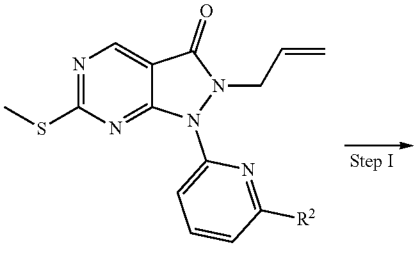

II-1A

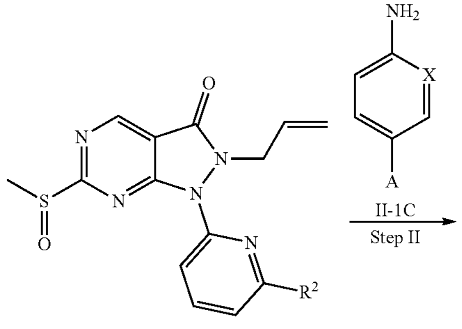

II-1B

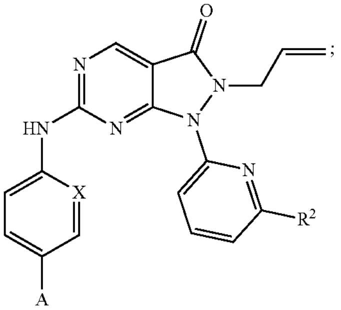

II method 2, comprising: step I, hydrolyzing compound II-2A ($R^1$ is —(C═O)—O—$C_2H_5$) to obtain compound II-2B ($R^1$ is —(C═O)—OH); and step II, a condensation reaction is carried out between compound II-2B and an amino compound in an organic solvent to obtain compound II ($R^1$ is —(C═O)—$NR^{1-5-1}R^{1-5-2}$);

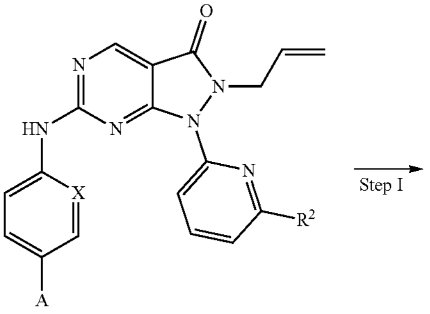

II-2A

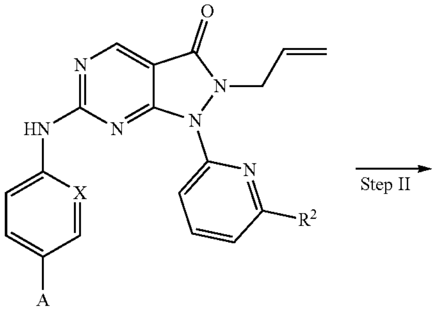

II-2B

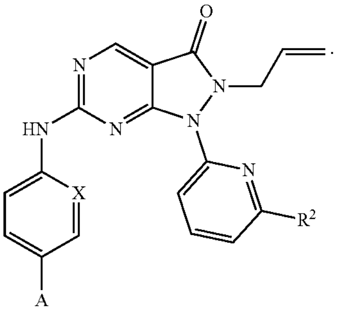

II

14. A pharmaceutical composition comprising a substance X and a pharmaceutical excipient;

the substance X is the pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof.

15. A combination comprising a substance X and an anticancer drug, the substance X is the pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof.

16. The pyrazolone-fused pyrimidine compound represented by formula II according to claim 12 or the pharmaceutically acceptable salt thereof, wherein, the pyrazolone-fused pyrimidine compound represented by formula II is I-8:

I-8

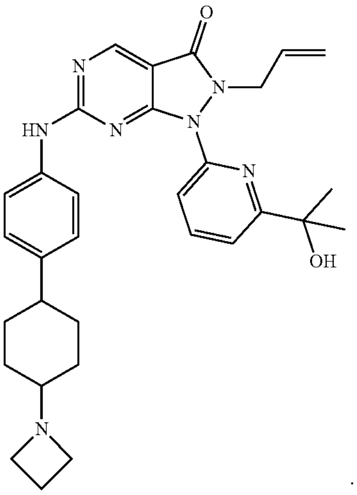

.

17. The pyrazolone-fused pyrimidine compound represented by formula II according to claim 12 or the pharmaceutically acceptable salt thereof, wherein, the pyrazolone-fused pyrimidine compound represented by formula II is I-8-1:

I-8-1

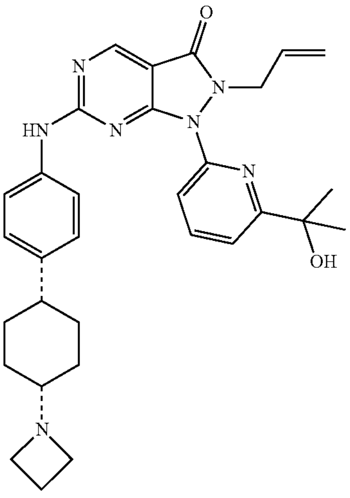

.

18. The pyrazolone-fused pyrimidine compound represented by formula II according to claim 12 or the pharmaceutically acceptable salt thereof, wherein, the pyrazolone-fused pyrimidine compound represented by formula II is I-23:

I-23

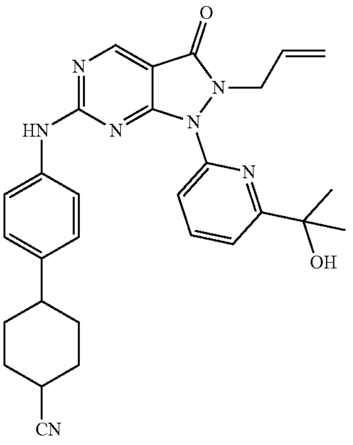

.

19. The pyrazolone-fused pyrimidine compound represented by formula II according to claim 12 or the pharmaceutically acceptable salt thereof, wherein, the pyrazolone-fused pyrimidine compound represented by formula II is I-15-1:

I-15-1

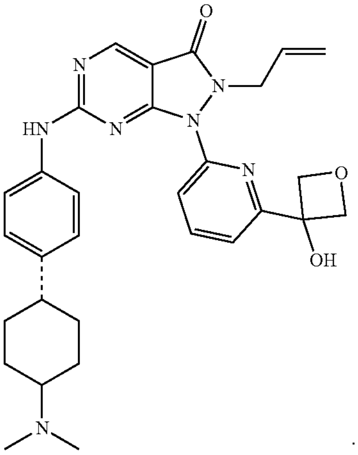

.

20. A method for inhibiting WEE1 kinase in a subject, comprising administering a therapeutically effective amount of a substance X to the subject;

the substance X is the pyrazolone-fused pyrimidine compound represented by formula II according to claim 1, the pharmaceutically acceptable salt thereof, the solvate thereof, the solvate of the pharmaceutically acceptable salt thereof, the metabolite thereof or the prodrug thereof.

* * * * *